US006329188B1

(12) United States Patent
Yan et al.

(10) Patent No.: US 6,329,188 B1
(45) Date of Patent: Dec. 11, 2001

(54) ISOLATED HUMAN PROTEASE PROTEINS, NUCLEIC ACID MOLECULES ENCODING HUMAN PROTEASE PROTEINS, AND USES THEREOF

(75) Inventors: Xianghe Yan, Gaithersburg; Karen A. Ketchum, Germantown; Valentina Di Francesco, Rockville; Ellen M. Beasley, Darnestown, all of MD (US)

(73) Assignee: PE Corporation(NY), Norwalk, CT (US)

( * ) Notice: Subject to any disclaimer, the term of this patent is extended or adjusted under 35 U.S.C. 154(b) by 0 days.

(21) Appl. No.: 09/797,906

(22) Filed: Mar. 5, 2001

Related U.S. Application Data

(63) Continuation-in-part of application No. 09/797,000, filed on Mar. 2, 2001, now abandoned.

(51) Int. Cl.[7] .............................. C12N 9/48; C12N 1/20; C12N 15/00; C12Q 1/68; C07H 21/04

(52) U.S. Cl. .................. 435/212; 435/252.3; 435/320.1; 435/6; 536/23.2

(58) Field of Search ................................ 435/212, 252.3, 435/320.1, 6; 536/23.2

(56) References Cited

PUBLICATIONS

Parsonage et al. The Journal of Biological Chemistry, vol. 273, No. 37, pp23812–23822. (Sep., 1998).*

Matsuoka et al. JP10150985–A. Sep., 1998. (English translation).*

* cited by examiner

*Primary Examiner*—Ponnathapu Achutamurthy
*Assistant Examiner*—Yong Pak
(74) *Attorney, Agent, or Firm*—Celera Genomics; Robert A. Millman; Justin D. Karjala

(57) ABSTRACT

The present invention provides amino acid sequences of peptides that are encoded by genes within the human genome, the protease peptides of the present invention. The present invention specifically provides isolated peptide and nucleic acid molecules, methods of identifying orthologs and paralogs of the protease peptides, and methods of identifying modulators of the protease peptides.

10 Claims, 48 Drawing Sheets

```
   1 CGCCAACATG GCGGCGCCCA GTGGCGTCCA CCTGCTCGTC CGCAGAGGTT
  51 CTCATAGAAT TTTCTCTTCA CCACTCAATC ATATCTACTT ACACAAGCAG
 101 TCAAGCAGTC AACAAAGAAG AAATTTCTTT TTTCGGAGAC AAAGAGATAT
 151 TTCACACAGT ATAGTTTTGC CGGCTGCAGT TTCTTCAGCT CATCCGGTTC
 201 CTAAGCACAT AAAGAAGCCA GACTATGTGA CGACAGGCAT TGTACCAGAC
 251 TGGGGAGACA GCATAGAAGT TAAGAATGAA GATCAGATTC AAGGGCTTCA
 301 TCAGGCTTGT CAGCTGGCCC GCCACGTCCT CCTCTTGGCT GGGAAGAGTT
 351 TAAAGGTTGA CATGACAACT GAAGAGATAG ATGCTCTTGT TCATCGGGAA
 401 ATCATCAGTC ATAATGCCTA TCCCTCACCT CTAGGCTATG GAGGTTTTCC
 451 AAAATCTGTT TGTACCTCTG TAAACAACGT GCTCTGTCAT GGTATTCCTG
 501 ACAGTCGACC TCTTCAGGAT GGAGATATTA TCAACATTGA TGTCACAGTC
 551 TATTACAATG GCTACCATGG AGACACCTCT GAAACATTTT TGGTGGGCAA
 601 TGTGGACGAA TGTGGTAAAA AGTTAGTGGA GGTTGCCAGG AGGTGTAGAG
 651 ATGAAGCAAT TGCAGCTTGC AGAGCAGGGG CTCCCTTCTC TGTAATTGGA
 701 AACACAATCA GCCACATAAC TCATCAGAAT GGTTTTCAAG TCTGTCCACA
 751 TTTTGTGGGA CATGGAATAG GATCTTACTT TCATGGACAT CCAGAAATTT
 801 GGCATCATGC AAACGACAGT GATCTACCCA TGGAGGAGGG CATGGCATTC
 851 ACTATAGAGC CAATCATCAC GGAGGGATCC CCTGAATTTA AAGTCCTGGA
 901 GGATGCATGG ACTGTGGTCT CCCTAGACAA TCAAAGGTCG GCGCAGTTCG
 951 AGCACACGGT TCTGATCACG TCGAGGGGCG CGCAGATCCT GACCAAACTA
1001 CCCCATGAGG CCTGAGGAGC CGCCCGAAGG TCGCGGTGAC CTGGTGCCTT
1051 TTTAAATAAA TTGCTGAAAT TTGGCTGGAG AACTTTTAGA AGAAACAGGG
1101 AAATGACCGG TGGTGCGGTA ACCTGCGTGG CTCCTGATAG CGTTTGGAAG
1151 AACGCGGGGG AGACTGAAGA GCAACTGGGA ACTCGGATCT GAAGCCCTGC
1201 TGGGGTCGCG CGGCTTTGGA AAAACAAATC CTGGCCCTGG ACTCGGTTTC
1251 CCAGCGCGGT CAACGCATCT GGAGGGGACT GGAGGAAACC CCCTTGTTGG
1301 AAGAGATTCC AAGAGAAGCA CGGTTTTCTC TTTCCCTTGC CCTGACTGTT
1351 GGAGTAAAAA ACCTCTTAAA TCCATTGTAT CAGAGGTCCT TACCTCTCTG
1401 ACAGTTACAA TGATCTTTGT ATCTGAACTT TGCACGTCTG CCGAAAAATC
1451 CGAACCTGTT GACTGGGATT TTTAAGAATC CGTTTCTCCC TTTTGTGTAT
1501 TCCATATTGG CCGGCCCCAA GGATGCTCGC AGAAGCCAGC CCCCAACCCC
1551 AGCCCTTCCG TATCTTTCCC CTCCATCGCG GCTTTGCGAT GAAAGATTAG
1601 CCCGCGAACA GAGGCATTGA TTACAAACAT GTCCTTGGCA GTGGAAAAAA
1651 AAAAAAAAAA AAAAAAAAAA AAAAAAAAAA AAAAAAAAAA AAAAAAAAAA
1701 AAAAAAAAAA AAAAAAAAAA AAAAAAAAAA AAAAAAAAAA AAAAAAAAAA
1751 AAAAAAAAAA AAAAAAAAAA AAAAAAAAAA AAAAAAAAAA AAAAAAAA
 (SEQ ID NO: 1)

FEATURES:
5'UTR:        1 - 7
Start Codon: 8
Stop Codon:  1013
3'UTR:       1016

Homologous proteins:
CRA|150000079513852 /altid=gi|9958075 /def=gb|AAG09564.1|AC0118...   294  3e-78
CRA|335001098677471 /altid=gi|11320956 /def=gb|AAG33975.1|AF250...   294  3e-78
CRA|89000000199735 /altid=gi|7297697 /def=gb|AAF52949.1| (AE003...   288  1e-76
CRA|18000005191372 /altid=gi|4006872 /def=emb|CAB16790.1| (Z997...   283  4e-75
CRA|335001098677475 /altid=gi|11320950 /def=gb|AAG33977.1|AF250...   283  4e-75
```

```
   1 CGCCAACATG GCGGCGCCCA GTGGCGTCCA CCTGCTCGTC CGCAGAGGTT
  51 CTCATAGAAT TTTCTCTTCA CCACTCAATC ATATCTACTT ACACAAGCAG
 101 TCAAGCAGTC AACAAAGAAG AAATTTCTTT TTTCGGAGAC AAAGAGATAT
 151 TTCACACAGT ATAGTTTTGC CGGCTGCAGT TTCTTCAGCT CATCCGGTTC
 201 CTAAGCACAT AAAGAAGCCA GACTATGTGA CGACAGGCAT TGTACCAGAC
 251 TGGGGAGACA GCATAGAAGT TAAGAATGAA GATCAGATTC AAGGGCTTCA
 301 TCAGGCTTGT CAGCTGGCCC GCCACGTCCT CCTCTTGGCT GGGAAGAGTT
 351 TAAAGGTTGA CATGACAACT GAAGAGATAG ATGCTCTTGT TCATCGGGAA
 401 ATCATCAGTC ATAATGCCTA TCCCTCACCT CTAGGCTATG GAGGTTTTCC
 451 AAAATCTGTT TGTACCTCTG TAAACAACGT GCTCTGTCAT GGTATTCCTG
 501 ACAGTCGACC TCTTCAGGAT GGAGATATTA TCAACATTGA TGTCACAGTC
 551 TATTACAATG GCTACCATGG AGACACCTCT GAAACATTTT TGGTGGGCAA
 601 TGTGGACGAA TGTGGTAAAA AGTTAGTGGA GGTTGCCAGG AGGTGTAGAG
 651 ATGAAGCAAT TGCAGCTTGC AGAGCAGGGG CTCCCTTCTC TGTAATTGGA
 701 AACACAATCA GCCACATAAC TCATCAGAAT GGTTTTCAAG TCTGTCCACA
 751 TTTTGTGGGA CATGGAATAG GATCTTACTT TCATGGACAT CCAGAAATTT
 801 GGCATCATGC AAACGACAGT GATCTACCCA TGGAGGAGGG CATGGCATTC
 851 ACTATAGAGC CAATCATCAC GGAGGGATCC CCTGAATTTA AAGTCCTGGA
 901 GGATGCATGG ACTGTGGTCT CCCTAGACAA TCAAAGGTCG GCGCAGTTCG
 951 AGCACACGGT TCTGATCACG TCGAGGGGCG CGCAGATCCT GACCAAACTA
1001 CCCCATGAGG CCTGAGGAGC CGCCCGAAGG TCGCGGTGAC CTGGTGCCTT
1051 TTTAAATAAA TTGCTGAAAT TTGGCTGGAG AACTTTTAGA AGAAACAGGG
1101 AAATGACCGG TGGTGCGGTA ACCTGCGTGG CTCCTGATAG CGTTTGGAAG
1151 AACGCGGGGG AGACTGAAGA GCAACTGGGA ACTCGGATCT GAAGCCCTGC
1201 TGGGGTCGCG CGGCTTTGGA AAAACAAATC CTGGCCCTGG ACTCGGTTTC
1251 CCAGCGCGGT CAACGCATCT GGAGGGGACT GGAGGAAACC CCCTTGTTGG
1301 AAGAGATTCC AAGAGAAGCA CGGTTTTCTC TTTCCCTTGC CCTGACTGTT
1351 GGAGTAAAAA ACCTCTTAAA TCCATTGTAT CAGAGGTCCT TACCTCTCTG
1401 ACAGTTACAA TGATCTTTGT ATCTGAACTT TGCACGTCTG CCGAAAAATC
1451 CGAACCTGTT GACTGGGATT TTTAAGAATC CGTTTCTCCC TTTTGTGTAT
1501 TCCATATTGG CCGGCCCCAA GGATGCTCGC AGAAGCCAGC CCCCAACCCC
1551 AGCCCTTCCG TATCTTTCCC CTCCATCGCG GCTTTGCGAT GAAAGATTAG
1601 CCCGCGAACA GAGGCATTGA TTACAAACAT GTCCTTGGCA GTGGAAAAAA
1651 AAAAAAAAAA AAAAAAAAAA AAAAAAAAAA AAAAAAAAAA AAAAAAAAAA
1701 AAAAAAAAAA AAAAAAAAAA AAAAAAAAAA AAAAAAAAAA AAAAAAAAAA
1751 AAAAAAAAAA AAAAAAAAAA AAAAAAAAAA AAAAAAAAAA AAAAAAAA
```

(SEQ ID NO: 1)

FEATURES:
5'UTR: 1 - 7
Start Codon: 8
Stop Codon: 1013
3'UTR: 1016

Homologous proteins:

```
CRA|150000079513852 /altid=gi|9958075 /def=gb|AAG09564.1|AC0118...    294  3e-78
CRA|335001098677471 /altid=gi|11320956 /def=gb|AAG33975.1|AF250...   294  3e-78
CRA|89000000199735 /altid=gi|7297697 /def=gb|AAF52949.1| (AE003...    288  1e-76
CRA|18000005191372 /altid=gi|4006872 /def=emb|CAB16790.1| (Z997...    283  4e-75
CRA|335001098677475 /altid=gi|11320960 /def=gb|AAG33977.1|AF250...   283  4e-75
```

FIG. 1A

| | | |
|---|---|---|
| CRA\|116000004179495 /altid=gi\|7939560 /def=dbj\|BAA95761.1\| (AB0... | 273 | 3e-72 |
| CRA\|335001098677473 /altid=gi\|11320958 /def=gb\|AAG33976.1\|AF250... | 273 | 3e-72 |
| CRA\|18000004928575 /altid=gi\|1703270 /def=sp\|P53582\|AMP1_HUMAN ... | 257 | 4e-67 |
| CRA\|335001114775549 /altid=gi\|12229672 /def=sp\|Q9SLN5\|AMP1_ARAT... | 250 | 3e-65 |
| CRA\|89000000202702 /altid=gi\|7301196 /def=gb\|AAF56327.1\| (AE003... | 237 | 3e-61 |

EST:

| | | |
|---|---|---|
| gi\|10730680 /dataset=dbest /taxon=96... | 676 | 0.0 |
| gi\|12768344 /dataset=dbest /taxon=960... | 603 | e-170 |
| gi\|5527904 /dataset=dbest /taxon=9606 ... | 559 | e-157 |
| gi\|953708 /dataset=dbest /taxon=9606 /... | 557 | e-156 |
| gi\|10283734 /dataset=dbest /taxon=96... | 391 | e-106 |
| gi\|5675411 /dataset=dbest /taxon=9606 ... | 311 | 2e-82 |
| gi\|11447216 /dataset=dbest /taxon=96... | 299 | 8e-79 |
| gi\|11951311 /dataset=dbest /taxon=96... | 285 | 1e-74 |

EXPRESSION INFORMATION FOR MODULATORY USE:

gi|10730680 Adrenal cortico adenoma for Cushing's syndrome
gi|12768344 Prostate embryonal carcinoma
gi|5527904 Colon tumor
gi|953708 Adult brain
gi|10283734 Heaptocellular carcinoma
gi|5675411 Pooled (fetal lung, testis and B cell)
gi|11447216 Kidney
gi|11951311 Prostate Tissue Expression:

Human Fetal whole brain

FIG.1B

```
  1 MAAPSGVHLL VRRGSHRIFS SPLNHIYLHK QSSSQQRRNF FFRRQRDISH
 51 SIVLPAAVSS AHPVPKHIKK PDYVTTGIVP DWGDSIEVKN EDQIQGLHQA
101 CQLARHVLLL AGKSLKVDMT TEEIDALVHR EIISHNAYPS PLGYGGFPKS
151 VCTSVNNVLC HGIPDSRPLQ DGDIINIDVT VYYNGYHGDT SETFLVGNVD
201 ECGKKLVEVA RRCRDEAIAA CRAGAPFSVI GNTISHITHQ NGFQVCPHFV
251 GHGIGSYFHG HPEIWHHAND SDLPMEEGMA FTIEPIITEG SPEFKVLEDA
301 WTVVSLDNQR SAQFEHTVLI TSRGAQILTK LPHEA
 (SEQ ID NO:2)
```

FEATURES:
Functional domains and key regions:
Prosite:
[1] PDOC00001 PS00001 ASN_GLYCOSYLATION
N-glycosylation site 269-272 NDSD

---

[2] PDOC00004 PS00004 CAMP_PHOSPHO_SITE
cAMP- and cGMP-dependent protein kinase phosphorylation site 12-15 RRGS

---

[3] PDOC00005 PS00005 PKC_PHOSPHO_SITE
Protein kinase C phosphorylation site

Number of matches: 3

| | |
|---|---|
| 1 | 15-17 SHR |
| 2 | 114-116 SLK |
| 3 | 321-323 TSR |

---

[4] PDOC00006 PS00006 CK2_PHOSPHO_SITE
Casein kinase II phosphorylation site 120-123 TTEE

---

[5] PDOC00008 PS00008 MYRISTYL
N-myristoylation site

Number of matches: 5

| | |
|---|---|
| 1 | 96-101 GLHQAC |
| 2 | 162-167 GIPDSR |
| 3 | 224-229 GAPFSV |
| 4 | 231-236 GNTISH |
| 5 | 278-283 GMAFTI |

---

FIG.2A

```
[6] PDOC00009 PS00009 AMIDATION
Amidation site

          202-205 CGKK

  _____

[7] PDOC00575 PS00680 MAP_1
Methionine aminopeptidase subfamily 1 signature

          249-267 FVGHGIGSYFHGHPEIWHH


Membrane spanning structure and domains:
 Helix Begin   End   Score Certainity
     1    47    67   0.640 Putative
          2   241   261   0.651 Putative
BLAST Alignment to Top Hit:
Alignment to top blast hit:
>CRA|150000079513852 /altid=gi|9958075
          /def=gb|AAG09564.1|AC011810_23 (AC011810) Putative
          methionine aminopeptidase [Arabidopsis thaliana]
          /org=Arabidopsis thaliana /taxon=3702 /dataset=nraa
          /length=369
         Length = 369

 Score =  294 bits (744), Expect = 3e-78
 Identities = 152/300 (50%), Positives = 185/300 (61%)
 Frame = +2

Query: 98  QSSSQQRRNFFFRRQRDISHSIVLPAAVSSAHPVPKHIKKPDYVTTGIVPDWGDSIEVKN 277
            ++ S+ RRN   RR R            VS    VP HI +P YV +G++PD     ++
Sbjct: 80  ETKSKVRRNPPLRRGR-----------VSPRLLVPDHIPRPPYVESGVLPDISSEFQIPG 128

Query: 278 EDQIQGLHQACQLARHVLLLAGKSLKVDMTTEEIDALVHREIISHNAYPSPLGYGGFPKS 457
             + I   +   AC+LA  VL  AG  +K  +TT EID  VH  II   AYPSPLGYGGFPKS
Sbjct: 129 PEGIAKMRAACELAARVLNYAGTLVKPSVTTNEIDKAVHDMIIEAGAYPSPLGYGGFPKS 188

Query: 458 VCTSVNNVLCHGIPDSRPLQDGDIINIDVTVYYNGYHGDTSETFLVGNVDECGKKLVEVA 637
            VCTSVN  +CHGIPDSR LQ GDIINIDVTVY +GYHGDTS TF  G VDE  K+LV+V
Sbjct: 189 VCTSVNECMCHGIPDSRQLQSGDIINIDVTVYLDGYHGDTSRTFFCGEVDEGFKRLVKVT 248

Query: 638 RRCRDEAIAACRAGAPFSVIGNTISHITHQNGFQVCPHFVGHGIGSYFHGHPEIWHHAND 817
              C +  IA C+ GA F  IG  IS    + G+ V   FVGHG+G  FH  P I+H+ ND
Sbjct: 249 EECLERGIAVCKDGASFKKIGKRISEHAEKFGYNVVERFVGHGVGPVFHSEPLIYHYRND 308

Query: 818 SDLPMEEGMAFTIEPIITEGSPEFKVLEDAWTVVSLDNQRSAQFEHTVLITSRGAQILTK 997
                M EG  FTIEPI+T G+ E      D WT ++ D    +AQFEHT+LIT  G++ILTK
Sbjct: 309 EPGLMVEGQTFTIEPILTIGTTECVTWPDNWTTLTADGGVAAQFEHTILITRTGSEILTK 368
(SEQ ID NO:4)
```

FIG.2B

```
>CRA|335001098677471 /altid=gi|11320956
          /def=gb|AAG33975.1|AF250961_1 (AF250961) methionine
          aminopeptidase-like protein [Arabidopsis thaliana]
          /org=Arabidopsis thaliana /taxon=3702 /dataset=nraa
          /length=369
         Length = 369

 Score =  294 bits (744), Expect = 3e-78
 Identities = 152/300 (50%), Positives = 186/300 (61%)
 Frame = +2

Query: 98  QSSSQQRRNFFFRRQRDISHSIVLPAAVSSAHPVPKHIKKPDYVTTGIVPDWGDSIEVKN 277
            ++ S+ RRN   RR R           VS    VP HI +P YV +G++PD     ++
Sbjct: 80  ETKSKVRRNPPLRRGR-----------VSPRLLVPDHIPRPPYVESGVLPDISSEFQIPG 128

Query: 278 EDQIQGLHQACQLARHVLLLAGKSLKVDMTTEEIDALVHREIISHNAYPSPLGYGGFPKS 457
              + I  +  AC+LA  VL  AG  +K  +TT EID  VH  II   AYPSPLGYGGFPKS
Sbjct: 129 PEGIAKMRAACELAARVLNYAGTLVKPSVTTNEIDKAVHDMIIEAGAYPSPLGYGGFPKS 188

Query: 458 VCTSVNNVLCHGIPDSRPLQDGDIINIDVTVYYNGYHGDTSETFLVGNVDECGKKLVEVA 637
            VCTSVN  +CHGIPDSR LQ GDIINIDVTVY +GYHGDTS TF  G VDE  K+LV+V
Sbjct: 189 VCTSVNECMCHGIPDSRQLQSGDIINIDVTVYLDGYHGDTSRTFFCGEVDEGFKQLVKVT 248

Query: 638 RRCRDEAIAACRAGAPFSVIGNTISHITHQNGFQVCPHFVGHGIGSYFHGHPEIWHHAND 817
              C ++ IA C+ GA F  IG  IS    + G+ V   FVGHG+G  FH  P I+H+ ND
Sbjct: 249 EECLEKGIAVCKDGASFKKIGKRISEHAEKFGYNVVERFVGHGVGPVFHSEPLIYHYRND 308

Query: 818 SDLPMEEGMAFTIEPIITEGSPEFKVLEDAWTVVSLDNQRSAQFEHTVLITSRGAQILTK 997
                M EG  FTIEPI+T G+ E     D WT ++ D   +AQFEHT+LIT  G++ILTK
Sbjct: 309 EPGLMVEGQTFTIEPILTIGTTECVTWPDNWTTLTADGGVAAQFEHTILITRTGSEILTK 368
(SEQ ID NO:5)
Hmmer search results (Pfam):
Scores for sequence family classification (score includes all domains):
Model     Description                                    Score    E-value  N
--------  -----------                                    -----    -------  ---
PF00557   metallopeptidase family M24                    241.1    1.6e-68    1
PF01982   Domain of unknown function                       7.1       0.85    1

Parsed for domains:
Model     Domain  seq-f seq-t    hmm-f hmm-t      score  E-value
--------  ------- ----- -----    ----- -----      -----  -------
PF01982     1/1     169   180 ..   113   124 .]     7.1     0.85
PF00557     1/1      87   326 ..     1   292 []  241.1  1.6e-68
```

FIG.2C

```
   1 CACCCAGCTT ATATCCCATA AGTTGATGGT TTTGGCGGAC ATGTGCTGGC
  51 AGCTTTTAAC CCTTCTGCGG TGAGAAGGAT GTGTATGAGA GAAGCCAGAT
 101 CCAGGGTCAG TGGATGAGCT ATCACCTGTG CAAGTTCATA TTTGCTTCAT
 151 TTCTAGCTCA TCCCAGATAT CTACATTCCA TGCCGAACTT ATTGAGGATT
 201 TCCTCACTGG ATTCCACTAC TGCTGGTGCC ACCTGGGTCC TCATAGTGTT
 251 TCCTTTTCCT TTTAGTTGTA GGGGAATAAA GCATTCATTT ATTTTCCAAG
 301 GGTTGGCTGA GTTAAGTCAC ATGAACATGT GTTCTATTTC AGATGGGTTT
 351 GAAACTAGGC TTGATGCCTT AAGGAATAGG GATGTCTAGA TTTCTTTTTT
 401 CTGTACACTT CTTAAGACTC TGTGGCCAGC TAACTCTCAG GCTCCTTTGC
 451 TGCACTCAGA TTGCTGGCCT CAGTTACACA GAGGACAGAT TTGCCACATT
 501 CAAAAATGCT CTCCCTGGAA TTGAAATGAG TTTGCAAAAG GTAGGAGTAC
 551 ATTTTATTCT CATTCTTGTG CATCTTATTT ACCCTGATGG AAAGCATTAC
 601 TTCTCTTTAT CTTTCAAGGT GACCCAAAAG CATCCAAAAC CAGGTTTTCC
 651 AGAATTATAG CATGTGTCCT CTAATGAAAT GCCAACATTC ACTCTCTTTA
 701 AAAGTAAAAA TATCAAGATT ATATAGTCAT TAAAAAGAAT AAGTCTGAAC
 751 TAAGTGTTCT AAGATTTGAT GCCTATGATG ACTGGAATGG AAAAAGCAAG
 801 TCATATGATT CTATTTAAAA TACTTACATT TGCCTGTGTG TAAAAGGCAA
 851 AGATCTCAAT TGAGCACACG GTGGTTAACT GGGGAGTGGG ACTATGGTAT
 901 GTACAGAGGG CGAGGAAGGG GCTTGCACTT GTTCCTTATT TCTGAATTGT
 951 TCTGAATTGT CTAGATTATT CACTGAGTGT GTAGTGCTTA AAAATTAATT
1001 AGAAGACATC ACACACATTC ACTGAGAATC CTAATCAATC TTCACTGCAT
1051 TTAAAGTCTG GAAACGGTTA CATTCTCAGT TTGACTGGTT TCATGCAGTG
1101 TTCAATTGCT TCACCTGACA TTCCTCGGGT ATCGGGTTCT GTGCCGGGCA
1151 CGGAGGCTAC TAAGATGAAT AACACCTGGT CCATGACAGG ATGGCATCTA
1201 CCCCAGAACA CAGGTAAGAG AGACAGTGAA TTTGGTAAAA ATGGGCACCG
1251 TCATCAGTAG GCATACATCA GCTCCCTCAT CTGATTCACA ATTGGCCTTC
1301 TGTAGGCTTC TTCTCTTGGC AATGCAATTG GCAGGCGTCA TCCTTTTATA
1351 CTTAAACTCC AAATTTAGGA TTAAGACTCC AGTTAATACT GCCAAGCAGA
1401 AGGCGTCCTT GGAGAAAGAG AAGTCTCCTG AACATACCCA CTGGGGTACC
1451 TAGAATAGAT TTTGCAGCGA CACACAGATC CTGTGTTGTC TGGAGTCTCT
1501 GCTGAGTAAT GTAGATTCTG GGACAGCAAA AGGGGAGCTG GTGACTTTGA
1551 ACCAAATTTT ACCTTTCAAC TGAATCCAGG GGAATAATTT GCAACAGAGT
1601 GGCAGACGAT ACAAAGTGCT ATGTTGAACA CTAGATTGTG CTTTATTTTT
1651 TCCGCCCAAC TTCACGTTTC CATGCACCAA AATGTTGATG CTATAAATAT
1701 TGGATGCCAC GCTTACCTGA CAGGCTTCTT CCATCCCACC TGGGCGCGGG
1751 GGCTCAGAGC GAGCGCGCGA GCCGCGGCTG GAGCCCGCCT CTCGCGGCTG
1801 GAGAGGACTC AGCCGGCCGC GGGTTCTGCT GCTTGCCCGG GTGCCCTAGC
1851 CGCTTCCCAG CCAGGGCTCC CGCAGTCAGC CCCGCGCGCG CACGCGCGCT
1901 CCCCTCGGGC GGCCTCGACG CCTCAGGGCT TCGGCAGGGC TGCGACTGGC
1951 CGGCTCCAGC GGGCGGGGCG GCGAGCGAGT GCTCGCGGCC ACGTGACCGA
2001 CGCCAACATG GCGGCGCCCA GTGGCGTCCA CCTGCTCGTC CGCAGAGGTA
2051 AGCGCGTGGA GGAGAGCCCC GTGAGGGTTC GCACGGTTGC TCACTAGGTA
2101 CGCACCCGGG TCCAAAGGGA TGCGCACCCG CGCTCAGACT TCTCGGCGCA
2151 CACGACTGTA CTTTCAGTGT TTACGAACAC ACGCAGGCAC ACACGATGAC
2201 ACATTCACAC ACCACAGGAT CACACATACA AATTTGTTCA CTGATCACCC
2251 GCCTAGAACA CGTCACCACG TGGCATCTTT TCGCAATTAC TCCTTGAGAT
2301 TTGCGGGCCA TTGTCTGAAG TTTTTTTCCC CAACTTCGGT TGTATCATTA
```

FIG.3-1

2351 GTGTAACCAA CATTTATTCT GTATGCCGAG CAAGGAAACC TATGGTAATT
2401 CTGAAATGCA TCTGGACACC CGGTTCCCTT CCCTAGAGCT TTTATGCAGG
2451 CATGCTTTTT GGGGACTTGC AAAATGTGAT GGTTTTCTTC CAGTGACTTA
2501 AAGTTAAGAA GATAAGAAAG GATGTCTGGG TAGTTCTAAG TAGGTTTTAT
2551 CCTGCGTGAG TGTTGAGATT TTAGTAAATA TACAAATGCC TTTGCAGCAG
2601 AATTGGGGAA ATCTTTGTTG GATTTGAACT AGGTGCTGAA TCTTTGTTGG
2651 AAAGAACTAG AAAGTTTTTC CAAGGACGGG GGAAGAGGAA AACTATCATA
2701 TTTTGAGGAG CTACTTAAGC GTCAGGCATG TAGGAACAGT TTTGTGAGGT
2751 AAATATTATT TTCATAGTAA CAGCTACTGT TTATTAAGTG CCTTTTAAGT
2801 ACACGATACT GTGTTAAGCG CCTTACATAT GCTTGCTTCC TTTTAAAACT
2851 CAATGAATGA GACCCCGTCT CTACAAAAAA TTTTAAAAAT TAGTCGGGCG
2901 TGGTGACACA TGCCTGTAGT CTCAGCTATT CTGGGGGTTG AGGTGGTAGG
2951 ATCGCTTGAG CCTGGGAGGT CAAGAGGCTG CAGTGAGCCG TGATCGTACC
3001 ACTGAACTCC AGACTTGGCA ATAGAGCCAG ACCCTGTCTC AAAAACAAAA
3051 ACAAAAACCC AGTGAGTTAG GAATTATTTT CTCTTTGCAG AAGGGAAAAG
3101 TAAGGCTAGA GAGGTTAAGT AACATTACTA AGGTCGCATA AATGGTAAGA
3151 GGCAGATTGC TCATTTGAAC ATGACTCTAA TTTTTTTTTT TAAGACTCAT
3201 TTCTCGGTAC TGCATGACGT GGTCACTCCA TAGAAGTCAG TGTGTAAAGT
3251 TCAGCAGAGA CAGTGCAGGA TGAGTGTGTA CAAAAAGTGA AGAGAGCCTG
3301 GGCACGGTGG CTCACACCTG TAAACCCAGC ACTTTGGGAG GCCGAGGCAG
3351 GTGGCTCACT TGAGGTCAGA AGTTCAAGAC CAGCCTGGCC AACATGGTGA
3401 AACCCCGTCT CTACTAATAT ACACAATTAG CTGGGCGTGG TGGCGCATGC
3451 CTGTAATCCC AGCTACTCGG GAGACTGAGG TAGGAAAATT GCTTTAACCC
3501 AGGAGGTGGA GGTTGCAGTG AGCTGAGATC ATACCACTAC ACTCTAGCCT
3551 GGGCGACAGA GCGAGACTCC GTCTCAGAAA AAAAAAATAA ATAAAAATAA
3601 TAAAAAATAA GAAGTGAAGA GGAAGATATT TTTAGAGAGG AAGAAGGTTG
3651 GTAATCGAAT AGACTTCAGT ATTTCAGTGT TAGTGGAGAT GAGAAAGGGG
3701 CCACAGGAAG ATTTGAGGGG AGAGATGTGT ATGGGGAAGG TGATGTAGCG
3751 AGCATTTTGG ACTGGTTGCA TGAAGGAATG GACATCAGCA TGAGAGTGTA
3801 GCCTTGTGAA AAGACAGCCA ATTTACATCT CTCAAGATCT GGGTGCCAGG
3851 CCTGGCAAGG TGGCTAATGC CTGTAATATT ACCCAGCACT TTGGGAGGCC
3901 AAGGCGGGCA GATCACTTGA GGCCAGGAGT TCAAGACCAG CCTGGCCAAC
3951 ATGGTGAAAC CTGTCTCTAC TAAAAATACA AAAATTAGCC AGGTGTGGTG
4001 GCACATGCTG GTAATCCCAG CTACTTGGGA GGTGGAGGTG GGAGGGATCG
4051 CCTGAACCCA GGAGGCGGAG GTTGTAGTGA GCTGAAAAAA AAAAAAAAAA
4101 AGATCTGGGT TCCAGTCCAA ACTTTCTTTA CTAATTACTT TTCTGTTTCC
4151 TCTTTTCACA AGAAATCATG GCTTTTAGAC TTCATTTTTG TATGCTTCAG
4201 GTAATGGTGA GAAGGATCTG AGGAGATAGT CAATGTAGAG GAGGAGCCAA
4251 AAAAAAAACA ACCTGAAAAC ATACATAGGT GTATGTATGT ATATATATAT
4301 ACACCTATGC ATGTATAAAC GTATTTTTAT ATGTGTGTAT ATATGTATTA
4351 GGTTGGTACA AAAGTAATTG CAGTTTTAGA ATCAATGACA AAAACTGTGA
4401 TTACTTTGCA CCAACTGTAT ATATAACATC TCTTTGCAGA TAACAGAAAT
4451 AGCATTAATC TTTTCTTTCT TTTTGATCAC TTATTATTTT GACAAATGGT
4501 GGTTTAGACA GTCTTGAGAA AATATATTAT ATGGAAGTCA GGCCAAGTTA
4551 TTGGTTCCTA TAATCCATCC CACTGTATCC CAAAGTGTTG CAACAACCAA
4601 GAAGTGGATC CTCTGATTAG AGGAGAGAAG AAAAATGTGT CATCAGGAAG
4651 CTATTTTAAT GATGGAGAAA GGGCCCCTTT TTGGACTACC CATAGCTAGT

FIG.3-2

```
4701 TTTAAATTGC AGAGAGGTTT TCCTGCTCCC CACCCCCAAG AATTGAAAAT
4751 GAAGGGTAAA TTCACGAAGA CTCCTCTCTC CACCCTCTTC CTCCCTTTCA
4801 CCCATCTAGA TTTATGTAAA GCAATCCATT ACAAGTCTTC ATGTACCAGG
4851 ATTTATTATC AGCATTTATG AGCATCATTT CTTCTTGAAA TAGAGGAAGA
4901 CTTTTTTTTA ACCTTTTAAA AAAGGCATGA GGTTTCTCTT GTGACGCCTC
4951 AACTCATTGT GGCTTTGGTC ACAGTATACC CTGTATACAG TAGTTACCTA
5001 GCTCCTCTCA CCATTTCTGC TCCTTACTAG ATTATTAATT CTTGTTGAAC
5051 AGAAGCTTTG TCTTATGTAT CTTTCTGTCT TTATAAGCAC AGTACCTGGC
5101 TCAAAGTTAA GCTCATTAAA AGTATACAGA ATTGAGAGGC TGTTAAGATT
5151 TGTTCTCTTC CATCATGGTC TAAGGAGGGT TGGGTAGAAA CTATGAGTAG
5201 TGACATTGGA AAGAGGAAAA GACAGATCAG CCTCTTGGAA CCAAGAGAGA
5251 AGGTAACAAG GGCCTTTAAG GGACTAAAAT ACTCCCAAGT ATTAGTGCTG
5301 GCAGGAAATC CCTTCCTCAG AGTACAGAAT CCCTACCCTG GGGCCCCAGG
5351 AACTCTCTCC TATCTCAGTC TCACTCCCAG CCCTCGCTTC ACTGGAATCC
5401 CAGGTCTAGC TCGGGCCACG AAGCAAGATC CCAGTGAATA TGAAGAGGAA
5451 CAAGGAAATC TCAGCTTGAA TTGTAATAAT CCCCATGTGT CAAGGGCAGG
5501 ACCAGGTAGA GGTAATTGGA TCATGGGGAT AGTTTCCCCC ATTCTGTTCT
5551 TGTGATAATG AGTGAGTCTC AGGAGATCTG ATAGTTTTAT AAGCGTCTGG
5601 CATTTTCTCC TGCTTGCACT CATTCTCTCT CCTGCCACCC TGTGAAGAGG
5651 TGCCTTCTGC CATGATTATA CATTTCCTGA GGCCTCCCGA GCCATGCAGA
5701 ACTGTGAGTC AATTAAACCC CTTTTCTTTA TAAATTACCC AGTCTCAGGA
5751 ATTTCTTCAT AGCAGTGTGA GAACAGACTA ATACAGCAAG TAAGAGGGCA
5801 TATTTTCTTT CTTTTTTTTT TGAGACAGAG TCTCGCCCTG TAGCACAGGG
5851 TGAAGTGCAG TGGTGCGATC TTGGCTCACT GCAACCTCTG CCTCCCGGGT
5901 TGAAGTGATT CTCCTGCCTC AGCCTCCCGA GTAGCTGGGA CCACAGGTGC
5951 CCACCACCAC GCCTGGCTAA TTTTTGTATT TTTAAGTAGA CACGGGGTTT
6001 TGCCATGTTG GCCAGGCTGG TCTCTCTTGA ACTTCTGACT TCAAGTGATC
6051 CGCCTGCCTC AGCCTCCCAC AGTGCTGGGA TTACAGGCAT GAACCACCGC
6101 ACCTGGCCAT TTACTTATTT TTAACAAATA TAAAAAAAAC TTAGAAGTAC
6151 TTTTGTTCAC TTGTGACTGT AAGGCCCTAG ACTCCTCCAC TGAGAATTTT
6201 GTTACCTTAG TGGTTTTTCA AAAATGTAAT AGCCAGGCAG GGGAGGGGCT
6251 GTTATACATC ATGAGTTAAG TACTTTAAAC TTTTGCCAAC TGCCCTGAGA
6301 TCCTTGCTAT CTTGTATAGC TTCTGCAGGA AAATGTCTGC TCAGTTTTGC
6351 CAAACCAACT TTTCTTTTTT TTTTTAAATC GAGACGGAGT CTTGCTCTGT
6401 TGCCCAGGCT GGAATGCAGT GGTGTGATCT TGGCCCACTG CAACCTCTGC
6451 CACCCAAATT CAAGTGATTC TCCTGCCTCA GCCTCTTGAG TAGTGGGAAT
6501 TACAAGCATC CGCCGCCATG CCCGGCTAAT TTTTGTATTT TTAGTAGAGA
6551 CGGGGGTTTC GCCATGTTGG CCAGGCTGGT CTCGAACTCC TGACCTCTGG
6601 TGACGCACCT GCCTCGGCCT CCCAAAGTGC TGGGATTATA AGCATGAGCC
6651 ACCACGCCCA GCCGCCAAAC CAACTTATAA TTAAACTTTT GGGATGCAAT
6701 TCATGGGTGA TTTGGAAAAT GCTAACATTC CTAAGTTTAG CTTCCTATTA
6751 CTTAGACTAC ATTCCTGTTG ACATCCAGAG AATGGAAATG GAGTTTTGCC
6801 GTATGACATC TTTTAACAAA TACATTCCAA TTCTATTATA ATATGGCATG
6851 TTACTACACA GATTAAGAAA TACTTATGAA ACCTTGGCTC TAAAGTGCTC
6901 CTAAATCCAT ACATACTTGT ATGTGTTTTC CTCTATTTGA AACAGCTAGC
6951 TTGCTTCCTT TCTTCCTTCC TTTTTTTTTT CTTTTTTCAG GGTCTCTGTC
7001 ACGAAGGCTG GAGTGCAGTG GCACAATCAC AGGTCACTAC AGCCTCAACT
```

FIG.3-3

```
7051 TCCTGGGCTC GACCAGTCCT CCCACCTCAA CCTCCTGAGT GGCTAGGCGC
7101 ACACCACCAC ACCCAGCTAA TTTTTTGTTT TTTTCATAAA GACAGGTTAT
7151 CATCATGCTG CCCAGGCTGT GAAACAGTTT TCTTTCTTTC TTATTTATTT
7201 ATTTTATGTT TTATTTCAAT AGTTTTTGGG GTACAGGTAG TTTTTCGTTA
7251 CATGGATGAA TACTTTAGAA GTGAATTCTG AGATTTTAGT GCACCCATCA
7301 CCCAAGCAGT GTACATTGTA CCCAGTATGT TTTCTTTTAT CCTTCACCCC
7351 TGCATCCCTA GAGTTCATTA TATTGCTCTG TATGTTTTTG CATCCTCATA
7401 GCTTAGCTCC CACTTATAAG TGAGAACATA CAGTATTTGG TTTTCTTTTC
7451 CTGAGTTACT TCACTTAGAA TAATGGCCTC CAGTTCCATC CAAGTTGCTA
7501 CAAAAGACAT TATTTTGTTC CTTTTTATGT CTGAGTAGTA TTCCATGGTG
7551 TCTGAAAAAT ATATATATAT ATATATATAT ATATCTTTTT TTTTTTTTTT
7601 GAGAGTCTCT CTGTCACCCA GGCTGGAGTG CAGTGGTGCA GTCTCGGCTC
7651 ACTGCAACCT CCGCCTCCCG GGTTCAAGCA ATTCTCTTGC CTTAGCCTCC
7701 TGAATAGCTG GGACTACAGG CACCCGCCAC CATGCCCGGC TAATTTTTGT
7751 ATTTTTTTGT AGAGGCGGGA TTTCACCATG TTGGCCAGGC TGATCTCAAA
7801 CTCCTGACCC AAATGATCCA CCCACCTCGG CCTCCCAAAG TGCTGGGATT
7851 ACAGGCATAA GCTACCATGT ATAACACATT TTATTTATCT ACTCATTGGT
7901 TGATGTGAAA CAGCTTTCTG TACTACAAAT AGTTCTGTCT CCCATTGAAA
7951 TTATGAAATT TCGATGTATA CTACAGGGCA TATAGACCCT CAGTGATGAA
8001 TGCTTTGCAG TCATTAAAAA AAAATATATT GACCTGCATT TGTTGGTATG
8051 GAATGATGTC CACAAAATAC ATTATTATGG AAAAGCAAGT TATAAAACAA
8101 TATAAGCTAC TCACATTTTG TAAATAAAAT ATCAATATTT CTGTATATGT
8151 GTATACATGT GTCTAAGTGT ATATAACATG TATACACACA GAGTATGACA
8201 TACAAGCAGA TATTTATAGT TTTTGTTTTT TTTTTTTTTG AGACGAAGTC
8251 TCGCTCTGTC ACCCAGGCTG GAGTGCAGTG GCGGGATCTC GGCTCACTGC
8301 AAGCTCCGCC TCCCAGGTTC ATGCCATTCT CCTGCCTCAG CCTCCCAAGT
8351 AGCTGGGACT ACAGGCACCT GCCACCACGC CCAGCTAATT TTTTGTATTT
8401 TTAGTAGAGA TGGGGTTTCA CCGTGTTAGC CAGGCTGGTC TCGATCTCCT
8451 GACCTCGTGA TCTGCCTGCC TTGGCCTCCC AAAGTGCTGG GATTACAGGT
8501 GTGAGCCACT GCGCCTGGCC AATATTTATA GTTTCTATGA AATACCCGCT
8551 TTCCTCAAGC ATTAGAAATC CATAAAAATC AGTGTGGATG CTATATATCT
8601 TAGGGAACTT GGCAAAGATG GGAGAAGTAC TATGTGTATG CAGAACTTCA
8651 TTTGAACAAC ATCTAGTTTT AAGCTGAAAC AGCTTGTTTT TACGGAGACT
8701 GAATTTTCTT TTTTAGCTTT TGAACATGGA GACAGTTAAA CATAATGCAA
8751 AAGTAGAGAG AATAGTACAA TGAACTCCCA CGTAGCCATC ATCTAGTTAC
8801 AATAGTCATC AACCTATGGC CACTATTGTT ACATCTATAC TCCCAGTTAC
8851 TTTGCCTCCC CACAGGTGGA TTATTTTGAA GCACATTCCA GATATATTAT
8901 TTCATCTGTA GATTTTTTAC CGTGTATCTC TAAAAGATAG GGAGCCATTT
8951 TTTTCTTCTT ACGTTGTACA TATCAGTTCT AGAATTTGCA TTATAATTTC
9001 CATTTCTTGT TGAGATTTCC CACCTGTTCA CTCATTATGT TCATCTTTTC
9051 CTTTAAGTAC TTGAACATAC ATATTTATAA CAGCTTTTTA AAAATCTGTT
9101 AATTTTATTA TTGGGTCTCC TCAGAGTCTG TTTCTGTTTT GTTGACTGCT
9151 GTTTTTTTTT TTATTGTACA TTACGTTTTC CTGCTGCTTC CCATGTCATG
9201 TAATTTTTTT TTTTTTTTTT TTTTAAGAGA AGGGCCTTGT TCTGTCACCC
9251 AGGCTGGAGT GCAGTGGTAC AATCATAGCT CACTGCAACC TCAAACTCCT
9301 GGGCTCAAGC AATCCTCCTG CCTCAGCCTT CCAAGTAGCT GGGACTATAG
9351 GCGCACACCA CCATGTCTGG CTAATCATGT AATATTTAAT TTTATAAGTG
```

FIG.3-4

```
9401 GCATGACAGA TAATATCTTG GTGGAGATTA TGTTGTTTTT CTTTAACATA
9451 TGTTTTAAAC AACTGCCAGG CAATATGTTA AATCTGTTTG ATTCTTTCAG
9501 GCTTGGTTTT TATTCTCTGT TAGGATGGAT CTATTTGTGT TTTGCTGTTA
9551 GTTCTAGGGG GTGGCTGAGG CCAGTGTGGG CTCATGTGTT GTATTGTTTT
9601 CTTTTAAGGT TCATGGTCCT GCATTGCCTA ATATCCAGTG CCAAGATATA
9651 GTTGCTTCAC ATATTTTGTC TAATTGGTTA AGACAGGTGG GAATTCTAGT
9701 ACCAGTTATG CTGGAATGGA TGGAAAAGGA TATTAATTTT GTTTTTTTTG
9751 AGACAGAGTC TCTGTTGCCC AGGATGGAGT GCAGTGGCGC ATTCTCAGCT
9801 CACTGCAACC TTCTTCTCCT GGGTTCAAGC AGTTCTCCTG CCTCAGCCTC
9851 CTGTGTAGCT GAGATTACAG GCGCATGCCA CGACACCCGG CTAATTTTTG
9901 TATTTTTAGT AGAGACGGGG TTTCACCATG TTGGCCAGGC TGGTCTCCAA
9951 CTCCTGATCT CAAGTGATCC ACCTCAGCCT CCCAAAGTGC TGGGATTACA
10001 GGCATGAGCC ACCGCGCCTA GCCGGATATT ATTATTTTTT TTAATCTATA
10051 AGTTTACTTT CCCTTTTTTT TTTTTTTTGA AAATTATTTG TTGAAGCAAC
10101 TGGTTAGCCT ATTGGTTCTG TGGAGCTTTG CATTTTGTGG ATTTTGCTGA
10151 TGGTATTATA TTCCACAGGG CTTGTTGAAG ATGTTCCTCT ATAAAATGGT
10201 AGTTAGATCC AAGGCCTGAT TTAAGTTAGA CATTTTTTGG TACAAGTACT
10251 TCATAGTGGT GTTGCTGGAG ACATTGTGGC CTGGAGACAT TGGAGACATT
10301 AGTGGCCATT GGCAATCATG ACCTGGCTCA TTAGGAGTTT ACAAATGACA
10351 ATATTTTAAT TACTCCTTCT TTATTTATCA GCTAGAAAAC ATCTACAAAG
10401 AGAAACTTTC TCATCAAGTA TTTCATTACC CTGACAGGCC CTGTCCCAGC
10451 AAGGAAAGTT AAATGGTTTG TTCTCCTTAT TTATCAGTTT TTAAAATACC
10501 ATAGTCCCCC GCTTATCCAA TGGGGGTATG TTCCCAGACC CTCAGTGGAT
10551 GTCTGAAGCC ACAGATGGTA CTGAACCCTG CACGGTGCTG TACTATGCTT
10601 TTTCCTATAC ACACATTTCT GTGGTAAGGT TTAATTTATA AATTAGGCAG
10651 AGTATGAAAT TAACAACAAT CACTAAAAAT AGAACAATTT TAACAATATA
10701 CTGTAATAAA AGTTAGGTGA ATGTGGCCTT TCTCTCAAAA TATCTTTTTG
10751 CACTGTGCTC ACCCCTTTTT TTTTATGATG ATGTGAGATG ATAAAATGCT
10801 TACGTGATGA AGTGAGGTGA ATGAGAAAGC ATTGTGATGT AGTTTTAGAC
10851 TACATGTCTG AAGGAGAATC ATCTGCTTCA GGTGATCCTG GATCACTAAG
10901 CCATGACATG ATGTCAGAAG CAGAGAATGT GGATGACTAA TGGGTTGCTA
10951 GTGTGCAGGG TGTGGACCTG CTGACAAAAG GGAGGATTCA TGTCCTGAGC
11001 AGAATGGAGT GGGCCAGTGT GAGATTTCAT CACGCTGTGC AGAACGGTGT
11051 GTTTGTGAAT TGTTTATTTC TGGAATTTTC TTTCTTTTTT TTTTTTTGAG
11101 ACAGAGTCTC GCCGTGTCTC TCAGGCTGGA GTGCAGTGGC GCGATCTCTG
11151 CTCACTGCAA ACTCCACCTC CCGGGTTCCC GCCATTCTCC TGCCTCAGCC
11201 TCCCGAGTAG CTGGGACTAG GGGCGCCCAC CACCGCGCCA GGCTAATTTT
11251 TTTTGTATTT TTTAGTAGCG ACGGGGTTTC ACCGTGTTAG CCAGGATGGT
11301 CTCGATTTCC TGACCTCGTG GTCCGCCCAC TTCGGCCTCC CAAAGTGCTG
11351 GGATTACAGG CGTGAGCCAC CGCGCCCGGC CTGGAATTTT CTATTTAATA
11401 TTTTTAGACC TTGATTGACC TTGGATAACT GAAACTCTTA TCTAAGAGGA
11451 GACTACCGTA ACAGGTTTAT CCTCCAAAAG TGACCAATGA ATTTTTGTTT
11501 CGGGTCATTA TATGGGTTAA TTTTTTTTAT ATGGGTTTAT TTTTAATTGT
11551 GTATCTACTT CTTTAATTTT CTGAAAGTAT ATGAAACGTC ATGGAGCATT
11601 GAAATTGTGA GGCAGGATTG CAAGATTCAA GATAGAAGAG CTATTGACAG
11651 AAGTAGCATT TCTAATATAT GGAATTTAAG AAACTCTTAC TATACCTTAA
11701 TGTTAGAGTG GAAGACTGTA GGGTAAGAGA GGATTAACAA GAAAGTGAGA
```

FIG.3-5

```
11751 TGGTGTCTCC ATTTTAATCT GCTGCTTGTG TGTTCTGAAT GTATTGGAGA
11801 GGGAAAGCCA TTGCAGTCAG TTAGAAGATA ATGGCAGAAA CAGAAGGACC
11851 TGAACTAGGG TAATGACTGC GGGATGGAAA GGGAGAGATG GATGCCAAGG
11901 AAATGGTACA GAGGAGAAAT CATCATGACC TGGTGGTTTG CTGGAAAGGA
11951 GACCCGAGGA AGGGAAGGGG CATCAAAGCA GAAAAGGAGG AGTTGGCAGG
12001 AACAGAGAAC TTAGTAGGGA AAAGAGTCTC TAAGATGAAA TTGCAGGATG
12051 ACTAAGTATC AGTGAATTTG GCCACTAGTG ATGATGGCGG CTTGGAGCAA
12101 AATTTAGCAG TAGAAGGAGC TTGTGAAAAG TGACAGTTGG TGGTGGTTGT
12151 AGAGAATTGT GGAGGGGTTT TTGTCCCTT CTTTTTTTTT TTTTTTTGAG
12201 ACAGGGTCTC ACTTTGTCAC CCAGGCTGGA GTGCAGTGGC GCAATCTCAA
12251 CTCACTGCAG CCTTGACCTC CCAGGCCCAA GCGATCCTTC CACCTCAGCC
12301 CCCCAAGTAG CTGGGACTAC AGGTGCACAC CACCACACCT GGCTAATTTT
12351 TTGCATTTTT TGTAGAGATG GGGTTTCACC ATGTTGCCCA GGCTGGCTTT
12401 GAACTCTTGA GCTCAAGTGA TTGGTCAGCC CACCTTGGCC TCCCAGAGTA
12451 CTAGGATTAT AGATGTGAGC CACTGCACCC AGCCCTTTTT TTTTTTTTTT
12501 AACAACTTTT TTCCTTCTTT CCTTCTTTCC TCTTTTTTTT TTTTTTTTTT
12551 TTAACAGAAT CTCACTCTGT CACGCAAGCT AGAGGACAGT GGTGCAATCT
12601 CAGCTCACTA CAACCTGTGC CTCCGGGTTC AAGTGATTCT CCTGCCTCAG
12651 CCCCCCGAGT GGCTGAGATT GTAGGCGTGT GCCACCTCGC CTGGCTAGTT
12701 TTTGTATTTT TAGTAAGAGA CAGGGTTTCG CCATGTTGGC CAGGCTGGTC
12751 TTGAACTCCT GGCCTCAAGT GATTCACCTG CCCAATGTTT TTTTTTTTTT
12801 TTTTGAGATG AAGTCTCTGA TCTTTCACCC AGGCTGGAGT GCAGTGGCAT
12851 GATCTCGATC TCCACTCACT GCAACCTCCG CCTCCCAGGT TCAAGCGATT
12901 GTCCTGCCTC AGCCTCACGA GTGGCTGGGA TTACAGGTAC ATGCCACCAC
12951 ACCTGGCTAA CTTGTATTTT TAGTAGAGGT GGGGTTTCAC CATGTTGGCC
13001 AGGCTGGTCT CTTAAACTCC TGACCTCAAG TGATCTGCCT GCCTCAGTCT
13051 CCCATAGTGC TGGGATTACA GGCGTGAGCC ACCGCGCCCA GCCTGTCTGT
13101 TCAATCTTAA CAGCTTTTTT GAGATATAAT TCACAGTCCA TACAGTTCAC
13151 CTATTTAAGG TGTATAATTC AGTGATTTTT TAGTATATTC AAAGAGTTGT
13201 GCAAGCATCA CCACAATCAG TTTTACATTT TTATCACCCC AAAGAGAAAC
13251 CTCTTACCCA TTAGCAGTCA CTCCCCAATC TGCCCATCCC CTCATCCTTA
13301 AGCAACCACT AATCTTTCTG TTTCTTTTTT TTTTTTTTTT GGCGATGGAG
13351 TCTCACTCTG TCGCCCAGGC TGGAGTGCAG TGGCGCGATC TCGGCTCACT
13401 GCAAGCTCCG CATCCCAGGT TCATGCCATT CTCCTGCCTC AGCCTCCAGA
13451 GTAGCTGGGA CTACAGGCGC CCGCCACCAC GCCCAGCTAA TTTTTTGTAT
13501 TTTTAGTAGA GACGGGGTTT CACTGTGTTA GCCAGGCTGG TCTCGATCTC
13551 CTGACCTCGT GATCCTCCTG CCTTGGCCTC CCAAAGTGCT GGGATTACAG
13601 GCGTGAGCCA CCGCGCCCGG CCTAATCTTT CTGTTTCTAT AGATTTGCCT
13651 CTCCTGGACA TTTCATATAA TGGAATCATA CAACATGCAG TCTTTTGTGA
13701 CTGGCTTCTT TCATTTAGCA TGATGTTTTC ATGGTTCATC CCTATTGTGG
13751 CATGTGTCAG TTTATTGCTG TATAATATGC CACTGTATGG ATATATCACA
13801 TTTTGTTTAT CCATTCACCA GTTTGTGGAC ATTTGGGTCA TTTCTACTTT
13851 TTAGTTCTTA TGAATAATGC TACTATGAAT ATTTGTGTAT GTGTTTTTCT
13901 GCGGACATAT ATTTTGTTTT GGTTTTGAAA TAGGCTATGT TTAGATGCAG
13951 AGGGAAGCAA AGAAACTGGT AAGGATGTGG TAAAATTACC ACATCCACAA
14001 GACAACGTTT ATTAAGTACT GAAATATTCC TTTATGAAAG TTAACTCTTG
14051 CCATCCCTTT TATCTTTCAC ATTTAGAGTC TATATTATCA CAACCTTGTT
```

FIG.3-6

```
14101 TTTCCTTTGA GTCAGCATTG TGATCATTCT GGACGTGGGG TCCCACACAC
14151 CCTGTCTCTG TCAGTAAGAT TATGATTAAG ATCAAATAGA AATAGGTCAG
14201 GAGAGAAAAG AGCTCCCTGG CCTTATTCTC CTCAAACTAG CTGATGCTCC
14251 TGAATACCAA CCTCTTTAAG AATTGATATT TCAAAGGACA ACTCCTCTCT
14301 GTGGTCTTCT GTCCTCTCTC CCCTACTTTA TGCTCTGTGC ATAGCAGCTG
14351 TTCAGGACAT CGCCCGAGCG CAGGGGCACT GCAATCAGAA AAGCGAGTGA
14401 GGGACACAGC AGGAGAAGGC TGTTCTGGGG CTAGTGAGTG GGAGACGGGA
14451 CAAACAGCTA GATAGCAACG TGATGGCTTC ACCATGGGGT GAAGCGTGGG
14501 GGAGAGTATC AATTACCTAG ATTTTAAAAA GAGAGCCCTT GAACACCTCT
14551 GTCACTGGTC ACTTTTACCA AAGCCTTCTA ACTTAACGGA AGGAGATGCT
14601 GCACTTTAAA GAAAAATCAC AGCTGCGGAA GACAGTCTCG CAAAGCCAGT
14651 TTTTGTGGCT TAGTATTTTG GGGTAGCTTG TTTCATGAGG GTCAGATTAA
14701 TTTTCTAATG TTGTTTTCTA CCTTAATGTT ACTGCTTTAA TCATTAGAAT
14751 GCCACCAGTT CCTTCAGGCA ATAGGAAGCT ATTGAAGATT TAATGAGATT
14801 CATACTGCTT ATGCTTAAAT GTTGATGACT TCCTGCATGC ATATTAATCA
14851 TTCCTGACCT TGATCTCAAA TTCCTTCCCG GTACAAATTC TCATTAAACA
14901 TACCTACTAG ATCTCCCAGT GTTCACTGAA TACCTGGTTT GTTTCCAAAA
14951 GTACATAAAA GAACATTAAG TCTCATGTTC GGTATGTGTC AAATGTTCAG
15001 TTCCCTTGTC TGATTTGTTT TCCAATTCTT ATTGTGACTG TAAATCTGGA
15051 GAATTTAGGG GAAGAAAAAT CAGTAACTCT TAACAGGGGA TTTAGCCTAG
15101 TTTACAAGAG TATATGATCT GTGCAGCAGA CCTTGAACAC AGCTAATTGC
15151 TTGTCTAGGT CAGTATGTCC AACTGGCAAC TCTCAGAGCC CATCCAGGCC
15201 ACAGAGCATT TCCGGGTGGC TTGTGTGTGC GCTCCGGCTG TCGAGCAGCA
15251 GGACTTGGCT TCTGTCCCCG GCTTCGTTGG CCCCATCTTT TAGTTCAGGT
15301 CCACCCCCTC CTGCCTCAGA GGCCTGGGAA ACCCAGCCTG GCCACCTGGT
15351 GTCCTCATGC CCAGCATCTA CGCATCTGCC CCAGTTGTCC CCTCAGCCAC
15401 CTTGGCAGAT TTCTTGACTT AACAGTTCTT CCCTGAACTA GGACCGGGGG
15451 CAGGAGTTAT TAGAGAAGGG AGAGGAAAGG TGACAGGTCT CAGGAGTCTG
15501 AGGGAAGATG AAAGTGAGAG CGAAGTAGTG TGGGAGAGAG GGGGATCACA
15551 TACCATGGGA GAGAAAATAA ATATGTCAAT ATTAGGGTGG TGAGGCCTGT
15601 ATACAAAGAC AGGATGGCAG GGAGAAGAAG TAGGCAAGGA CATAAAGGGG
15651 CTTGGGTATG CAGATGCTGG TCACTGAAAA TGAGGAACAA AGGAGGGAAA
15701 TTTGCGTGTG AAAGAGGCCA CATGTGAGAG AATAGAGAGA GCAAAATGAC
15751 AGCTTTGCTT GGCAGAACGT GACCATGCAC AGCATTGGGA GACACAGTCT
15801 GATGAAGCAT TTTTTCCAAT TTGTAAATAT ATTTATAACA AAGAAACATT
15851 ATACTTTTTT TTTCTTTTTT TTTTTTTTTG AGACAGAGTC TTGCTCTGTC
15901 ACCCAGGCTG GAGTGCAGTG GCGTGATCTT GGCTCAGGGC AACCTCCGCC
15951 TCCTGGGTTC AAGCGATTCT CCTGGCTCAG CTTCCCGAGT AGCTGGGACT
16001 GCAGGTGCGC ACCACCATGC CCAGCTAATT TTTTGTATTT TTTAGTAGAG
16051 ACGGGGTTTC ACCATATTGG CCAGGCTGAT CTCGAACTCC TGACCTCAAG
16101 TGATCTGCCT GCCTCGGCCT CTGAAAGTGC TGGGATTACA GGCGTGAGCC
16151 ACTGCATCTG GACTACTTTT TTTTTTGAGA GGGAATCTCA CTCTGTCACC
16201 CAGGCTGGAG TGCAGTAGCA GGATCACTGC AACCTCCACC TCCTGGGTGC
16251 AAGCGATTCT CCTGCCTCAG CCTTCCCAAG TAGCTGGGAT TACAGGCACC
16301 TGCCACCATG CCTGGCTAAT TTTTGTATTT TTAATAGAGA CAGGGTTTCA
16351 CTATGTTGGC CAGGCTGGTC TTGCACTCTT GACCTCAGGT GATTTGCCTG
16401 CTTCAGCCTC CCAAAGTGCT GGGATTACAG GCATGAGCCA CTGTGCCTGG
```

FIG.3-7

```
16451 TCAGAAATTT ATTATTATAA AAACACAAAG AGATATATAC TTAGCATATT
16501 ACATTACATT GGGATTATTT TAGGTTGTCC CAAAGGTGTA GTCATTTGAT
16551 TCAGAGGCAT AGCCTGCTTC TGACATGTTG GTTGTTTAAA ATGTGGCCTG
16601 TTCTGACCAA GAAGTTGGAC AGTATTGGTT TTGATGACTA TCTTGCCACT
16651 TATTTTTTAC AATGTGGTAA TTTTTACATC CAGATAGTTT TTCATCTTTT
16701 TTTCTTTTTT TGAATCAGAG TCTGGCCCTG TTGCCCAGGC TGGAGTGCAG
16751 TGGTGCAATC TCGGCTCACT GCAACCTCCA TCTCCCGGGT TCAAGAAATT
16801 CTCCTGCCTC AGCCTCCCGA GTAGCTGGGA CTACAGGCGC CCGCCAGCAC
16851 ACCCGGCTAT TTTTTTTTAG TTTTAGTAGA GATGGGGTTT CACCATGTTA
16901 GCCAGGATGG TCTCGAACTC CTGACCTTGT AATCCGCCCA CCTCAGCCTC
16951 CCTAAGTGCT GGGATTACAG GCGTCAGCCA CTGCGCTGGC CTAGTTTTTC
17001 ATCTTTTTAA AGCACATTTC CGCTGATATA ATTTGACTGG ATAGGTGAAA
17051 AGATATCCAT TTTGCAAAGT AGATTTTTTA TATTTAATGA TCAAAATCTT
17101 TATCTTTTAA AAACAATTTT TATAAAATAG CCACAAAATT TCATACCCTT
17151 TAACTTATTT ACTTAATTCC ACTTCTAGAA ATCTATATTT AGAAAATAAT
17201 TAAGTCGGGC GTGGTGGCTC ACGCCTGTAA TCCCAGAGGT CAGGAATTTG
17251 AGACCAGCCT GGCCAAAAAT GGCGAAACCT CGTCTCTGCT AAAAGTACAA
17301 AAATTAGCCA GGCATGGTGG CGCCCACCTG TAATCCCAGC TACTTGGGAG
17351 GCTGAAGCAG GAGAATCACT TGAACCCAGG AGGTGGAGGT TGCAGTGAGC
17401 TGGGATTGCA CCACTGCACT CGAGCCTGGG CAACAGTGAG ACTCTGTCTC
17451 AAAAAAAAGA AAGAAAATAA TTAGAGATGC TGCCAAAGAT TTAGGTTCAA
17501 GAATGTTTAT TACAGTGTCG CTTATATTAA TATTAGCAAA GAACTGGAAA
17551 TAGTCTAAAT GTCCAATAAA ATAGAGAAAT GATTCAGTAA ATTATGATTT
17601 ATTCATAAGT TGAGATGGGC TGTTGTATGG TCATTAAAAT ACTGCCTATT
17651 AAACTATTAT ACTTCCTCCA GTTTATTCTC CACACTGCAG TCAAGTGACC
17701 TTTGAAAAAG TACATTGTGG CCAGACATGG TGGCTCACAC TTGTAATCCC
17751 AGCACTTTGG AAAGCCAAGA TGGGAGGATC GCTTAAGGCC AGGAGTTCCA
17801 GACCAGCCTG GGCAACATAG TGAGACCCCC ATCTTTATAA AACATTTAAA
17851 AATTAGCTGG GTATGGTGGC ATGTGCATGT AGCTACTCGG GAGGCTGAGG
17901 TAGAGGATTG CTTTAGCCCA GGAGTTTAAG GCTGCAGTGA GCTATGATTG
17951 TGCCACTGCA CTCCAGCCTG GGCAACAGAG TGGGACTCTT GTGTCTTAAA
18001 ACTATAAAAA TAGAGAGCCG GGCATGGTGG CTCATGCCTG TAATCTTAAC
18051 ACTTTGGGAG GCTGAGGCGG GCAGATCACT TGAGGTCAGG AGTTCGAGAT
18101 CGGCCTGGCT AATATAGTGA AACTCCGTCT CTATCAAAAA AAAAAAAACA
18151 AAAAAAGAAA AAAAAAATTA GCTGGGCGCG GTCACATGTG CCTGTAATCC
18201 CAGCTACTTA AGAGGCTGAG GCAGGAGAAT TGCTTGAACC CAGGAGTCCA
18251 AGGTTGCAGT GAGCTGAGAT CATGCCACTG CACTCCAGCC TGGGTGACAG
18301 AGTGAGACCC TGTCTCAAAA AAAAAAAAAA AAAAAAAAAA AAAAAAAAAA
18351 TATATATATA TATATATATA TATATAAATA GTCCAGGCGT GGTGACTAAT
18401 GCTTGTAATC CCCACCACTT TGGAAGGCCA AGGCAGGTGG ATGGCTTCAG
18451 CCCCAGAAGT TCGAGACCAG CCTGGGCAAC ATGGAAAAAC CCTGTCTCTA
18501 CAAAAAAAAA TACAAAAATT AGCTGGACGT GGTGGTGTGC ACCTGTAATC
18551 CCAGCTACTT GGGAGGCTGA GGTGGGAGGA TTGCTGAGCT GGGGAGGTGA
18601 AGGTTGCAGT GAGCCAGGAT GGCGCCACTG TACTGCAGCC TGGGCGATAG
18651 AGCCAGACCT TGCCCCCACC CCCCCAAAAA AGAAAGAAAG AAAGAAAAAT
18701 ATGAAAATAA AATAAATTTT AAAAGTACAT TGGATCATTT CACTCCCCCT
18751 TAAAATCTTT TCTTGGCTTC TCATTGTAGT CACTGTAAGT TCCTGACCTC
```

FIG.3-8

```
18801 CAAGGCTCTC TGGCCTCATC CCTTCACTCT GGTCTCCAGT CCTTCCACTC
18851 CTGTCCACTG GCCTGCCCCT CAGGTGCTGT AATTCTCTAG GCCCTTTCCT
18901 CCTTGGGATC TTTGCATATG CTATTCCTCG TGCTTGAACC ATCTTCCCCC
18951 AGCTCTTCAT CTGGCTAATT CCTGCTTGTT CTTGAGGTCT TCATCTCATT
19001 GTCACTTTAA GAGAGGGATT TCCTGACCTC TCTACCCAAA GGAGGGGCCT
19051 CAGATATATT CTGTCATTGT GGTCTATGCT TCTTTGTAAC GTATATCACA
19101 TTTTAAAATC ACGTTCATTT GTGTGGTTCT TTAATTCCCA GATCCCCTCT
19151 GGACTTGGTC TGTTTCCTTT CTTTTCTGGA GGAGTTCCTC AAGTTTCTTC
19201 TCTATCCCTT CAATTGAGGT TTTCATTTCT GTTGCCATAT TTTAAATCTC
19251 CAAGCAGTCT GTCTTGTTCC ATGAAAGGTT TTACACACAC ACACACACAC
19301 ACACACACAC ACACACATTT TATATATATA CACATATATA AAACCTTTCA
19351 TGGAACAAGA CAGACATATA TATGTGTATA TATATGTGTA TATATAGGTA
19401 TATATGTATA TATATGTGTA TATATATGTA TATATGTGTA TATATGTATA
19451 TATGTGTATA TATCTAAAAC CTTTCATACA TACATATATA TAAAAGGTGG
19501 CTCACGTTCA CCTGTATTAA ACTGTAAGTT CCCTCAGGGT AAGGACTGTG
19551 CTTTTTTCAT CCCATGAGTG GTAAGTGGTA GATTTCTGAC TAACAAAATT
19601 ACCAGACATG AAGTATGAGG GCAAAAAAAA GTTAAAGGAA AAATTAGGAA
19651 TATGGACAAA AATGTGATTC ATGGATAGTC TTCAAAGATT AACAGTGTTG
19701 TCTTGCCCAG AATTTAATAG AGAAAAAAAA ATGGACTTGC AGAAAAACTT
19751 GAGGCCCTTC AAGCTGTCAT CATATCAGAG GTGATAAGAC CCAGTGAACT
19801 GTTTGAGAAA TTGGGTAATT GTCACTAGGT AAAGGAAAAG GATTGAAAAT
19851 TAGATAAGGG TTAGTCCCAC AAAAGAAATT TTAAAACTGG GCTGGGCGCG
19901 GTGGCTTACA CCTGTAATCC CAACACTTTG GGAGGCTGAG GCGGGTGAAT
19951 CACGATATCA GGAGTTTGAG ACCAACCTGA CCAACATGGT GAAACCCCGT
20001 CTCTACTAAA AATACAAAAA TTAGCCGAGT GTGGTGGCAG GCACCTGTAA
20051 TCCCAGCTAC TTGGGAGGCT GAGGCAGGAG AATCGCTTGA ACCTGGGAGC
20101 AGGAGGTTGT AGTGAGCTGA GATCGCACCA CTGCACTCCA GCCTGGGTGA
20151 CAGAGTGAGA CTCTGTCTCA AAAAAAAAAA AAAAAAAAAG GAAATTGCAA
20201 AACTGAAGTA AAATGAAACA AAATATGACA CGTATAAGGG CAATATTTCT
20251 GGCCAAGATG CAACAAAATT CATTTCAGAA GTCCAAAGTT CAAATACACA
20301 TCTACCCTTG CTGCCTCTCT TGTAGATTAG GGCATGACCC TATAAGATTA
20351 GAGAACAGGA GAGGAGACAA CAGGAAACAA GCAAAAAAAG ACCAGAAGCT
20401 GAAAAGCAGA TAATAGGAAG TAAATGGCAG CAGAACCAAG AAAACATAAT
20451 CCTGTTCAGG TGGTAGAGAA AGCAAGAATT CCCAGGAATC AACTGGTGGC
20501 ACCAGGTATC TCTTGATACA AGAGTGAAGT GGAACTAAAA CGAAGAACTG
20551 CTAACCTCCA GATCTCATAC TCTACAAAAT GTAATGACTA CCCCTCTACC
20601 ATTCTGGCAG AATTATTCTT AGGAGAGAGT AAAACACTCT CAAGAGAGAA
20651 TAAAACAGAG AGGTCTCTGA CTGGAGAAGG CTAGCAACAT AGTATCCCGG
20701 TTAAGGGTGG GGTACTATGA TGAGTGATGA GGGAGATTAA GTGAACAACT
20751 GCATACTTGG TGTAGGGACA CCCCCCATCC CCCCCTCACC CCACCGCCAC
20801 CTGCTGCGGG CTATTACCTT TCTGCCCTCC TATTTATCTT CCAGAATGTA
20851 GGTAAATTTC ACCAATTTCT CCACTAAAAT TCTTTTTGTT TTCCAGGATC
20901 CAATTCGGTA TTCCACAATG TAATTTAGTT GTAAAGTCTT CTTAGTCTTC
20951 TATAATCTTC TGACAGTTCC TCAGTCTTTA CCTTGTCTTT CATGAGTCCA
21001 CTGAGGGTTT TAAATCCCCC ACTCTTACAT AGAAGCAGAC AACCATGGAT
21051 TTCCAGATAT CTGAGAACGC CTCTAATATA AAAGACAAAT ACCAAACAAA
21101 CAAAAGAAAG AAGCCAGGCG CAGTGGCTCA TACCTGTAAT CCCAGCACTC
```

FIG.3-9

```
21151 TGGGAGGCTG AGGTGGGAGG ATCACTTGAG ACGAGGAGTT CAAGACCAGC
21201 TTGGGCAACA CAGTGAGAAC CCATCTCTAC AGAATATTTA AAAATTAGCT
21251 GGGTGTGGTG ATGGATGTCT GTAGTCCTAT CTATGAAAGA GTGTGAGATA
21301 GGAGGATCAC TTGAGCTGCC ACTGCATTGT ACTCCAGCCT AGGTTAGAAA
21351 GAAAGAAAAA GAATTCAGAG ACTACACAGA GAAGAAATTT TCTAGAAAAC
21401 TATTAATAAT ATACTCAAGA AAAATTTTCC AACCGCAAAA CAAGAATAGA
21451 ATACTATTTT TAAAAACTTT CATGGGGCTG GGCATGGTGG CTCATGCCTG
21501 TAATTCCAGT ACTTTGGGAG GTGGAGGCGG GAGGATTGTT TGAACTCAGG
21551 AGTTCAAAAC CAGCCTGGGC AACATAGAGA GACCCCTCTG TCTATTGTAT
21601 ATATATAAAA TATATACATA TTATATATTT CCAAGGAGGA AAGGGCCTAG
21651 AGACTATATA TATGTATATA ATCTCCAAGA GGCCAGGTGC AGCGGCCTCT
21701 TCCGTCAAGC CTTAGCACCT ATAAACTTTA TAAAACCTAC TCTCTGTGAA
21751 TTGTGCATGC CACTAATCTT CATCTAGCAA TACATTTCTG CTCATTCTTT
21801 AAAATTCATC TCAAGTACCA TTTGATTTAG ACGAGCCACC TCTTGGTTCC
21851 AGTGGCTTCC TGATCATACC TCTAGTGCTA TATTGTAACC ATCACTTAAT
21901 TAGTTCATGA TTTTTTCTCT TCTAGACTAT AAGTTACTTG AACATATGGA
21951 TTTGAGTCAG TAGGTATAGG TGAGACATGG GAATCTGCAT GTTCAACAAA
22001 TTCCTCCTGG CATTCTAGGG CTCCAATCTC AGGTATGTTT GTTTCTTTTT
22051 TTTAGACAAG AGTCTTGCTC TGTCTCCAGG CTGGAGTGCA GTGGCGCAAT
22101 CTTGGCTTGT CGCAACCTCC CGGGTTCAAG CAATTTGCCT GCCTCAGCCT
22151 CCCAGGTAGC TGGGACTACA GGCGCACGCC ATCATGCCCG GCTAATTTTT
22201 ATGTTTTTAG TAGAGATGGG GTGTCACCAT GTTGGCCAGG ATGGTCTTGA
22251 TTTACTGACC TCATGATCCA CCCGCCTCAG CCTCCCAAAG TGCTGGGATT
22301 ACAGGCGTGA GCCACCGCGC CCGGCCTAAC CTCAGTTTTA AGTGGTTTTT
22351 AAAATCTACT TCAACTCTGA AATATCAAGG CTTTTCCTCC CTGCAATTTA
22401 ACTGGTATTG GGGAGGGCAG GTAAAGCTTT CGGGTAGTTG ATTAAAAACA
22451 ACAACAAAAA AAGCAGGGGC CGTCTTCTTT CGTGCCCACA ATAAGAGCTT
22501 ATACTGAAAT GTAGAGTAAG GTAGATAAGT AGAAATAAGA TAAATACCCT
22551 TATTTCATTT AACAGTGTTT GCACAATGTG TCCAATTTTT ATTCACTAGT
22601 TCTAAAACTA TTGAGGGCTT ACTATATGCC AGACACTGTT CTAGTCATTG
22651 GGAGTACATC AACACAGACA AAACCCCCTA CCCTATAGGA GTTTGCATTG
22701 GTAGGCAATA AGCAAATAAA ATAAGTAAAG CAAAGTATTT TAGAAGGTGA
22751 TAAGTATTGT GGAGAAAATA GAACATTTAG GGGAGCTTTC TTTTATTTGT
22801 CAGTGTTTAG TAATAAATTA CTAGAGAGAG TAATTTTTAA AAATTTGAGC
22851 TATTTAAATA AGCCATACTT TAAAAGGCAG GATTTAACCT ACATCTAATC
22901 AGAAGAGAAC TTGGGATTTG CAAAATTCAG GTCTGGTTTC CTGTTATAAA
22951 GTTGACAGTA AATGGCTTTC CCATTATGTC AATAGGAATG AAATAATTTA
23001 GTGGCTCAGG GAATTGCTTC CAAGGAGTCA AAAGTAAATT GTGTTTATAT
23051 AATTTTTTTT ACTACTATTA AAAAAAGCCA CAAACCAGAA AAAAATTGTT
23101 TTGTACTTGT CTACAAGGCA GAGTTAATTT TATTATTAAA AAAAATCCTA
23151 TACTCTAAAA CCTCTTCTAT TATCTCCTCA CTTCTTCGTT TTAATTTTTT
23201 GTTTGCATTT TCACGTTTAG GTAAAAAGAT ATTGGTCCTT TTAGGATATA
23251 TGGGGATAGA ATTATATGAG GAAGCACAGG ACTCCTGGTA TGGAATGAGG
23301 AAGCTGGAGA TTTGAGCTTA ACCTCTCTGG GGTGCTTAGA ACTAAGTAAG
23351 AGAAGCAGTC TGTTTCTGCA GGGAAAATCA CTTCTCCATC TTTACTCTCC
23401 AAATAACTTA CTTAATCAAA TGGTCTAATG TTTCATTGTA AAGAGTCTTA
23451 AAAGTCAAAA TTAATGTCAC CTGCAGAGTA AGCTAAACGA GTGATGAGCT
```

FIG.3-10

23501 TTGTTTTGCA CAGCAGTTGA AACTGATTTT CAAAGTCCCA CCAAACAGTA
23551 AAAGACTTTT CTTGCATTTC TGAAAAACTA GAACTGTGTG GTGATTCTGA
23601 AGACTGTCAG TTCCTGTGGG GTGTTTACAC AAAGGTACTT TTAAATGAAG
23651 AGTCATTTTT AGAGCAATTA GAGAAAAGGC TAGACAGAGA AGAGCGGCTC
23701 AGGGGCTTGG CAGGTCGGGG TTAAGGTTTA TTGACAGGAC AGGGTCAGGC
23751 GTCTGCTTAG CCACCACTGC CCCGAGTACC TGCCCTCCGG ATACACCCAA
23801 GACCTCCCTG GCCTTGGCTC CCTGCCATAG GCCAAACTCC CATGCAGAAT
23851 GAGGAGAGGG GAAAGGAGGA AGAGGAGAGC AAGTTCTGCT GGTTCAGTAT
23901 TGAACTGCAA GTATGAAAAT GTTTGTGTAT ATTTTTCTGG CCCAGATGTT
23951 GTGTTAACAT TAGGAAGAAG AAACTTTAAA ACAAAGAATT GTCTGTTCTT
24001 TCAACTTTGT AGTTTGCAGT TTGCATCCTG AAGAAAGAAA TTGCCTAGCT
24051 AAAGTAGTCT TTTAATTTCA TTTTTTAGTT TTGAGTTACA GGTTTCTGGC
24101 AAGCTCCCTG ACCACTACTG TTACCTGGTG GCGCCTATAT TTCATCAAAT
24151 TTAGACATGC AGACTACCTG GATCCAGGCC CAGATGAACT GTTGTGACTG
24201 ATAAACATGA TCCCACCCTG CCCCCATGCA GACTCCTGCT TTTCCCTTTA
24251 AGGGAATCTA AGACGTTGAG TCGCCGGATC CCCAAGGGAG TTAAAGAAAA
24301 ATGTCTTCCG GCATTCACAT TTGCTCTGTG GTTTTCTTGA GCTGCATCTC
24351 TGCTTGCCCA GAGGCTGGTG AACATCCCAG CAGTGCCCTG ACTTCTCCAG
24401 TGTTGGTAAC TAATGGAGGG AAATTTTTTT GTTTTTAATA AAAACAAGCA
24451 GAGACATCTA TCAGTACTCA CAGACAAGGC AGAATTTGTT TGACATCTTG
24501 TGATTGCTGC GTACAAAAAG AATGACAGCA GTTATTAAAC AAATAAGAAA
24551 AAAGATGCTG TTTATTGATA GTTTTCAGAT ATCCTAAGAA TATTTTTAGT
24601 AATCTTACTG CCTTTGCTTG CATAAGTAAA AAAAGTGGAA TTGTTAATTT
24651 TTGCAATCTG GGTTGTATTA GATTTGGAAT CATAATAAAA ATGTAAATAT
24701 TAAGCAAATA TGTGCTGTTT AGCTATGTAA CATACTCGTG GCTTTTCCTT
24751 TTATTAGAAT TTATTTCAAA TACTTGTTTT TAAGATGGTA AGGTGAGTAT
24801 TAGCAGTCAA TGCAATTAAA CTTAATTGCA TTTTCTATAT GAATTGTTTT
24851 TGTCTCTTTT TAAATGTATT TATGGTTCTT TTTCTCCATA CTAGCTATTC
24901 CTATAGGTTT GTCTTGACAA AAAATTATAA ACAATTGTTT GTTTGCAGCC
24951 GGGTGTGGTG GCTTAACATC TGTAATCCCA GCACTTTGGG AGGCCGAGGC
25001 GGGCTGATCA CCTGAGGTCG GGAGTTCGAG ATCAGCCTGA CCAACATGGA
25051 GAAACCTCGT CTCTACTAAA AATACAAAAA ATTAGCTGGG CGTGGTGGCA
25101 CATGCCTGTA ATTCCAGCTA CTCAGGAGGC TGAGGCAGGA GAATCGCTTG
25151 AACCCAGGAG GCGGAGGTTG CAGTGAGCCG AGATCATGCC ACTGTACTCC
25201 TGCCTGGGCA ACAAAAGCAA AACTCCATCT CAAAAAAAAA TTGTTTGTTT
25251 GCTTGGAAAC AGTCTAAAGT CACAAATTTG ATTTCAGTTT CATTTGGAAA
25301 TTTTAAAATG AAAAATTGGG ACACAGTCAA GTGGGAAAAG CATTTAAACT
25351 GTTCAGTGAC TGAACTTTCG TTTTCATATC ATGTTAATGT GATCTAAAAA
25401 AAATAATTTC TTCCTGGCCT AAGTTACCCC ACTTGAGGAT TGTTACAGTG
25451 ATTTCAATCC CTGACCTCAC CAGATGATGT GGAAGCATCA GGCCACATAT
25501 TTTTATAAGT ACTGGGTGAG GGCAAAGATT TGCTTGGAAG GGAGGAGAGA
25551 ACCTCCTGGA AGGTTGATAA TAGTTTGTAT CTTGATAGAT GTTGGTTACA
25601 CCAGTACATG CATTCGTCAG GACTCATCGA ATGGTACCTT AAGATTCGTG
25651 CATATCATGG TATGTAAATT TTACCTCAAG ACACCAACAA AGGAACTTAT
25701 AAACATATAT TAAAATCTAG CATGTTGAAG TATTATAGGA GAGTGAATAC
25751 TGATCTTGAT CTTTAAAACT TACTTTGAAA TGCACCCCCC AAAAAAGATG
25801 GGTGAATGGA TAGTGAAACG TTTAGAAATG TGGTAAAGAG TAAGTATAGT

FIG.3-11

```
25851 AAAATGTTAA TTGTCAAATC TAGGTAGTGT GAGTGTTCAC TGTAAAATTC
25901 TTTTTTTTTT TTTTTGAGAC AGAGTCTTGC TCTGTCACCC AGGCTGGAGT
25951 GCAGTGGTGT GATCTCAGCT CACTGCAAGC TCTGCCTCCT GGGTTCACGC
26001 CATTCCCCCA CCTCAGCCTC CCAAGTAGCT GGGACTACAG GCGCCCGCCA
26051 CCATGCCCGG CTAATTTTTG ATTTTGTATT TTTAGTAGAG ATGGGGTTTC
26101 ACTGTGTTAG CCAGGATAGT CTCGATCTCC TGACCTCGTG ATCCGCTCAC
26151 CTTGGCCTCC CAAAGTGCTG GGATTACAGG CATGAGCCAC TGTGCCTGGC
26201 CTCATTGTAA AATTCTTTCA GCTTTTTTGT GTGTTTGACA TAAAATGTTG
26251 TGTTCCATAA AATGTTGGGA AAAAATGAAG GTACTGGTTT TTGCTCATTT
26301 AAGGATCTGT GTACCTCCAT TTTAAATCCC CTCCTTAATT CAAAATCAGA
26351 CCACTTGGTA TTAATACCAA AAAGGGGAAG GGTGTGAAAG TAGCCATTTA
26401 GCATAAACAG AAAAATGTAC CCACCTCATA CTTTCTCTAG TTACCTGCTG
26451 AAAGACCATT ACCAAGCATG GAGGCCCAGG GGGTCTTTAC AAACAAGAAT
26501 AATTCTGAGA AACCCAAACC ACAAAGCCCA ACCAATGACC TCTCCAGGCA
26551 GATAAAAATT GGCCTCCAGA ACCCTAACCA TGAAAAAAGA CATGACTTCC
26601 TACATGTAAT CTTCACCAAT GGCAAGCAGG TAACCCCCCG CTATATACCT
26651 TATACTAAGA CCCTATGGAA TGAAAATGGG CTTTTGGTTT TCAGCCAAAT
26701 CCCCAGGATT TGGCCATGAA CACCTCCACT TTATCAGAAT GCCAAGCTAT
26751 TTTTTACATC CTGATAAAGC CTCCTTTTTA AAGACATATA GATTGTGTGT
26801 GTGTGTGTGT GTATGTGTGT GTGTGTGTGT GTGTGTGTGT GTGTGTTTTA
26851 ATCTTGAAGG GTCAAAAGGA TAAGTTGGTT CTGGTAGAAT TTGAGCCAAA
26901 CTTTTAAAAG CTAATGATAA TATATTTTTT AATTAGGCCA TATTGCTCAG
26951 TTGATGCTTG AGCAGTAAAC TAGAAAATCA AGATTTGAGA GGCTCAGTGA
27001 TCTCAATTCC TTCAGGGTCT CATAGTGAAC TCTGGCCAGT TAATTTATCT
27051 CCAAACTTTG ATTTTCTCAT TTGGAAAGTG AGAATAAAGC CTGACACAAA
27101 ATGGCTAGCC CATGGTTCTC AAACTTTTGT GTATGTAGGA ATCATTGGTT
27151 AAGAAACCTT GGTGTGTGTA AACATAATTT AGTTTATTAA AATAGAGATT
27201 CCTGGGTTTC AAACTGGGTT TTCTCAATCA ATTGTTCTAG GGCAGAGCCC
27251 AGAAATCTAC ATTTTAATAA GCACCTAGTG TGATACTGAT GCAATTATTG
27301 GACCACAGGA TATATGGTGT AGATGTGTTT TGATGGGTAT TATATTAACT
27351 GAGAATTTTT TTAGCTTTTT GTTATGGAAA AAAATTATTA TTATTATTAT
27401 TTTGAGACAA GATCTCACTC TGTGGCCCAG GCTTTAGTGC AGTGGCACGA
27451 TCAAGGCTCA CTGCAGCCTT AACCTCCAGG GCTCAATCAA TCCACCCACC
27501 TCAGCCTCCC GAGTAGCTGG GACTACAGGC AAGTGCCACC ATACCTGGAT
27551 AATTTTTGTA TTTTTTTGTA GAGATGGGGT ATCGCCATGT TTCCCAGGCT
27601 GGTTTTGAAC TCCTAGGTTC AAGCGTTCTG CCCACCTCAG CCTCCCAGGG
27651 CTTCCAAAGT GCTGGGATTA CAGGTATGCA CCATGTTATG GAAAATTTTA
27701 AATATGCATT AGAGAGAATA ATGGTATGAG TCTCCGTGTA AGAGATAGAA
27751 GCATCACCCA ACATCCATCA GATTTTTTTT TAAGAGTCTG GGTCGCTTCG
27801 TTGCCCAGGC TGGAGTGCAG TGACACAGTC AGCTCAGTGC ATCCTCAAAC
27851 TCCTGGACTC AGCGTGCCTG TCTTCACAAC TTCAATAATC TTGATTCACT
27901 TTGACATTCA CCCTTTCCTG CATCCCTCCT CCAAGGTGAT ATGTAGAAGC
27951 AATTGTTAGA TATATCATTA CATCTAGTAA ATATTTTAGT AGGCATCTCT
28001 AAAATATTAA AATATAAGTA CTCTTTTAAA GATATATGAT GGTTAAACCT
28051 TACCAAATTT GAGAGTAATT TCTTAGTATC AAATATGTCA GTGTCTAGAT
28101 TTCCTTGATT ATCTTTTTGT TTGTTTGTTT CAGTTGTTTT GTTAGAATTA
28151 GGAACCAAAC ATATTCCCAT GTTGCATTTG GCTGATATGT CTCTAATCGT
```

FIG.3-12

```
28201 TTATTCTATA GGTTCCTTCT CTCTCTGTTT TTCCCCTTGT GGTTTATTTG
28251 TTGATGAAAC CAGGTCATTT GTTCTATAGA TTTTCTCAGT CTAGATTTCG
28301 CTTTTTGGGT CCCCATGATG TCATTTACCT TTTTTTCCCC TCCTGTTTCC
28351 TGCAAATTGG TGGTTCCATC ACTTCCCTCC TGAAGTATGA TCAGATTCAA
28401 GTTCAGTTTT CTGGCAGGAA TACATCACAG ATAGCGTCTT GTACATCTTT
28451 CAGGAGGCAC ACGTTTGGTT GTCTCACTTT TTGTCATGTT AGCACCATTG
28501 ATGGTCATGG CTGAGATCCT TTATTTCCTT AGGGAGAGCC CCATATTTTA
28551 ACTTAGTGAG TAGCTCATGA ATCTCTCCCC TTCATCATGG AGTTTTTTCT
28601 TTTCTAAGTT AGACTTCTAG AGCTTTCACA GATTTCACAG TGAGCCCATA
28651 GCGCCTACCT AGACATTCTG TTTGCTGTAG AAACCAGAAA GGCTTTCTTG
28701 CTCTCATATC TTAGTTTAAT TTACACAATA TAGTAATCTT TAAAATTTGT
28751 CCTAGTGTCC CCCAAATTTG TTTCTATTTC TGAGACATGT TAAGATGAAT
28801 GGATGACAGA ACAGAAAGTT GAGGGCTCTA GAGTGAAATC ACAGTTGCAG
28851 GTAAGTTGAC GAGGTGCAAG TACAAATAAG ACACAGTCAC CAATTCTGTA
28901 CCAACATCCT ATCCAGAGGG AAGGGGATAA ATTTTTATTA TCTATATTTA
28951 CTTATTTTGT CCTGACAGCA AACATAAGGT TTCTGGGTCA GGAGCAGACA
29001 ATTATGACTT AGAGCATTAA CTAAGTCAAT TCCCCATACC CCAGTACCCT
29051 CCTTCAGGGC AACATAAAGG GGTCTAGAAG AAGAGGGCCT GGAAGAATGA
29101 GGTTGGATAT GCCAAGATTA CTCCAGGAAC TGAGAATGAA TGGAATCATT
29151 CCTTTATTCA GCAAACCCAC TGATTGTCGG CTGTATGCCA GACACTAGGG
29201 TAGATGATAA ATACTAGAAA ACTCCCAACC TAACACACAA AACCATATGC
29251 CTCTGTGTCT AGAGTTAGGC ATCAGGTGTC ATCTTGTGCT TATAGGTAAA
29301 TCACATACCC ACAGTTACAT GCCCTGCAAT GACATTTTGG TCAACAATGG
29351 ACTGCATATA TGATGGCAGG TCCCATAAGA ATATAATGCT GTTTTTACAG
29401 TACCTTTTCC ATGTTTAGAT ACACAAATAC TTACCATTGT GTTCCAGTTG
29451 CTGACCATAT TCAGTACACT GACATGCTAT ACAGGTTTGT AGGCTAGGAG
29501 CAATAGGCTA TCCCATATAG CATAGGGATG TAGTAGGTTA TACCATCTAG
29551 GTTTGTGTAA GTACCCTTTA GGATGTTCTC ACAATCACAG ATCACCTAAT
29601 GATGCATTTC TCAGAATGTA TCCCTGTTGT TAAGTGATGC ATGACTGTAT
29651 TTGTGTGTGT AAGGATATGA GTGTGTATGT GTATTTATGA TTTTGTACGT
29701 GTACACGTGT GTATGTCATA TTCCCTTCTG ACTTAACATT ATAATTTCTG
29751 AAAATCTTTT TCTTCATTTT TAATTTGTCT TCAGTTGTCG TTTGTGCTAA
29801 AGTTTGCATG AAGTTTTCTT ATCCCTCACT TTCCAGGTAG CAGTGGAATT
29851 TACTCTCTAC CTTCTGTTGT GTCTGCTCAT GTGACAAGTT CTTTTGGTAA
29901 GAAAGTAAAG TCTAAACTAT AAAAGTTAAA CTCTGAAAGA AGAAAATTCA
29951 GGTGCAAAGT GACAAGGATT TCACCAGACT GAAGAGACCT AAAGAAAGGG
30001 AGGGCCAGAT CCCTCAGCTG CAAGTCTCTT GATTTGGTGA GGGATTAAAT
30051 GTGCTAGGTC CCCTGGTACT AGTGGGGGCT GGGGTTTCAG ACCTCACGGA
30101 GTTGCCATTC TGATGGGGAA ACAATAGACG CAATTAGACA AACAAACATG
30151 ATAACTTCAA AATGAGAAAC GTGCGTTTAG GGAAATAAAC AAAGCTAAGA
30201 GGGTGCCAGT AACTAGGGGG GACCACTTTA GAGAGAGAGG TCCCAGAAGG
30251 CCTGCTGATG AAGTGACATT TGAGCTGAGG CTCAAAGGCC ATGAATGGGC
30301 CAGTGATGTG AGAACTTGGT GAAAGAGCAA ATGCAGAGCC CAGAAAGGGC
30351 TTAGTGTCTC TGAGGAGCAG AAAGGGGGCC CCTGTGGCTG GCGGCAGTGA
30401 GTGACAGGAG GGTGGAGTGC CAGGAGGCCA GAGGGAGGTG GGGTCAGACC
30451 ATTGCAGGCC CTCAAGGCCA TAATGGGAAG TTGAAACTAT GTTCAAAAAG
30501 CAGTGGATAA ACATTGAAGA GTTTGAAGCA GGAAAACTTA GTAATTATTC
```

FIG.3-13

30551 TCACCTAGAC TTTTTTTCCT ACACATGAGC AGACTTCTGT ATGTGTGTCT
30601 GTGTGTGTGT GTGTGTGTGT GTGTGTGTGT GTGTGTGTGT GTGTGTTTTC
30651 TTAGTGGTAA CATGCTGTGT ATATAATATG CAACTTGTTT TTCATTTACC
30701 AATAATATCT TGGTCATCTC TGAAAGGAAG ACTTATAAAG AAAAATAAGG
30751 TTTGCCACGA ACTATATAAC AAATTTAGAC ATGCAAAAAT GTGAAGCTGT
30801 GATGGAAAAT TAGTTTCTTA GGAATAAAAA AGGAAGGAGA GTGCTTGTTT
30851 TTAATGTCTG TTATACCTAT GAATTCCCTG TAATAATTTA AGGACATTAA
30901 AAATGTATTC TAACTTGATT CTTGATTTTC TCATAAACTT GCCATGATTA
30951 GTATGTTACT TTAATTATGT ATTTATTGTT AAAGCATCTT TACACACCAT
31001 TTTTAGTCTT CTAAAATATA GCAGAGACTG AACAAAGTAG GAAAATAGAA
31051 GAATAAGAAT TCAGTAGACA TGCATGGTCA AACCATAACA AACCCAAAGA
31101 TACTGAGACT CTAGAGAGAA TGTGTCACCT TTCAAAGTAC TGCTTACTAT
31151 TGCCAGTAGT TATAAATGTA CTTATTAGCT GGGCATGGTG GTTTACGCCT
31201 GTAATCCCAG CGCTTTGGGA GGCTGAGGCA GGAGGATTGC TTATCTCTGG
31251 AGTTTGAGAC CAGCCTGAGC AACTAGGTGA AAACCTGTCT CTACTAAAAA
31301 TAGAAAAATT AGCCAGGCCT AGTGGCATGT GCCTGTGGTA GTGCACGCCT
31351 GTGGTCCCAG CTACTTTGAA GGCTGAGGTG GGAGAATTGC TTGAACCCAG
31401 GAGGCTGAGT TTGCAGTAAG CTGAGATCAC ACCACTGCAC TCCAGCATAA
31451 GGGATAGAGC CAAACCTTGT CTCAAAGAAG AAGTACTTAT TTATTTGCTT
31501 TTAAAATATA CTTTTGTGAA AAGATATACC TAAAATCCCC AGCACATTTT
31551 AGTTCTTGCC CATTTACAAA ATAGTATATA GACAAAAGCC TGACTAAGAG
31601 AAACTGTCAA TATTACAGCG AAACAGAGAT AGGGATTGTT TTCTGGTCTT
31651 AGAGTTACCA TAACATGAGC ATCTGTGGTG AGCAAATATT TTCCAGAAAA
31701 GCAGGTGAAT GAAAAAACTA TAGCCCACAA AAATAACCGC CTCAAACTCA
31751 TGATCCCTAA TGTAGGCTCA TTTTTAAGTC TACATTTTAT TTTTATTTCT
31801 ACTTACTTAC TTATTTATTT TTTGAGACAA AGTCTCACTC TGTTGCCCAG
31851 GCTAGAGTGC AGTGGCACCA TCTCAGCTCA CTGCAACCTC CATCTCCCAG
31901 GTTCAAGCAA TTCTAATGCC TCAGCTTCCC TAGTAGCTGG GATTTACAGG
31951 CATGCGCCAC CACATCCAGC TAATTTTTGT ATTTTTAGTA GAGATGGGGT
32001 TTCACTATGT TGGCCAGGCT GGTCTCAAAC TCCTGACTTC AAGTGATCCA
32051 CCCGCCTGGG CCTCCCAAGG TGCTGGGATT ACAGACATGA GCCGCTGCAC
32101 CCGGCCTTTA AGCCTACATT TTATTTTATT TTATTTATTT ATTTATTTAT
32151 TTTTTTTGAG GCAGAGTTTC ACTCTTGTTG CCCAGGCTAG AGTGCAATGG
32201 TGTGATCTCG GCTCACCACA ACCTCCACCT CCTGGGTTCA AGCAATTCTC
32251 CTGCCTCAGA CTCCTGAGTA GCTGGGATTA CAGGCATGTG CCACCATGCC
32301 TGGCTAATTT TTTTTTATTT TTATTAGAGA CGGGGTTTCT TTATGTTGGT
32351 CAGGCTGGTC TCGAACTCCC GATCTCAGGT GATCTGCCCA CCTCGGCCTC
32401 CCAAAATACT GGGATTACAG GCGTGAGCCA CCACACCTGG CGTAAGCCTA
32451 CATTTTTAAA AAAATGTATT GCAGAGGTGG AAATGAACTA AAGTAGGCAT
32501 GAAGTAAGGG TCGAGGTCCA AGGGTGTGTG ACACAACATT GCTACCATGT
32551 TATAGAGGGA TATTCTAAAC AAAATCTCTG CATTCTTACC CCATGAACCC
32601 TATCTTCAGC CTTTACCACT GGAAAGCATC TTTCTAAATT CAAATCCTTG
32651 ATTTGCTTCT GGTTTTGTAA TAAAGTCATG AGCAATAGGA ATGCAGCCAG
32701 CAATTACGTT TCTGCTTTTG TCTTAAATTG GAGACCATGG AGCGACATCA
32751 ATTCGCAGGA AATATACTGT TTCTTAAGAA AGTCTTTCAT TTAACTTTCT
32801 TCTGTACTTA AAATTGGAAA TATATTTAGC TTCTCTAAAT ATTTAGTTGT
32851 ATGTGAACCA GTTGTTAAAG AATGTCTTAA TTCTACAGTT AAGCTCACTC

FIG.3-14

```
32901 ACATGTATGT ATGTCTCATA CATTAAAAAT GTCATCCTGC TGTGTAGTTT
32951 TAAGAAATTA CTTTTCAGAA GTAAAGACTT TAGGTATGAT AATGATAATT
33001 TAGGAAATGA TAATTTAGGA AAATTTTCTC AAGTACTCAT CATTTTTAAA
33051 AATTCATAAT TCAGAAATAT TTTATTGGGA GACTAAAGAC ATTTATAGTA
33101 TTTTCCCCCA GAGTGTCATA TTTTTATAAA ACAGGTTATT ATTAACAAAT
33151 GATATAATTT GAAATAATTG GAAAGGTCCA CTGGCCCTAA AATATGTCCC
33201 CTACAGCCTT CTTGGAACAT AAAATGTCCA ACTACGTATT AGAATTTTCT
33251 TTGGGTTAAT GGAGTATCCT CATAAAGGCT TAGTTTAATA GGAGTTATCA
33301 CTCTGGGTTT TGCCAAGATT GCTTTAGAAG GAATGAGTTG GGTATGTTTT
33351 CAGTAGTCTT GGTGAAGACC CCAGAGGAAG AGCAGAGGGT AGGGATCTTG
33401 GTGGGAGAGA AGGGAGACAC TCCCCTACCA GGGGCTCCAA AAGAGGGCTT
33451 TAGGTTGTAG GAAAGGTGGG CAAAGCCTGT CCTTTATAAT AATAAAATGT
33501 TTAGTTAGAG GGGAGCCATA TTTAAAACTA TAGCACTAGA CTTATCTCAG
33551 TTGTAAAATG GATATTATAT AATAAGATGG AGGAAGTCAT TCACATATGC
33601 TTTCTCTCTC TTTTTGAGCA CAATACCAAA GTGTTTCCAG AATAATTTGG
33651 CACCTTCACT TCCTGCACAG ACTTGGAGTA GAGTCCAGAA AACAGTCTAG
33701 TTGAATTCTC AGATGGGTTT TTGGCAAGAA TACAAAGTAG CTTTATACAG
33751 CTCATCTCTG ATGCTTTTCA CTGAGTGTCT GAAAGAAAAG GGAGGATTTG
33801 AGGACCTGAT TTAAACAAGG AAGTAACCCA GTGACTTAAA GAGGAGTGTT
33851 GTGGAATTCG AATCCCAAAA TAAAGCCCTA CGTCGTTGAC TTTTCAGCCA
33901 TGGGAATAAC CAGTTGCTTC ATTGTGTGTT TTGTCAAAGT GCCTCAGCCA
33951 TTTGGTCGGC CTGATGGTTA CCTGCTGCCT CTATTCATAG TTTCTGCGTC
34001 CTTTCTTGTT GCCCGGCTGG TCAAACATGT GTAACGGTGC CCTGGGGCAC
34051 CAAGCATGCC CTCGGGGAGC TAAATGCTGC CAGATGTAGG GAGCAAGGGT
34101 TGATTCACAT AGCCATAGTT TCAATAGCTA ATTTTACCTG TTTTCTTTTG
34151 GTTTTGGGTT TCCTTCTTAA AGAAAAACCC ATTTGGAGTT GAGTTTTTCC
34201 CCCTTTAAAT TGCAGTCTTA TCTTGTTACC TCTAATCTCC CAGCCTCATC
34251 CCACTCCCGA AATAAAAGTG TGAGAAGAAA AGAATAGAAA AGATACGTGA
34301 TTTATTAAGT CTGAGAGATT AATAGTTTTA CTTTATGATA AAATCAGTAA
34351 AATGTTTCTG TTTTACTGGA TTCTGATTAG TATTCTTATT TCAAAGTGAA
34401 ATTATGTTTC ACTTGACTCA ACCTTCCCTG TAGAAATCAT TTAGATAGAA
34451 ATAGATCATC TTCTAGATAG ATACTTTATG TAATCTCTGA TTAGGAACAC
34501 TGAATTTGTT GTTGAAAGCC CTATATTTTT TAACTCACTC TTGAAAACTG
34551 GTTAAGTAGA AGGAAAGAAT CAAGCCCTTA ACTTGATATA TCCTGTATGG
34601 AACTGAACCT CAGGATGACC AAATATTTGA TGAAAGAAAG TTTCTCTTTT
34651 TAGAAGTATT TCTGCCAACA AATTAAGAAG GTCTGAGAGA ATATCACCAT
34701 TTGGCAAACC CCTCGTGAAA TAATGAATCT ATCTACTGGT CATCAATGGT
34751 TGCTAACATC ACAAAAAGAG CCACAGCTAT CAGAGCACAC CACTGTCCAT
34801 TAAATATTCT TGCCAAAAAA ATTGAACTTG AGGCCGGGCG TGGTGGCTCA
34851 CGCCTGTAAT CCCAACACGT TGGGAGGCCG AGGCAGGTGG ATCACGAGGT
34901 CAGGCGATCG AGACCATCCT GGATAACACG GTGAAACCCC ATCTCTACTA
34951 AAAATAAAAA TTAGCTGAGC CTGGTGGCGG GCGTCTGTAG TCCCAGCTAC
35001 TCGGGAGGCT GAGGCAGGAG AATGGCGTGA ACCCGGGAGG TGGAGCTTGC
35051 AGCGAGCTGA GATCACACCA CTGCACTCCA GCCTGGGCGA CAGAGCAAGA
35101 CTCCATCTCT AAATAAATAA ATAAATAAAT AAATAAAAAT AAAAAAATCA
35151 AACTTGAATC AGAACAAATC CCTAGATTTA ATATGTCTAC AGGAAATACA
35201 AAGGACAGAG AAACATATTA ATTGACACCA CCAAGATACA ACTGGTAAGT
```

FIG.3-15

35251 TACAGAATGT GAGAAGTGCT AGGGACAAAT TCATTTTCTT AACAAATAAT
35301 TTACGAGAAA GAAAAAAGGG AGGAATTCAT TAAAACTGGC ATAAGAGACA
35351 TAGCAATCAA GTACAATAGA CCTTATTTGG CTCCTATTTT AATAATACAT
35401 TTGTTTAATT TTTTTTTTTT TTGAGACGGA ATCTCACTCT GTCACCCAGG
35451 CCAGAGTGCA GTGGTGCGAT CTTGGCTCAC TGCAACCTCC GCCTCCCGAG
35501 TTCAAGCAAT TCTCCTGCCT CAGCTTCCCA AGTAACTGGG ATTACAGGTG
35551 CCTGCCACCA TGCCCGGGCT AATTTTTTTG TATTTTTAGA GAGGCAAGGT
35601 TTCACTACGT TGGCCAGGCT GGTTTCGAAT TCCTGACCTC AAGTGATGTG
35651 CCTGTCTCGG CCTCCCAAAG TGCAGGGATT ACAGGTGTGA GCCACCGGGC
35701 CCAGCCCATT TGTTTAATTT AAAAAAGAAT ATATGACAAA AGGAGAATAT
35751 CTAAAGGCTG ATAAAATATT TGATGGTACT AAGGAACTAT TGTTAATTTC
35801 TAAAGGTATA ATATTATATT ATTAAACCAT TAAAAAGAGT TCTCATCACA
35851 GGCCGGGTAT GGTGGCTCAC GGCCTCCAGC ACTTTGGGAG GCCGAGGCGG
35901 GGGGGATCAC GAGGTCAGGG ATTTGGGACC AGCCTGGCCA ACATGGTGAA
35951 ACCCTGTCTC AACTAAAAAT ACAAAACATT AGCTGGCAGT GGTGGTGCGT
36001 GCCTGTAATC CCGGCTACTC GGGAGGCTGA GGTAGGAAAA TCACTTGAAC
36051 CCAGGAGGCG GAGGTTGCGG CGAGTGGAGA TCATGCCATT GTACTCCAGT
36101 CTGGGCAACA GAGCAAGACT TCATCTCAAA AAAAAAAAAA AAAAAAAAAG
36151 TCCTCATCTT TTGGATGTAC ACATGGAAAT ATTTACAGTT GAAATTATAT
36201 GATATCTGAA TAGGCTTCAA AATTATCCAG TGGGAAGGGA TGATGGTTAT
36251 GGATGAAACA AGATTGGCCA TCTATTGGCC ATTGTTGAAG CTGAATGATA
36301 GATACATGGG GATTTGTTAC ACTAATCTAC TTTTGTGTGT TTTTGAAATT
36351 GTCTATAATA AAAAGTTTTT AAAATAGGCT TAGGTAAATC CCAGATTTGC
36401 CACTTGTAAA TTTGTGATCG TGGACAAATT CATTAGCCTC CATAAGTCTC
36451 AGTTTTTGTG TGTGTGTGTG TGTGTGTGTG TGTTATTTCT GGTTAGGGCG
36501 TTGCCTATAA AATAGGTACA AGGTTATTTT CCCAGTTTAC CACCTGGTCC
36551 GGGTTGTTGT GCCAAACTTA ATAATATGTA TGATGTTACT TTGTAAATTG
36601 CCACAAATAT ATCAACTGTT TTATTATTAT GAAGTTCCTG AAAGGATCCA
36651 GGTTTTCTGC TTAGAAAATT TAGTAGCTTT TTCTGCTTCA ACAAGCAGTA
36701 TGGCTGTCTA CATAGATTAT ATCAACTAAA AAGCTCTGGA ATAAGAATAT
36751 AATTATGTAT CCAACAAGGG TTTTATCAAT TAGTTTGTAG TAATAGAGTA
36801 ATTATAAGAC TTCATTTTAA AAAATTTGCA AATATAAATT TCTCATGGCC
36851 TAGTAAATTA AATGTCGTGT AGACAACTGT GCTATTAATG TTTTCCCTGT
36901 ATAGTAAGAA TTGTGAATTA TTTCTGATTT CTTATTTTTC TTGATTGGAA
36951 GAAATTGCTT GAATTTAACA CATCAATAAA GATTTTAAAT TTATTCCTTC
37001 AAAATATAGA GAAACCCTGA TTGTTAGAAT TTTTTTCTTT TTTTTTTTTT
37051 TGTTGTTTTA TTTTCTAATT CTGGCCTCAT TTCTTCCTTC CTAACTCCCA
37101 GCATTTTATT GTGAAATATG TAGAGAGAAA CGTGTAAAAG AAATATACAA
37151 TTTAATGAAT GATTATGAAG CAAATACCTA TGTAACTACT GTACTGTGTT
37201 TTTTTTTTGT TTGTTTGTTT GTTTGTTTGT TTTGAGACGG AGTCTCGCCC
37251 TGTCACCCAG GCTGGAGTGC AGTGGCCCGA TCTCAGCTCA CTGCAAGCTC
37301 CGCCTCCCGG GTTCACGCCA TTCTCCTGCC TCAGCCTCCC GAGTAGCTGG
37351 GACTGCAGGC GCCGGCCACC ACGCCCGGCT AACTTTTTGT ATTTTTAGTA
37401 GAGATGGGGT TTCACCGTAT TAGCCAGGAT GGTCTCCATC TCCTGACCTC
37451 GTGATCCTAC CGCCTCCGCC TCCCAAAGTG CTGGGATTAC AGGTGTGAGC
37501 CACCACCCCC GGCCTACTGT ACTGTGTTTT AAGAAAAATC AGAATATCAC
37551 CAGCACCTCA GAAAACCTCT GCATGCTTCT TCCCAGTCCA AATCTCTTTC

FIG.3-16

37601 ATCCCCTGGG TAGCCACTAT CCTGACTTTA GTAGTATTCA CTTTCTTGCT
37651 TACCTTTATA GTTTTACCAC TTGTGTATAG ATTCCTAAAC AGTGTGATTT
37701 TGTTTGTTTG TTTGTTTTGA GACAGGGTCT TCTTTGTCAC CCAGGCTGGA
37751 ATGCAGTGGC ATGATCACAG CTCACTGCAT CCTCAACCTA CCAGGCTCAA
37801 GTGATCCTCC CACCTCCACC TCCCAAGTAG CTGGGACCAC AGATGCATGC
37851 CATCATGCCT GGCTAATTTT TAATTTTTTT TAGAGACAGA GTCTTCCTAT
37901 GTTGCCCAGG CTGATCTCGA ATGCTTGGGC TCAAGCAGTC CTCCCACCTC
37951 TGTCTCCCAA AGTGCTAAGA TTACAGGTGT GAGAGACCAC ACTGGGACTG
38001 ATTTTTATAT TTTAAGGATC CATTTATATT GTATCTGTAG TGAATTCATT
38051 TTTTTTGCTG TATAGTCTTC TGTTTTAAGA ATTTATGGCT GGGCATGATG
38101 GTTCATGCCT GTAATGCCAG CACTTTGGGA GGCCAAGGTG GGCGGATCAC
38151 TAGGTCAGGA GATCAAGACC ATCCTGGCTA ACCCGGTGAA ACCCCATCTC
38201 TACTAAAAAT ACAAAAAGTT AGCTGGGCGT GGTGGCGGGC GCCTGTAGTC
38251 CCAGCTACTT GGGAGGCTGA GGTAGGAGAA TGGCGTGAAC CCGGGAGGCG
38301 GAGCTTGCAG AGAGCCGAGA TCGCGCCATT GCACCCCAGC CTAGGCGACA
38351 GAGCGAGACT CTGTCTCAAG AAAAAAAAAA AAAGAATTTA CTGTAATTTA
38401 TTCTGTAGTT GATGGACATC TGGGTTGTTT CCACCTTTTT CTTTTTTTTT
38451 TTGTCGCCCA GGCTGAAGTG CAGTGGCGTG ATCTTGGCTC AATGCAAGCT
38501 CCGCCTTCCG GGTTCACGCC ATTCTCCTGC CTCAACCTCC CAAGTAGCAG
38551 GGACTACAGG CGCCTGCCAC CACGCCCGGC TAATTTTTTG TATTTTTAGT
38601 AGAGACGGGG TTTCACAGTG TTAGCCAGGA TGGTCTCGAT CTCCTGACCT
38651 CGTGATCCAC CTGTCTCGGC CTCCCAAAGT ACCGAGATTA CAGGCGTGAG
38701 CCACCGCACC CGGCCCGTTT CCACCTTTTT CTATTACAAA CAGTCTGAGT
38751 ATGTCTTTTG GATGCACTTC TGTATGCATT TCTTTTATGT GTATACCTAG
38801 GATTGAATTA GTGACTTCAT AATTGACAGG CAGTTTTCCA AGGTGGTTGT
38851 ACCAGTTGAC TCTCCAGCAG TATTCGAGAG ATCTTGTTTT CCCACATCTT
38901 CAACCTGTAC TTGGCATTGT CAGACTTTTA AATGCTTTAT TTTAAAATAT
38951 TATTAGTAAA ACAACATAGA TAAGTTTACT GTTGTCTATT ACTTACATGT
39001 ACTTGTAATG TTAAAGTCTA GGTTTTATGG CTGGGGGCGG TGGCTCACGC
39051 CTGTAATTCC AGCACTTTGG TAGGCCAAGG TGGGCGGATC ACTTGAGGTC
39101 GGGAGTTCAA GACCAGCCTG ACCAACATGG AGAAACCCTG TCTCTACTAA
39151 AAATACAAAA ACATTAGCTG GGCATGGTGG TGCATACCTA TAATCCCAGC
39201 TGCTTGGGAG GCTGAGACAG GAGAATCGCT TGAACCCGGG AGGCGGAGGT
39251 TGCTGTAAGC CAAAATCGTG CCGTTGCACT CCAGCCTGGG CAACAAGAGG
39301 GAAACTCCAT CTCAAGAAAA AAAAAAAAGT CTAGGTTTTA CTTGGGGTGT
39351 GTGTGTGTGT GTGTGTGTGA ATATTTCAGA GGTACAGAGA CTCTTTCTGG
39401 TCATCGATAT CTACTTGCTA AATTACGTCT TCCTACCTAA CAACTGCTAC
39451 GCTAGAGACC AGAAAAAAAA ATAGTAGAGC TTTAAAAAAG GAGAGAGCAT
39501 TTTTGTACCT TTTTCACTTG TTGTGATATT AAACCTATGA GTGATAGCTC
39551 AATTTATCAA TTGCTACATG CCAGGCGCTG TGCTAATGAA CTCTTAAGAC
39601 ATGTAAACTC ATTTAATCTT TACAACAGTT TTTTATTTCC CCATTTTTTA
39651 ACAGATGAAG AAACTGAGGC ATTAAATGGT TAAGTAACTT GCTGAAGATT
39701 GTAAGCTAGT AAATCATAGA GCCAGAGCTG AAGCTCAACA GTTGAGCTTC
39751 ACTGGTTCCA TCTGGGTTCT GAACACTTAA TATCTAGACC TCCTACCCCG
39801 TTGGTGAGTT CTGGTTAGTG ACATTAGTCC TCCAGAGCCA CCATGTTTTG
39851 TCTCCGGGTG GCTGTATTTG AGCTTGACAT GTTGTTTCTG GTGCTAAACAG
39901 TTAGGAAAGC AGGGTTGCTT GAACTTCAAG ACAGAGACTT ACTTCCTTTC

FIG.3-17

39951 ACTTGTTGTA GAAGTTGAAA GAAGCTGAAG CAGCATGAGA ATCCTGGCTC
40001 TGGGGCTGGT ACAGCTATTA CAGGAAGGGA CAGGACTTGG CCCTCTCTTC
40051 TCCTCTCTAG ATTTTCCTGG GGGTACTCAG CCTTCATCTT CTGCCACTTA
40101 GGGTTTGAGT GGAAATGGCC GAGAATATGT GGTAGGAAGC AGTAAAGTGG
40151 ACGTTTCAAT TTCCTTAATT GTCCAAAAAT GTGGAATATG TTATCCTTTA
40201 GAAACCATGT TGTAAATGGC AGCAACATTC CCAGGCCAGC TCAAAAAACC
40251 TATAATGTGG CCAAAATATA TGCTTACAGC TGTATTGTTT CCTAGTTTTT
40301 TGTTTTCATT GCAATTGTGT AGCATTTTAT TTGTCTTATG AGCTACTGGG
40351 CTAGCTGAGA ACTTAGCCAC ATTGTTTATG TCGGAAAATG CATTCCAAAC
40401 AGCTAAGACC ACGTATTTAT CTTAGTGTAG AGCTAACTAT CCATAGCTTA
40451 GATCATTGAC TACCTGAACA CTCTGCTCCA AGTAAACTGA ACAATACCAT
40501 CACCAATTTT TTGACGGTAA AGAGAAAAAC ATCTCAGTAA GATAGAGAAA
40551 CATTTTCTAT GGATTTACTG TGACCGAGAC CAAATTTTAA TTAGCTAGGA
40601 TATTTTTTAA ATTGTAGCAT TATATAAATG CATCTGTTTT TCATTTGTTA
40651 CATATGGGTT TTTATTTACC CACCCTCCTA AAACATTGAA ATATATTCAT
40701 GTAGCTACCT GAACCACTTG TAGATCTTCA GACTTGTGCG GCAAAAGGAA
40751 TGATAATTAT AATCTGCTTC AGGCTACAGG CTAGAATAAT TCAAAAGGAA
40801 ATGTGCATTA CTAATGCAGC AGAGCTCATA AATTCTCAAT GTCAGTTTGC
40851 CATTTATGCA GTCAGTCTGG TTGGCCAGAG GCAAAAAGAC TAGGGTTACA
40901 TAATATTTAT GAGGTCTGAA GTTAGCCATC ACCAAAGCCA AATATTGCCA
40951 GTGTTTCAGA TTACTCATTA AAGTCAGCAT CATCTAGTCA CGCCAATGGA
41001 GTTGGGAGCA GGGTGGATTT GGTAGTGATG AAACATTAGT TATAAGTATA
41051 AATTCTGTCC ATTTTAGTCC ACTACTACCT CCTTTACAGG ATTTATAGCC
41101 TTCCTATTTT ATATATTATC CCTGAGATGC CTACCTAAGG AGGGTTCCCA
41151 TACCATTCTG CAAAAATCTA CTTGCCACCT AAGGTTTCAT AACACAAAAG
41201 TGGGAATGGG ACTTTCTTTG CTCTGCATTG TTTCTCCAAC CCTCTTCATG
41251 TTTAACTCCT GAGAAGACCT CCTGCCTCTC TGTACATCAT CACAATGGCC
41301 AAGTCTCAAA AACTTTTAGA TCCCAGCTAG CACCTTATGT CATACTGTGC
41351 TCAGAAATAA TTAAGTGTCC AGACCCATAC TCTTGTGCTC TAGTGCACTT
41401 CAGGAGTTTG ACTTGTATAG GGTAATGAGC AGCTACAACT CCAGGCCTCA
41451 GGGTTACTCC CAGGAAACAC TGTGGCTGTG AACTCCAAAT TAAAAATGTG
41501 TGTACAATTG TACAGTTTCC AACATCAAGA AGCACTAGTC CCTGGGGCTG
41551 TTCATAACGG CTTTCTTTGT ATTTTCACAA AAGAACAGTC CCAGAATTAA
41601 AATAACCCTT TCATTTCCTA CACTTCACTT CTTAGAAGTC GTCAGGAAAG
41651 ATGAGTTTTG GTATGATTGT TGATGGTGAG TTTTTTGTGG GGTGGGGGTG
41701 ATGGAGCAAA TACCTTTAAA ACTTTTTTTT TTTTTTTTTT GAGATGAACT
41751 CTCGCTCTAT CGCCCAGGCT GGAGTGCAGG GGCTCCATCT CAGCTCACTG
41801 CAACCTCCGC CTCCCGGGTT CTAAAGCAAT TCTCCTGCCT CAGCCTCCTG
41851 AGTAGCTGGG ATTACAGGCA CCCACCACCA GTAATTAGTC CCAGCTAATT
41901 TTTGTATTTT TAGTAGAGGC GGGATTTCGC CATGTTGGCC AGGCTGGTCT
41951 CGAACTCCTG ACCTCGTGAT CTGCCCACCT TGGCCTCTCA GAGTGCTGGG
42001 ATTACAGGCG TGAGCCACTG CACCCAGCCA AAACTTTTTT TTGTTTTATT
42051 TTGTTTTGAG ACAGAGTCTC GCCCTGTCGC CCAGGCTGGA GTGCAACTGC
42101 CTGCCGGGTT CAAGCGATTC TTCTGCCTCA GCCTCCTGAG TAGCTGGGAT
42151 TACAGGCGCT CGCCATCACG CCCGGCTAAT TTTTGTATTT TCAGTAGAGA
42201 CGGGGTTTCA CCATGTTGGC CAGGCTGGTC TCGAACTCCT GACCTCGTGA
42251 TCCACCCACC TCAGCCTCCC AAAGTGCTGG GATTACAGGC GTGAGCCACT

FIG.3-18

```
42301 GCGCCCGGCC GAAAACTTTT TATTAGTGAG AAAAGTTTTA AGGATTTCAG
42351 TTAAACCAGG ATTATAGCTT AACTTTAAGG ATTTCATTTT ACCCCTTTCT
42401 CTACTTTTAC CTATATTTAA AAATATTAAA AAGTCCGTTT TTTTCTGTCA
42451 ACTATATGGC ATAGTGATTT TCTTCCAGAC TAGTAGGTGG AGTCGGAAGT
42501 AGTATTCTGA AACATGTGGA GGAAACTACA TCAGGAGAGC ATTTGCCCCA
42551 AGGGAGCAAT AGTGAGAGGA TTCCCCACAC TCTCTTCGAA AATTTTAAGA
42601 CATACTGCTA CTCCCAGGGG GAGATCAAAC TAAATACACA GCGTTTTAGG
42651 AACTAGAGAT ATACAGAGTC CTTGTTCAGC GGAGTGGCAG ATTTGTTTTA
42701 AGTTTATTTT TGTTCAAAGT TTTTGATCTC TTTTACTGTT ACAAGACTAG
42751 GGGAAATATC GTAATCGATT GTGCTATTTG CTTTGATACA TTCAGGCCCT
42801 CTTTTTTTTT TTTTTTTTTT TGAGATGGAG TCTCACTCTC TCTCCCAGGT
42851 TAGAGTGCAG TGGCACAACC TCGGCTCACT GCAGCCTCTG CCTCCCGGGT
42901 TCAAGCAATT TTCCTGCCTC AGCCTCCTGA GTAGCTGGGA TTACAGGCGC
42951 ACACCACCAC GCGCGGCTAA CTTGTGTATT TTTAGTAGAG ACGCCCGGCT
43001 AACTTGTGTA TTTTTAGTTT CACCATGATG GCCAGGATGG TCTCAATCTC
43051 TTGACCTTGT GATCCGCCCG CCTCGGCCTC CCAAAGTGCT GGGATTACAG
43101 GCGTGAGCCA CCACACCTGG CCCATTCAGG CCCTCTTGTA CCTGATAGCC
43151 ACAGTATACA AGAACTGAAG GAGTCTGAGG CCCCCCAAAG GCATATTATA
43201 TAAAGCAAAA ACAAACAAAC AAAAAACCCA CTTAAGGCTG GATGCGGTGG
43251 CTCATTCCTG TAATCGCAGC ACTTGGGGAG GACGAGGTGG GTGGACCATG
43301 AGGTCAGGAG TTCAAGACCA GCCTGGCCAA TATGGTGAAT CCCTGTCTCT
43351 ACTAAAAATA CCCAAATTAG CTGGGCGTGG TGGTGTGCAC CTATAGTCCC
43401 AGCTACGTGG GAGGCTGAGG CATAAGAATC GCTTGAATCC AGGAGGCGGA
43451 GGTTTCAGTG AGCCGATAGT CGGCCACTGT ACTCCAGCCT GGGTGACAGC
43501 GCAAGACTCT GTATCAAAAA AAAAAAAAAG AATCCACTTA AATGCTCATC
43551 ATTGGTTAAA TAAGGTGTTG TGTGACCTGT CCGTAAAGGA ATTCATGAAA
43601 CAACTAAAAA AGATCATGTA GATCTATATT GTTTTGTTAG AGACANNNNN
43651 NNNNNNNNNN NNNNNNNNNN NNNNNNNNNN NNNNNNNNNN NNNNNNNNNN
43701 NNNNNNNNNN NNNNNNNNNN NNNNNNNNNN NNNNNNNNNN NNNNNNNNNN
43751 NNNNNNNNNN NNNNNNNNNN NNNNNNNNNN NNNNNNNNNN NNNNNNNNNN
43801 NNNNNNNNNN NNNNNNNNNN NNNNNNNNNN NNNNNNNNNN NNNNNNNNNN
43851 NNNNNNNNNN NNNNNNNNNN NNNNNNNNNN NNNNNNNNNN NNNNNNNNNN
43901 NNNNNNNNNN NNNNNNNNNN NNNNNNNNNN NNNNNNNNNN NNNNNNNNNN
43951 NNNNNNNNNN NNNNNNNNNN NNNNNNNNNN NNNNNNNNNN NNNNNNNNNN
44001 NNNNNTACAT ATATGTGTGT GTACATGTGT ACATATATAC ATATGTGTGT
44051 ATGTGTACAT GTGTACACAT ATACATGTGT GCGTATGTGT ACACATATAC
44101 ATGTGTGCGT ATGTGTACAC ATATACATGT GTGCGTATGT ACACATATAC
44151 ATGTGTGTGT ATATGTACAC ATATACATGT GTGTGTATAT GTACATATAT
44201 GTGTATATGT GTAAATATAT ACATATATGT GTATGTGTAC ATATGTATAC
44251 ATATATGCGT ACATGTGTAT ACACGTATGC GTACCTGTGT ATATATATGC
44301 ATGCATGTGC ATGCATATGT GTGCGTGTGT ACACATATAT GTGTACGTGT
44351 ACACATATAT GTGTATATGT GTACACGTGT ACACATATAT GTGTATATAT
44401 ATACGTGTGT GTGTACATAT ATTTACATAT ATATATATTT TTTTTTTTAG
44451 GATACAGGAT CTCACTTTGT TCCCCAGGCT GGTCTCAAAC TCCTGAGCTC
44501 AAGCAATCTT CCCATCTCAG CCTCCCAAGT AGCTGGGATT ATAGGCACCC
44551 AGCTATGAGA AATATTTTAA ATATCAGATC CTTACAAAAA AAATAGTATT
44601 CTTTTATTGG AACTTCACTT GGTTTGCACT TCCAACACCT GTTAGTTTAT
```

FIG.3-19

```
44651 CCAGTCAGGC ACTCCATATT TGGAAGGAAG GAGGATAATA TTTGGGGAGA
44701 GGAAAGGTAA GAGAGGGGTG AGTTGGCAGT GATGGAAAGC AAAGTCAACC
44751 CCACTTGGTC ACGACTCACT AACCTCCAAT GGAGAAAGTG TGTGAGTCTG
44801 CATGTATGTT TGATTTTTGA TACATGAAAG AACATAAAAA TATGACATTA
44851 GACTATTATA CTTCAATTTT TAAAACTTAA GTTTTTTAAA GAAAAGTACG
44901 TTTAATGTTT TACAAAAATT ATTGTATTTA TATTTAATAG CATTATATTC
44951 CATTATAAAA ATTTCATTTA TTGTAGCAAC CAAGGAGTTA AAAAAAACCA
45001 AGGATAGACA AATAACAAGA AATGTACAAG GCCTGTATGG AGAAAACATT
45051 AGATCTCCAG TGATGGACAT TTAAGAACAC TGGAGGAAAT GTGAAGGCAT
45101 TTCTTATCTT AAAGAAGACG TTAAATATTT TAGAGTCAAC TGGACATGGT
45151 GGCTCACGCC TGTAATTCCA GCACTGTGGG AGACCAAGGC AGGGAGGATC
45201 ACTTGAATCC AGGAGTTTGA GACTAGCCTG GGCAACATAG TGAGACCCTG
45251 TCTCTGCAAA ATAAAAAAAA ATATTGGGCA TTGGTGGCAT GTGCCTGTAG
45301 TCCCAGCTAC TTGGGAGGCT GAGGCAGGAG GATTGCTTGA GCCCAGGAAG
45351 TTAAAACTGC AGTGGGCTAT GATTGCACCA CTGCACTTCG TCTGGGTGAC
45401 AGAGCAAGAC CCTGTCCCCC CAAAAAATTA TAGTCATATT GTCCTTAGAT
45451 TAATCCCATA AATTCCAATG TAAACCCAAT TTTGTGGCCA AAAACACTTT
45501 AAATATGGTG GAAATACAAA AAGCAAGCTG AAAAGATAGT TGAAACAATG
45551 TAGTACACAC ATTTAATATT TGTAATTCAC AGAATACTCT TAAAAATAAG
45601 TCAGGTGGGC TGGGCACGGT GGCTCACACC TGTAATCTCA GCACTTTGGG
45651 AGGCCGAGGC AGGTGGATCA CGAGGTCATG AGATCAAGAC CATCCTGGCA
45701 AACATGGTGA AACCCTGTCT CTCTTAAAAA TACAAAAAAA AAAAAAAAAA
45751 ACCCAAAACA AACAAAAAAC CTAGCTGGGC GTGGTGGCAT GCACCTGTAA
45801 TCCCAGCTAC TTAGGAGGCT GAGGCAGGAG AATCGCTTGA ACCTGGGAGG
45851 CAGAGGTGGC AGTGAGCCGA GATCGTGCCA CTGCACTCCA GCTTGGTGAT
45901 AGAGCGAGAC TCTGTCTAAA AAATAAAAAT AAAATAAGTC AGGTGAAAAG
45951 GCTGGGCGTG GTGGCTCACG CCTATAATCC CAGCAATTTG GGAAGCCGAG
46001 GAGGGTGGAT CACTTGAAGT CAGGAGTTCG AGACCAGCCT GGTCAACATG
46051 GCGAAACCCC ATTTCTACTT AAAATACAAA ATTAGCTGGT CGTGGTGGCA
46101 CATGCCTGTA ATCCCAGTTA CTTGGGAAGC TGAGGCAGGA GAATTCTTGA
46151 ACCTGGATGA TGGAGGTCAT GCCACTGCAC TCCAGCCTGG GTGACAGAAC
46201 GAGACTTTAT CTCAAAAAAA ATAAATAAAT AAATAAATCA GGTGAAAAAC
46251 AACCCAAGAG ACCTAATAGG AGACTTCACA AAAGAGGATA CAGAAATAAA
46301 CAAAGGAAAA TATCTTTAAC CTCAGGAGTA TCTGAAGAAA AATAAGTAAA
46351 AGTGAGATAC AGTTTTTCAT TTATCAGACT AACAGATTTT AACATTAAAC
46401 TGTTGGTAAA GGTATAGGAA ATAGGCATCA TTAGGAAGAC AAGTTGCAGT
46451 GTTTGTGAAC AGTTTTGCAA ATATGTTAAA GTTTGCATAT TTCTTAACCC
46501 ACAAATACTA CTTTTACACA TTTAAACTAA AAAGAAGTCA TCACTTGTGC
46551 AACTGTACTT GTAAAAAACA CATTATATAA AGCAAAAAAA TCAAACCAAA
46601 ACAAAAAGGA CCTACCAAAA TGCTCATCAT TGTTTAAATA AGGTACTATG
46651 TGATCCCTTC GTATAAGGGA ATGCTCCAAA ACCACTAAAA AGGATCCTAT
46701 ATAAGCCGGG CGCGGTGGCT CACCCCTGTA ATCCCAGCAC TTTGAGAGGC
46751 CGAGGCGGGC AGATCACTTG AGGTTGGGAG TTCAAGACCA GCCTGACCAA
46801 CATGGAGAAA CCCCGTCTCT ACTAAAAAAT ATAAAATTAG CCGGGCGTGG
46851 TGGCGCACGC CTCTAATCCC AGCTACTCGG TAGGCTGAGG CAGGAGAATC
46901 ACTTGAGCCT GGGAGGTGGA GGTTGCGGTG AGCCGAGATT GTGCCATTGC
46951 ACTCCAGCCT GGGCAACAAG AGTGAAACTC CGTCTCAGGA AAAAAAAAAA
```

FIG.3-20

```
47001 AAAAAAAAGG ATCATTCATA TATATGTGTG NNNNNNNNNN NNNNNNNNNN
47051 NNNNNNNNNN NNNNNNNNNN NNNNNNNNNN NNNNNNNNNN NNNNNNNNNN
47101 NNNNNNNNNN NNNNNNNNNN NNNNNNNNNN NNNNNNNNNN NNNNNNNNNN
47151 NNNNNNNNNN NNNNNNNNNN NNNNNNNNNN NNNNNNNNNN NNNNNNNNNN
47201 NNNNNNNNNN NNNNNNNNNN NNNNNNNNNN NNNNNNNNNN NNNNNNNNNN
47251 NNNNNNNNNN NNNNNNNNNN NNNNNNNNNN NNNNNNNNNN NNNNNNNNNN
47301 NNNNNNNNNN NNNNNNNNNN NNNNNNNNNN NNNNNNNNNN NNNNNNNNNN
47351 NNNNNNNNNN NNNNNNNNNN NNNNNNNNNN NNNNNNNNNN NNNNNNNNNN
47401 NNNNNNNNNN NNNNNNNNNN NNNNNNNNNN NNNNNNNNNN NNNNNNNNNN
47451 NNNNNNNNNN NNNNNNNNNN NNNNNNNNNN NNNNNNNNNN NNNNNNNNNN
47501 NNNNNNNNNN NNNNNNNNNN NNNNNNNNNN NNNNNNNNNN NNNNNNNNNN
47551 NNNNNNNNNN NNNNNNNNNN NNNNNNNNNN NNNNNNNNNN NNNNNNNNNN
47601 NNNNNNNNNN NNNNNNNNNN NNNNNNNNNN NNNNNNNNNN NNNNNNNNNN
47651 NNNNNNNNNN NNNNNNNNNN NNNNNNNNNN NNNNNNNNNN NNNNNNNNNN
47701 NNNNNNNNNN NNNNNNNNNN NNNNNNNNNN NNNNNNNNNN NNNNNNNNNN
47751 NNNNNNNNNN NNNNNNNNNN NNNNNNNNNN NNNNNNNNNN NNNNNNNNNN
47801 NNNNNNNNNN NNNNNNNNNN NNNNNNNNNN NNNNNNNNNN NNNNNNNNNN
47851 NNNNNNNNNN NNNNNNNNNN NNNNNNNNNN NNNNNNNNNN NNNNNNNNNN
47901 NNNNNNNNNN NNNNNNNNNN NNNNNNNNNN ATAGCATTAA ATATTAAACT
47951 CTTCAAATGG TAATTGTCAG TAAAAACAAC TTTTAAACCA AAACAACTAG
48001 TAGCATTTCT GCTTTAGTAG TTAATTAGAG GAAGTGGAGG TGGTTGCATG
48051 CAACAGTATT AATTTAAGAA AAGTCTTTAT GTGAAAGTGT CTGTTAATAT
48101 TACTTGACTA TTATGGGACT TACTGTAAAT AGTTGAGTTT TTCAGTTAAT
48151 CAGTGGTTGT GAAATAATAG TTTTCTGACA AAATTAGAAA AATTTGTTTG
48201 ACATTTTTAT CATAGTTTCA TTAAACGGTC TCCGCATAAT TTTAAAGATA
48251 ACTAATTTAT AGCTGAAACT ATTTCAATCA ATGATCTAAT AACAAAGATA
48301 AGCTTTGACA GCTTTAAAAA TATTTAAATT TTGTAAGGAC ATCATTTGCA
48351 CAGTGATTAA ATAAATGCAA AATTTAAAGG TACTGAATTT AGGCTATCAG
48401 GTTTCCATGG TTACACCTTT CCAAGTTATT TTGTGTATTG TGTAAATAGG
48451 TCTGTGAGTC ACTGGTAATT ATTTGTTTTT TTGTTTGTTC TGTTGGTAAT
48501 TCTGTGTTTA GCTGAATTTA ATACAGTTCA CACGGCGTGC TTTGGTTTAT
48551 GTATATTTTA GTGTTTGTGA TTGACAGTGA TTGAGCATTT CTTATGGAGT
48601 GCTTGCCTTT TTTGTCATAA GTGATGTATG TTGGTAGTGC TTGAAATGTA
48651 AATAAGTTCT TCCTGTATCA CTGTTTAATA AACAGGAATT TTTATGCAAA
48701 GAAGACTTCT TGATACATTT AAACAATAAG GTTTGTTGAG CTCTGAAATA
48751 TTTCTGCTAA ACAGATTGTG CACCAAGACA AATAGGTTTA AATTCTTACA
48801 AACTGAGGTT ACCAAGGGCA ACGTTAAAGT TTATGGCTAA GCACAGCATT
48851 GACTGAATGG TATTTAGTAA CAGAATAAAA AAGGCTGAAT TCTTTTTTTT
48901 TTTTGAGACA GGGTCTCACT TTGTTGCCCA GGCTGGAATG CAGTGGTGCA
48951 ATCTCCACTC ACTACAGCCT CAGCCTCCTG GGCTCAAGTC ATCCTCCCAC
49001 CTCAGTCTTC TGAGTAGCTG GGACTACAGG AGCATGCCAC CACGCCTGGC
49051 TAATTTTTGT ATTTTTCATA GAGATGCGGT TTCACCATGT TGCCCCAGGC
49101 TGGCCTTGAA CTCCTGAGCT CAAAGGATCC GCACACCTCG GCCTCCCAAA
49151 GTGCTCAGAT TATAGGCGTG AGCCACTGCG CTCAGCCAAA ATAGCAGCAT
49201 TCTGATCTAA CTCTTAAAAT TGTTTGTGAT AGTACACTTT ACAGGGAATG
49251 TCTTCAATGC AAAGTAGAAT CTTCCTATAA CATAATTTCT CCCATCCCAC
49301 CCTTTGCACA AATTTAAGAA GTATTCTTAT ATGTTTAGAA AGATATGATT
```

FIG.3-21

```
49351 CTTGAAAAAA GCCAGGGCCT TTTATGGATG TAGGAAGGAA TTTTCCTTAG
49401 ACCTCACCAT TAACCATCAG CATACTAGCA AGGGCCCAGC AGGAACTCTC
49451 AGGAAAACAT CAAAATTAGG CTGTCCGTAA TTCATCCTAC TGAGTGTGAG
49501 CCTTCTCTCA TACACTACAA TCATGAAATG CTGTCCAGTT TGTAAAGTGT
49551 TTCTACATCT GCAGTCTCAT TTGGGGTTCA GGTTGGCCCT GTGATGGAGT
49601 GAGGAGAGGC CCAGTGCTTT GGATGGTGTC ACTTTTAAGT AGCAGCTCTG
49651 GGACCCAACC TAGGATCTCA TGATTACTTT GTGAATTACT TGCTTTGTGG
49701 ATTATCCAAG GCACATTTTA AAATTCAGGC TGGTTTCTAC CTACTGATTA
49751 GTCCATTTTA GAGTGACCTC CTCCCACAGT CAGGTAACCA ATGATAGTAA
49801 TTACCATTTA TTGAGTGCTT ACCTTATGCC ACTTTCGATA TATCATGTCA
49851 TACAATTATC ATAGCAACCC TGTGAGGAAG GTATTATTAT CCACATTAAC
49901 AAATGAAGAA ACTAAGGCTT AAAGAATTTA ACTAACTTGT TTAAGTAAAC
49951 CAATAGTACT CAGAGAAGGA AAACCAATTT AAACAAGAGC TCAAGTGAAT
50001 ATAAATAGGA AGGCATATCT TTTGGAGGAA ATTCTCATGG TGCATTCACA
50051 AGCAAAATAT AAAATTTTAA ATTTCACACT GTTTCCTTCT TTTTTACCCC
50101 CAAATTGACT ATACCTTATT AGGCATTGAA GAGTTGAGGT TTCTTTGTAA
50151 CACTCCAGTA GAAGCATACT TCAAAAAGTG TCCCATCCCC TCAGACAATA
50201 AATATGTTTC AAATGTTTTA CACATCAAAT ATTTTGGTAT TGTGGCAATA
50251 TTAAAAACTT TAAATATGAG ATGATGAATT TGTCATTTTA CTGTGTGAAT
50301 AATCTTGGTG TTGGCTAAGG TTTTCAAGTA ATGTGTTTTC AGATATGAGA
50351 AGCAAGCAGC CTGCTATATA CAGATAAAGA GTACATGTTT TTTTGGTGGT
50401 TGGGGTGGTT TTAATTTTTA ACGTTTTTAA ATTTTTATTT TATTTTAACT
50451 TTTTTAAGGC AGGGTTTCGC TCTGTTGCCT AGGCTGAAGT GCAGCAGCGC
50501 AATCTTGGCT CACTGCAACC TCTGCCTCCT GGGCTCAAAC GGTCTTCCCA
50551 CCCCAACCTC CCAAGTAGCT GGGACTACAG TTGTGTGCCA CCATGCCTGG
50601 CTAATGTTTG TATTTTTTGT AGAAACAAGG TTTCACCATG TTTCCCAGGC
50651 TGGTCTCAAA TTCCTGGACT CAAGCGATTC ACAGGCCTTA GTCTCCCAAA
50701 GTGCTGGGTT TATAGGCGTC AGCCTGGCTT AATTTTTAAT CTTTAGTACA
50751 AAAAGTAACA GATAGTTGAA CATTCATATC CTTAAATATA TAAGTATATA
50801 TATTTAAATA AATGTTTATT TATATTTATG TTTACTTATA TACATATATT
50851 TACTTATATA CATATTTATA TTTATGTTTA CTTATATACA TATACACACA
50901 CATACACATA TATATGGGCC AAATTGTAAG CAGGCATCTA TGGAGCTCCC
50951 CTTTTAAGCC TGTGCCATTT TAACACTTTG TACTTTTTGA ATTAATACCA
51001 AAAACTGTCG AGTGAGTATT CATATGGTCA ACCAGGTATA CCTAGTAGAA
51051 TTGAGTGTAA AATTATTTGG GCAACATAAC TATACCAGTC CAAAAAGCTG
51101 CCTTCAGAAA ATTTGGAGCT TTTGCTTTTA CTAAAGAGGT TACTGTATAC
51151 TTTCTCTTTA TTTTTCTGGT TGAAAATAAC TCCTTGATGA GTGATCTTGG
51201 CTTCTGTTGT CTTGAATCTG TGTACTCTCA ACTGCAGAAG CTTGGAAATA
51251 TATTGTTTTC CTGAAGCATT AGCTTTCTCA TTTTAGGTAG TAATTATTGA
51301 CCTATCTACC TACCGATTTA CCACTCCTAT TGACTGGTTA CAGGGCAGAG
51351 ACAAAACTCC TACAGTTGTC AAAATACCAC GATAAGATTG ATATTCAAAT
51401 GTTTTCTTTC TATCCCATGC CTTTCACTTA GAGATGTACA GTGAAAATCT
51451 TCTCAGGAAG TTTAAGATGT AGGGTTTTTT GTTTTTTGTC TTATTTGTTT
51501 TTGATATTGA TACTACAATT TTGGTCAAAG CTCTGAGCTA TTTCATCCCA
51551 ATGGTTTGCT TGTGTGGCAA TAACTTTCAA TGGCCCATTG AAAAGAAAAA
51601 AGGAAAGAAA GACATCCAGC AATATACCTA GGGCATGCTG TATCTAGAAT
51651 TCAGTTGACA CTATTGTAAT ATGAAGACTA AAATCATGCT CTTTTCAAAT
```

FIG.3-22

```
51701 GCTTTAATGT AATTTAAAAA TATATTAAAG CTGTGCTTTT GATCATAGAT
51751 TATAAGCCCT CATATCTTCT GTTATTGGGC ATTTTAATAC AAAATAACTA
51801 ATATTTTAAG TAGTATATGA CAGTAGTATT TATGAATAGT CTGGAGGTTT
51851 TTTTAAGAAT TAAAGAAGGA TTTTGTTACT ATATCAGTTT TTTTTTAAAA
51901 AACTCATGAT GTTTTTATAT AGACTTTCTC TAAAATTCAG TTCCATGTGT
51951 GATTCCTATG AAATTGCTCT TTCTGGTTCT GATTTGTGTG CTTTAATATA
52001 AAATCATTCT ATTTTCCTCT TCTTTAACCA AAGTGTGTGA GGTAACAGGA
52051 ATGTTTCTTT TGAGAGACTT TGGAAGGTTG AAATTTGCCA GATGTTCTGT
52101 GCTAACCTAG AAGTGTGCAT TCCCTGGGTA GCAGGACTGT GTGAAATTCT
52151 TTCCTATAAC TTTGACAGAG CATTTGGTTT TGGTTCATTT TAGTGTTGTG
52201 CTTCTACTCT GATCAGAGCT TGTCTTTTAT TCTGTGTTTA AATGATATTA
52251 AGGCATCCAG AAAATCTGAC AAAGAAAATG ATATTTTGAT GACATTTTTC
52301 ACAGGGCTCA ACTAGAATGA ATTATTACAT TTTAACCACG GCCCTAATAA
52351 ACAGCTTCTT TATTTCCTCT GTAAGGATAC AATATTTCTT TGTCCAAGAA
52401 GTTGCCTGAG TATATGTATT GTTGAAGTGC TAAAAAGCTG CTTTTCTCTA
52451 AACTTTAGCT GAGAGACAAT GGGATTTGCC AAGTATATAC CATTTCATTG
52501 TGACTCAATA CTTTATAAAG ATGAATTTAA TTTAAATTTT GAAGTAAACT
52551 TTTTTTGTCT CAAATGGAGA AATTCCATGC AATAGCCCTA TTGTACAAAT
52601 TAAACATTTC TATGTAACTT CTACTTATCC ACCAAATGAT CAGCTTTTAG
52651 TTTTATACTT GAGTTCTGAC TATAATCTTT GGCACCCTTC CCCCAGCTAT
52701 AATTCGGCTA GCCTAAAGGA ATTTTTTTTC CTAGACTCAC AAGCAGGAGC
52751 CTATATTATT AAGTAGGAAT GTTTATAGAT CTGTGTTTCT AGAGTAGGTT
52801 GAGGTGTTTT AGTTTCCCAA AAAGAGGGGA ATGCTTCTTG TTTTAAATAC
52851 AGATGCCTGT GTGCTGGTGG TGTACATTAG TGAATAATCA CATATTAACA
52901 GATTTAGCTT TTGTAAAGAA GCAAAATGAA GTGTTTTCGT AAACCATTTC
52951 TGAACTTGTC ATTGATGTTA TACTCTATCA GTTGCTATTG ATAATTTTAT
53001 TTAAAGGAGG AGGTATATAG TATAGCGCCA ACTTCCTGAT TAGGCCTTGG
53051 GGAAGGTCAC GTTTTGCAGT GACCTGGGCA CCACTCTTAA ATGTTGTTAT
53101 TATTGGAAGA GGGTACCCTC AGGCTGCTGC CCTTCCTCTC CCCAGAAGCG
53151 CTCTGTGACT GACTTTCCAG TTCATCTTTT CTAGAACCAA GACTCCCAGG
53201 CTGTAGATGA ATTCTGACAT CTACAGACCA GTATCCATCT CAACTTCATT
53251 TGAGGTGAAT TTTATTAGTA GTAGTGACCC AGTCCTACCT TAATATGAGA
53301 ATGATGCATC CTCATAAAAA TTGCAAACTT AGAGCAGTAA ACAACTAGGA
53351 TAAACTTTTA TGTTTCAGCA TAAAAGTGAG TTATGACTTT TTTGTCATTT
53401 AAAATATTGC ACACATTTCC TTTTTATTTC TGTGGGATCT TTGTTACTGT
53451 TTTAGTGGTC TTAAGTAAAA ATAACTTCAA GGACAACACG GTTGGATGTG
53501 AGGTAGAATA TTTATTTCAG ACAAGTATTA TGCCCACATA TTTTAGATTC
53551 AACTATGTGC TTTATTTTCA GCATTAAAGA AAATGAGCTG TTTTCCAACA
53601 CCTGCATACC AACTGGGCCT GCATCCTCTT TAGAAATGTT GTTTAATAAA
53651 CACTGTGGCT TTATCATCCA GAGGCTGTTG CCAAATGCTG TTAATTAGGC
53701 CAAAAAAATG TTTTTTAAAG GTTGGTGAAA CAGATCCACT TTTCTCTCTG
53751 TAATGGCATC TTAGCTTGAA ATCCAGGAAG CAGTGGTGTA TGGTGTCCAT
53801 ATCCATGATT TCCTGCATTG GAGAAAAAGT GTGGAAAGCA TCTGGGGAAA
53851 AGGAGGCTCT TTACCAGCTT GTTTCCTGTA AGTTCAATTG GAAGACCTTG
53901 TCTGTGCAAA TAGATTTCAA AATAGAGCCT GCCCTTTGAC TGTCTCCATA
53951 ATTACATGGC TCGCTCTGTA TTTTATTTGG CAGCCAGAGC AGTTAACCCC
54001 TGGAAGGAAG GGGCTGATGG TATGGCCAGC TTGGCTTCCC AGGCATGTCC
```

FIG.3-23

```
54051 ATGGGAATGA ATAAACCACT GTTTGGAGAA GCCCATAGCT AAAAACACAC
54101 TAGAATAGTC TGTAACTGAA CTGAAACTCT TTTAAAACAA GTTCACTAAT
54151 GTTTATTATG ATCGGTTAAA AAACTTAACT TTGTCCTTAT TGTGTAGATT
54201 ATAGAGCTGT ATTAATTGTT TTAAAAATTG GGAATTGGGG GAGTTCCTTG
54251 TTGCTTTGAT GTAATCAACA TCTGTCAACA GATGAATTTG CTTTTGTTTA
54301 GTTTCAAGGG CTCTTGTCCT TTAGCTTTGC CCAATCAGTA TCTGCTTCAG
54351 CCTGGGGCAT TCCCTAGTAG TGCATGTGGT TTTTTTTCCC TCAGCAAATG
54401 CATAGGTTAT TTCTCATGAA ATGTGAGCTT CTCTTCTGCT TTATAGTTGC
54451 CTTGAGATGG GAAGGAACCT TCAATCTTTC TCATTTATTT TGAAACGTAC
54501 ACCTTAGTAC TAGATTATAA AAATCAATAA AAGAGTTATA TCAAGTGATG
54551 CAGACTATTT AATTTTTCTT TAGCAACATT TGTACAAGTT ATGAAACATG
54601 TCAAGCAATC AGTGTTTTAG GTCAAGAAAT ATAAGGCATG GATGCATTTG
54651 CAGTGTTCTC ATGGACTTGA AGCACACAGC GCTGTAAGAG CCTGTGCTCC
54701 TACTCTGAGT AATTGGTTGG AGTTCATGAA GTGTGATCTT TCTGTGGGTC
54751 TAAATCAGCA CCCCGAAAAT ATATTCCTAT GCTATAGTCC CTTCTGAGCT
54801 TACTGTAGGA GGCAACATTT TTAAACAGTT AAAAATGTAT CAGATTGCTG
54851 TCACAAAGTA AGTTGGGTTT TTTTTCTTGT TAAAGTTAAT ATATTATTAA
54901 GCAAATCATT TGGTTTAAAA TTAAAATCAT CAATGAATGT AAGAACCATA
54951 TTTGAAAATG AATTAGCAAA ACATTGTTGT TTTTCTCTCT TGGTAATCAT
55001 AAATCATTTA AATCTGGCAG GCATTCCTCT CTTCATCCAA AATAATTGCC
55051 TCCATTTGTA AAATCAATTA GATGTTAACA TGCTATAAAT AATAGTTTTG
55101 TTACTAGACT TTGGCATTTA CTGATCATTA TGAAAAAATA TATTCAGTAA
55151 GACATTTTAC AGGGTGTCTT TTAAATCACA TATTATCTCT GGTTGACATT
55201 GTTAGCTAAT GTAAAGTAGT GCCAAGCTAC ATTATTGTGT TGTTTTCTAC
55251 CCAGATATTT GATACCTCTG CAGTGTAACG TAACTGAGGA TTGATGGCAC
55301 ACTGCAGGGT GAAAGTGCTT CCCTGGAAAC ATACAATGAA AAATATATGT
55351 GTTGGTAGTC CAAACTTGAG TACAAATGTA CTTTGTTCAG TTTTACAACT
55401 GCTTAAAATA ATAAGCATTT TAAATGTCTC TTTGAAAGTT CATTCAGACC
55451 TCTCCCTTAA AAATACTTAT TGACCAAAAG AAAACTCACA TTTTCAGGGA
55501 TAAAATCAGC TTAATTAAGG GTCATTAGTA AAGGTGCACA TGAAAACCCA
55551 GGGCTCAGTG GGTGAAATGG AAGCATTTCA TTATGTGGTA TAGGATGCAT
55601 GAGCAGATAA CAATTAAAAT GGACCCTGAG TAAGAGGCCA ATAAATATAG
55651 GGCATGTTGT GTGCAGCAAC ATTCGTTATT TAAAATGCAT TCCTCCTGGC
55701 CAGGCACGGT GGCTCATGCC TGTAATCCCA GCACTTTGGG AGGCCCGAGG
55751 TGGGCCGGAT CACGAGGTCA GGGAGATCGA GACCATCCTG GCCAACATGG
55801 TGAAACCCGT CTCTATTAAA AATACAAAAA TTAGCTGGAC GTGGTGGTGG
55851 GTGCCTGTAA TCCCAGCTAC TCGGGAGGCT GAGGCAGGAA AATGACTTGA
55901 ACCCGGGAGG CAGAGGTTGC AGTGAGCCGA GATCGTGCTA CTGCACTCTA
55951 GCCTGGTGAC AGAGCAAGAA GACTCTGTCT CAAAATAAAT AAATAAATAA
56001 ATAAATAAAA TGCATTCCTC CCTCCATCAT ACTTGAATTC TATAATCCTA
56051 CCTTCAGATT TAACCTATAA AGGAAAATAA AATGCAGCTT TTAGAAATGG
56101 ATGTTATTAC TGAATATGAA AATATTTAAA ACCATAACCT AGATTTACAT
56151 TCCAAATACA AATTTTAAAT ATGAAAAAAT GTGCTGCAGG ATCCAGAGGA
56201 CATAGAGCAA TTTCAAGAGA TGTTCAGACT GCACAGTGTG CTCTTCCATG
56251 GAGTGCAGGA AGAAGTTGCC TATAATTTTC AGCGTTCAAC TCAGACTAGG
56301 TGCTGATAGA ATTTTTGTAA CACTAAAAAT AATTCTTATT ATTACCTTTG
56351 ATAACAGTAA CTATTCTAGT ATTCATAAAA AATAACATGT AGATTTACTC
```

FIG.3-24

```
56401 CCTAAGAAAA CCCTATATAG AGTTGCTGTT AGGTCATCAA CAGTAGCAAT
56451 ACTACGATCA TCTCTTGCAA GATCAAATTA GTATAAAGCA ACTCCTCACT
56501 GTTCTGGGCT CTCCTACTCC CCTGAGGTTT CTGGTGATTT CCCACTGGTG
56551 TCTCTAAAAA CATCAGATTA GTCCACTTGC CCCTTGTAGT AATTAGTACA
56601 CACCTGAGTC TTGTTTCCCC AAATAGCTTT ACCAAAACAC CGTGTGCAGT
56651 GAATCCTGAA TGAATGATAG TGTGTGGGAG ACGGAGGGAC TATTTCTGTC
56701 TCTGAAGATG GTCATCATGC ATCAAATTTG TTGTAACATT GGTGGTAGCA
56751 ATTTGGAAAT TAGATGTAGT TATAAGGTAT CAGCAGTGCT TTTGTCAAGA
56801 AATGAATTAT ATAGGAAATT CAAGAGACCA TTTCTACATT GATCTACATT
56851 AGTTACTGTA GTTCGGGTAT CCTTTCTGTG ACCCTGAATA TAATAGAGAC
56901 TGGGGATTTT AATTTTGCTC ACTCTGCATT TAGAAAATTT ACTACTTATT
56951 TGTATTGTGA TAAACAAAGT TGAGGGCCCG CCCCTCTTTC TTTGCCAGGC
57001 TAGTTGGAGG ACCATTATCT TCTAAAGGTA CCATGACTTA TGCCCATTTC
57051 TTCATTTCCC CTGTGAAAAC ACCAGATTTT ATTTCTAATA AAAAGATGGA
57101 ATCATTTGTA ATGAGTAGTT AGTGGAATAA ACACAGTATG GCACCTTATT
57151 ATCCTGTTGC CTTGTGACAA CATTTGTAAG GGTGTCTTTC ATCAGATTGA
57201 AAGAAAAGAA TTCGTTTCAA ATACAAAAGT GTCTTATGAA AGTGAAATTG
57251 CTGAATACAG TGTAGAACCA TAATTGTCAA CAGATTGGAT ATGTTCAGGC
57301 TGTGTTCCTG ACGTTTCGAA TTTTACCATC CAGTCATGTG TGGGTGTGTC
57351 TGCATCTTTT CGGCAGTGAG GCTGTCATTT GGCAGGACAG GTACCTTGGC
57401 AACACTGTTC ATCCTAAAAG TGAATGTCTC AAAAGCCTCA TCCAGATATC
57451 TAGTGGAGGC CTGATGACTT CATGCTTCAA GTTTAAGTAC ATAGAAAAGA
57501 TTCCCCCTAT AATGACTGTG TACTTGAACT TGATAACACT GATAAAGATG
57551 ATCTTTTGTG TAATCAACCA CATTGAAAAA AATCTTCATG AGTCCTAAAA
57601 TTGATCAGAG GCTACATCTT CCCATTTCCT GGGATGTAGC ATGACAATCA
57651 GATGGTGCTG AATGAAGGCA CACATTTCAG AGCTGAAGGG ACCTCAAAGA
57701 TTGTGAAGCC CAACTCTCAT TTTACTGAGC TTCTGCATCT CACAGGGTAA
57751 TGTCTTTGAA GTACTCAGCA CCGAGCTTGG CACCAGTAAG CTCTTGGTCA
57801 GTCAGCATCC ACTGTTATTG TTATTGCTCA AGATCACATA GCTCTTAGCA
57851 GGACCAGGGG TAGAACTTTC TGTCCAATGC TGTGCCACTT TGGTTATTTT
57901 TTCATCATGC ATAGCACTGT CTGATGTAAT CAAATGCATT TGTTGATTTG
57951 CCTATGTCTG CCTCCCACTA CAAGGATGTA AGCTCCCTGG GAGTCGGGAC
58001 CTTGTCACCT CATTCACCAC TGAATTCTCT AATCCAGAGC ATGGCACATG
58051 CAATGAGTTC ATTAAGTAGT TGTTGAATGA ATGAAGGCAT TTAGAGACCC
58101 CACAGGTAAA CATGTTGAAG AATGGAGAAG GAAAAGGAAA AGAAAGGAGC
58151 ATTTATGGAG CACCTATTTT TTAAAAGATG GTTTACCTAT TTATGTTATC
58201 TCAGCAAATG CTCACATCAG CTCGTGGTAG GGAGAGCACT ACTACTCCCA
58251 TTTAATAGTG AAGAAAATGA GTCTCAGAAG TTTTGGTAAC TCACACCTGT
58301 TTGACCTCCA AGCTCATGCT GTTGTCACTA CCATAGTGCC TCCCAACTGG
58351 ATCATTTCTA AGAATTTTCA TGAAAAGTGT CTTCATTCTA AATGCTAACT
58401 AGTTACATGA TATTTACATT TTTCATGATA AAAAAAACTG ACCTTGAAAT
58451 CTAGTACCCT GAAAGAATAC ATTATGTAAC AAAACACACT AGCGAATAGA
58501 ACTCATAGAG CCCCTGCACA CTGCTGAGAG GCAACTGGAA TGGCAGACAC
58551 AGCCCTGGAT TTGCATTTAC AGGATTAAGC TTGGGGCCTG GTCATTGATT
58601 ACCAGACTTG TGAGCCTTAG TTCCTCATCT ATAAAGCAGT GATGTTAACA
58651 GCTACCTGCC TAATGACAGA GCTGGTAAGA GGTAATGTAT GTAGAGCACC
58701 TAGCACTGAG CTTAATCTAA GTGTCCATTA AATTTTAACC ACTGTTATTA
```

FIG.3-25

```
58751 TTACTATTTA TATTAGCATT ATCATTATTA ATAGTAATTA TAATACTTTC
58801 CTCAGAAGAG AAACACTTGT GAGTTTGTGT CTTGTATGTG GTCCTGCCTA
58851 GCAATGCAAT TAGGGAGGTG GAATCATAGA TTGAGTCCAC CTGTGTCTTT
58901 CCAAATTTTC CATTTCATAT CCACAGACTG TCCAACTAAT AGTTCTGGCA
58951 GCCACCTCCC CAAAGCGTGT GTTTGGTCAG CGAAGGCAGC TTGGCTTAAG
59001 GTAGTGGGTG GATTAGGCCA ACCCATCACC ACTTTTGGAA AAATAATAGT
59051 AGTAGTAACA ATAGTTTTGT GATGCCTTTT CAATTTTCTG GGTATTTCCC
59101 TGTGTTTTAG CTCCTGTTTT TTCTCATGCC TGTGAGAGAA GTAATACATT
59151 TTGTAGAGGC AACTTAGCCT GCTTTCCCTC TCAGCTTTGG CACTTACTGC
59201 ATGTTCCTTT GTGTGCCTCA GTATCTTCAA CTGTGACATG GAGTAATAAC
59251 AGTTCACAAT TCATACAGTT TCTGTGAAGA TTAATGAGCT AACATATGTA
59301 AAGTGCCTAG TACAGTAATT GAGGCATAAT AAGTGTTCAG TATTAGAAGC
59351 TATACTGGAG GTCATGTTTT CTTTCCCATT TTATTTTTTG TGCAGACTTT
59401 TTTTTTTTTT TTGAGACAGG ATCTTACTCT GTTGCCCAGG CTGGAGTGCA
59451 GTGGTGTGAT CATAGCTCAG TGCATAACTC AGTGATCATA GCTCCAGGGC
59501 TCAAGTGATT CTCCTGCCTC AGCCTCCTGA GTAGCTGGAC TCCTGAGTAG
59551 CTGGACTGAC TCCTGAGTAG CTGAACTCCT GAGTAGCTGG ACTACAGTAG
59601 CTGATGGCCC AAGCCACCAC ATCTGGCTAA TTCTTTTATT TTTTGTAGAG
59651 ATGGGATCTC ACGATCCTCC CACCTCGACC TCCCAAAGCG CTGGGATTAC
59701 AGGTTTTTAT GTATTCTTGA AAGAACTATT ATTTATTGGG TATCTTCTTA
59751 AATGCAAGAC ACTTTCACAT TTCTTATTTC AATTCTCACC TGAGACTGAA
59801 ATGAAGAAAC TTGTGCAGGG CCACACAGCT AATAAGTGGT AGAGCTGAAA
59851 CAAAAGTCCA GGCTTCTGCC TTCCAACTGT CTGCTTTTCC TAGGACACTA
59901 CCCTGTCCCT CATATATCAG TTGACAATAC TAGGGTTGGT GATATTGTCA
59951 TTAGGGAAAT ATTATACTTT AAAAGCTTTA CACAATACAT ACCTGCCTCT
60001 ATCAAGCAAC TTTTTTTTTT TTAGAGAGAC AGGAGTCTTG CTTTGTTGCC
60051 CAAGCTGGTC TCAGACTCCT GGGTTTAAGC AATCCCACAT CAGCTGCCCT
60101 CCAAAGTAGC TGGGACTACA TGTATGTGCC ACTGTACCTG AGTTTTGTAA
60151 CTTCTTTTTA AAGAAATGAT ATTACTGACA TTTTGTCTAG TGCTTGAAAT
60201 TGTTTAAAAT AGTACCAAAA ACACCTCTAT AAGTTAGATT CAACAATATT
60251 GCAGTCCACT TTAAGGAGGG ACATAATTGA GTGAAACCTA TCACCCTGAA
60301 TCACTGATCA TTGCGGTTTG TTTGCATCAG TGCCTTTCCC CAAGTCAATT
60351 AGAGATCCAG AGTTTTGAAG CCAGTACTTA CCTGCAATTC ACGTTTTCAT
60401 TATGTTTCAC AGCTGAAATG TTACTCTAGG CCAGTTCTCA AGCTTCGTGT
60451 GCGTCAGGAT TACCTGAGGG CTGGTTAAGG CACAGATTGC CCGCCTCCAT
60501 CACCAGTTTC TATGTTTGTA GGTCGATACG GGGCCCAAGA ATTTGCATCT
60551 TTTTTCTTTT TCTTTCTTTC TTTCTTTTTT TTTTTTTCTG AGACAGAGTC
60601 TTGCTCTGTC ACCCAGGCTG GAGTGCAGTG GCGCGATCTT GGCTCACTGC
60651 ACCCTCTGCC TTCCGGGTTC GAGTAGTTCT CCTGCCTTAG CCTCCCGAGT
60701 AGCTGGGATT ACAGGCGCGC GCCACCATGC CCGGCTAATT TTTGTATTTT
60751 TAGTAGAGAC AAGGTGTGGG ATTACAGGCG TGACCCACCG CACTCAGCCT
60801 TGCATCTTTT TTCTATGTGA CATTATACTG CTGGTCTGTG AACCTCATTT
60851 TAAGGACTAC TGCTCTAGAC CAGGATTCAG CAAATGTCTC CTGTAGAGGG
60901 CCAAAGAGTA CATTTTTTAG GCTCTGTGGA ACATGTGTTC ACAACTACTC
60951 AGCTACCACT GTAGCTCAAA ATCCTCCATA GACATTTGTA AGCAAATGAG
61001 GGTAGCTATG GTCCAATGAA CCTTTTATTT ATGGGCACCA AGATTTGAAT
61051 TTCATGTATT ACAAAATATT GGGTTAAAAA GTTTTTTTCA ACCATTTATA
```

FIG.3-26

```
61101 AATGTAAAAA CCTTTTTAGG TTTTGTGCTG TATAAAAACA GTCAGCAGTC
61151 CAGATTTGGC CCTTGAGCTG TAGTTTTCTG ACCCCTGCCA TGTAGTTGTG
61201 ACCTGTTGGG GACTTCTAAA ACTATTGTTC TGGCCAGGCG CGGTGGCTAC
61251 GCCCGTAATC CCAGCACTTT GGGAGACCAA GGCGGGCAGA TTACGAGGTC
61301 AGGAGATTGA GACCAGCATG GCCAACATGG TGAAACCCCG TCTCTACTAA
61351 AAATACAAAA AAATTAGCCG GGCCTGGTGG TGCGCGCCTG CAGTCCCAGC
61401 TACTCTGGAG GCTGAGGCAG GAGAATTGCT TGGACCTGGG AGGCGGAGGT
61451 TGCAGTGAGC CAAGATCGCG CCACTGTACT CCAGCCTGGG CGACTGAGTG
61501 AGACTCCGTC TCAAAAAAAA GAAACCAAAA AACAAAAAAC AAAAAAAAGA
61551 TTGTTCTAAA TATGAAAGTA ATAAAATGAA TCAAAATGTC TTCCTGGCTG
61601 GATGCAGTAG CTCACGCCTG TAACCTCAAC ACTTTGGGAG GCCGAGGTGG
61651 GAGGATCGCT TGAGCCCAGG AGTTTAAAAC CAGCCTGGGC CACATAGCAG
61701 GACCCCATCT CTACAAAAAA TACAAAAATT AGCCAGGCAT GGTAGCATGT
61751 GCCTGTGGTT CCAGCTACTC AAGAGGCTGA AGTGGGAGGA TTCCTTGAGC
61801 CTGGGAATCC AAGGCTGCAG TGAACCATGA TCGCACCACT GTTGCCTTAG
61851 CCTGGGCGAC AGAGCAAGAC CCTGTCTCAA AAAAAAAAAA AAAAAAAAAG
61901 TCTTCCTCTC TACCTCTAGC CCCAACCACA AGCCACAGAA AGAGCCACTG
61951 TTTACAAATA TCAATTTCCA GAAATTTTAT GAGCACGTGC AAGCTTATAT
62001 AAATGTATAA GCTCCTTTTA CATTAATGGG CTTTTTATAT GTATTTGTTA
62051 AGCATTCACT TTTTTCCTAA CAGTGTATTG TGACCTCTTT CCATATCAAC
62101 ACATAGAGAT GATGATTTAG CCTATTCTTT TTAATAGCTC CAGAATTTTC
62151 TGTAAGTATA CCATAATATA TTTAATCAGT CCCCTACTGG TATTTCCTAT
62201 TTGGAAACAT TTGAGTTGTT TCCCACTTTC TTCTACCACA AATAATGCTG
62251 CCATGAGGGT ACATCTTCAT TCATCCATCA GTGCATAGTG TCTGCAGGAT
62301 AAAGTCCTAG GAGATGAACT GCTGAGTCAA AGGATATGTG CATTTAAAAT
62351 TTTGATAGAC ATTTCTAAAT TCCTGTTGTG AGTACTTCAA ACCCTATATT
62401 CATTTTCTTT CAGTGTTATA CTTACATTTT TGCTATTTAG TCTTTATCTG
62451 ACTTGAACAT TCATCACAAT GAATTTCAGT ATAATGCCTC ACTGCACGTG
62501 AACTTAACAC AGAGTAGTAA TCCTATGGAG GGCAAAAAGT GCAGCTGGCA
62551 ATTTGTCCGT GATTCTTGAA AGGAAACGGC TTTACAGAGT ATAAAGCCAT
62601 CAAAACAGTG CCCTGAATCT AGGGTCGTCT TGGACATTGC CACATAAGGT
62651 ATTACAGCAG AAATTGTTCT TTTTACAGAC CTGGTGCTTA GCAGATGTTT
62701 CTATATGTTT GTTTCCCGTT AGAGTAGAGT TTTCCATTGT CACGCATTTA
62751 TGTAAACATA GTATTAGCTA ATAAATACGC TGTGTTACTA TTGTACTAGA
62801 ATTCAGAATA CCACTGTTTT CATTTCTATT TGGGGCTTTT CCTTTTTCAG
62851 TCAATAAGGT ATTAGAATAA TGATTTAATA GACAACACCA CAACATCTTA
62901 AAGTGGAGGA CTGTGTTAGG TTGTTTTTTT ACTTAAAATA TGTCTGTTTC
62951 TGCTCACAGG TTCTCATAGA ATTTTCTCTT CACCACTCAA TCATATCTAC
63001 TTACACAAGC AGTCAAGCAG TCAACAAAGA AGAAATTTCT TTTTTCGGAG
63051 ACAAAGAGAT ATTTCACACA GTATAGTTTT GCCGGCTGCA GTTTCTTCAG
63101 CTCATCCGGT TCCTAAGGTA CTGTATTGCC TATTATCTCC TGCTTTTTCC
63151 AGCCAAGATA AAAGTTGACT GCAGAAGTGA TCAAATATTT TTGCACCTTT
63201 GATTTCTGAG CCATTTGGGT TTTAATTTTC AAACTAGGTT TGTGATCTAA
63251 AACTGTGATT TGAGAAGTTT TAATATCCTG CAATTCTATA GCATTAATTT
63301 TTTAAAACAA AGCTCTAAGC TTTCAATTGC TTAGAGTATT TAGAATTAAA
63351 ATTTTTAACA TGAAATTTTC TATATTAAAT TTCTAACATG AAGATAAAAC
63401 TATACGTATG TAGTTTTCTA ACTGTTTTAG AGAAAAAAAT TGACTATAAA
```

FIG.3-27

```
63451 ATTGTGATGA TTCAAAAGAG ATTACTTAAA ACTAACATAC TAGATTTTTT
63501 TAAGCCTGTT CTTACATTTT CCTTGTTATT GATGCTGGTG TCTTTGAATT
63551 GTCTTTTAGA CTAAATTAAA TAAAATATGT CTCAGAGCAG TCTTGGCTTT
63601 TTTTTTTCAG AGATTGCAAT TCTGTGGAAA GGCAATCTAT CCATTTTTCA
63651 AAATGCAATA TAAAGGGAGT GTGCGAGTGA GCCCTTTAGG AAGAAGGAGA
63701 GTAGCTAAAG AAATATAGAT TGGTCACAAA AATCATCTGC TTTCTCCCTT
63751 TTATGAACTT TGTTTACAGC GAGCCCATAT TTAGTATGTT ATACTTCTGA
63801 AGGTGAGTGG CCCACTTTTA TGGCAAAGGC CAGTGACACA GAAGGGCCAC
63851 CAGGATGTAT CCCCTGGCCT GGCCATCACA GTGAGAGTGA GAATTTGGTA
63901 TTAGTTACAA AACTGACACT TTTTTCCTTA GAAGAAAAGA AAAAGAAATC
63951 TCTGGTGAGG TGAATTGTAT TGCTTTAGCC ATTTCAGTCA ATTTCAGCAT
64001 GACAGCCCAA CAGCCCTTCT GCCTGCAAGT TATAACCTTG CCAGATCACA
64051 GAGCAGAGTG GAGACAAGAA CACAGGCTCT TTGGGGGAGA CCTGGTGAGC
64101 ATTTGTGGGC ATTTGTGGTG TAGCTGTGGG AGAGTAGATG TTCCTCTGGA
64151 GCTCAGCTGT GGCAAACCAG GCAGTAGTGT TACCTGTATC AGAAAACCCA
64201 TCTGAACAGG GGAGCAAGTG AAGACCCGTA ACTCCTGCAG GACAGGCTTC
64251 ACAAAGAAGA GAGCCCTAAC CTCAGCCCTT CCAGAGCTGC TGCAATGTTT
64301 CAATTGAAGA GTGTTATCTC CCTCAGCTTC CTGTCCCAAA CTGCTGTGGA
64351 GCCTAACTGT GGACTGTCCA ATAATGCTTA TAGTTTGTAA TGCATTATAA
64401 ACTATAAATA GTTTGTAAAG AGCTGTGCAA AACCTTGGGA CTGAAAGAAG
64451 CTTTGTGTGT AAGATGGTAT TTATTTCCTG AATACTGCCC ATGGTGGAGA
64501 ATGGTCTGCA AAAGTGATCA GGGTTGCACG TCTTGAGTTT TGGGGTGGCT
64551 TTTTGTTTAC TCTTGACAAA TAATGGAAAT GTTCTAGGTA ATTTTTATGT
64601 ATTTGAAGAA TAAAACTTGT TTCATTTTAT TCTAGTGTCT CAGTGTAAGT
64651 ACGGTTGCAA AATGTAAGAA AAGTGTATAT GTAATAGGCT TTAGGGAACT
64701 TGATAGTCAG CCTTTTTACA TATGTTCATT TTGAGAGGGT GTTGGGAGCT
64751 ATCTTTTGCA TAAATTATAT TTTTGTGTTA AGAAGATGAA AGTGCTCTTA
64801 ATTAACCATT TGGTGAATTG GAAGCTTGGT GCTATTTTTC ATCAATGGTG
64851 AATATGCTTC TAACTGGGTT GGGAGGAGGA AAAAGAGAAA ACTACTGTTT
64901 GTTTTGACCA GAAGTCTACT TCAGTCCAGT TTGACTCAAA GCATGGTAAG
64951 GTTAACAGAC CATCCAGAGG CAGCACTAAC AGGCAATGTT AAGTTCAAAA
65001 GGGCAGGGGA AGGAACTGGG GGCAGCCTGG AGGGTCTGTT GTGCTGGCTT
65051 CGGAGGTCGG TGCTCCGGCA GGAAGGGCAG AGCTCCATGA AGCAGGAGGC
65101 TGTGTCTGAA AAAATGATCC CATTGTCGTG CGCTGGGTTC TGATCTTCGT
65151 TTTCAATCCT TTTTCCTCAA GCACATAAAG AAGCCAGACT ATGTGACGAC
65201 AGGCATTGTA CCAGACTGGG GAGACAGCAT AGAAGTTAAG AATGAAGATC
65251 AGATTCAAGG GCTTCATCAG GCTTGTCAGC TGGCCCGCCA CGTCCTCCTC
65301 TTGGCTGGGA AGAGTTTAAA GGTGGCGTCT CACCAAGCCT CAGAACGACT
65351 TACATAAGGG GCAACAAACA CTCCTCTTTT TTTCCTTCTC CTTAACTCTT
65401 CTTTTAGGTT GACATCTAAT TTGTTTTAAA AATTTATTTG TTTTAAATTA
65451 ATTTGTTTTT AAAAATTAAG TAAAGCCTTG GGATGGGGAA AAGGAATTTT
65501 ATTATTTTAT GTGTTTATTC AAGAAGTAAT TTAAAATCCA AATTCAATTT
65551 TAACTAGCAG AATTCTAGAG ATACTTTGGT CTCAGTCAAC CTATCCAAGT
65601 TGATCAATGG CAGACAGCTT TGATTTTTGC CCCCCTACTC CTGCCTGTAG
65651 TTTCAGCTTT TACTCCCCAC ATTATTTCTG TGTGCTTGAA GATTTGCTCT
65701 ACCTTGTCCT TTGTCTCCTA TTTTCTTGCA TTTGCCCTGC AAAGAAAGAT
65751 CAGATCACAT ACACAAAGCT GTAGGTAATA TAGCAGTGTA ATTACATACA
```

FIG.3-28

```
65801 ACTTCCTACT ACAAGATTTA GTTCTTTTAG GCCAGGCGCA GTGACTCATG
65851 GCTGTGGATC ATTTGAGGTC AGGAGTTCGA GACCAGCCTG GCCAACATGG
65901 TGAAACCCCA CCTCTACTAA AAATATAAAA ATTAGCCAGG CATGGTGGCG
65951 GGCACCTGTA GTCCCAGCTA CTTGGGAGGC TGAGGCAGGA GAATCACTTG
66001 AACCCAGGAG GTGGAGGTTG CAGTGAGCCA AGATCATGCT ACTGTACTCC
66051 AGTCTGGGCA ACAGAGTGAG ACTCCATCTC AAAAAAAAAA AAAAAAAGAT
66101 TTAGTTCTTT CATTTAGTTC TTTCATAATA ATCTGAAGCA CCCTTCTGTA
66151 TAAGGATTAT AAAAGAAAAA TATGAGCCTA TTTTCTGCCA AAAGGTGGGC
66201 AGAATTTAGG AAGTGAGACT CAAAGATAAA ATCACTCACA GTATCTTCTG
66251 TGTAATAAAC TTACAACACG GCTAAACATA ATGTATATAT ACAAAATGAA
66301 GAAAATTATT GAAGAAATGG TTAATTTTTA ATAAAAGATT TTATTTTTGT
66351 TTTAGAATTT TATTTATGTT TATGGAGTTT ATGGAAATAG TCTTCATATA
66401 CTTATAAAAC TCAATTTCAG TTTTCTTTTA GTTTGGGAGC AATTTAGTTT
66451 GGAATACCTT TAGTAAGGAA AAAATATTTT AAAAATTACA TTTATTTAGA
66501 CATGAAAGAA ATGAAGATTA CTTAAAATCA AATCTCTACA AACTATATTA
66551 GACTCACTCT TTTAAATATC AACCATAATC TCTGTGCCAT TGCTGCAAAA
66601 CCCCTGTAAT GTTTTACTGA GATAAAAAGA TGCGAGTTGA CCTACTTTTC
66651 AAGCTTTTCA AGGTTCAACT GATGAACCTT TTGAGCATTT ATTCACATGC
66701 GCTGGGTAGC CCAGGGCACC AATCATTGAG AAAGAGTAAG GAATTGCCGA
66751 AGAACATAAT TTTGAAATCC TCAGGCCAAA AGGGAGTTAT GTCATTTAAT
66801 GACTCACAAA TGATTTAGAG GATCGTAGGG TTTAACATTT CTATTTCCTA
66851 ATGGTCCATA ACACCATCAT ATGCCCAAAT GATTGTCCAC AAGGCACAGT
66901 TGAGGATTCT AACACTAATC ATAATTAATT CAAATGTTGT ACCATAACTT
66951 TATCATAGTA AATTTATACA GTCTCACATG GAAGTACTGT TGCTATAGCA
67001 TAGTTGATAA ATACAAGAAA TGTCTTCAAT TGTTGCTGCA CAATTTCTTT
67051 ATTTAACATT TTAGGTTGAC ATGACAACTG AAGAGATAGA TGCTCTTGTT
67101 CATCGGGAAA TCATCAGTCA TAATGCCTAT CCCTCACCTC TAGGCTATGG
67151 AGGTTTTCCA AAATCTGTTT GTACCTCTGT AAACAACGTG CTCTGTCATG
67201 GTATTCCTGA CAGGTATTCA GTTCTTAATA ACATATTGTT CCTTTGGAAA
67251 CTAAAACATG AAGCTAAGAT CTGTAACATA TGTTGAAAGA CACTATCATT
67301 CAATTGAAAC CCACCGGTAA ACTTCTGAAA TTGATTATGA TAAAACAGAA
67351 ATTTTGAAGT ATTTTACTTC TAAATGGATA CACCACCACC ATTTAATGTT
67401 TGTTAAAGCA GTGCATAATC TAAATGGGGG TTGTGCATTA CGTATGTCTT
67451 TTACTTCTTA GATTTTAATC ATATAAGTGG TAAAATTCAA ATGTGGCAAA
67501 TTTTTCTTAT CAACTCTTGT TTTGGTTCTT GGCAAAATTA AGGTAATAAA
67551 TTAAGTGCAT CTTTTGAAAT AAAGATTAGA TTTAGTTATC CTGTGTAGTC
67601 CTCCTTCACT CCAAATTATC ACTGCATCCC ATTGGGTTTG TGACAGTAGT
67651 CATTAAGTAT TTATTTTTAT TTTCCTTTTA TTGAGATCTG TCTATCACCA
67701 TTTTTTTTTC TGTTTACGTT TTAGTCGACC TCTTCAGGAT GGAGATATTA
67751 TCAACATTGA TGTCACAGTG AGTAAATCAT ATAAAAAATT GTCTTTGATC
67801 AACTTCAGAA TTGCTGGTAG CAACAGGAAG AGTGGATTGA AAATGTGAAC
67851 TGCACCAGTG GAAGTGCTGT TTACTTCTAG ACCCAGACGC AAGCAGCTGG
67901 TTTCCTTTTT TGTCTTTAAC TCTGTGTTTA TTCCAAGTAA ACCCAGGCCT
67951 GACTTGAATT TAGGGCTGCA ATCAGATGCA CTGAGATCAA TGTTGGCCTA
68001 AGTGAAATGT CAACCCAATC CTGCTATGTG TCATGTTTTT GAGAAGGTGT
68051 AATTGTTATT GATCCACTGT GTAGTTAACG CAGAGCACCA CAGCACTGGG
68101 CAGCTGCTGA AGCTAGATAT GTATGAGATG AGCTAACACG AAGAAAGCCA
```

FIG.3-29

68151 GCATTTTTCC TTCACTCTGC CAAGATTGAT CTTCCTCTTC CTGCTGATTT
68201 TGAGTGGGGC CTGTCATTAT CTTACTCTGT CATTAGGGGC TACATTGGCC
68251 TGTGTATGTC AGTCTATTTG GACAGCAACT CTTTTGCTAG CCGTGTTCCC
68301 TAGATTTATT AAAATCCCTG AAGGTAACGT TGAGTTCCAT TTCTGGTATA
68351 GAGAGCCTTG TGCTCAAAGT AAGCAGAGTG GTTTTTTTGT CTGAACTTAA
68401 GTTTTCACCA AATGGTTAAT AGCCTTTCTT TTAAGTAACA AGCCTAAGTA
68451 ATTTATCATA GGGACTTCAA ATTGTACAAG ATGTAGCTTT TTCTCATTTT
68501 CTTAGCCTTT TACCATTCTC AGACTTGGAT TATATGTGCT TTTACATTTC
68551 TGTTTATTAA AGAATTTTGT AATGATACCT TTGGATTACC TAGATTATAA
68601 ATAAATTCTG TACATCTAAT GATTAACAAA TACATTTTAA ATAAATAAAC
68651 AAAATTTAAA CATCTTAGGA GAACTAGTTG AAATGACAAT ATTCAGGGAA
68701 TACAATTTCT ATTAATAAGG AAGTGTTTTT AAGAATAGTA TCTAGACCAT
68751 GAAACTGAAG TAGGAGTGGG AATGAGATAA AAATAGGAAT CCAATGGTGG
68801 AATTCAGTCT GACTTTTAGT TTAAGTTAAC TAAACCTTTT TTCTTCATAT
68851 CAATCATATG AGGAGATAGC CAACGATTCT TTCATTGCTG ATGCTATTTC
68901 CTGTATCATT TTATCCTACT TAAAATGCTT GAACACTTGC ACCACATACA
68951 TCCTGTTGGT ATCTTTCCAA CTCAGAATCA TGTGGAAGGA GGTATTTTAT
69001 GAAGTATACC TAAAACAGAG TTCTTTTCAT GAGACACTTT TATTTTGGAT
69051 TGTACCTGAT TTTACGGTTT TACATCTATT TTCTCATCTA GTCACCCTAT
69101 CATGAAATGT TACCATTTTA ATGTTTTGAA TGAAATCAAC TACTCTTCCC
69151 TACTGTTTCC AGTGTGTCCA AAGAAAATAC TCTATTCCTT TTCTAAGTTT
69201 CCTGAATACT TAATAAACAG TTTTGTATTT AACATTCAAA TTACTTCACA
69251 ATTGCAAAAC TTATAAAGCA AAGTGAAATA TTTCCAAGTG TCTAGAAATG
69301 TGAAGGAATC TAGGAAACAT ATAGGTCCAT ATCTTAACAA ATTATATTTC
69351 TTATAAAATA TTTTATTAAG TGAAGGACTC CATTATCAGA TCCTATGTTT
69401 CTATCAGAAA ATACTCATTG CATCTTAGAA TTATTGACGT CTAGTATACA
69451 TCACAAGAAA TTAGATTTCC TTCCCCCCTT TAAAACTGAA AAATGTTTTT
69501 CTTAAAGACA ATGCGATGTC CATAGTAGTT GCTCAATAAA TATTTGTTAA
69551 ATGAAGTACA AGGGCCAGGC GCAGTGGCTC ATGCCTGAAA TCCCAGCACT
69601 TTGGGAGGCC AAGGCAGGCG GATCACCTGA GGTCAGGAGT TCAAGACCAG
69651 CCTGGCCAAC ATGGTGAAAT CCCATCTCTA CTAAAAATAC TAAAAATATA
69701 AAAATTAGCC CTGTGTGGGG GCAGGAGCCT CTAATCCCAG CTACTTAGGA
69751 GGCTGAGGCA GGGAGAATTG CTTGAACCTG AGAGGCAGAG GTTGCAGTGA
69801 GCTGAAATCG CGCCCCTGCA CTCCAGCCTG GGTGACAGAG CGAGACTCTG
69851 TCTCAAAAAA TAAATAAATA AATAAATGAA GTACAAGTAC TAGTTTATGG
69901 GTATAAATAG AAATTGTAGA TGACTGCCAC AGACTTTCAA AAGTATTGTA
69951 TTTCTGTATA TAGTGAATCT TTTAAGTAGT CTTTTTTTTT TTCAGACGGA
70001 GTTTCCCTCT GTTGCCCAGG CTGGAGCACA ATGGCAGGAT CTCAGCTCAC
70051 TGCAAACTCC GCCTTAAGGG TTCAAGTGAT TCTCCTGCCT CAGCCTCCCC
70101 AGTAACTGAG ACTACAGGCA CACGCCACCA CACCCAGCTA ATTTTTGTAT
70151 TTTAAGTAGA GGCTGGGTTT ACCATGTTGG CCAGACTGGT CTTGAACTCC
70201 TGACCTCAAG TGATCCGCCC ACCTCCGCCT CCCAAAGTGC TGGAATTATG
70251 GGTGTGAGCC ACTGCACCAG TCTCAAATAG TCATTTTGAT ATTCCTTCCT
70301 TCCTTCCTTC CTTCCTTCGT TCCTCCCTTC CTCCCTCCCT TCCTCCCTTC
70351 CTTTCTTTTT CTTTTTCTTT GTTTCCTTTT CTTTTTTTAC TTTTTCAGAT
70401 ATAGGGTCTT GCTCTGTCAC TCAGGATGCA GTGCAGTGGT GCCATCATGG
70451 CTTACTGTAA GCTTGAACTC CTGGGCTCAA GTGATCCTTC TACCGTAGCC

FIG.3-30

70501 TCCCAAGTAG CTAGAACTAC AGGCGTGTGC CACCACACCT GGTTAATTTT
70551 TTAATTTTGT AGAGATGGGG TTTCACTATG TTTCCCAAGC TGGTCTTAAA
70601 CTCCTGGTCT CACGCAATCC TCTCATCCCA GCCTCCCAAA GGATTGCAGG
70651 CGTGAGCTAC TGCACCCAGC CTCAAGTAAT CATTTTCAAA GCTAGGAAAA
70701 AGTAATATGA AAAGATGAAT AAAGATTTTT TAAAATAGTA CATTTTTACT
70751 TAAAAAGCAG TTATATAAAC ATTCATTTAT ACATTTTCTT GACTACGCCT
70801 ATATTAGCAA ATTTTATATT CTTGTATTTT GAATGAAATC GTATTTTGTA
70851 TTTTGAAATA GTATTCTTGT ATTTTGAATG AAATATAAGA ATATAAAAAT
70901 TTGAATTTTT GAACGAAATC AGCATAGTCT TCCCTACTGT TTCCAATGTG
70951 TCCAAAGAGA ATACTCTATT CCTTTTCTAA GTTTCCTGAA GACTTTTAAT
71001 AGTTTCATTA TTAACATTCA AACTATTTCA AAATTGTAAA ACCTATGAAG
71051 CAAAGTGAAA TACTGCCAAG TGTATAAAAT AAAAACTCAT ACTTTCCTGG
71101 ATTGCAAAGG ACTGTAAGTG GGAGTAAATG TATAAAACAC TATTCTGTTG
71151 CAAGGTAATT AAGATAATTT GATATAGTAG AGAAAACACT CGATTAGAAG
71201 CCAATAATCC ATCATATTAA CCTGAATCTA CCTCTATATT CTGCCACCAA
71251 CCTTAAACAA GTTACTTATC TGTGCCTCAG TTTCCTGAAT TATAAACTGA
71301 AGATCTAATA AAGACCTTTC TTGCTTCCTT CACAGAATAT GAGAGCATTT
71351 TTTAAGAAAT GCAGAGTAGT ATACAGATTT AAGACATTAA TTCAGTATCA
71401 CAACAGACTG AAAGCTCATA TAAACATCTT TTTTATAACA GTTTCTACAT
71451 TCTACCTTAT GAGCAAGAGA AATGTGAAAA ATAATTAGAT AGGACAAATT
71501 TATGCAAAGT AGCAAATTCC ATGCTACATC AAAGGATCAG TATCCAAACA
71551 GTTGCCTCTG CCTTTTATAT TTACTATAGT GCTTGGTTAT CAATGATTTA
71601 TAATGAATCT GGTATCTTTC AAGATCCTAC TTGGCTTCTG AATCACTGAA
71651 GACTGATAAA ATTATACTTT CTGTAATTGT GCTTTTAAGC TTGTTTTATT
71701 ATATTCTAAT TCTTTAGATA TCCATATATA GTGCTTTCTG TTAACGTTCG
71751 GCTGTCTGGA ACATTTGATT AAGATTTCAC TTCTAGACAT AGGATTTTTC
71801 TGTAACACAT TTCATTCCTA TATGGAACCA CTTCAATTCT TAGAACTGAA
71851 TTCTCCTATT TGTTTGTTAG AATACAGACA TGTCTATCTT ACTTCTTCTT
71901 GTCATTATAT ATCACTTCAA ATGTAGAACT GGTAAATACA AAATCAAGTA
71951 AGTCTTCATG ACATTGAAGA AACTTTTCAC TATGTTAAAT ACTTTTTGGT
72001 TCTCTAAACC TGTTGTGGTA ATTGTAGATC AAGGTCTTTG GCTACTAATT
72051 TTTGCTTATA TAATTTTGTC TTCTCAGAAA TAAAGTGAGG AATCAAAATA
72101 TTACAGTAGT ATTGTTCATC ATAATGCTGA AATAACCATA CTAGTTAACA
72151 TAGTTGTTTT TAAATTTTGC AATATCATTG CATGGCTTCA TCTTTTAAAT
72201 TTCTGCAAGG TTTCAATATA TCTATTTCTT CTTTTTTTGA TAGGCAAATG
72251 AATAATTCTG GAAGGGTAAA ACATGAGTCT ACTAAATACA TAAATGAATA
72301 CAATGTATAC TTTAGGAAAG TAGATTTTTA AACAAGGACA TATTTTTAAA
72351 TTTCTGCTTA TGTTTAGGTC TATTACAATG GCTACCATGG AGACACCTCT
72401 GAAACATTTT TGGTGGGCAA TGTGGACGAA TGTGGTAAAA AGTTAGTGGA
72451 GGTTGCCAGG AGGTGTAGAG ATGAAGCAAT TGCAGCTTGC AGAGCAGGGG
72501 CTCCCTTCTC TGTAATTGGA AACACAATCA GGTAAGCCTT ACATTGACAA
72551 GTAAAGGGAG GGTTGGCAAA TGGTACAAAG GTTATTGGTG GCTTGGTATA
72601 AAGTTGATGA CATGTTTTAT GATTCAGAAC CATCATTTCA GTCTGATATC
72651 AGTATGTGAA CTGCCAGGCT GCAATATTGT TCCCTGAGTT GAAAAAAAAA
72701 AAAGATTTTA TAAAAATGAA TTATACCAGG GTCAGCAAAG AAACTTATAG
72751 AAGGAGCAAG CAATATTTAC ATGGCTGCTT TTGTTTTAGC TTGACATACT
72801 GGTCTATAGT TTCCCTTTAT TCAAAATCAC ACCAAATATG GAAGGGAGTA

FIG.3-31

```
72851 CCTAAGAAGG GGATGAGCAT CTCAACCCTG GGGTTTTTAA TAAGACAGGA
72901 GAAAAACTAA ATTTTATAAA GGAATGAAGT GAAATGTATT TCTGTGATAT
72951 GAAGATAATA AAGTGTTAGT TCAAGCAAGC CTTACCTTTC AAATTGGTAG
73001 ATTAACAAAT AGCCTGAAAC GGTGATCTTC TGTTCTTTTT TTGTCTGGTT
73051 CATTTTTCCT GTAAACCGTT GTTTATTTTT CACAGAGTAT TCTATCCTTA
73101 CTTTTTGAAT GTATGTGTAT GTGTGTTTTC TGAATTTAAG ACTTTTCTTT
73151 ATAATCTGTT ACCTACTTTT AGGTCTTTTT TCCCCCATAA CTGTTTTGAA
73201 GTAGACATGC CGAATATATG TTTTCATTTT AAAGTAATGC ATTCTGTTAA
73251 AGATGATCAC ATCAGTGCCC TTTAAAGTAC TGTTCTCATT AATATGAACC
73301 ATTGAATACT TCCCATTTGT CTAAAGGATG GAAGGCTTAG TCACCTTGAA
73351 AAGATGCTGC CTTTTTTTCT TCGTAAGCCT TCAAATACTT TAAGAAAAAA
73401 GCCAGTAAAA TATCAGTTAA ATGTATTTAT GGCTTTAAAA ATATTGTAAC
73451 AGTGTCTGAA TCAAACTTTA GTAAAATCTC TTTGGGTTAT ATCTGAGAAG
73501 CTTTTATTGA AGACTTTGAA CAAAATTGTG TTTTTGACAG TTTTAAATTA
73551 TAGGCTAACT AGCCTGGGAA AAAAGGATAG TGTCTCTCTG TTCTTTCATA
73601 GGAAATGTTG AATCAGACCC CTACTGGGAA AAGAAATTTA ATGCATATCT
73651 CACTATCTTA CTGTCCATGA ATATAATAGA AATGAATTCA AAATGCAGTT
73701 TTATTTTTGC AAATGGGATG AGTCGATAGA TGCACCTCAT ATTTTTGAAC
73751 ACCTAGGGTT CAACAAATTT ACTGGTGGTG CTCTTGCATT TTAACAAAAT
73801 TTATTCTTCA GTAGAAGGGG GCAGAGAACA CTAGATTCTT ATTCAAGCAT
73851 TCTATCGAGC TCTGCATTCA TGGCTGTGTC TAAAGGGCAT GTCAGCCTTT
73901 GATTCTCTCT GAGAGGTAAT TATCCTTTTC CTGTCACGGA ACAACAAATG
73951 ATAGCTAACT ACAGAGGCAC ATTTGCAGTA GTCACATTCA TCAACTGCAG
74001 AAAAAAAAAT TCAATTTAAT TGTGCAACAC AGCTGCACAT GGGCTTTTGA
74051 GCATTTCTGT TGTTCTCCCT GTCTCGCTAT TCCTCCCTCC AGATCTATTT
74101 TTTAAACTTT TTTTCTGGTT ATTTTTTCCC CTTTTTGTCT CTTCTTCCAT
74151 TTTTACTCTC TGTACTTTCT TGTTAAAGTA ATTTTCCTTT GTGGCTCTCA
74201 TTCTTTTTCC CCCATTGAAG GCTATGAATG TAGAAAATTA TCACAATTAC
74251 TCATATAATT GAGCCTCTTT GTAGCAAGTG CAACTCCAGT AGCCTTTCTC
74301 CATCAGAAAA GGTTTCATTA TAGGGTTTTT CATATTCTCT GACACCATCT
74351 ACACAGAGGA ACAGGCGTGC AGATGAGATG TGCTAGGAAC AGGCTAGATC
74401 AGTAAGGTCA CAGTAGGAAT AATTAGCTCT GCTATGGAAA GAGCATCTAG
74451 GCCTTTTACT GCTACATAAA TGTACTGTCC ATGGCTTTTA GTCACAAAAA
74501 AAACTTACTA ACAAATGGAG CTCCCGCCTA CTACTTTGAA AAAAAGATTT
74551 GTATCAACAC TACAATTTTC CATCATTAAG ACTAATAACA CAGAGCCTAG
74601 TATACATCAA GGGGAATAAA AAGAAAAATC TCACATTCAA GTGGCGGCTG
74651 GGTGCTGACC TTTGTTCCCT TTTTTTGTGT ACGACTTAAC TCTTTACAAA
74701 AAAGAGCCAC ACGCCACACC AACATGCAGG TGAACTCCAG CTAGTACTAG
74751 CAAAGCATAG CATTCAGTTG GAAAATTTGA TAAATCTCCA TGCAGGATAA
74801 TGCATTTCAT TACATATTCA CTACATTAAT TCTAGCTACA TTAAAAAAAA
74851 AAGAAGAAGA AGAAGAAGAG TAGAATTGAA AGTGACATTG GATTTTAGCT
74901 ATCTGGATAC AAAGGTCAGT TTTCACAGAG TATGAATTTG CATGTACAAG
74951 CTTTTTTGAA AACCAGATCA GTCAGTCCCA ACAACTGCAC TTAAAAAAAC
75001 TATGTGGAAA ATAACAGACA ATGAACTTTT TACTTGTACC CTAATACATT
75051 TCATTATTTA GATGGTTTAT GTCTGCCGCT AGAAAGGAAA CTGGCCCCGA
75101 TTCTAACAAA TATTTGTTCT GATGTGTTAA AGCAGTGTTT CTGGACACCT
75151 ATTATCTTGC CTTTTCTTAT TCTGGCAAAA TCTTAGGGGA ATAAGTAAAC
```

FIG.3-32

75201 AAACCATATT TACCTTTAAG CCAAAAGTAC TTGAAATCAT TACAGACCAA
75251 AGGTTTACAA ACATCTTTCA ACTCGGTCTT GTTTATTTTA AGATATTCAC
75301 CATCTTTTGC GTAGCCTCTC TCTACTGATA CACTAGGAAA AGAACAAGCA
75351 ACTTGTATTA GTATCATGTT ATCAAAAACC TTGAGATCTC TACAGGAAAT
75401 TTTGGAATTC TCCTCTGAAA CCTAAAGAAG ATAATGTCTT TGAGGAAGTA
75451 TCAGCTAAAA TGTTTTAATG GAAAGAGTTC TCTCTGGGCC CTTTTGCTTT
75501 TGTGAGGAAT GTCTAGTAAT CTTTAGGTCA TAGTGTTACT AGACTCACTG
75551 TATCTCCATT TGCTTTAAAA TATTTCTAAA TCTGTATTTT TATAATTATC
75601 TCTAGATTAT ACAATCTGTA CATATGAGTA TATTGTGAAT GTGTAGATTC
75651 ATGCATCATG AATATGTGAC AGTTCAATCA AAAATAATTT AAACTTGTAA
75701 ATGTCATGAT GAAAGTATCA ATAAATGGTT TTTAATGTTT AATTCATAAC
75751 TATATGTTTT GATATTAATT TGGAACAATA TAAAGCAGAT TTTTAAAAAA
75801 TAATCTCTTT CTATTAGATT ACGCACATTT AAACAATAAG TGGCTCAGGC
75851 AAAATAAGTC ATTTTAATGT CATCTGTGAT GGATTTTTCT TGACAGCTAC
75901 TGTAAATTAC AATTATACTG CTTCTCTCTG CACATGAAAG TAAGCATTGC
75951 AATAAATTAT CTTTTATTTC AATCCATCAT GTCTGCTTTT CAGAAACAGA
76001 AAACCTCAAA TAAAAGTTCA GCACTATTGT AAGAAAAATA CAGTAATTTG
76051 TGATCTGGTT TGAAACAAAA AAAATCTACT ACTTTTTTGG AAAACAGTTG
76101 TTGGCTTTCA AAAATATTAC TAATTGTACT TAAACATTCC TTTTCATTAG
76151 AAGGAATCCC TGGATTTGTG CATTTCTTCA TTCATAACTA CTGCCTAAAA
76201 TAAATATCTA GAAAGAGTAA AGAAAAATTT CATAACTTAT GAAATAACAT
76251 GCCATTTGAG ATCATTTATT AGAGATGTGA CTATTTGGAG ATTAGTGCTG
76301 TTTATAGGAT TAATGTAAAA TTGGCAATAA ATCTATTTTC ATGTGCATTT
76351 TTATTTCTTT ATAACAGCAT GTACGTAAAC ATAGTACTCC TCTGCCCTCT
76401 TGGGGAATGT ATTTTTAGTC AAAAAACTAG TTGAAAAGTA TTAAGAAATT
76451 TAATTTACCT AGGTGACATT TAAATTGAGT ATAACTGCCT CATGAAAAGG
76501 AATTAAACTG AAGAAAATGG TCACAAGATG AAATTCCTTA AAAGAGGTAT
76551 CTTTTTCATG TATAAACTGT AACTACAACA TGAATTGTAA TCAGACAGTA
76601 TAATAGGAAA GTAAGTTCAT AAACAACCTT TATGTATCCT CCTCTCCCTC
76651 TCCAAATATT CCATATAAAA GGCCTCAAAT CACAAGTGTG CTTGGGTTCA
76701 TGGGCAGATG TCACACTGTC TTAAAGGATT TTTAGTTAGA GAAAATCAGA
76751 AGATCTACTA CCAGGAGAAT TCTTTTCAGT AGGTTTCAGC AGAGCGAAGA
76801 CAGATTTTAT CCGTGAAATG TCCAGGGCAA GAAAACTCTT GTGCACAGCA
76851 AAAGGGTTAT GGCCTGTGGT GACTGGTGTT TGGGAGCACT TCGGTGCTTC
76901 TGCCTGCCCT GCTGTTTCCA TTTTCCCCAG CATGCCAGTC AAGAGCTGCA
76951 GACATACTCC AACTCCCCAT GCCACAGTTA GGGTTACCAG TACTTTCTTT
77001 CAAATTAGAG GAGTGAAATT TGCTACTACT GGTCACTTGG ATTGTCTCTG
77051 TGAATTTGGA CTTAAACCCT ACAATCAGGT AAATAATCTT GTGCTCCCCA
77101 TTTATTCCAA AATAATAGAA AGGGAATGCT TTTAAACAGT AATTAGGAAT
77151 ATTAATGAGA TCCTATCTGA CTTAGTTCCA GTAAGTGCTA AAAACCACCT
77201 ACCAATCCAG AAGGAAAATA CTCTGCAAAG CAAACAGGAG TGTATACTCA
77251 GCTCCTGAGA GTCAGGCATT AAGATGTGCT CAAGCAGGGA ACTGGGGGAA
77301 ATTTGGCCTG TTCTTTTCCT CTTTCCACCT GGCTGTGAAA TCCTCTAACC
77351 TTTGCATCCA TGACACACAG ATTCTATGAT ACTCCTGGAG CCAGAAGTTC
77401 CAGCAGGACC CACGGAGTAA ATTGTTGTAG GAGAATGCTC TTAGATATCT
77451 TTAGCCACCT AGTAATTGCA CAGCTTCTTT TATGCAGAGG AACGAGAGGT
77501 ATGATGGGGG GAGGGACCCT AAGTGTTTTT TCAGAGTGGG CTTTCTTCCT

FIG.3-33

```
77551 CTCCTCTCAT CGGAAATTAA AATGAAGATT GCCATTGTAA CACACATTTA
77601 AGATGTAGCC GTGATGCCTG CCAATCAGCC GGATCCTCTA AAAACAAAAA
77651 AAAAAGAACC TAGATTTTTT TTTTTAGAAG AGAAAATAGA ATAGTTTATA
77701 TTGAGTGTTC TTAGAATCAT TGAGGTTTGT TGGGATTGAA CTAACATAAT
77751 TTATAGGTTT AGGGAGAAAC TGTTCCTGTA AAAAAAAAAA AATCTAGATT
77801 ATTATGTCCT ATTTAATTAT CTTTCTTCCA CCCTGTATTC ACTCTTCATC
77851 CTCAGTGTTT ATTCAGAAAC TGTGTGGCAC AAATAAAAAC ACCTTGGGAA
77901 ACACCAAATA GAAATACTTG CCCACCAAAG ATCCACAGAA ATAACCATAA
77951 AGTACAACGT AAGAGATAAA AACCTTGACT TACCGTTCCT GTCCTCAACA
78001 TATGTATAGC TTACCTATTT CTGCACTAAC AGTTACATCA AAATTAAATC
78051 TGAATAAGAG GCTGCCCATC TGCTGGTTAT AGTGACATCC AGGTCTAAGT
78101 GAAGCTGTCT TACAAGTCTG GGGATGGTTA AAATTATTTA GAAAAATGTA
78151 TAAACATGAA TGGCCATAAA GATGCTGGCT GAAAGCCTGT GGGTTCATGT
78201 TAAACTAAAC TTAGAGTCTG TTAGAGACTC TAGTTTGAGA TCTAGAAACT
78251 TAGTTCTGTT AATAATTGAA ATAGTAGTCC TGTAAATCCC AATCTAGTGT
78301 TAGGGTTAGG GGCATTTTGC CCTTTGTCCA CATGAAAATA TAAATTCTTA
78351 ATAGTATATA TGTTCTTGTT TGTCTGATGC TCCCCAAAAT AAACATGTTA
78401 GCTGATTTCA AGGACTACTT TTCAATCTTG TAGATGAAGA TTTTAGAATT
78451 GGAGTCTGTG TGCTTGGTTT CAGATGGAAT GTAAAACATT TGCATGTAAC
78501 TAATGTAGTG CATGCAATGT ACTTCTCCAC ATACATGTAA TGAAGTAACT
78551 AATGAAGCAC TAAGAATTGG GAATCACAAT ACTAGCTTAT CTTAAGCATC
78601 CTAGTGATTA AAAAGCATTC TTTATGAATT TTGTTAATGG TGCAGGTCTT
78651 GAATGGAACT CTCAAATGAT CTCACGGTTT TGGAGTATTT CAAGAATATT
78701 GACAAAGTAG ATTGAGCTTT TCGTGTGAGT GTGCCTGTTG GTAAAATGTG
78751 TAACACTTTG AAATAGAGCA GAAAAAGGGA ACCATAGAAG TAGAAAGTCA
78801 TATTTCTATA TTGTAATTTG TTTTATATTT GGTTCCCCAA TCAGGAGTAA
78851 TTTATAGTCT TTTTGTGAAA CCTCAAAAAA GCCAGGCAGG TTTTTATGAC
78901 CTGCATTATA TGCACATATA TCCCGGTTAT GTATGGCAAT CACTATGTGT
78951 GTATACACAC TCACTTGTTG TCTAAAAGTG GCTTTGTTTG AATGCTGTAC
79001 AAAGGTAAAT GACTCAAACG ACTGTGTTGG ATAGATATGT ACCTTCTCTC
79051 TTCATATATC CAAAGACAGT GGTTGCAGGC AACAGCAAAA ATTAAAATTA
79101 TTACAGCATA ATGAAAACAC ATGAATGTTA TTATCTGACT CTAAATATTA
79151 CTGACTTTTT CTTTTTCAGA GAATATTTTA AAGTGACTTT GTTTTATCTT
79201 AGTATGCCTG AAAAACTTAT CTAATTTAAT TAAATATTTT TTGGTCACTT
79251 TTAAAGCCAC ATAACTCATC AGAATGGTTT TCAAGTCTGT CCACATTTTG
79301 TGGGACATGG AATAGGATCT TACTTTCATG GACATCCAGA AATTTGGCAT
79351 CATGGTAAGA AAGTTCATTT GGAGGCTGTT TCTTGATCAG AGATCAAGAT
79401 GTGGCAGCTT TGACCCTGAA GCTCTTCCTC TGACTTTGAA TCTGCATTAT
79451 CAACCTTGTG TTTGTGTGTG TGTTTATGTG CAGGGGGCAG GGGAGGGGGG
79501 TCTGCTTAAT TTTAACCGGG ACATTACTGT GTTACTGGAT TAGAGCCCAG
79551 CTGTTTCAAT CCCAAAATAA GGTTTATTTT GCTCTCTGTC TTCTCCTGAA
79601 GGGTGCATGG CTGGAAGGCA CAAGGGATAT TTGTGTAGAA AAAGTTACTG
79651 AAAACAAAAC GCCACTGCAT CAGTGTCCCA GCAGCATGCA CATATGACTG
79701 TTTCTGTTTT TCTTTTTCTA CCCCCTTTTC TAGCTGCTGA CTGTTGTGGT
79751 TAAACTTCAT TACATCCTAC ACAGCGTTGA CAGCTGATGT ATTTAGCAGC
79801 ATGTACTCCT TCGTGATTTC TAGATTATGC CCACCCTTGT CTTCCTTCCC
79851 CAGAATCTCT TGTTTTTCAC TGCCTGGGTG TGCACCCTAT AGTGAGAAGA
```

FIG.3-34

```
79901 CAGGGGTGGG CCCAGAGGGG TGGGAGGATT TGGATTGAGG TAGGAGGCAG
79951 CTCAGTGGAG CACCCTCAAG GCAGGTCCAC ACCTGGACGG GGATCAAAGG
80001 AAAGTTGGTC CTGGGGCCTT GACCTGTGCC CCTATGGACT TGATTGGTCC
80051 ATAGAAGGAC TACTCTTTCG GACCCATGCC CTCGAGGATC GCTGGACACC
80101 CAGCAGGTCC AAACCCTCTT TGGACCAAAG AGCCCCCACC TAGGCAGCTC
80151 AAGAGGTTCA GGTGAGAGTG CAGAAACGGC TTGTCAGCCT TGTGCCCTAC
80201 CTGGTGCCAA TGTCTGGAGT GAAGCTATTT GAAGTCAGGC CCCTGCTCCC
80251 CACAACCTGC ACCAAAGGAG GCTTCCCTCC TTTGCATCCT TCCCCAGGAC
80301 TTCTTTGAGT GAGGGGTGTG GGCAAGGCCC AGGACCCAGT AGTAGGCTGG
80351 GAGACCTAGT AGCCTGGGGG ACAGGGAGAG GGGGCGAGGA AGCCTGACGT
80401 GTCTGAAACA ACCAGGCTGC CCCTGCCAGG CCTTGGAAAA CTCTTCTGGG
80451 GGAGTCTTGA CCCAGAGCAC AGATAATGCA AAGACTCAGG CCCAGTAGCC
80501 CCGTGTTTAA CTCCTGGTCA CTATCCAGGA CTCCAGAAAT CTCCACCCTT
80551 CCTTCTCTAA AAGAAGAGAA ATAAAACGAC CAAGTTTTTT AAAGGGGCCT
80601 GACCCCTGTA ATCTGTTTTT TTTTTCTGTC CTCCCCATTT CCTATTCTCA
80651 CCCCCCATGT TTTTTGTTTT GCAGCAAACG ACAGTGATCT ACCCATGGAG
80701 GAGGGCATGG CATTCACTAT AGGTAAATTG AGCTCCTCTT CCGAGTGAGT
80751 GCGTAGCTCC TGGTGGAAGC TTTTGCCACT GGCCTAGGCC CGGCAGTCCG
80801 GTGAAGGACC AATAAAGCCA ATCAGTGTAA TGAAATAATT CGGATGCACT
80851 GGAAATCTGA TTAAATAATA TCCTCAAGCC CCATCTTCCT AAATCAGATA
80901 CTTACCGACA CATTTAGGAG AAGGCAGCCA TCCAACCTCT AATTCTGTTA
80951 CCAGCATAAT GTGGTGTTGG GTTTTTTGTT TTGTTTTGTT TTTTCATTAA
81001 CACCCAGTAA CTAGACACGA TTATGTCCCT TGCTCCCTGT CAGCAAGTGG
81051 CATGTGCTCT CTGGTGGCCC GTTCCTGGCT GATCCTGTGA TTGGTATCAC
81101 CACCAAATTC CAGTCACCTA GGGCCGTAAA GACATCCTGT TTCTGACTGT
81151 GGGACTTAAT GGAGAAGCAA TTAGAGTGAA ATAAGAAAAT TGTTATTTGC
81201 TGATGAATGA ACATCTCGAG CATGTTTTTA AAATTTAAAT ATTTTTTTAA
81251 AAATTGGTAT TTATAAGAGG GACTGGTGTT TGGGTGGTTA TTATCCACGG
81301 GGTCCTAATT AAAGCTTGAT TAAAATGCCC TTCTTTCTCT AAAAAATTAC
81351 GAACTAGGCA ACTTCATACA TTTTGAATGG CGCAGTGTTT CCTCTTCCAA
81401 CTGTTTAGTT TGTAGTATAC TATGTAAGCA ACATCAATTA TCAACCCTTG
81451 CAAGATGACA ACATGAGCCT GTGGGGGAAG CACTTGAGGG GAGGGAGGAG
81501 AAACTTCTCT TTTTTAATAA TCAGCCGGAA ACAATGTTTA ACAAGAATCT
81551 GATGAGGTCA CTGCAGTAAA TATTTTTCCT CTTACAGAGC CAATCATCAC
81601 GGAGGGATCC CCTGAATTTA AAGTCCTGGA GGATGCATGG ACTGTGGTCT
81651 CCCTAGACAA TCAAAGGTGT TTGCTTTCTG CTCTGTTGCT TTTAAATTGT
81701 ATGGGAAAGG AAGATTGGTC CGACGGCGCG CTTGTGGCCC GGCCGGAGCT
81751 TGCGTGCGCG TTCTGACGGC TGGGTGCTGT GTTACAGGTC GGCGCAGTTC
81801 GAGCACACGG TTCTGATCAC GTCGAGGGGC GCGCAGATCC TGACCAAACT
81851 ACCCCATGAG GCCTGAGGAG CCGCCCGAAG GTCGCGGTGA CCTGGTGCCT
81901 TTTTAAATAA ATTGCTGAAA TTTGGCTGGA GAACTTTTAG AAGAAACAGG
81951 GAAATGACCG GTGGTGCGGT AACCTGCGTG GCTCCTGATA GCGTTTGGAA
82001 GAACGCGGGG GAGACTGAAG AGCAACTGGG AACTCGGATC TGAAGCCCTG
82051 CTGGGGTCGC GCGGCTTTGG AAAAACAAAT CCTGGCCCTG GACTCGGTTT
82101 CCCAGCGCGG TCAACGCATC TGGAGGGGAC TGGAGGAAAC CCCCTTGTTG
82151 GAAGAGATTC CAAGAGAAGC ACGGTTTTCT CTTTCCCTTG CCCTGACTGT
82201 TGGAGTAAAA AACCTCTTAA ATCCATTGTA TCAGAGGTCC TTACCTCTCT
```

FIG.3-35

82251 GACAGTTACA ATGATCTTTG TATCTGAACT TTGCACGTCT GCCGAAAAAT
82301 CCGAACCTGT TGACTGGGAT TTTTAAGAAT CCGTTTCTCC CTTTTGTGTA
82351 TTCCATATTG GCCGGCCCCA AGGATGCTCG CAGAAGCCAG CCCCCAACCC
82401 CAGCCCTTCC GTATCTTTCC CCTCCATCGC GGCTTTGCGA TGAAAGATTA
82451 GCCCGCGAAC AGAGGCATTG ATTACAAACA TGTCCTTGGC AGTGGACTCT
82501 GGGCCTGGCC ATTCTTCAGG TTTCTGTCAA TCCAGAAACG CGACTTTCCT
82551 GGACCCCTGC GGCTCTTCCT CCCCCGCCCA CATCCAGCCC TCCAAGGCCA
82601 GTCCAGAGGT GAAGTTTGAG GCCCTCCCCC CACCCACCCC ACACGCACGC
82651 ACGCACGCTA GAGCGTTTGC TGCACTAGGA ATTCGAGCTT GGGCCCCACT
82701 CGCCCAGGTG TGAACAGTGG CTGATTAGTG GGCGGTCTAG TCTCTAAAAT
82751 GACCCCTCCC CAGACTGGCC CTTCTCGCAT CGGGACCCGC GCTTGCACGC
82801 TGCAGGAGCC GCAAACGTCA GCTGTTCTGG AAACCGAGAG GGTCCCAGAG
82851 AGAGGAGATA CGGGCGCATT TGAGAGCAAG GGCCTACTTG GCCGGGACTG
82901 AAGCTTGCGA GTTGAGCTCC AGTTCGGCCG GCAGTTCCAT CCCGCTTCAG
82951 GAACAGGAAT CCAAGGGCCC ACGCTCTGTC TGCCAAGGGC CATTCCTGCC
83001 CGGAGCACCC TCCTTTCCCT TGCGCTTGCT CTCCGGTACC TGTTCCGCAC
83051 CTGAGCTCAA GGGCAGGGAG AGGCCGGGCC TCTGGCAGTC CACGAAGGAA
83101 GCCGTCTGCC TTCGGTTATG ATTTTAGGAA CAAGTCCAAC GAGGGTGTTC
83151 AAGCAGTTAA TGGTTGTGCT AACTCTTGTT TCTACTGAAG CGGGTTTTGC
83201 AAAGCTGACA TCCCTTAAAG ATAACTTGGG CTTTCGGAAG CGGCAAGGAA
83251 ATGGCACCTG TAGTTGCCAG GACAGGTGGT GTCCTCGGCC AGGACTAAGA
83301 GCCAGCTCAT CTTTGTAACA TTCATAATAC GGGAAACTGA GGACCAGGTG
83351 GCTCGGAAAA GAGATGAGTT CCAGCTTTTA CCTAACACAG GGTTCTCTCG
83401 TCGTCCCCCA ACCCCTCCAG CTCGGCTTCT TTGTGTCCAG GGTTGTAGAT
83451 TTTTGGATAG AGGTGTTTCT GATTCTAGTG AGTCTGAGAA CTGGAAAAGA
83501 CCAAGGAGGG GTTGATGATT TACAAGGTCC ATAGAAAAAC TTTTTGTGTG
83551 GTCGGAAGTT GGCCAAGCAG AGGCCCACAG CCTGATGCTA CTGCCCCCCA
83601 CCCCCCCAAA GATCTGAATT CCCTAAAGAT CAAGAGGGTT CAGCTGGCCT
83651 TGGGAGATGT TTGCTGGAGA ATGACTTCAG TTTTCTCCTA AGGCAATCAG
83701 ATTGCAACCA TTAGCATTGT ATCTTATCTG CAAATCAGTT TACTCCGAGG
83751 TTCCCCAAGG ATAGTTTTAT TAGGACCACA GGACTTTACT AACCACTGAG
83801 GTAACACGCT GCTTGTGCAG CAATTATTTT GAGGTGGAGG TATTTATGGG
83851 ACAAGTTTAT AATTCCATTT ATTAAAGGGA CTAACCTAAA GTGTGTGGGT
83901 GTATATATAT ATGTGTGTAT GTGTGTACCA ACACTCAGCA GCTCCCTAAA
83951 GAACTCCCTT TAACATGCTT TGAAGTTGAG ATTAGGAAGT AGATTTAAAA
84001 ATACCTCGTC CACGCCTTCC TGTCCCTCTT CCAGCTGAAC TGGCCGAAAA
84051 CCTCACCCAG AGCCACTGGG ATTCCAGCCA AGAGTGGCTG CGGCTAACAC
84101 CACCAGGACC TCCTGGTCCT GAGGTGACTC CAGTAGGCTC CATGAGGAAT
84151 CCCGGACCCT CAGGACAAAT GGGAGAGTTT TGTTTTCTCT CAGAGTGAGG
84201 GCAGGCAACA ATTTAAGCAA ACCGGCATTC AGAACAGGTG TCACCTTAGC
84251 AGTAGGGGGT GGGAGGGATC CACTCCAAGT TCACTGAGTG CAGCTAAGAT
84301 CCCACATTGA GAAACCAGCT ACCGCCAGCG GCTCGGCATC AGAGGGCCCG
84351 CGCTCAGTGC TCCTCCCTAG ACCTTTCTGA GCTAAGAAAT AATTCCCGGA
84401 GTGTAGCCAT CTCTTGCTCA CACACAACCC GCTTCTAAAT TAAGCAAGGC
84451 TCTGAAACAG TATCCCGAGG GGCTCATGCC GGACTTTTGT TCCAA
(SEQ ID NO:3)

FIG.3-36

FEATURES:

| | |
|---|---|
| Start: | 2008 |
| Exon: | 2008-2047 |
| Intron: | 2048-62959 |
| Exon: | 62960-63117 |
| Intron: | 63118-65171 |
| Exon: | 65172-65321 |
| Intron: | 65322-67064 |
| Exon: | 67065-67213 |
| Intron: | 67214-67724 |
| Exon: | 67725-67767 |
| Intron: | 67768-72367 |
| Exon: | 72368-72531 |
| Intron: | 72532-79256 |
| Exon: | 79257-79354 |
| Intron: | 79355-80674 |
| Exon: | 80675-80722 |
| Intron: | 80723-81587 |
| Exon: | 81588-81666 |
| Intron: | 81667-81787 |
| Exon: | 81788-81863 |
| Stop: | 81864 |

SNPs:

| DNA Position | Major | Minor | Domain | Protein Position | Major | Minor |
|---|---|---|---|---|---|---|
| 48815 | G | A | Intron | | | |
| 48823 | G | A | Intron | | | |
| 50709 | C | T | Intron | | | |
| 52214 | G | C | Intron | | | |
| 52944 | C | A | Intron | | | |
| 56446 | G | A | Intron | | | |
| 56691 | T | C | Intron | | | |
| 56692 | A | G | Intron | | | |
| 56739 | - | T | Intron | | | |
| 56740 | - | T | Intron | | | |
| 57478 | C | T | Intron | | | |
| 59407 | T | - | Intron | | | |
| 64097 | - | A G | Intron | | | |
| 64098 | - | C A | Intron | | | |
| 65938 | A | G | Intron | | | |
| 66092 | A | - | Intron | | | |
| 69016 | C | T | Intron | | | |
| 69517 | T | G | Intron | | | |
| 80083 | C | T | Intron | | | |

FIG.3-37

| | | | | | | |
|---|---|---|---|---|---|---|
| 80750 | T | A | Intron | | | |
| 81839 | C | T | Exon | 327 | I | I |

Context:

DNA
Position

48815 AATTTAATACAGTTCACACGGCGTGCTTTGGTTTATGTATATTTTAGTGTTTGTGATTGA
CAGTGATTGAGCATTTCTTATGGAGTGCTTGCCTTTTTTGTCATAAGTGATGTATGTTGG
TAGTGCTTGAAATGTAAATAAGTTCTTCCTGTATCACTGTTTAATAAACAGGAATTTTTA
TGCAAAGAAGACTTCTTGATACATTTAAACAATAAGGTTTGTTGAGCTCTGAAATATTTC
TGCTAAACAGATTGTGCACCAAGACAAATAGGTTTAAATTCTTACAAACTGAGGTTACCA
[G,A]
GGGCAACGTTAAAGTTTATGGCTAAGCACAGCATTGACTGAATGGTATTTAGTAACAGAA
TAAAAAAGGCTGAATTCTTTTTTTTTTTTTGAGACAGGGTCTCACTTTGTTGCCCAGGCTG
GAATGCAGTGGTGCAATCTCCACTCACTACAGCCTCAGCCTCCTGGGCTCAAGTCATCCT
CCCACCTCAGTCTTCTGAGTAGCTGGGACTACAGGAGCATGCCACCACGCCTGGCTAATT
TTTGTATTTTTCATAGAGATGCGGTTTCACCATGTTGCCCCAGGCTGGCCTTGAACTCCT

48823 ACAGTTCACACGGCGTGCTTTGGTTTATGTATATTTTAGTGTTTGTGATTGACAGTGATT
GAGCATTTCTTATGGAGTGCTTGCCTTTTTTGTCATAAGTGATGTATGTTGGTAGTGCTT
GAAATGTAAATAAGTTCTTCCTGTATCACTGTTTAATAAACAGGAATTTTTATGCAAAGA
AGACTTCTTGATACATTTAAACAATAAGGTTTGTTGAGCTCTGAAATATTTCTGCTAAAC
AGATTGTGCACCAAGACAAATAGGTTTAAATTCTTACAAACTGAGGTTACCAAGGGCAAC
[G,A]
TTAAAGTTTATGGCTAAGCACAGCATTGACTGAATGGTATTTAGTAACAGAATAAAAAAG
GCTGAATTCTTTTTTTTTTTTTGAGACAGGGTCTCACTTTGTTGCCCAGGCTGGAATGCAG
TGGTGCAATCTCCACTCACTACAGCCTCAGCCTCCTGGGCTCAAGTCATCCTCCCACCTC
AGTCTTCTGAGTAGCTGGGACTACAGGAGCATGCCACCACGCCTGGCTAATTTTTGTATT
TTTCATAGAGATGCGGTTTCACCATGTTGCCCCAGGCTGGCCTTGAACTCCTGAGCTCAA

50709 TTTTAATTTTTAACGTTTTTAAATTTTTATTTTATTTTAACTTTTTTAAGGCAGGGTTTC
GCTCTGTTGCCTAGGCTGAAGTGCAGCAGCGCAATCTTGGCTCACTGCAACCTCTGCCTC
CTGGGCTCAAACGGTCTTCCCACCCCAACCTCCCAAGTAGCTGGGACTACAGTTGTGTGC
CACCATGCCTGGCTAATGTTTGTATTTTTTGTAGAAACAAGGTTTCACCATGTTTCCCAG
GCTGGTCTCAAATTCCTGGACTCAAGCGATTCACAGGCCTTAGTCTCCCAAAGTGCTGGG
[C,T]
TTATAGGCGTCAGCCTGGCTTAATTTTTAATCTTTAGTACAAAAAGTAACAGATAGTTGA
ACATTCATATCCTTAAATATATAAGTATATATATTTAAATAAATGTTTATTTATATTTAT
GTTTACTTATATACATATATTTACTTATATACATATTTATATTTATGTTTACTTATATAC
ATATACACACACATACACATATATATGGGCCAAATTGTAAGCAGGCATCTATGGAGCTCC
CCTTTTAAGCCTGTGCCATTTTAACACTTTGTACTTTTTGAATTAATACCAAAAACTGTC

52214 TTTATATAGACTTTCTCTAAAATTCAGTTCCATGTGTGATTCCTATGAAATTGCTCTTTC
TGGTTCTGATTTGTGTGCTTTAATATAAAATCATTCTATTTTCCTCTTCTTTAACCAAAG

FIG.3-38

TGTGTGAGGTAACAGGAATGTTTCTTTTGAGAGACTTTGGAAGGTTGAAATTTGCCAGAT
GTTCTGTGCTAACCTAGAAGTGTGCATTCCCTGGGTAGCAGGACTGTGTGAAATTCTTTC
CTATAACTTTGACAGAGCATTTGGTTTTGGTTCATTTTAGTGTTGTGCTTCTACTCTGAT
[G,C]
AGAGCTTGTCTTTTATTCTGTGTTTAAATGATATTAAGGCATCCAGAAAATCTGACAAAG
AAAATGATATTTTGATGACATTTTTCACAGGGCTCAACTAGAATGAATTATTACATTTTA
ACCACGGCCCTAATAAACAGCTTCTTTATTTCCTCTGTAAGGATACAATATTTCTTTGTC
CAAGAAGTTGCCTGAGTATATGTATTGTTGAAGTGCTAAAAAGCTGCTTTTCTCTAAACT
TTAGCTGAGAGACAATGGGATTTGCCAAGTATATACCATTTCATTGTGACTCAATACTTT

52944 CTTTTAGTTTTATACTTGAGTTCTGACTATAATCTTTGGCACCCTTCCCCCAGCTATAAT
TCGGCTAGCCTAAAGGAATTTTTTTTCCTAGACTCACAAGCAGGAGCCTATATTATTAAG
TAGGAATGTTTATAGATCTGTGTTTCTAGAGTAGGTTGAGGTGTTTTAGTTTCCCAAAAA
GAGGGGAATGCTTCTTGTTTTAAATACAGATGCCTGTGTGCTGGTGGTGTACATTAGTGA
ATAATCACATATTAACAGATTTAGCTTTTGTAAAGAAGCAAAATGAAGTGTTTTCGTAAA
[C,A]
CATTTCTGAACTTGTCATTGATGTTATACTCTATCAGTTGCTATTGATAATTTTATTTAA
AGGAGGAGGTATATAGTATAGCGCCAACTTCCTGATTAGGCCTTGGGGAAGGTCACGTTT
TGCAGTGACCTGGGCACCACTCTTAAATGTTGTTATTATTGGAAGAGGGTACCCTCAGGC
TGCTGCCCTTCCTCTCCCCAGAAGCGCTCTGTGACTGACTTTCCAGTTCATCTTTTCTAG
AACCAAGACTCCCAGGCTGTAGATGAATTCTGACATCTACAGACCAGTATCCATCTCAAC

56446 TACATTCCAAATACAAATTTTAAATATGAAAAAATGTGCTGCAGGATCCAGAGGACATAG
AGCAATTTCAAGAGATGTTCAGACTGCACAGTGTGCTCTTCCATGGAGTGCAGGAAGAAG
TTGCCTATAATTTTCAGCGTTCAACTCAGACTAGGTGCTGATAGAATTTTTGTAACACTA
AAAATAATTCTTATTATTACCTTTGATAACAGTAACTATTCTAGTATTCATAAAAAATAA
CATGTAGATTTACTCCCTAAGAAAACCCTATATAGAGTTGCTGTTAGGTCATCAACAGTA
[G,A]
CAATACTACGATCATCTCTTGCAAGATCAAATTAGTATAAAGCAACTCCTCACTGTTCTG
GGCTCTCCTACTCCCCTGAGGTTTCTGGTGATTTCCCACTGGTGTCTCTAAAAACATCAG
ATTAGTCCACTTGCCCCTTGTAGTAATTAGTACACACCTGAGTCTTGTTTCCCCAAATAG
CTTTACCAAAACACCGTGTGCAGTGAATCCTGAATGAATGATAGTGTGTGGGAGACGGAG
GGACTATTTCTGTCTCTGAAGATGGTCATCATGCATCAAATTTGTTGTAACATTGGTGGT

56691 AGATTTACTCCCTAAGAAAACCCTATATAGAGTTGCTGTTAGGTCATCAACAGTAGCAAT
ACTACGATCATCTCTTGCAAGATCAAATTAGTATAAAGCAACTCCTCACTGTTCTGGGCT
CTCCTACTCCCCTGAGGTTTCTGGTGATTTCCCACTGGTGTCTCTAAAAACATCAGATTA
GTCCACTTGCCCCTTGTAGTAATTAGTACACACCTGAGTCTTGTTTCCCCAAATAGCTTT
ACCAAAACACCGTGTGCAGTGAATCCTGAATGAATGATAGTGTGTGGGAGACGGAGGGAC
[T,C]
ATTTCTGTCTCTGAAGATGGTCATCATGCATCAAATTTGTTGTAACATTGGTGGTAGCAA
TTTGGAAATTAGATGTAGTTATAAGGTATCAGCAGTGCTTTTGTCAAGAAATGAATTATA
TAGGAAATTCAAGAGACCATTTCTACATTGATCTACATTAGTTACTGTAGTTCGGGTATC
CTTTCTGTGACCCTGAATATAATAGAGACTGGGGATTTTAATTTTGCTCACTCTGCATTT
AGAAAATTTACTACTTATTTGTATTGTGATAAACAAAGTTGAGGGCCCGCCCCTCTTTCT

56692 GATTTACTCCCTAAGAAAACCCTATATAGAGTTGCTGTTAGGTCATCAACAGTAGCAATA

FIG.3-39

CTACGATCATCTCTTGCAAGATCAAATTAGTATAAAGCAACTCCTCACTGTTCTGGGCTC
TCCTACTCCCCTGAGGTTTCTGGTGATTTCCCACTGGTGTCTCTAAAAACATCAGATTAG
TCCACTTGCCCCTTGTAGTAATTAGTACACACCTGAGTCTTGTTTCCCCAAATAGCTTTA
CCAAAACACCGTGTGCAGTGAATCCTGAATGAATGATAGTGTGTGGGAGACGGAGGGACT
[A,G]
TTTCTGTCTCTGAAGATGGTCATCATGCATCAAATTTGTTGTAACATTGGTGGTAGCAAT
TTGGAAATTAGATGTAGTTATAAGGTATCAGCAGTGCTTTTGTCAAGAAATGAATTATAT
AGGAAATTCAAGAGACCATTTCTACATTGATCTACATTAGTTACTGTAGTTCGGGTATCC
TTTCTGTGACCCTGAATATAATAGAGACTGGGGATTTTAATTTTGCTCACTCTGCATTTA
GAAAATTTACTACTTATTTGTATTGTGATAAACAAAGTTGAGGGCCCGCCCCTCTTTCTT

56739 AACAGTAGCAATACTACGATCATCTCTTGCAAGATCAAATTAGTATAAAGCAACTCCTCA
CTGTTCTGGGCTCTCCTACTCCCCTGAGGTTTCTGGTGATTTCCCACTGGTGTCTCTAAA
AACATCAGATTAGTCCACTTGCCCCTTGTAGTAATTAGTACACACCTGAGTCTTGTTTCC
CCAAATAGCTTTACCAAAACACCGTGTGCAGTGAATCCTGAATGAATGATAGTGTGTGGG
AGACGGAGGGACTATTTCTGTCTCTGAAGATGGTCATCATGCATCAAATTTGTTGTAACA
[-,T]
TGGTGGTAGCAATTTGGAAATTAGATGTAGTTATAAGGTATCAGCAGTGCTTTTGTCAAG
AAATGAATTATATAGGAAATTCAAGAGACCATTTCTACATTGATCTACATTAGTTACTGT
AGTTCGGGTATCCTTTCTGTGACCCTGAATATAATAGAGACTGGGGATTTTAATTTTGCT
CACTCTGCATTTAGAAAATTTACTACTTATTTGTATTGTGATAAACAAAGTTGAGGGCCC
GCCCCTCTTTCTTTGCCAGGCTAGTTGGAGGACCATTATCTTCTAAAGGTACCATGACTT

56740 ACAGTAGCAATACTACGATCATCTCTTGCAAGATCAAATTAGTATAAAGCAACTCCTCAC
TGTTCTGGGCTCTCCTACTCCCCTGAGGTTTCTGGTGATTTCCCACTGGTGTCTCTAAAA
ACATCAGATTAGTCCACTTGCCCCTTGTAGTAATTAGTACACACCTGAGTCTTGTTTCCC
CAAATAGCTTTACCAAAACACCGTGTGCAGTGAATCCTGAATGAATGATAGTGTGTGGGA
GACGGAGGGACTATTTCTGTCTCTGAAGATGGTCATCATGCATCAAATTTGTTGTAACAT
[-,T]
GGTGGTAGCAATTTGGAAATTAGATGTAGTTATAAGGTATCAGCAGTGCTTTTGTCAAGA
AATGAATTATATAGGAAATTCAAGAGACCATTTCTACATTGATCTACATTAGTTACTGTA
GTTCGGGTATCCTTTCTGTGACCCTGAATATAATAGAGACTGGGGATTTTAATTTTGCTC
ACTCTGCATTTAGAAAATTTACTACTTATTTGTATTGTGATAAACAAAGTTGAGGGCCCG
CCCCTCTTTCTTTGCCAGGCTAGTTGGAGGACCATTATCTTCTAAAGGTACCATGACTTA

57478 AAGGGTGTCTTTCATCAGATTGAAAGAAAAGAATTCGTTTCAAATACAAAAGTGTCTTAT
GAAAGTGAAATTGCTGAATACAGTGTAGAACCATAATTGTCAACAGATTGGATATGTTCA
GGCTGTGTTCCTGACGTTTCGAATTTTACCATCCAGTCATGTGTGGGTGTGTCTGCATCT
TTTCGGCAGTGAGGCTGTCATTTGGCAGGACAGGTACCTTGGCAACACTGTTCATCCTAA
AAGTGAATGTCTCAAAAGCCTCATCCAGATATCTAGTGGAGGCCTGATGACTTCATGCTT
[C,T]
AAGTTTAAGTACATAGAAAAGATTCCCCCTATAATGACTGTGTACTTGAACTTGATAACA
CTGATAAAGATGATCTTTTGTGTAATCAACCACATTGAAAAAAATCTTCATGAGTCCTAA
AATTGATCAGAGGCTACATCTTCCCATTTCCTGGGATGTAGCATGACAATCAGATGGTGC
TGAATGAAGGCACACATTTCAGAGCTGAAGGGACCTCAAAGATTGTGAAGCCCAACTCTC
ATTTTACTGAGCTTCTGCATCTCACAGGGTAATGTCTTTGAAGTACTCAGCACCGAGCTT

FIG.3-40

59407 TTAGCTCCTGTTTTTTCTCATGCCTGTGAGAGAAGTAATACATTTTGTAGAGGCAACTTA
GCCTGCTTTCCCTCTCAGCTTTGGCACTTACTGCATGTTCCTTTGTGTGCCTCAGTATCT
TCAACTGTGACATGGAGTAATAACAGTTCACAATTCATACAGTTTCTGTGAAGATTAATG
AGCTAACATATGTAAAGTGCCTAGTACAGTAATTGAGGCATAATAAGTGTTCAGTATTAG
AAGCTATACTGGAGGTCATGTTTTCTTTCCCATTTTATTTTTTGTGCAGACTTTTTTTTT
[T,-]
TTTTTGAGACAGGATCTTACTCTGTTGCCCAGGCTGGAGTGCAGTGGTGTGATCATAGCT
CAGTGCATAACTCAGTGATCATAGCTCCAGGGCTCAAGTGATTCTCCTGCCTCAGCCTCC
TGAGTAGCTGGACTCCTGAGTAGCTGGACTGACTCCTGAGTAGCTGAACTCCTGAGTAGC
TGGACTACAGTAGCTGATGGCCCAAGCCACCACATCTGGCTAATTCTTTTATTTTTTGTA
GAGATGGGATCTCACGATCCTCCCACCTCGACCTCCCAAAGCGCTGGGATTACAGGTTTT

64097 CTGAAGGTGAGTGGCCCACTTTTATGGCAAAGGCCAGTGACACAGAAGGGCCACCAGGAT
GTATCCCCTGGCCTGGCCATCACAGTGAGAGTGAGAATTTGGTATTAGTTACAAAACTGA
CACTTTTTTCCTTAGAAGAAAAGAAAAAGAAATCTCTGGTGAGGTGAATTGTATTGCTTT
AGCCATTTCAGTCAATTTCAGCATGACAGCCCAACAGCCCTTCTGCCTGCAAGTTATAAC
CTTGCCAGATCACAGAGCAGAGTGGAGACAAGAACACAGGCTCTTTGGGGGAGACCTGGT
[-,A,G]
AGCATTTGTGGGCATTTGTGGTGTAGCTGTGGGAGAGTAGATGTTCCTCTGGAGCTCAGC
TGTGGCAAACCAGGCAGTAGTGTTACCTGTATCAGAAAACCCATCTGAACAGGGGAGCAA
GTGAAGACCCGTAACTCCTGCAGGACAGGCTTCACAAAGAAGAGAGCCCTAACCTCAGCC
CTTCCAGAGCTGCTGCAATGTTTCAATTGAAGAGTGTTATCTCCCTCAGCTTCCTGTCCC
AAACTGCTGTGGAGCCTAACTGTGGACTGTCCAATAATGCTTATAGTTTGTAATGCATTA

64098 TGAAGGTGAGTGGCCCACTTTTATGGCAAAGGCCAGTGACACAGAAGGGCCACCAGGATG
TATCCCCTGGCCTGGCCATCACAGTGAGAGTGAGAATTTGGTATTAGTTACAAAACTGAC
ACTTTTTTCCTTAGAAGAAAAGAAAAAGAAATCTCTGGTGAGGTGAATTGTATTGCTTTA
GCCATTTCAGTCAATTTCAGCATGACAGCCCAACAGCCCTTCTGCCTGCAAGTTATAACC
TTGCCAGATCACAGAGCAGAGTGGAGACAAGAACACAGGCTCTTTGGGGGAGACCTGGTG
[-,C,A]
GCATTTGTGGGCATTTGTGGTGTAGCTGTGGGAGAGTAGATGTTCCTCTGGAGCTCAGCT
GTGGCAAACCAGGCAGTAGTGTTACCTGTATCAGAAAACCCATCTGAACAGGGGAGCAAG
TGAAGACCCGTAACTCCTGCAGGACAGGCTTCACAAAGAAGAGAGCCCTAACCTCAGCCC
TTCCAGAGCTGCTGCAATGTTTCAATTGAAGAGTGTTATCTCCCTCAGCTTCCTGTCCCA
AACTGCTGTGGAGCCTAACTGTGGACTGTCCAATAATGCTTATAGTTTGTAATGCATTAT

65938 CTCCTGCCTGTAGTTTCAGCTTTTACTCCCCACATTATTTCTGTGTGCTTGAAGATTTGC
TCTACCTTGTCCTTTGTCTCCTATTTTCTTGCATTTGCCCTGCAAAGAAAGATCAGATCA
CATACACAAAGCTGTAGGTAATATAGCAGTGTAATTACATACAACTTCCTACTACAAGAT
TTAGTTCTTTTAGGCCAGGCGCAGTGACTCATGGCTGTGGATCATTTGAGGTCAGGAGTT
CGAGACCAGCCTGGCCAACATGGTGAAACCCCACCTCTACTAAAAATATAAAAATTAGCC
[A,G]
GGCATGGTGGCGGGCACCTGTAGTCCCAGCTACTTGGGAGGCTGAGGCAGGAGAATCACT
TGAACCCAGGAGGTGGAGGTTGCAGTGAGCCAAGATCATGCTACTGTACTCCAGTCTGGG
CAACAGAGTGAGACTCCATCTCAAAAAAAAAAAAAAAAAGATTTAGTTCTTTCATTTAGT
TCTTTCATAATAATCTGAAGCACCCTTCTGTATAAGGATTATAAAAGAAAAATATGAGCC
TATTTTCTGCCAAAAGGTGGGCAGAATTTAGGAAGTGAGACTCAAAGATAAAATCACTCA

FIG.3-41

66092
TTACATACAACTTCCTACTACAAGATTTAGTTCTTTTAGGCCAGGCGCAGTGACTCATGG
CTGTGGATCATTTGAGGTCAGGAGTTCGAGACCAGCCTGGCCAACATGGTGAAACCCCAC
CTCTACTAAAAATATAAAAATTAGCCAGGCATGGTGGCGGGCACCTGTAGTCCCAGCTAC
TTGGGAGGCTGAGGCAGGAGAATCACTTGAACCCAGGAGGTGGAGGTTGCAGTGAGCCAA
GATCATGCTACTGTACTCCAGTCTGGGCAACAGAGTGAGACTCCATCTCAAAAAAAAAAA
[A,-]
AAAAAGATTTAGTTCTTTCATTTAGTTCTTTCATAATAATCTGAAGCACCCTTCTGTATA
AGGATTATAAAAGAAAAATATGAGCCTATTTTCTGCCAAAAGGTGGGCAGAATTTAGGAA
GTGAGACTCAAAGATAAAATCACTCACAGTATCTTCTGTGTAATAAACTTACAACACGGC
TAAACATAATGTATATATACAAAATGAAGAAAATTATTGAAGAAATGGTTAATTTTTAAT
AAAAGATTTTATTTTTGTTTTAGAATTTTATTTATGTTTATGGAGTTTATGGAAATAGTC

69016
TAAGGAAGTGTTTTTAAGAATAGTATCTAGACCATGAAACTGAAGTAGGAGTGGGAATGA
GATAAAAATAGGAATCCAATGGTGGAATTCAGTCTGACTTTTAGTTTAAGTTAACTAAAC
CTTTTTTCTTCATATCAATCATATGAGGAGATAGCCAACGATTCTTTCATTGCTGATGCT
ATTTCCTGTATCATTTTATCCTACTTAAAATGCTTGAACACTTGCACCACATACATCCTG
TTGGTATCTTTCCAACTCAGAATCATGTGGAAGGAGGTATTTTATGAAGTATACCTAAAA
[C,T]
AGAGTTCTTTTCATGAGACACTTTTATTTTGGATTGTACCTGATTTTACGGTTTTACATC
TATTTTCTCATCTAGTCACCCTATCATGAAATGTTACCATTTTAATGTTTTGAATGAAAT
CAACTACTCTTCCCTACTGTTTCCAGTGTGTCCAAAGAAAATACTCTATTCCTTTTCTAA
GTTTCCTGAATACTTAATAAACAGTTTTGTATTTAACATTCAAATTACTTCACAATTGCA
AAACTTATAAAGCAAAGTGAAATATTTCCAAGTGTCTAGAAATGTGAAGGAATCTAGGAA

69517
ACAGTTTTGTATTTAACATTCAAATTACTTCACAATTGCAAAACTTATAAAGCAAAGTGA
AATATTTCCAAGTGTCTAGAAATGTGAAGGAATCTAGGAAACATATAGGTCCATATCTTA
ACAAATTATATTTCTTATAAAATATTTTATTAAGTGAAGGACTCCATTATCAGATCCTAT
GTTTCTATCAGAAAATACTCATTGCATCTTAGAATTATTGACGTCTAGTATACATCACAA
GAAATTAGATTTCCTTCCCCCCTTTAAAACTGAAAAATGTTTTTCTTAAAGACAATGCGA
[T,G]
GTCCATAGTAGTTGCTCAATAAATATTTGTTAAATGAAGTACAAGGGCCAGGCGCAGTGG
CTCATGCCTGAAATCCCAGCACTTTGGGAGGCCAAGGCAGGCGGATCACCTGAGGTCAGG
AGTTCAAGACCAGCCTGGCCAACATGGTGAAATCCCATCTCTACTAAAAATACTAAAAAT
ATAAAAATTAGCCCTGTGTGGGGGCAGGAGCCTCTAATCCCAGCTACTTAGGAGGCTGAG
GCAGGGAGAATTGCTTGAACCTGAGAGGCAGAGGTTGCAGTGAGCTGAAATCGCGCCCCT

80083
GCTGATGTATTTAGCAGCATGTACTCCTTCGTGATTTCTAGATTATGCCCACCCTTGTCT
TCCTTCCCCAGAATCTCTTGTTTTTCACTGCCTGGGTGTGCACCCTATAGTGAGAAGACA
GGGGTGGGCCCAGAGGGGTGGGAGGATTTGGATTGAGGTAGGAGGCAGCTCAGTGGAGCA
CCCTCAAGGCAGGTCCACACCTGGACGGGGATCAAAGGAAAGTTGGTCCTGGGGCCTTGA
CCTGTGCCCCTATGGACTTGATTGGTCCATAGAAGGACTACTCTTTCGGACCCATGCCCT
[C,T]
GAGGATCGCTGGACACCCAGCAGGTCCAAACCCTCTTTGGACCAAAGAGCCCCCACCTAG
GCAGCTCAAGAGGTTCAGGTGAGAGTGCAGAAACGGCTTGTCAGCCTTGTGCCCTACCTG
GTGCCAATGTCTGGAGTGAAGCTATTTGAAGTCAGGCCCCTGCTCCCCACAACCTGCACC
AAAGGAGGCTTCCCTCCTTTGCATCCTTCCCCAGGACTTCTTTGAGTGAGGGGTGTGGGC
AAGGCCCAGGACCCAGTAGTAGGCTGGGAGACCTAGTAGCCTGGGGACAGGGAGAGGGG

FIG.3-42

80750 GGGAGTCTTGACCCAGAGCACAGATAATGCAAAGACTCAGGCCCAGTAGCCCCGTGTTTA
ACTCCTGGTCACTATCCAGGACTCCAGAAATCTCCACCCTTCCTTCTCTAAAAGAAGAGA
AATAAAACGACCAAGTTTTTTAAAGGGGCCTGACCCCTGTAATCTGTTTTTTTTTTTCTGT
CCTCCCCATTTCCTATTCTCACCCCCCATGTTTTTTGTTTTGCAGCAAACGACAGTGATC
TACCCATGGAGGAGGGCATGGCATTCACTATAGGTAAATTGAGCTCCTCTTCCGAGTGAG
[T,A]
GCGTAGCTCCTGGTGGAAGCTTTTGCCACTGGCCTAGGCCCGGCAGTCCGGTGAAGGACC
AATAAAGCCAATCAGTGTAATGAAATAATTCGGATGCACTGGAAATCTGATTAAATAATA
TCCTCAAGCCCCATCTTCCTAAATCAGATACTTACCGACACATTTAGGAGAAGGCAGCCA
TCCAACCTCTAATTCTGTTACCAGCATAATGTGGTGTTGGGTTTTTTGTTTTGTTTTGTT
TTTTCATTAACACCCAGTAACTAGACACGATTATGTCCCTTGCTCCCTGTCAGCAAGTGG

81839 TAACAAGAATCTGATGAGGTCACTGCAGTAAATATTTTTCCTCTTACAGAGCCAATCATC
ACGGAGGGATCCCCTGAATTTAAAGTCCTGGAGGATGCATGGACTGTGGTCTCCCTAGAC
AATCAAAGGTGTTTGCTTTCTGCTCTGTTGCTTTTAAATTGTATGGGAAAGGAAGATTGG
TCCGACGGCGCGCTTGTGGCCCGGCCGGAGCTTGCGTGCGCGTTCTGACGGCTGGGTGCT
GTGTTACAGGTCGGCGCAGTTCGAGCACACGGTTCTGATCACGTCGAGGGGCGCGCAGAT
[C,T]
CTGACCAAACTACCCCATGAGGCCTGAGGAGCCGCCCGAAGGTCGCGGTGACCTGGTGCC
TTTTTAAATAAATTGCTGAAATTTGGCTGGAGAACTTTTAGAAGAAACAGGGAAATGACC
GGTGGTGCGGTAACCTGCGTGGCTCCTGATAGCGTTTGGAAGAACGCGGGGGAGACTGAA
GAGCAACTGGGAACTCGGATCTGAAGCCCTGCTGGGGTCGCGCGGCTTTGGAAAAAACAAA
TCCTGGCCCTGGACTCGGTTTCCCAGCGCGGTCAACGCATCTGGAGGGGACTGGAGGAAA

Chromosome map:
Chromosome 2

FIG.3-43

SEQUENCE LISTING

```
<160> NUMBER OF SEQ ID NOS:  5

<210> SEQ ID NO 1
<211> LENGTH: 1798
<212> TYPE: DNA
```

<213> ORGANISM: Human

<400> SEQUENCE: 1

```
cgccaacatg gcggcgccca gtggcgtcca cctgctcgtc cgcagaggtt ctcatagaat     60
tttctcttca ccactcaatc atatctactt acacaagcag tcaagcagtc aacaaagaag    120
aaatttcttt tttcggagac aaagagatat ttcacacagt atagttttgc cggctgcagt    180
ttcttcagct catccggttc ctaagcacat aaagaagcca gactatgtga cgacaggcat    240
tgtaccagac tggggagaca gcatagaagt taagaatgaa gatcagattc aagggcttca    300
tcaggcttgt cagctggccc gccacgtcct cctcttggct gggaagagtt taaaggttga    360
catgacaact gaagagatag atgctcttgt tcatcgggaa atcatcagtc ataatgccta    420
tccctcacct ctaggctatg gaggttttcc aaaatctgtt tgtacctctg taaacaacgt    480
gctctgtcat ggtattcctg acagtcgacc tcttcaggat ggagatatta tcaacattga    540
tgtcacagtc tattacaatg gctaccatgg agacacctct gaaacatttt tggtgggcaa    600
tgtggacgaa tgtggtaaaa agttagtgga ggttgccagg aggtgtagag atgaagcaat    660
tgcagcttgc agagcagggg ctcccttctc tgtaattgga aacacaatca gccacataac    720
tcatcagaat ggttttcaag tctgtccaca ttttgtggga catggaatag gatcttactt    780
tcatggacat ccagaaattt ggcatcatgc aaacgacagt gatctaccca tggaggaggg    840
catggcattc actatagagc caatcatcac ggagggatcc cctgaattta aagtcctgga    900
ggatgcatgg actgtggtct ccctagacaa tcaaaggtcg gcgcagttcg agcacacggt    960
tctgatcacg tcgaggggcg cgcagatcct gaccaaacta ccccatgagg cctgaggagc   1020
cgcccgaagg tcgcggtgac ctggtgcctt tttaaataaa ttgctgaaat ttggctggag   1080
aacttttaga agaaacaggg aaatgaccgg tggtgcggta acctgcgtgg ctcctgatag   1140
cgtttggaag aacgcggggg agactgaaga gcaactggga actcggatct gaagccctgc   1200
tggggtcgcg cggctttgga aaaacaaatc ctggccctgg actcggtttc ccagcgcggt   1260
caacgcatct ggaggggact ggaggaaacc ccttgttgg aagagattcc aagagaagca    1320
cggttttctc tttcccttgc cctgactgtt ggagtaaaaa acctcttaaa tccattgtat   1380
cagaggtcct tacctctctg acagttacaa tgatctttgt atctgaactt tgcacgtctg   1440
ccgaaaaatc cgaacctgtt gactgggatt tttaagaatc cgtttctccc ttttgtgtat   1500
tccatattgg ccggccccaa ggatgctcgc agaagccagc cccaaccccc agcccttccg   1560
tatctttccc ctccatcgcg gctttgcgat gaaagattag cccgcgaaca gaggcattga   1620
ttacaaacat gtccttggca gtggaaaaaa aaaaaaaaaa aaaaaaaaaa aaaaaaaaaa   1680
aaaaaaaaaa aaaaaaaaaa aaaaaaaaaa aaaaaaaaaa aaaaaaaaaa aaaaaaaaaa   1740
aaaaaaaaaa aaaaaaaaaa aaaaaaaaaa aaaaaaaaaa aaaaaaaaaa aaaaaaaa     1798
```

<210> SEQ ID NO 2
<211> LENGTH: 335
<212> TYPE: PRT
<213> ORGANISM: Human

<400> SEQUENCE: 2

```
Met Ala Ala Pro Ser Gly Val His Leu Leu Val Arg Arg Gly Ser His
 1               5                  10                  15

Arg Ile Phe Ser Ser Pro Leu Asn His Ile Tyr Leu His Lys Gln Ser
            20                  25                  30

Ser Ser Gln Gln Arg Arg Asn Phe Phe Phe Arg Arg Gln Arg Asp Ile
```

-continued

```
        35                  40                  45

Ser His Ser Ile Val Leu Pro Ala Ala Val Ser Ser Ala His Pro Val
    50                  55                  60

Pro Lys His Ile Lys Lys Pro Asp Tyr Val Thr Thr Gly Ile Val Pro
65                  70                  75                  80

Asp Trp Gly Asp Ser Ile Glu Val Lys Asn Glu Asp Gln Ile Gln Gly
                85                  90                  95

Leu His Gln Ala Cys Gln Leu Ala Arg His Val Leu Leu Leu Ala Gly
            100                 105                 110

Lys Ser Leu Lys Val Asp Met Thr Thr Glu Glu Ile Asp Ala Leu Val
        115                 120                 125

His Arg Glu Ile Ile Ser His Asn Ala Tyr Pro Ser Pro Leu Gly Tyr
    130                 135                 140

Gly Gly Phe Pro Lys Ser Val Cys Thr Ser Val Asn Asn Val Leu Cys
145                 150                 155                 160

His Gly Ile Pro Asp Ser Arg Pro Leu Gln Asp Gly Asp Ile Ile Asn
                165                 170                 175

Ile Asp Val Thr Val Tyr Tyr Asn Gly Tyr His Gly Asp Thr Ser Glu
            180                 185                 190

Thr Phe Leu Val Gly Asn Val Asp Glu Cys Gly Lys Lys Leu Val Glu
        195                 200                 205

Val Ala Arg Arg Cys Arg Asp Glu Ala Ile Ala Ala Cys Arg Ala Gly
    210                 215                 220

Ala Pro Phe Ser Val Ile Gly Asn Thr Ile Ser His Ile Thr His Gln
225                 230                 235                 240

Asn Gly Phe Gln Val Cys Pro His Phe Val Gly His Gly Ile Gly Ser
                245                 250                 255

Tyr Phe His Gly His Pro Glu Ile Trp His His Ala Asn Asp Ser Asp
            260                 265                 270

Leu Pro Met Glu Glu Gly Met Ala Phe Thr Ile Glu Pro Ile Ile Thr
        275                 280                 285

Glu Gly Ser Pro Glu Phe Lys Val Leu Glu Asp Ala Trp Thr Val Val
    290                 295                 300

Ser Leu Asp Asn Gln Arg Ser Ala Gln Phe Glu His Thr Val Leu Ile
305                 310                 315                 320

Thr Ser Arg Gly Ala Gln Ile Leu Thr Lys Leu Pro His Glu Ala
                325                 330                 335


<210> SEQ ID NO 3
<211> LENGTH: 84495
<212> TYPE: DNA
<213> ORGANISM: Human
<220> FEATURE:
<221> NAME/KEY: misc_feature
<222> LOCATION: (1)...(84495)
<223> OTHER INFORMATION: n = A,T,C or G

<400> SEQUENCE: 3

cacccagctt atatcccata agttgatggt tttggcggac atgtgctggc agcttttaac     60

ccttctgcgg tgagaaggat gtgtatgaga gaagccagat ccagggtcag tggatgagct    120

atcacctgtg caagttcata tttgcttcat ttctagctca tcccagatat ctacattcca    180

tgccgaactt attgaggatt tcctcactgg attccactac tgctggtgcc acctgggtcc    240

tcatagtgtt tccttttcct tttagttgta ggggaataaa gcattcattt attttccaag    300

ggttggctga gttaagtcac atgaacatgt gttctatttc agatgggttt gaaactaggc    360
```

-continued

```
ttgatgcctt aaggaatagg gatgtctaga tttctttttt ctgtacactt cttaagactc    420
tgtggccagc taactctcag gctcctttgc tgcactcaga ttgctggcct cagttacaca    480
gaggacagat ttgccacatt caaaaatgct ctccctggaa ttgaaatgag tttgcaaaag    540
gtaggagtac attttattct cattcttgtg catcttattt accctgatgg aaagcattac    600
ttctctttat ctttcaaggt gacccaaaag catccaaaac caggttttcc agaattatag    660
catgtgtcct ctaatgaaat gccaacattc actctcttta aaagtaaaaa tatcaagatt    720
atatagtcat taaaaagaat aagtctgaac taagtgttct aagatttgat gcctatgatg    780
actggaatgg aaaaagcaag tcatatgatt ctatttaaaa tacttacatt tgcctgtgtg    840
taaaaggcaa agatctcaat tgagcacacg gtggttaact ggggagtggg actatggtat    900
gtacagaggg cgaggaaggg gcttgcactt gttccttatt tctgaattgt tctgaattgt    960
ctagattatt cactgagtgt gtagtgctta aaaattaatt agaagacatc acacacattc   1020
actgagaatc ctaatcaatc ttcactgcat ttaaagtctg gaaacggtta cattctcagt   1080
ttgactggtt tcatgcagtg ttcaattgct tcacctgaca ttcctcgggt atcgggttct   1140
gtgccgggca cggaggctac taagatgaat aacacctggt ccatgacagg atggcatcta   1200
ccccagaaca caggtaagag agacagtgaa tttggtaaaa atgggcaccg tcatcagtag   1260
gcatacatca gctccctcat ctgattcaca attggccttc tgtaggcttc ttctcttggc   1320
aatgcaattg gcaggcgtca tccttttata cttaaactcc aaatttagga ttaagactcc   1380
agttaatact gccaagcaga aggcgtcctt ggagaaagag aagtctcctg aacataccca   1440
ctggggtacc tagaatagat tttgcagcga cacacagatc ctgtgttgtc tggagtctct   1500
gctgagtaat gtagattctg ggacagcaaa aggggagctg gtgactttga accaaatttt   1560
acctttcaac tgaatccagg ggaataattt gcaacagagt ggcagacgat acaaagtgct   1620
atgttgaaca ctagattgtg ctttattttt tccgcccaac ttcacgtttc catgcaccaa   1680
aatgttgatg ctataaatat tggatgccac gcttacctga caggcttctt ccatcccacc   1740
tgggcgcggg ggctcagagc gagcgcgcga gccgcggctg gagcccgcct ctcgcggctg   1800
gagaggactc agccggccgc gggttctgct gcttgcccgg gtgccctagc cgcttcccag   1860
ccagggctcc cgcagtcagc cccgcgcgcg cacgcgcgct cccctcgggc ggcctcgacg   1920
cctcagggct tcggcagggc tgcgactggc cggctccagc gggcggggcg gcgagcgagt   1980
gctcgcggcc acgtgaccga cgccaacatg gcggcgccca gtggcgtcca cctgctcgtc   2040
cgcagaggta agcgcgtgga ggagagcccc gtgagggttc gcacggttgc tcactaggta   2100
cgcacccggg tccaaaggga tgcgcacccg cgctcagact tctcggcgca cacgactgta   2160
ctttcagtgt ttacgaacac acgcaggcac acacgatgac acattcacac accacaggat   2220
cacacataca aatttgttca ctgatcaccc gcctagaaca cgtcaccacg tggcatcttt   2280
tcgcaattac tccttgagat ttgcgggcca ttgtctgaag ttttttttccc caacttcggt   2340
tgtatcatta gtgtaaccaa catttattct gtatgccgag caaggaaacc tatggtaatt   2400
ctgaaatgca tctggacacc cggttccctt ccctagagct tttatgcagg catgcttttt   2460
ggggacttgc aaaatgtgat ggttttcttc cagtgactta aagttaagaa gataagaaag   2520
gatgtctggg tagttctaag taggttttat cctgcgtgag tgttgagatt ttagtaaata   2580
tacaaatgcc tttgcagcag aattggggaa atctttgttg gatttgaact aggtgctgaa   2640
tctttgttgg aaagaactag aaagtttttc caaggacggg ggaagaggaa aactatcata   2700
```

-continued

```
ttttgaggag ctacttaagc gtcaggcatg taggaacagt tttgtgaggt aaatattatt   2760
ttcatagtaa cagctactgt ttattaagtg ccttttaagt acacgatact gtgttaagcg   2820
ccttacatat gcttgcttcc ttttaaaact caatgaatga gaccccgtct ctacaaaaaa   2880
ttttaaaaat tagtcgggcg tggtgacaca tgcctgtagt ctcagctatt ctgggggttg   2940
aggtggtagg atcgcttgag cctgggaggt caagaggctg cagtgagccg tgatcgtacc   3000
actgaactcc agacttggca atagagccag accctgtctc aaaaacaaaa acaaaaaccc   3060
agtgagttag gaattatttt ctctttgcag aagggaaaag taaggctaga gaggttaagt   3120
aacattacta aggtcgcata aatggtaaga ggcagattgc tcatttgaac atgactctaa   3180
tttttttttt taagactcat ttctcggtac tgcatgacgt ggtcactcca tagaagtcag   3240
tgtgtaaagt tcagcagaga cagtgcagga tgagtgtgta caaaaagtga agagagcctg   3300
ggcacggtgg ctcacacctg taaacccagc actttgggag gccgaggcag gtggctcact   3360
tgaggtcaga agttcaagac cagcctggcc aacatggtga aaccccgtct ctactaatat   3420
acacaattag ctgggcgtgg tggcgcatgc ctgtaatccc agctactcgg gagactgagg   3480
taggaaaatt gctttaaccc aggaggtgga ggttgcagtg agctgagatc ataccactac   3540
actctagcct gggcgacaga gcgagactcc gtctcagaaa aaaaaaataa ataaaaataa   3600
taaaaaataa gaagtgaaga ggaagatatt tttagagagg aagaaggttg gtaatcgaat   3660
agacttcagt atttcagtgt tagtggagat gagaaagggg ccacaggaag atttgagggg   3720
agagatgtgt atggggaagg tgatgtagcg agcattttgg actggttgca tgaaggaatg   3780
gacatcagca tgagagtgta gccttgtgaa aagacagcca atttacatct ctcaagatct   3840
gggtgccagg cctggcaagg tggctaatgc ctgtaatatt acccagcact ttgggaggcc   3900
aaggcgggca gatcacttga ggccaggagt tcaagaccag cctggccaac atggtgaaac   3960
ctgtctctac taaaaataca aaaattagcc aggtgtggtg gcacatgctg gtaatcccag   4020
ctacttggga ggtggaggtg ggagggatcg cctgaaccca ggaggcggag gttgtagtga   4080
gctgaaaaaa aaaaaaaaaa agatctgggt tccagtccaa actttcttta ctaattactt   4140
ttctgtttcc tcttttcaca agaaatcatg gcttttagac ttcatttttg tatgcttcag   4200
gtaatggtga gaaggatctg aggagatagt caatgtagag gaggagccaa aaaaaaaaca   4260
acctgaaaac atacataggt gtatgtatgt atatatatat acacctatgc atgtataaac   4320
gtatttttat atgtgtgtat atatgtatta ggttggtaca aaagtaattg cagttttaga   4380
atcaatgaca aaaactgtga ttactttgca ccaactgtat atataacatc tctttgcaga   4440
taacagaaat agcattaatc ttttctttct ttttgatcac ttattatttt gacaaatggt   4500
ggtttagaca gtcttgagaa aatatattat atggaagtca ggccaagtta ttggttccta   4560
taatccatcc cactgtatcc caaagtgttg caacaaccaa gaagtggatc ctctgattag   4620
aggagagaag aaaaatgtgt catcaggaag ctattttaat gatggagaaa gggccccttt   4680
ttggactacc catagctagt tttaaattgc agagaggttt tcctgctccc cacccccaag   4740
aattgaaaat gaagggtaaa ttcacgaaga ctcctctctc caccctcttc ctccctttca   4800
cccatctaga tttatgtaaa gcaatccatt acaagtcttc atgtaccagg atttattatc   4860
agcatttatg agcatcattt cttcttgaaa tagaggaaga cttttttttta accttttaaa   4920
aaaggcatga ggtttctctt gtgacgcctc aactcattgt ggctttggtc acagtatacc   4980
ctgtatacag tagttaccta gctcctctca ccatttctgc tccttactag attattaatt   5040
cttgttgaac agaagctttg tcttatgtat ctttctgtct ttataagcac agtacctggc   5100
```

-continued

```
tcaaagttaa gctcattaaa agtatacaga attgagaggc tgttaagatt tgttctcttc   5160
catcatggtc taaggagggt tgggtagaaa ctatgagtag tgacattgga aagaggaaaa   5220
gacagatcag cctcttggaa ccaagagaga aggtaacaag ggcctttaag ggactaaaat   5280
actcccaagt attagtgctg gcaggaaatc ccttcctcag agtacagaat ccctaccctg   5340
gggccccagg aactctctcc tatctcagtc tcactcccag ccctcgcttc actggaatcc   5400
caggtctagc tcgggccacg aagcaagatc ccagtgaata tgaagaggaa caaggaaatc   5460
tcagcttgaa ttgtaataat ccccatgtgt caagggcagg accaggtaga ggtaattgga   5520
tcatggggat agtttccccc attctgttct tgtgataatg agtgagtctc aggagatctg   5580
atagttttat aagcgtctgg cattttctcc tgcttgcact cattctctct cctgccaccc   5640
tgtgaagagg tgccttctgc catgattata catttcctga ggcctcccga gccatgcaga   5700
actgtgagtc aattaaaccc cttttcttta taaattaccc agtctcagga atttcttcat   5760
agcagtgtga gaacagacta atacagcaag taagagggca tattttcttt cttttttttt   5820
tgagacagag tctcgccctg tagcacaggg tgaagtgcag tggtgcgatc ttggctcact   5880
gcaacctctg cctcccgggt tgaagtgatt ctcctgcctc agcctcccga gtagctggga   5940
ccacaggtgc ccaccaccac gcctggctaa tttttgtatt tttaagtaga cacggggttt   6000
tgccatgttg gccaggctgg tctctcttga acttctgact tcaagtgatc cgcctgcctc   6060
agcctcccac agtgctggga ttacaggcat gaaccaccgc acctggccat ttacttattt   6120
ttaacaaata taaaaaaaac ttagaagtac ttttgttcac ttgtgactgt aaggccctag   6180
actcctccac tgagaatttt gttaccttag tggtttttca aaaatgtaat agccaggcag   6240
gggaggggct gttatacatc atgagttaag tactttaaac ttttgccaac tgccctgaga   6300
tccttgctat cttgtatagc ttctgcagga aaatgtctgc tcagttttgc caaaccaact   6360
tttctttttt tttttaaatc gagacggagt cttgctctgt tgcccaggct ggaatgcagt   6420
ggtgtgatct tggcccactg caacctctgc cacccaaatt caagtgattc tcctgcctca   6480
gcctcttgag tagtgggaat tacaagcatc cgccgccatg cccggctaat tttgtattt    6540
ttagtagaga cggggggtttc gccatgttgg ccaggctggt ctcgaactcc tgacctctgg  6600
tgacgcacct gcctcggcct cccaaagtgc tgggattata agcatgagcc accacgccca   6660
gccgccaaac caacttataa ttaaactttt gggatgcaat tcatgggtga tttggaaaat   6720
gctaacattc ctaagtttag cttcctatta cttagactac attcctgttg acatccagag   6780
aatggaaatg gagttttgcc gtatgacatc ttttaacaaa tacattccaa ttctattata   6840
atatggcatg ttactacaca gattaagaaa tacttatgaa accttggctc taaagtgctc   6900
ctaaatccat acatacttgt atgtgttttc ctctatttga aacagctagc ttgcttcctt   6960
tcttccttcc tttttttttt cttttttcag ggtctctgtc acgaaggctg gagtgcagtg   7020
gcacaatcac aggtcactac agcctcaact tcctgggctc gaccagtcct cccacctcaa   7080
cctcctgagt ggctaggcgc acaccaccac acccagctaa ttttttgttt ttttcataaa   7140
gacaggttat catcatgctg cccaggctgt gaaacagttt tctttctttc ttatttattt   7200
attttatgtt ttatttcaat agtttttggg gtacaggtag tttttcgtta catggatgaa   7260
tactttagaa gtgaattctg agattttagt gcacccatca cccaagcagt gtacattgta   7320
cccagtatgt tttcttttat ccttcacccc tgcatcccta gagttcatta tattgctctg   7380
tatgtttttg catcctcata gcttagctcc cacttataag tgagaacata cagtatttgg   7440
```

-continued

```
ttttcttttc ctgagttact tcacttagaa taatggcctc cagttccatc caagttgcta   7500
caaaagacat tattttgttc ctttttatgt ctgagtagta ttccatggtg tctgaaaaat   7560
atatatatat atatatatat atatcttttt tttttttttt gagagtctct ctgtcaccca   7620
ggctggagtg cagtggtgca gtctcggctc actgcaacct ccgcctcccg ggttcaagca   7680
attctcttgc cttagcctcc tgaatagctg ggactacagg cacccgccac catgcccggc   7740
taatttttgt atttttttgt agaggcggga tttcaccatg ttggccaggc tgatctcaaa   7800
ctcctgaccc aaatgatcca cccacctcgg cctcccaaag tgctgggatt acaggcataa   7860
gctaccatgt ataacacatt ttatttatct actcattggt tgatgtgaaa cagctttctg   7920
tactacaaat agttctgtct cccattgaaa ttatgaaatt tcgatgtata ctacagggca   7980
tatagaccct cagtgatgaa tgctttgcag tcattaaaaa aaaatatatt gacctgcatt   8040
tgttggtatg gaatgatgtc cacaaaatac attattatgg aaaagcaagt tataaaacaa   8100
tataagctac tcacattttg taaataaaat atcaatattt ctgtatatgt gtatacatgt   8160
gtctaagtgt atataacatg tatacacaca gagtatgaca tacaagcaga tatttatagt   8220
ttttgttttt tttttttttg agacgaagtc tcgctctgtc acccaggctg gagtgcagtg   8280
gcgggatctc ggctcactgc aagctccgcc tcccaggttc atgccattct cctgcctcag   8340
cctcccaagt agctgggact acaggcacct gccaccacgc ccagctaatt ttttgtattt   8400
ttagtagaga tggggtttca ccgtgttagc caggctggtc tcgatctcct gacctcgtga   8460
tctgcctgcc ttggcctccc aaagtgctgg gattacaggt gtgagccact gcgcctggcc   8520
aatatttata gtttctatga aatacccgct ttcctcaagc attagaaatc cataaaaatc   8580
agtgtggatg ctatatatct tagggaactt ggcaaagatg ggagaagtac tatgtgtatg   8640
cagaacttca tttgaacaac atctagtttt aagctgaaac agcttgtttt tacggagact   8700
gaattttctt ttttagcttt tgaacatgga gacagttaaa cataatgcaa aagtagagag   8760
aatagtacaa tgaactccca cgtagccatc atctagttac aatagtcatc aacctatggc   8820
cactattgtt acatctatac tcccagttac tttgcctccc cacaggtgga ttattttgaa   8880
gcacattcca gatatattat ttcatctgta gattttttac cgtgtatctc taaaagatag   8940
ggagccattt ttttcttctt acgttgtaca tatcagttct agaatttgca ttataatttc   9000
catttcttgt tgagatttcc cacctgttca ctcattatgt tcatcttttc ctttaagtac   9060
ttgaacatac atatttataa cagcttttta aaaatctgtt aattttatta ttgggtctcc   9120
tcagagtctg tttctgtttt gttgactgct gttttttttt ttattgtaca ttacgttttc   9180
ctgctgcttc ccatgtcatg taattttttt tttttttttt ttttaagaga agggccttgt   9240
tctgtcaccc aggctggagt gcagtggtac aatcatagct cactgcaacc tcaaactcct   9300
gggctcaagc aatcctcctg cctcagcctt ccaagtagct gggactatag gcgcacacca   9360
ccatgtctgg ctaatcatgt aatatttaat tttataagtg gcatgacaga taatatcttg   9420
gtggagatta tgttgttttt ctttaacata tgttttaaac aactgccagg caatatgtta   9480
aatctgtttg attctttcag gcttggtttt tattctctgt taggatggat ctatttgtgt   9540
tttgctgtta gttctagggg gtggctgagg ccagtgtggg ctcatgtgtt gtattgtttt   9600
cttttaaggt tcatggtcct gcattgccta atatccagtg ccaagatata gttgcttcac   9660
atattttgtc taattggtta agacaggtgg gaattctagt accagttatg ctggaatgga   9720
tggaaaagga tattaatttt gttttttttg agacagagtc tctgttgccc aggatggagt   9780
gcagtggcgc attctcagct cactgcaacc ttcttctcct gggttcaagc agttctcctg   9840
```

```
cctcagcctc ctgtgtagct gagattacag gcgcatgcca cgacacccgg ctaatttttg   9900
tatttttagt agagacgggg tttcaccatg ttggccaggc tggtctccaa ctcctgatct   9960
caagtgatcc acctcagcct cccaaagtgc tgggattaca ggcatgagcc accgcgccta  10020
gccggatatt attatttttt ttaatctata agtttacttt cccttttttt ttttttttga  10080
aaattatttg ttgaagcaac tggttagcct attggttctg tggagctttg cattttgtgg  10140
attttgctga tggtattata ttccacaggg cttgttgaag atgttcctct ataaaatggt  10200
agttagatcc aaggcctgat ttaagttaga catttttttgg tacaagtact tcatagtggt  10260
gttgctggag acattgtggc ctggagacat tggagacatt agtggccatt ggcaatcatg  10320
acctggctca ttaggagttt acaaatgaca atattttaat tactccttct ttatttatca  10380
gctagaaaac atctacaaag agaaactttc tcatcaagta tttcattacc ctgacaggcc  10440
ctgtcccagc aaggaaagtt aaatggtttg ttctccttat ttatcagttt ttaaaatacc  10500
atagtccccc gcttatccaa tgggggtatg ttcccagacc ctcagtggat gtctgaagcc  10560
acagatggta ctgaaccctg cacggtgctg tactatgctt tttcctatac acacatttct  10620
gtggtaaggt ttaatttata aattaggcag agtatgaaat taacaacaat cactaaaaat  10680
agaacaattt taacaatata ctgtaataaa agttaggtga atgtggcctt tctctcaaaa  10740
tatctttttg cactgtgctc accccttttt ttttatgatg atgtgagatg ataaaatgct  10800
tacgtgatga agtgaggtga atgagaaagc attgtgatgt agttttagac tacatgtctg  10860
aaggagaatc atctgcttca ggtgatcctg gatcactaag ccatgacatg atgtcagaag  10920
cagagaatgt ggatgactaa tgggttgcta gtgtgcaggg tgtggacctg ctgacaaaag  10980
ggaggattca tgtcctgagc agaatggagt gggccagtgt gagatttcat cacgctgtgc  11040
agaacggtgt gtttgtgaat tgtttatttc tggaattttc tttctttttt tttttttgag  11100
acagagtctc gccgtgtctc tcaggctgga gtgcagtggc gcgatctctg ctcactgcaa  11160
actccacctc ccgggttccc gccattctcc tgcctcagcc tcccgagtag ctgggactag  11220
gggcgcccac caccgcgcca ggctaatttt ttttgtattt tttagtagcg acggggtttc  11280
accgtgttag ccaggatggt ctcgatttcc tgacctcgtg gtccgcccac ttcggcctcc  11340
caaagtgctg ggattacagg cgtgagccac cgcgcccggc ctggaatttt ctatttaata  11400
tttttagacc ttgattgacc ttggataact gaaactctta tctaagagga gactaccgta  11460
acaggtttat cctccaaaag tgaccaatga atttttgttt cgggtcatta tatgggttaa  11520
tttttttat atgggtttat ttttaattgt gtatctactt ctttaatttt ctgaaagtat  11580
atgaaacgtc atggagcatt gaaattgtga ggcaggattg caagattcaa gatagaagag  11640
ctattgacag aagtagcatt tctaatatat ggaatttaag aaactcttac tataccttaa  11700
tgttagagtg gaagactgta gggtaagaga ggattaacaa gaaagtgaga tggtgtctcc  11760
attttaatct gctgcttgtg tgttctgaat gtattggaga gggaaagcca ttgcagtcag  11820
ttagaagata atggcagaaa cagaaggacc tgaactaggg taatgactgc gggatggaaa  11880
gggagagatg gatgccaagg aaatggtaca gaggagaaat catcatgacc tggtggtttg  11940
ctggaaagga gacccgagga agggaagggg catcaaagca gaaaaggagg agttggcagg  12000
aacagagaac ttagtaggga aaagagtctc taagatgaaa ttgcaggatg actaagtatc  12060
agtgaatttg gccactagtg atgatggcgg cttggagcaa aatttagcag tagaaggagc  12120
ttgtgaaaag tgacagttgg tggtggttgt agagaattgt ggaggggttt tttgtccctt  12180
```

-continued

```
cttttttttt ttttttttgag acagggtctc actttgtcac ccaggctgga gtgcagtggc  12240
gcaatctcaa ctcactgcag ccttgacctc ccaggcccaa gcgatccttc cacctcagcc  12300
ccccaagtag ctgggactac aggtgcacac caccacacct ggctaatttt ttgcattttt  12360
tgtagagatg gggtttcacc atgttgccca ggctggcttt gaactcttga gctcaagtga  12420
ttggtcagcc caccttggcc tcccagagta ctaggattat agatgtgagc cactgcaccc  12480
agccctttttt tttttttttt aacaactttt ttccttcttt ccttctttcc tctttttttt  12540
tttttttttt ttaacagaat ctcactctgt cacgcaagct agaggacagt ggtgcaatct  12600
cagctcacta caacctgtgc ctccgggttc aagtgattct cctgcctcag ccccccgagt  12660
ggctgagatt gtaggcgtgt gccacctcgc ctggctagtt tttgtatttt tagtaagaga  12720
cagggtttcg ccatgttggc caggctggtc ttgaactcct ggcctcaagt gattcacctg  12780
cccaatgttt tttttttttt ttttgagatg aagtctctga tctttcaccc aggctggagt  12840
gcagtggcat gatctcgatc tccactcact gcaacctccg cctcccaggt tcaagcgatt  12900
gtcctgcctc agcctcacga gtggctggga ttacaggtac atgccaccac acctggctaa  12960
cttgtatttt tagtagaggt ggggtttcac catgttggcc aggctggtct cttaaactcc  13020
tgacctcaag tgatctgcct gcctcagtct cccatagtgc tgggattaca ggcgtgagcc  13080
accgcgccca gcctgtctgt tcaatcttaa cagctttttt gagatataat tcacagtcca  13140
tacagttcac ctatttaagg tgtataattc agtgattttt tagtatattc aaagagttgt  13200
gcaagcatca ccacaatcag ttttacattt ttatcacccc aaagagaaac ctcttaccca  13260
ttagcagtca ctccccaatc tgcccatccc ctcatcctta agcaaccact aatctttctg  13320
tttctttttt tttttttttt ggcgatggag tctcactctg tcgcccaggc tggagtgcag  13380
tggcgcgatc tcggctcact gcaagctccg catcccaggt tcatgccatt ctcctgcctc  13440
agcctccaga gtagctggga ctacaggcgc ccgccaccac gcccagctaa tttttttgtat  13500
ttttagtaga gacggggttt cactgtgtta gccaggctgg tctcgatctc ctgacctcgt  13560
gatcctcctg ccttggcctc ccaaagtgct gggattacag gcgtgagcca ccgcgcccgg  13620
cctaatcttt ctgtttctat agatttgcct ctcctggaca tttcatataa tggaatcata  13680
caacatgcag tcttttgtga ctggcttctt tcatttagca tgatgttttc atggttcatc  13740
cctattgtgg catgtgtcag tttattgctg tataatatgc cactgtatgg atatatcaca  13800
ttttgtttat ccattcacca gtttgtggac atttgggtca tttctacttt ttagttctta  13860
tgaataatgc tactatgaat atttgtgtat gtgtttttct gcggacatat attttgtttt  13920
ggttttgaaa taggctatgt ttagatgcag agggaagcaa agaaactggt aaggatgtgg  13980
taaaattacc acatccacaa gacaacgttt attaagtact gaaatattcc tttatgaaag  14040
ttaactcttg ccatcccttt tatctttcac atttagagtc tatattatca caaccttgtt  14100
tttcctttga gtcagcattg tgatcattct ggacgtgggg tcccacacac cctgtctctg  14160
tcagtaagat tatgattaag atcaaataga aataggtcag gagagaaaag agctccctgg  14220
ccttattctc ctcaaactag ctgatgctcc tgaataccaa cctctttaag aattgatatt  14280
tcaaaggaca actcctctct gtggtcttct gtcctctctc ccctacttta tgctctgtgc  14340
atagcagctg ttcaggacat cgcccgagcg caggggcact gcaatcagaa aagcgagtga  14400
gggacacagc aggagaaggc tgttctgggg ctagtgagtg ggagacggga caaacagcta  14460
gatagcaacg tgatggcttc accatggggt gaagcgtggg ggagagtatc aattacctag  14520
attttaaaaa gagagccctt gaacacctct gtcactggtc acttttacca aagccttcta  14580
```

-continued

```
acttaacgga aggagatgct gcactttaaa gaaaaatcac agctgcggaa gacagtctcg  14640
caaagccagt ttttgtggct tagtattttg gggtagcttg tttcatgagg gtcagattaa  14700
ttttctaatg ttgttttcta ccttaatgtt actgctttaa tcattagaat gccaccagtt  14760
ccttcaggca ataggaagct attgaagatt taatgagatt catactgctt atgcttaaat  14820
gttgatgact tcctgcatgc atattaatca ttcctgacct tgatctcaaa ttccttcccg  14880
gtacaaattc tcattaaaca tacctactag atctcccagt gttcactgaa tacctggttt  14940
gtttccaaaa gtacataaaa gaacattaag tctcatgttc ggtatgtgtc aaatgttcag  15000
ttcccttgtc tgatttgttt tccaattctt attgtgactg taaatctgga gaatttaggg  15060
gaagaaaaat cagtaactct taacagggga tttagcctag tttacaagag tatatgatct  15120
gtgcagcaga ccttgaacac agctaattgc ttgtctaggt cagtatgtcc aactggcaac  15180
tctcagagcc catccaggcc acagagcatt tccgggtggc ttgtgtgtgc gctccggctg  15240
tcgagcagca ggacttggct tctgtccccg gcttcgttgg ccccatcttt tagttcaggt  15300
ccaccccctc ctgcctcaga ggcctgggaa acccagcctg gccacctggt gtcctcatgc  15360
ccagcatcta cgcatctgcc ccagttgtcc cctcagccac cttggcagat ttcttgactt  15420
aacagttctt ccctgaacta ggaccggggg caggagttat tagagaaggg agaggaaagg  15480
tgacaggtct caggagtctg agggaagatg aaagtgagag cgaagtagtg tgggagagag  15540
ggggatcaca taccatggga gagaaaataa atatgtcaat attagggtgg tgaggcctgt  15600
atacaaagac aggatggcag ggagaagaag taggcaagga cataaagggg cttgggtatg  15660
cagatgctgg tcactgaaaa tgaggaacaa aggagggaaa tttgcgtgtg aaagaggcca  15720
catgtgagag aatagagaga gcaaaatgac agctttgctt ggcagaacgt gaccatgcac  15780
agcattggga gacacagtct gatgaagcat tttttccaat ttgtaaatat atttataaca  15840
aagaaacatt atactttttt tttctttttt tttttttttg agacagagtc ttgctctgtc  15900
acccaggctg gagtgcagtg gcgtgatctt ggctcagggc aacctccgcc tcctgggttc  15960
aagcgattct cctggctcag cttcccgagt agctgggact gcaggtgcgc accaccatgc  16020
ccagctaatt ttttgtattt tttagtagag acggggtttc accatattgg ccaggctgat  16080
ctcgaactcc tgacctcaag tgatctgcct gcctcggcct ctgaaagtgc tgggattaca  16140
ggcgtgagcc actgcatctg gactactttt ttttttgaga gggaatctca ctctgtcacc  16200
caggctggag tgcagtagca ggatcactgc aacctccacc tcctgggtgc aagcgattct  16260
cctgcctcag ccttcccaag tagctgggat tacaggcacc tgccaccatg cctggctaat  16320
ttttgtattt ttaatagaga cagggtttca ctatgttggc caggctggtc ttgcactctt  16380
gacctcaggt gatttgcctg cttcagcctc ccaaagtgct gggattacag gcatgagcca  16440
ctgtgcctgg tcagaaattt attattataa aaacacaaag agatatatac ttagcatatt  16500
acattacatt gggattattt taggttgtcc caaaggtgta gtcatttgat tcagaggcat  16560
agcctgcttc tgacatgttg gttgtttaaa atgtggcctg ttctgaccaa gaagttggac  16620
agtattggtt ttgatgacta tcttgccact tattttttac aatgtggtaa tttttacatc  16680
cagatagttt ttcatctttt tttctttttt tgaatcagag tctggccctg ttgcccaggc  16740
tggagtgcag tggtgcaatc tcggctcact gcaacctcca tctcccgggt tcaagaaatt  16800
ctcctgcctc agcctcccga gtagctggga ctacaggcgc ccgccagcac acccggctat  16860
tttttttttag ttttagtaga gatggggttt caccatgtta gccaggatgg tctcgaactc  16920
```

-continued

```
ctgaccttgt aatccgccca cctcagcctc cctaagtgct gggattacag gcgtcagcca  16980
ctgcgctggc ctagtttttc atctttttaa agcacatttc cgctgatata atttgactgg  17040
ataggtgaaa agatatccat tttgcaaagt agatttttta tatttaatga tcaaaatctt  17100
tatcttttaa aaacaatttt tataaaatag ccacaaaatt tcataccctt taacttattt  17160
acttaattcc acttctagaa atctatattt agaaaataat taagtcgggc gtggtggctc  17220
acgcctgtaa tcccagaggt caggaatttg agaccagcct ggccaaaaat ggcgaaacct  17280
cgtctctgct aaaagtacaa aaattagcca ggcatggtgg cgcccacctg taatcccagc  17340
tacttgggag gctgaagcag gagaatcact tgaacccagg aggtggaggt tgcagtgagc  17400
tgggattgca ccactgcact cgagcctggg caacagtgag actctgtctc aaaaaaaaga  17460
aagaaaataa ttagagatgc tgccaaagat ttaggttcaa gaatgtttat tacagtgtcg  17520
cttatattaa tattagcaaa gaactggaaa tagtctaaat gtccaataaa atagagaaat  17580
gattcagtaa attatgattt attcataagt tgagatgggc tgttgtatgg tcattaaaat  17640
actgcctatt aaactattat acttcctcca gtttattctc cacactgcag tcaagtgacc  17700
tttgaaaaag tacattgtgg ccagacatgg tggctcacac ttgtaatccc agcactttgg  17760
aaagccaaga tgggaggatc gcttaaggcc aggagttcca gaccagcctg ggcaacatag  17820
tgagaccccc atctttataa aacatttaaa aattagctgg gtatggtggc atgtgcatgt  17880
agctactcgg gaggctgagg tagaggattg ctttagccca ggagtttaag gctgcagtga  17940
gctatgattg tgccactgca ctccagcctg ggcaacagag tgggactctt gtgtcttaaa  18000
actataaaaa tagagagccg ggcatggtgg ctcatgcctg taatcttaac actttgggag  18060
gctgaggcgg gcagatcact tgaggtcagg agttcgagat cggcctggct aatatagtga  18120
aactccgtct ctatcaaaaa aaaaaaaaca aaaaaagaaa aaaaaaatta gctgggcgcg  18180
gtcacatgtg cctgtaatcc cagctactta agaggctgag gcaggagaat tgcttgaacc  18240
caggagtcca aggttgcagt gagctgagat catgccactg cactccagcc tgggtgacag  18300
agtgagaccc tgtctcaaaa aaaaaaaaaa aaaaaaaaaa aaaaaaaaaa tatatatata  18360
tatatatata tatataaata gtccaggcgt ggtgactaat gcttgtaatc cccaccactt  18420
tggaaggcca aggcaggtgg atggcttcag ccccagaagt tcgagaccag cctgggcaac  18480
atggaaaaac cctgtctcta caaaaaaaaa tacaaaaatt agctggacgt ggtggtgtgc  18540
acctgtaatc ccagctactt gggaggctga ggtgggagga ttgctgagct ggggaggtga  18600
aggttgcagt gagccaggat ggcgccactg tactgcagcc tgggcgatag agccagacct  18660
tgcccccacc cccccaaaaa agaaagaaag aaagaaaaat atgaaaataa aataaatttt  18720
aaaagtacat tggatcattt cactccccct taaaatcttt tcttggcttc tcattgtagt  18780
cactgtaagt tcctgacctc caaggctctc tggcctcatc ccttcactct ggtctccagt  18840
ccttccactc ctgtccactg gcctgcccct caggtgctgt aattctctag gccctttcct  18900
ccttgggatc tttgcatatg ctattcctcg tgcttgaacc atcttccccc agctcttcat  18960
ctggctaatt cctgcttgtt cttgaggtct tcatctcatt gtcactttaa gagagggatt  19020
tcctgacctc tctacccaaa ggaggggcct cagatatatt ctgtcattgt ggtctatgct  19080
tctttgtaac gtatatcaca ttttaaaatc acgttcattt gtgtggttct ttaattccca  19140
gatcccctct ggacttggtc tgtttccttt cttttctgga ggagttcctc aagtttcttc  19200
tctatccctt caattgaggt tttcatttct gttgccatat tttaaatctc caagcagtct  19260
gtcttgttcc atgaaaggtt ttacacacac acacacacac acacacacac acacacattt  19320
```

-continued

```
tatatatata cacatatata aaacctttca tggaacaaga cagacatata tatgtgtata  19380
tatatgtgta tatataggta tatatgtata tatatgtgta tatatatgta tatatgtgta  19440
tatatgtata tatgtgtata tatctaaaac ctttcataca tacatatata taaaaggtgg  19500
ctcacgttca cctgtattaa actgtaagtt ccctcagggt aaggactgtg ctttttttcat  19560
cccatgagtg gtaagtggta gatttctgac taacaaaatt accagacatg aagtatgagg  19620
gcaaaaaaaa gttaaaggaa aaattaggaa tatggacaaa aatgtgattc atggatagtc  19680
ttcaaagatt aacagtgttg tcttgcccag aatttaatag agaaaaaaaa atggacttgc  19740
agaaaaactt gaggcccttc aagctgtcat catatcagag gtgataagac ccagtgaact  19800
gtttgagaaa ttgggtaatt gtcactaggt aaaggaaaag gattgaaaat tagataaggg  19860
ttagtcccac aaaagaaatt ttaaaactgg gctgggcgcg gtggcttaca cctgtaatcc  19920
caacactttg ggaggctgag gcgggtgaat cacgatatca ggagtttgag accaacctga  19980
ccaacatggt gaaaccccgt ctctactaaa aatacaaaaa ttagccgagt gtggtggcag  20040
gcacctgtaa tcccagctac ttgggaggct gaggcaggag aatcgcttga acctgggagc  20100
aggaggttgt agtgagctga gatcgcacca ctgcactcca gcctgggtga cagagtgaga  20160
ctctgtctca aaaaaaaaaa aaaaaaaaag gaaattgcaa aactgaagta aaatgaaaca  20220
aaatatgaca cgtataaggg caatatttct ggccaagatg caacaaaatt catttcagaa  20280
gtccaaagtt caaatacaca tctacccttg ctgcctctct tgtagattag ggcatgaccc  20340
tataagatta gagaacagga gaggagacaa caggaaacaa gcaaaaaaag accagaagct  20400
gaaaagcaga taataggaag taaatggcag cagaaccaag aaaacataat cctgttcagg  20460
tggtagagaa agcaagaatt cccaggaatc aactggtggc accaggtatc tcttgataca  20520
agagtgaagt ggaactaaaa cgaagaactg ctaacctcca gatctcatac tctacaaaat  20580
gtaatgacta cccctctacc attctggcag aattattctt aggagagagt aaaacactct  20640
caagagagaa taaaacagag aggtctctga ctggagaagg ctagcaacat agtatcccgg  20700
ttaagggtgg ggtactatga tgagtgatga gggagattaa gtgaacaact gcatacttgg  20760
tgtagggaca ccccccatcc ccccctcacc ccaccgccac ctgctgcggg ctattacctt  20820
tctgccctcc tatttatctt ccagaatgta ggtaaatttc accaatttct ccactaaaat  20880
tctttttgtt ttccaggatc caattcggta ttccacaatg taatttagtt gtaaagtctt  20940
cttagtcttc tataatcttc tgacagttcc tcagtcttta ccttgtcttt catgagtcca  21000
ctgagggttt taaatccccc actcttacat agaagcagac aaccatggat ttccagatat  21060
ctgagaacgc ctctaatata aaagacaaat accaaacaaa caaaagaaag aagccaggcg  21120
cagtggctca tacctgtaat cccagcactc tgggaggctg aggtgggagg atcacttgag  21180
acgaggagtt caagaccagc ttgggcaaca cagtgagaac ccatctctac agaatattta  21240
aaaattagct gggtgtggtg atggatgtct gtagtcctat ctatgaaaga gtgtgagata  21300
ggaggatcac ttgagctgcc actgcattgt actccagcct aggttagaaa gaaagaaaaa  21360
gaattcagag actacacaga gaagaaattt tctagaaaac tattaataat atactcaaga  21420
aaaattttcc aaccgcaaaa caagaataga atactatttt taaaaacttt catggggctg  21480
ggcatggtgg ctcatgcctg taattccagt actttgggag gtggaggcgg gaggattgtt  21540
tgaactcagg agttcaaaac cagcctgggc aacatagaga gacccctctg tctattgtat  21600
atatataaaa tatatacata ttatatattt ccaaggagga aagggcctag agactatata  21660
```

-continued

```
tatgtatata atctccaaga ggccaggtgc agcggcctct tccgtcaagc cttagcacct  21720
ataaacttta taaaacctac tctctgtgaa ttgtgcatgc cactaatctt catctagcaa  21780
tacatttctg ctcattcttt aaaattcatc tcaagtacca tttgatttag acgagccacc  21840
tcttggttcc agtggcttcc tgatcatacc tctagtgcta tattgtaacc atcacttaat  21900
tagttcatga ttttttctct tctagactat aagttacttg aacatatgga tttgagtcag  21960
taggtatagg tgagacatgg gaatctgcat gttcaacaaa ttcctcctgg cattctaggg  22020
ctccaatctc aggtatgttt gtttcttttt tttagacaag agtcttgctc tgtctccagg  22080
ctggagtgca gtggcgcaat cttggcttgt cgcaacctcc cgggttcaag caatttgcct  22140
gcctcagcct cccaggtagc tgggactaca ggcgcacgcc atcatgcccg gctaattttt  22200
atgtttttag tagagatggg gtgtcaccat gttggccagg atggtcttga tttactgacc  22260
tcatgatcca cccgcctcag cctcccaaag tgctgggatt acaggcgtga gccaccgcgc  22320
ccggcctaac ctcagtttta agtggttttt aaaatctact tcaactctga aatatcaagg  22380
cttttcctcc ctgcaattta actggtattg gggagggcag gtaaagcttt cgggtagttg  22440
attaaaaaca acaacaaaaa aagcaggggc cgtcttcttt cgtgcccaca ataagagctt  22500
atactgaaat gtagagtaag gtagataagt agaaataaga taaataccct tatttcattt  22560
aacagtgttt gcacaatgtg tccaattttt attcactagt tctaaaacta ttgagggctt  22620
actatatgcc agacactgtt ctagtcattg ggagtacatc aacacagaca aaacccccta  22680
ccctatagga gtttgcattg gtaggcaata agcaaataaa ataagtaaag caaagtattt  22740
tagaaggtga taagtattgt ggagaaaata gaacatttag gggagctttc ttttatttgt  22800
cagtgtttag taataaatta ctagagagag taatttttaa aaatttgagc tatttaaata  22860
agccatactt taaaaggcag gatttaacct acatctaatc agaagagaac ttgggatttg  22920
caaaattcag gtctggtttc ctgttataaa gttgacagta aatggctttc ccattatgtc  22980
aataggaatg aaataattta gtggctcagg gaattgcttc caaggagtca aaagtaaatt  23040
gtgtttatat aatttttttt actactatta aaaaaagcca caaaccagaa aaaaattgtt  23100
ttgtacttgt ctacaaggca gagttaattt tattattaaa aaaaatccta tactctaaaa  23160
cctcttctat tatctcctca cttcttcgtt ttaatttttt gtttgcattt tcacgtttag  23220
gtaaaaagat attggtcctt ttaggatata tggggataga attatatgag gaagcacagg  23280
actcctggta tggaatgagg aagctggaga tttgagctta acctctctgg ggtgcttaga  23340
actaagtaag agaagcagtc tgtttctgca gggaaaatca cttctccatc tttactctcc  23400
aaataactta cttaatcaaa tggtctaatg tttcattgta aagagtctta aaagtcaaaa  23460
ttaatgtcac ctgcagagta agctaaacga gtgatgagct ttgttttgca cagcagttga  23520
aactgatttt caaagtccca ccaaacagta aaagactttt cttgcatttc tgaaaaacta  23580
gaactgtgtg gtgattctga agactgtcag ttcctgtggg gtgtttacac aaaggtactt  23640
ttaaatgaag agtcattttt agagcaatta gagaaaaggc tagacagaga agagcggctc  23700
aggggcttgg caggtcgggg ttaaggttta ttgacaggac agggtcaggc gtctgcttag  23760
ccaccactgc cccgagtacc tgccctccgg atacacccaa gacctccctg gccttggctc  23820
cctgccatag gccaaactcc catgcagaat gaggagaggg gaaaggagga agaggagagc  23880
aagttctgct ggttcagtat tgaactgcaa gtatgaaaat gtttgtgtat atttttctgg  23940
cccagatgtt gtgttaacat taggaagaag aaactttaaa acaaagaatt gtctgttctt  24000
tcaactttgt agtttgcagt ttgcatcctg aagaaagaaa ttgcctagct aaagtagtct  24060
```

-continued

```
tttaatttca ttttttagtt ttgagttaca ggtttctggc aagctccctg accactactg  24120
ttacctggtg gcgcctatat ttcatcaaat ttagacatgc agactacctg gatccaggcc  24180
cagatgaact gttgtgactg ataaacatga tcccaccctg cccccatgca gactcctgct  24240
tttcccttta agggaatcta agacgttgag tcgccggatc cccaagggag ttaaagaaaa  24300
atgtcttccg gcattcacat ttgctctgtg gttttcttga gctgcatctc tgcttgccca  24360
gaggctggtg aacatcccag cagtgccctg acttctccag tgttggtaac taatggaggg  24420
aaattttttt gtttttaata aaaacaagca gagacatcta tcagtactca cagacaaggc  24480
agaatttgtt tgacatcttg tgattgctgc gtacaaaaag aatgacagca gttattaaac  24540
aaataagaaa aaagatgctg tttattgata gttttcagat atcctaagaa tatttttagt  24600
aatcttactg cctttgcttg cataagtaaa aaaagtggaa ttgttaattt ttgcaatctg  24660
ggttgtatta gatttggaat cataataaaa atgtaaatat taagcaaata tgtgctgttt  24720
agctatgtaa catactcgtg gcttttcctt ttattagaat ttatttcaaa tacttgtttt  24780
taagatggta aggtgagtat tagcagtcaa tgcaattaaa cttaattgca ttttctatat  24840
gaattgtttt tgtctctttt taaatgtatt tatggttctt tttctccata ctagctattc  24900
ctataggttt gtcttgacaa aaaattataa acaattgttt gtttgcagcc gggtgtggtg  24960
gcttaacatc tgtaatccca gcactttggg aggccgaggc gggctgatca cctgaggtcg  25020
ggagttcgag atcagcctga ccaacatgga gaaacctcgt ctctactaaa aatacaaaaa  25080
attagctggg cgtggtggca catgcctgta attccagcta ctcaggaggc tgaggcagga  25140
gaatcgcttg aacccaggag gcggaggttg cagtgagccg agatcatgcc actgtactcc  25200
tgcctgggca acaaaagcaa aactccatct caaaaaaaaa ttgtttgttt gcttggaaac  25260
agtctaaagt cacaaatttg atttcagttt catttggaaa ttttaaaatg aaaaattggg  25320
acacagtcaa gtgggaaaag catttaaact gttcagtgac tgaactttcg ttttcatatc  25380
atgttaatgt gatctaaaaa aaataatttc ttcctggcct aagttacccc acttgaggat  25440
tgttacagtg atttcaatcc ctgacctcac cagatgatgt ggaagcatca ggccacatat  25500
ttttataagt actgggtgag ggcaaagatt tgcttggaag ggaggagaga acctcctgga  25560
aggttgataa tagtttgtat cttgatagat gttggttaca ccagtacatg cattcgtcag  25620
gactcatcga atggtacctt aagattcgtg catatcatgg tatgtaaatt ttacctcaag  25680
acaccaacaa aggaacttat aaacatatat taaaatctag catgttgaag tattatagga  25740
gagtgaatac tgatcttgat ctttaaaact tactttgaaa tgcacccccc aaaaaagatg  25800
ggtgaatgga tagtgaaacg tttagaaatg tggtaaagag taagtatagt aaaatgttaa  25860
ttgtcaaatc taggtagtgt gagtgttcac tgtaaaattc tttttttttt tttttgagac  25920
agagtcttgc tctgtcaccc aggctggagt gcagtggtgt gatctcagct cactgcaagc  25980
tctgcctcct gggttcacgc cattccccca cctcagcctc ccaagtagct gggactacag  26040
gcgcccgcca ccatgcccgg ctaatttttg attttgtatt tttagtagag atggggtttc  26100
actgtgttag ccaggatagt ctcgatctcc tgacctcgtg atccgctcac cttggcctcc  26160
caaagtgctg ggattacagg catgagccac tgtgcctggc ctcattgtaa aattctttca  26220
gctttttgt gtgtttgaca taaaatgttg tgttccataa aatgttggga aaaaatgaag  26280
gtactggttt ttgctcattt aaggatctgt gtacctccat tttaaatccc ctccttaatt  26340
caaaatcaga ccacttggta ttaataccaa aaaggggaag ggtgtgaaag tagccattta  26400
```

-continued

```
gcataaacag aaaaatgtac ccacctcata ctttctctag ttacctgctg aaagaccatt  26460
accaagcatg gaggcccagg gggtctttac aaacaagaat aattctgaga aacccaaacc  26520
acaaagccca accaatgacc tctccaggca gataaaaatt ggcctccaga accctaacca  26580
tgaaaaaaga catgacttcc tacatgtaat cttcaccaat ggcaagcagg taaccccccg  26640
ctatatacct tatactaaga ccctatggaa tgaaaatggg cttttggttt tcagccaaat  26700
ccccaggatt tggccatgaa cacctccact ttatcagaat gccaagctat tttttacatc  26760
ctgataaagc tcctttttta aagacatata gattgtgtgt gtgtgtgtgt gtatgtgtgt  26820
gtgtgtgtgt gtgtgtgtgt gtgtgtttta atcttgaagg gtcaaaagga taagttggtt  26880
ctggtagaat ttgagccaaa cttttaaaag ctaatgataa tatatttttt aattaggcca  26940
tattgctcag ttgatgcttg agcagtaaac tagaaaatca agatttgaga ggctcagtga  27000
tctcaattcc ttcagggtct catagtgaac tctggccagt taatttatct ccaaactttg  27060
attttctcat ttggaaagtg agaataaagc ctgacacaaa atggctagcc catggttctc  27120
aaacttttgt gtatgtagga atcattggtt aagaaacctt ggtgtgtgta aacataattt  27180
agtttattaa aatagagatt cctgggtttc aaactgggtt ttctcaatca attgttctag  27240
ggcagagccc agaaatctac attttaataa gcacctagtg tgatactgat gcaattattg  27300
gaccacagga tatatggtgt agatgtgttt tgatgggtat tatattaact gagaattttt  27360
ttagcttttt gttatggaaa aaaattatta ttattattat tttgagacaa gatctcactc  27420
tgtggcccag gctttagtgc agtggcacga tcaaggctca ctgcagcctt aacctccagg  27480
gctcaatcaa tccacccacc tcagcctccc gagtagctgg gactacaggc aagtgccacc  27540
atacctggat aatttttgta tttttttgta gagatggggt atcgccatgt ttcccaggct  27600
ggttttgaac tcctaggttc aagcgttctg cccacctcag cctcccaggg cttccaaagt  27660
gctgggatta caggtatgca ccatgttatg gaaaatttta aatatgcatt agagagaata  27720
atggtatgag tctccgtgta agagatagaa gcatcaccca acatccatca gatttttttt  27780
taagagtctg ggtcgcttcg ttgcccaggc tggagtgcag tgacacagtc agctcagtgc  27840
atcctcaaac tcctggactc agcgtgcctg tcttcacaac ttcaataatc ttgattcact  27900
ttgacattca ccctttcctg catccctcct ccaaggtgat atgtagaagc aattgttaga  27960
tatatcatta catctagtaa atattttagt aggcatctct aaaatattaa aatataagta  28020
ctcttttaaa gatatatgat ggttaaacct taccaaattt gagagtaatt tcttagtatc  28080
aaatatgtca gtgtctagat ttccttgatt atctttttgt ttgtttgttt cagttgtttt  28140
gttagaatta ggaaccaaac atattcccat gttgcatttg gctgatatgt ctctaatcgt  28200
ttattctata ggttccttct ctctctgttt ttccccttgt ggtttatttg ttgatgaaac  28260
caggtcattt gttctataga ttttctcagt ctagatttcg ctttttgggt ccccatgatg  28320
tcatttacct ttttttcccc tcctgtttcc tgcaaattgg tggttccatc acttccctcc  28380
tgaagtatga tcagattcaa gttcagtttt ctggcaggaa tacatcacag atagcgtctt  28440
gtacatcttt caggaggcac acgtttggtt gtctcacttt ttgtcatgtt agcaccattg  28500
atggtcatgg ctgagatcct ttatttcctt agggagagcc ccatatttta acttagtgag  28560
tagctcatga atctctcccc ttcatcatgg agttttttct tttctaagtt agacttctag  28620
agctttcaca gatttcacag tgagcccata gcgcctacct agacattctg tttgctgtag  28680
aaaccagaaa ggctttcttg ctctcatatc ttagtttaat ttacacaata tagtaatctt  28740
taaaatttgt cctagtgtcc cccaaatttg tttctatttc tgagacatgt taagatgaat  28800
```

-continued

```
ggatgacaga acagaaagtt gagggctcta gagtgaaatc acagttgcag gtaagttgac  28860
gaggtgcaag tacaaataag acacagtcac caattctgta ccaacatcct atccagaggg  28920
aaggggataa atttttatta tctatattta cttattttgt cctgacagca aacataaggt  28980
ttctgggtca ggagcagaca attatgactt agagcattaa ctaagtcaat tccccatacc  29040
ccagtaccct ccttcagggc aacataaagg ggtctagaag aagagggcct ggaagaatga  29100
ggttggatat gccaagatta ctccaggaac tgagaatgaa tggaatcatt cctttattca  29160
gcaaacccac tgattgtcgg ctgtatgcca gacactaggg tagatgataa atactagaaa  29220
actcccaacc taacacacaa aaccatatgc ctctgtgtct agagttaggc atcaggtgtc  29280
atcttgtgct tataggtaaa tcacataccc acagttacat gccctgcaat gacattttgg  29340
tcaacaatgg actgcatata tgatggcagg tcccataaga atataatgct gtttttacag  29400
taccttttcc atgtttagat acacaaatac ttaccattgt gttccagttg ctgaccatat  29460
tcagtacact gacatgctat acaggtttgt aggctaggag caataggcta tcccatatag  29520
catagggatg tagtaggtta taccatctag gtttgtgtaa gtacccttta ggatgttctc  29580
acaatcacag atcacctaat gatgcatttc tcagaatgta tccctgttgt taagtgatgc  29640
atgactgtat ttgtgtgtgt aaggatatga gtgtgtatgt gtatttatga ttttgtacgt  29700
gtacacgtgt gtatgtcata ttcccttctg acttaacatt ataatttctg aaaatctttt  29760
tcttcatttt taatttgtct tcagttgtcg tttgtgctaa agtttgcatg aagttttctt  29820
atccctcact ttccaggtag cagtggaatt tactctctac cttctgttgt gtctgctcat  29880
gtgacaagtt cttttggtaa gaaagtaaag tctaaactat aaaagttaaa ctctgaaaga  29940
agaaaattca ggtgcaaagt gacaaggatt tcaccagact gaagagacct aaagaaaggg  30000
agggccagat ccctcagctg caagtctctt gatttggtga gggattaaat gtgctaggtc  30060
ccctggtact agtgggggct ggggtttcag acctcacgga gttgccattc tgatggggaa  30120
acaatagacg caattagaca aacaaacatg ataacttcaa aatgagaaac gtgcgtttag  30180
ggaaataaac aaagctaaga gggtgccagt aactaggggg gaccacttta gagagagagg  30240
tcccagaagg cctgctgatg aagtgacatt tgagctgagg ctcaaaggcc atgaatgggc  30300
cagtgatgtg agaacttggt gaaagagcaa atgcagagcc cagaaagggc ttagtgtctc  30360
tgaggagcag aaagggggcc cctgtggctg gcggcagtga gtgacaggag ggtggagtgc  30420
caggaggcca gagggaggtg gggtcagacc attgcaggcc ctcaaggcca taatgggaag  30480
ttgaaactat gttcaaaaag cagtggataa acattgaaga gtttgaagca ggaaaactta  30540
gtaattattc tcacctagac ttttttttcct acacatgagc agacttctgt atgtgtgtct  30600
gtgtgtgtgt gtgtgtgtgt gtgtgtgtgt gtgtgtgtgt gtgtgttttc ttagtggtaa  30660
catgctgtgt atataatatg caacttgttt ttcatttacc aataatatct tggtcatctc  30720
tgaaaggaag acttataaag aaaaataagg tttgccacga actatataac aaatttagac  30780
atgcaaaaat gtgaagctgt gatggaaaat tagtttctta ggaataaaaa aggaaggaga  30840
gtgcttgttt ttaatgtctg ttatacctat gaattccctg taataattta aggacattaa  30900
aaatgtattc taacttgatt cttgattttc tcataaactt gccatgatta gtatgttact  30960
ttaattatgt atttattgtt aaagcatctt tacacaccat ttttagtctt ctaaaatata  31020
gcagagactg aacaaagtag gaaaatagaa gaataagaat tcagtagaca tgcatggtca  31080
aaccataaca aacccaaaga tactgagact ctagagagaa tgtgtcacct ttcaaagtac  31140
```

-continued

```
tgcttactat tgccagtagt tataaatgta cttattagct gggcatggtg gtttacgcct  31200
gtaatcccag cgctttggga ggctgaggca ggaggattgc ttatctctgg agtttgagac  31260
cagcctgagc aactaggtga aaacctgtct ctactaaaaa tagaaaaatt agccaggcct  31320
agtggcatgt gcctgtggta gtgcacgcct gtggtcccag ctactttgaa ggctgaggtg  31380
ggagaattgc ttgaacccag gaggctgagt ttgcagtaag ctgagatcac accactgcac  31440
tccagcataa gggatagagc caaaccttgt ctcaaagaag aagtacttat ttatttgctt  31500
ttaaaatata cttttgtgaa aagatatacc taaaatcccc agcacatttt agttcttgcc  31560
catttacaaa atagtatata gacaaaagcc tgactaagag aaactgtcaa tattacagcg  31620
aaacagagat agggattgtt ttctggtctt agagttacca taacatgagc atctgtggtg  31680
agcaaatatt ttccagaaaa gcaggtgaat gaaaaaacta tagcccacaa aaataaccgc  31740
ctcaaactca tgatccctaa tgtaggctca tttttaagtc tacattttat ttttatttct  31800
acttacttac ttatttattt tttgagacaa agtctcactc tgttgcccag gctagagtgc  31860
agtggcacca tctcagctca ctgcaacctc catctcccag gttcaagcaa ttctaatgcc  31920
tcagcttccc tagtagctgg gatttacagg catgcgccac cacatccagc taatttttgt  31980
atttttagta gagatggggt ttcactatgt tggccaggct ggtctcaaac tcctgacttc  32040
aagtgatcca cccgcctggg cctcccaagg tgctgggatt acagacatga gccgctgcac  32100
ccggccttta agcctacatt ttattttatt ttatttattt atttatttat ttttttttgag  32160
gcagagtttc actcttgttg cccaggctag agtgcaatgg tgtgatctcg gctcaccaca  32220
acctccacct cctgggttca agcaattctc ctgcctcaga ctcctgagta gctgggatta  32280
caggcatgtg ccaccatgcc tggctaattt tttttttattt ttattagaga cggggtttct  32340
ttatgttggt caggctggtc tcgaactccc gatctcaggt gatctgccca cctcggcctc  32400
ccaaaatact gggattacag gcgtgagcca ccacacctgg cgtaagccta catttttaaa  32460
aaaatgtatt gcagaggtgg aaatgaacta aagtaggcat gaagtaaggg tcgaggtcca  32520
agggtgtgtg acacaacatt gctaccatgt tatagaggga tattctaaac aaaatctctg  32580
cattcttacc ccatgaaccc tatcttcagc ctttaccact ggaaagcatc tttctaaatt  32640
caaatccttg atttgcttct ggttttgtaa taaagtcatg agcaatagga atgcagccag  32700
caattacgtt tctgcttttg tcttaaattg gagaccatgg agcgacatca attcgcagga  32760
aatatactgt ttcttaagaa agtctttcat ttaactttct tctgtactta aaattggaaa  32820
tatatttagc ttctctaaat atttagttgt atgtgaacca gttgttaaag aatgtcttaa  32880
ttctacagtt aagctcactc acatgtatgt atgtctcata cattaaaaat gtcatcctgc  32940
tgtgtagttt taagaaatta cttttcagaa gtaaagactt taggtatgat aatgataatt  33000
taggaaatga taatttagga aaattttctc aagtactcat catttttaaa aattcataat  33060
tcagaaatat tttattggga gactaaagac atttatagta ttttccccca gagtgtcata  33120
tttttataaa acaggttatt attaacaaat gatataattt gaaataattg gaaaggtcca  33180
ctggccctaa aatatgtccc ctacagcctt cttggaacat aaaatgtcca actacgtatt  33240
agaattttct ttgggttaat ggagtatcct cataaaggct tagtttaata ggagttatca  33300
ctctgggttt tgccaagatt gctttagaag gaatgagttg ggtatgtttt cagtagtctt  33360
ggtgaagacc ccagaggaag agcagagggt agggatcttg gtgggagaga agggagacac  33420
tcccctacca ggggctccaa aagagggctt taggttgtag gaaaggtggg caaagcctgt  33480
cctttataat aataaaatgt ttagttagag gggagccata tttaaaacta tagcactaga  33540
```

-continued

```
cttatctcag ttgtaaaatg gatattatat aataagatgg aggaagtcat tcacatatgc  33600
tttctctctc tttttgagca caataccaaa gtgtttccag aataatttgg caccttcact  33660
tcctgcacag acttggagta gagtccagaa aacagtctag ttgaattctc agatgggttt  33720
ttggcaagaa tacaaagtag ctttatacag ctcatctctg atgcttttca ctgagtgtct  33780
gaaagaaaag ggaggatttg aggacctgat ttaaacaagg aagtaaccca gtgacttaaa  33840
gaggagtgtt gtggaattcg aatcccaaaa taaagcccta cgtcgttgac ttttcagcca  33900
tgggaataac cagttgcttc attgtgtgtt ttgtcaaagt gcctcagcca tttggtcggc  33960
ctgatggtta cctgctgcct ctattcatag tttctgcgtc ctttcttgtt gcccggctgg  34020
tcaaacatgt gtaacggtgc cctggggcac caagcatgcc ctcggggagc taaatgctgc  34080
cagatgtagg gagcaagggt tgattcacat agccatagtt tcaatagcta attttacctg  34140
ttttcttttg gttttgggtt tccttcttaa agaaaaaccc atttggagtt gagtttttcc  34200
ccctttaaat tgcagtctta tcttgttacc tctaatctcc cagcctcatc ccactcccga  34260
aataaaagtg tgagaagaaa agaatagaaa agatacgtga tttattaagt ctgagagatt  34320
aatagtttta ctttatgata aaatcagtaa aatgtttctg ttttactgga ttctgattag  34380
tattcttatt tcaaagtgaa attatgtttc acttgactca accttccctg tagaaatcat  34440
ttagatagaa atagatcatc ttctagatag atactttatg taatctctga ttaggaacac  34500
tgaatttgtt gttgaaagcc ctatattttt taactcactc ttgaaaactg gttaagtaga  34560
aggaaagaat caagccctta acttgatata tcctgtatgg aactgaacct caggatgacc  34620
aaatatttga tgaaagaaag tttctctttt tagaagtatt tctgccaaca aattaagaag  34680
gtctgagaga atatcaccat ttggcaaacc cctcgtgaaa taatgaatct atctactggt  34740
catcaatggt tgctaacatc acaaaaagag ccacagctat cagagcacac cactgtccat  34800
taaatattct tgccaaaaaa attgaacttg aggccgggcg tggtggctca cgcctgtaat  34860
cccaacacgt tgggaggccg aggcaggtgg atcacgaggt caggcgatcg agaccatcct  34920
ggataacacg gtgaaacccc atctctacta aaaataaaaa ttagctgagc ctggtggcgg  34980
gcgtctgtag tcccagctac tcgggaggct gaggcaggag aatggcgtga acccgggagg  35040
tggagcttgc agcgagctga gatcacacca ctgcactcca gcctgggcga cagagcaaga  35100
ctccatctct aaataaataa ataaataaat aaataaaaat aaaaaaatca aacttgaatc  35160
agaacaaatc cctagattta atatgtctac aggaaataca aaggacagag aaacatatta  35220
attgacacca ccaagataca actggtaagt tacagaatgt gagaagtgct agggacaaat  35280
tcattttctt aacaaataat ttacgagaaa gaaaaaaggg aggaattcat taaaactggc  35340
ataagagaca tagcaatcaa gtacaataga ccttatttgg ctcctatttt aataatacat  35400
ttgtttaatt tttttttttt ttgagacgga atctcactct gtcacccagg ccagagtgca  35460
gtggtgcgat cttggctcac tgcaacctcc gcctcccgag ttcaagcaat tctcctgcct  35520
cagcttccca agtaactggg attacaggtg cctgccacca tgcccgggct aatttttttg  35580
tatttttaga gaggcaaggt ttcactacgt tggccaggct ggtttcgaat tcctgacctc  35640
aagtgatgtg cctgtctcgg cctcccaaag tgcagggatt acaggtgtga gccaccgggc  35700
ccagcccatt tgtttaattt aaaaaagaat atatgacaaa aggagaatat ctaaaggctg  35760
ataaaatatt tgatggtact aaggaactat tgttaatttc taaaggtata atattatatt  35820
attaaaccat taaaaagagt tctcatcaca ggccgggtat ggtggctcac ggcctccagc  35880
```

-continued

```
actttgggag gccgaggcgg gggggatcac gaggtcaggg atttgggacc agcctggcca  35940
acatggtgaa accctgtctc aactaaaaat acaaaacatt agctggcagt ggtggtgcgt  36000
gcctgtaatc ccggctactc gggaggctga ggtaggaaaa tcacttgaac ccaggaggcg  36060
gaggttgcgg cgagtggaga tcatgccatt gtactccagt ctgggcaaca gagcaagact  36120
tcatctcaaa aaaaaaaaaa aaaaaaaaag tcctcatctt ttggatgtac acatggaaat  36180
atttacagtt gaaattatat gatatctgaa taggcttcaa aattatccag tgggaaggga  36240
tgatggttat ggatgaaaca agattggcca tctattggcc attgttgaag ctgaatgata  36300
gatacatggg gatttgttac actaatctac ttttgtgtgt ttttgaaatt gtctataata  36360
aaaagttttt aaaataggct taggtaaatc ccagatttgc cacttgtaaa tttgtgatcg  36420
tggacaaatt cattagcctc cataagtctc agtttttgtg tgtgtgtgtg tgtgtgtgtg  36480
tgttatttct ggttagggcg ttgcctataa aataggtaca aggttatttt cccagtttac  36540
cacctggtcc gggttgttgt gccaaactta ataatatgta tgatgttact ttgtaaattg  36600
ccacaaatat atcaactgtt ttattattat gaagttcctg aaaggatcca ggttttctgc  36660
ttagaaaatt tagtagcttt ttctgcttca acaagcagta tggctgtcta catagattat  36720
atcaactaaa aagctctgga ataagaatat aattatgtat ccaacaaggg ttttatcaat  36780
tagtttgtag taatagagta attataagac ttcattttaa aaaatttgca aatataaatt  36840
tctcatggcc tagtaaatta aatgtcgtgt agacaactgt gctattaatg ttttccctgt  36900
atagtaagaa ttgtgaatta tttctgattt cttatttttc ttgattggaa gaaattgctt  36960
gaatttaaca catcaataaa gattttaaat ttattccttc aaaatataga gaaaccctga  37020
ttgttagaat ttttttcttt tttttttttt tgttgtttta ttttctaatt ctggcctcat  37080
ttcttccttc ctaactccca gcattttatt gtgaaatatg tagagagaaa cgtgtaaaag  37140
aaatatacaa tttaatgaat gattatgaag caaataccta tgtaactact gtactgtgtt  37200
tttttttgt ttgtttgttt gtttgtttgt tttgagacgg agtctcgccc tgtcacccag  37260
gctggagtgc agtggcccga tctcagctca ctgcaagctc cgcctcccgg gttcacgcca  37320
ttctcctgcc tcagcctccc gagtagctgg gactgcaggc gccggccacc acgcccggct  37380
aactttttgt atttttagta gagatggggt ttcaccgtat tagccaggat ggtctccatc  37440
tcctgacctc gtgatcctac cgcctccgcc tcccaaagtg ctgggattac aggtgtgagc  37500
caccaccccc ggcctactgt actgtgtttt aagaaaaatc agaatatcac cagcacctca  37560
gaaaacctct gcatgcttct tcccagtcca aatctctttc atcccctggg tagccactat  37620
cctgacttta gtagtattca ctttcttgct tacctttata gttttaccac ttgtgtatag  37680
attcctaaac agtgtgattt tgtttgtttg tttgttttga gacagggtct tctttgtcac  37740
ccaggctgga atgcagtggc atgatcacag ctcactgcat cctcaaccta ccaggctcaa  37800
gtgatcctcc cacctccacc tcccaagtag ctgggaccac agatgcatgc catcatgcct  37860
ggctaatttt taattttttt tagagacaga gtcttcctat gttgcccagg ctgatctcga  37920
atgcttgggc tcaagcagtc ctcccacctc tgtctcccaa agtgctaaga ttacaggtgt  37980
gagagaccac actgggactg atttttatat tttaaggatc catttatatt gtatctgtag  38040
tgaattcatt ttttttgctg tatagtcttc tgttttaaga atttatggct gggcatgatg  38100
gttcatgcct gtaatgccag cactttggga ggccaaggtg ggcggatcac taggtcagga  38160
gatcaagacc atcctggcta acccggtgaa accccatctc tactaaaaat acaaaaagtt  38220
agctgggcgt ggtggcgggc gcctgtagtc ccagctactt gggaggctga ggtaggagaa  38280
```

```
tggcgtgaac ccgggaggcg gagcttgcag agagccgaga tcgcgccatt gcaccccagc  38340
ctaggcgaca gagcgagact ctgtctcaag aaaaaaaaaa aaagaattta ctgtaattta  38400
ttctgtagtt gatggacatc tgggttgttt ccaccttttt cttttttttt ttgtcgccca  38460
ggctgaagtg cagtggcgtg atcttggctc aatgcaagct ccgccttccg ggttcacgcc  38520
attctcctgc ctcaacctcc caagtagcag ggactacagg cgcctgccac cacgcccggc  38580
taattttttg tatttttagt agagacgggg tttcacagtg ttagccagga tggtctcgat  38640
ctcctgacct cgtgatccac ctgtctcggc ctcccaaagt accgagatta caggcgtgag  38700
ccaccgcacc cggcccgttt ccaccttttt ctattacaaa cagtctgagt atgtcttttg  38760
gatgcacttc tgtatgcatt tcttttatgt gtatacctag gattgaatta gtgacttcat  38820
aattgacagg cagttttcca aggtggttgt accagttgac tctccagcag tattcgagag  38880
atcttgtttt cccacatctt caacctgtac ttggcattgt cagactttta aatgctttat  38940
tttaaaatat tattagtaaa acaacataga taagtttact gttgtctatt acttacatgt  39000
acttgtaatg ttaaagtcta ggttttatgg ctgggggcgg tggctcacgc ctgtaattcc  39060
agcactttgg taggccaagg tgggcggatc acttgaggtc gggagttcaa gaccagcctg  39120
accaacatgg agaaaccctg tctctactaa aaatacaaaa acattagctg ggcatggtgg  39180
tgcataccta taatcccagc tgcttgggag gctgagacag gagaatcgct tgaacccggg  39240
aggcggaggt tgctgtaagc caaaatcgtg ccgttgcact ccagcctggg caacaagagg  39300
gaaactccat ctcaagaaaa aaaaaaaagt ctaggtttta cttggggtgt gtgtgtgtgt  39360
gtgtgtgtga atatttcaga ggtacagaga ctctttctgg tcatcgatat ctacttgcta  39420
aattacgtct tcctacctaa caactgctac gctagagacc agaaaaaaaa atagtagagc  39480
tttaaaaaag gagagagcat ttttgtacct ttttcacttg ttgtgatatt aaacctatga  39540
gtgatagctc aatttatcaa ttgctacatg ccaggcgctg tgctaatgaa ctcttaagac  39600
atgtaaactc atttaatctt tacaacagtt ttttatttcc ccatttttta acagatgaag  39660
aaactgaggc attaaatggt taagtaactt gctgaagatt gtaagctagt aaatcataga  39720
gccagagctg aagctcaaca gttgagcttc actggttcca tctgggttct gaacacttaa  39780
tatctagacc tcctaccccg ttggtgagtt ctggttagtg acattagtcc tccagagcca  39840
ccatgttttg tctccgggtg gctgtatttg agcttgacat gttgtttctg gtgctaacag  39900
ttaggaaagc agggttgctt gaacttcaag acagagactt acttcctttc acttgttgta  39960
gaagttgaaa gaagctgaag cagcatgaga atcctggctc tggggctggt acagctatta  40020
caggaaggga caggacttgg ccctctcttc tcctctctag attttcctgg gggtactcag  40080
ccttcatctt ctgccactta gggtttgagt ggaaatggcc gagaatatgt ggtaggaagc  40140
agtaaagtgg acgtttcaat ttccttaatt gtccaaaaat gtggaatatg ttatccttta  40200
gaaaccatgt tgtaaatggc agcaacattc ccaggccagc tcaaaaaacc tataatgtgg  40260
ccaaaatata tgcttacagc tgtattgttt cctagttttt tgttttcatt gcaattgtgt  40320
agcattttat ttgtcttatg agctactggg ctagctgaga acttagccac attgtttatg  40380
tcggaaaatg cattccaaac agctaagacc acgtatttat cttagtgtag agctaactat  40440
ccatagctta gatcattgac tacctgaaca ctctgctcca agtaaactga acaataccat  40500
caccaatttt ttgacggtaa agagaaaaac atctcagtaa gatagagaaa cattttctat  40560
ggatttactg tgaccgagac caaattttaa ttagctagga tattttttaa attgtagcat  40620
```

-continued

```
tatataaatg catctgtttt tcatttgtta catatgggtt tttatttacc caccctccta  40680
aaacattgaa atatattcat gtagctacct gaaccacttg tagatcttca gacttgtgcg  40740
gcaaaaggaa tgataattat aatctgcttc aggctacagg ctagaataat tcaaaaggaa  40800
atgtgcatta ctaatgcagc agagctcata aattctcaat gtcagtttgc catttatgca  40860
gtcagtctgg ttggccagag gcaaaaagac tagggttaca taatatttat gaggtctgaa  40920
gttagccatc accaaagcca aatattgcca gtgtttcaga ttactcatta aagtcagcat  40980
catctagtca cgccaatgga gttgggagca gggtggattt ggtagtgatg aaacattagt  41040
tataagtata aattctgtcc attttagtcc actactacct cctttacagg atttatagcc  41100
ttcctatttt atatattatc cctgagatgc ctacctaagg agggttccca taccattctg  41160
caaaaatcta cttgccacct aaggtttcat aacacaaaag tgggaatggg actttctttg  41220
ctctgcattg tttctccaac cctcttcatg tttaactcct gagaagacct cctgcctctc  41280
tgtacatcat cacaatggcc aagtctcaaa aacttttaga tcccagctag caccttatgt  41340
catactgtgc tcagaaataa ttaagtgtcc agacccatac tcttgtgctc tagtgcactt  41400
caggagtttg acttgtatag ggtaatgagc agctacaact ccaggcctca gggttactcc  41460
caggaaacac tgtggctgtg aactccaaat taaaaatgtg tgtacaattg tacagtttcc  41520
aacatcaaga agcactagtc cctggggctg ttcataacgg ctttctttgt attttcacaa  41580
aagaacagtc ccagaattaa aataaccctt tcatttccta cacttcactt cttagaagtc  41640
gtcaggaaag atgagttttg gtatgattgt tgatggtgag ttttttgtgg ggtgggggtg  41700
atggagcaaa tacctttaaa actttttttt tttttttttt gagatgaact ctcgctctat  41760
cgcccaggct ggagtgcagg ggctccatct cagctcactg caacctccgc ctcccgggtt  41820
ctaaagcaat tctcctgcct cagcctcctg agtagctggg attacaggca cccaccacca  41880
gtaattagtc ccagctaatt tttgtatttt tagtagaggc gggatttcgc catgttggcc  41940
aggctggtct cgaactcctg acctcgtgat ctgcccacct tggcctctca gagtgctggg  42000
attacaggcg tgagccactg cacccagcca aaactttttt ttgttttatt ttgttttgag  42060
acagagtctc gccctgtcgc ccaggctgga gtgcaactgc ctgccgggtt caagcgattc  42120
ttctgcctca gcctcctgag tagctgggat tacaggcgct cgccatcacg cccggctaat  42180
ttttgtattt tcagtagaga cggggtttca ccatgttggc caggctggtc tcgaactcct  42240
gacctcgtga tccacccacc tcagcctccc aaagtgctgg gattacaggc gtgagccact  42300
gcgcccggcc gaaaactttt tattagtgag aaaagtttta aggatttcag ttaaaccagg  42360
attatagctt aactttaagg atttcatttt accccttttct ctacttttac ctatatttaa  42420
aaatattaaa aagtccgttt ttttctgtca actatatggc atagtgattt tcttccagac  42480
tagtaggtgg agtcggaagt agtattctga aacatgtgga ggaaactaca tcaggagagc  42540
atttgcccca agggagcaat agtgagagga ttccccacac tctcttcgaa aattttaaga  42600
catactgcta ctcccagggg gagatcaaac taaatacaca gcgttttagg aactagagat  42660
atacagagtc cttgttcagc ggagtggcag atttgtttta agtttatttt tgttcaaagt  42720
ttttgatctc ttttactgtt acaagactag gggaaatatc gtaatcgatt gtgctatttg  42780
ctttgataca ttcaggccct cttttttttt tttttttttt tgagatggag tctcactctc  42840
tctcccaggt tagagtgcag tggcacaacc tcggctcact gcagcctctg cctcccgggt  42900
tcaagcaatt ttcctgcctc agcctcctga gtagctggga ttacaggcgc acaccaccac  42960
gcgcggctaa cttgtgtatt tttagtagag acgcccggct aacttgtgta tttttagttt  43020
```

-continued

```
caccatgatg gccaggatgg tctcaatctc ttgaccttgt gatccgcccg cctcggcctc  43080
ccaaagtgct gggattacag gcgtgagcca ccacacctgg cccattcagg ccctcttgta  43140
cctgatagcc acagtataca agaactgaag gagtctgagg ccccccaaag gcatattata  43200
taaagcaaaa acaaacaaac aaaaaaccca cttaaggctg gatgcggtgg ctcattcctg  43260
taatcgcagc acttggggag gacgaggtgg gtggaccatg aggtcaggag ttcaagacca  43320
gcctggccaa tatggtgaat ccctgtctct actaaaaata cccaaattag ctgggcgtgg  43380
tggtgtgcac ctatagtccc agctacgtgg gaggctgagg cataagaatc gcttgaatcc  43440
aggaggcgga ggtttcagtg agccgatagt cggccactgt actccagcct gggtgacagc  43500
gcaagactct gtatcaaaaa aaaaaaaaag aatccactta aatgctcatc attggttaaa  43560
taaggtgttg tgtgacctgt ccgtaaagga attcatgaaa caactaaaaa agatcatgta  43620
gatctatatt gttttgttag agacannnnn nnnnnnnnnn nnnnnnnnnn nnnnnnnnnn  43680
nnnnnnnnnn nnnnnnnnnn nnnnnnnnnn nnnnnnnnnn nnnnnnnnnn nnnnnnnnnn  43740
nnnnnnnnnn nnnnnnnnnn nnnnnnnnnn nnnnnnnnnn nnnnnnnnnn nnnnnnnnnn  43800
nnnnnnnnnn nnnnnnnnnn nnnnnnnnnn nnnnnnnnnn nnnnnnnnnn nnnnnnnnnn  43860
nnnnnnnnnn nnnnnnnnnn nnnnnnnnnn nnnnnnnnnn nnnnnnnnnn nnnnnnnnnn  43920
nnnnnnnnnn nnnnnnnnnn nnnnnnnnnn nnnnnnnnnn nnnnnnnnnn nnnnnnnnnn  43980
nnnnnnnnnn nnnnnnnnnn nnnnntacat atatgtgtgt gtacatgtgt acatatatac  44040
atatgtgtgt atgtgtacat gtgtacacat atacatgtgt gcgtatgtgt acacatatac  44100
atgtgtgcgt atgtgtacac atatacatgt gtgcgtatgt acacatatac atgtgtgtgt  44160
atatgtacac atatacatgt gtgtgtatat gtacatatat gtgtatatgt gtaaatatat  44220
acatatatgt gtatgtgtac atatgtatac atatatgcgt acatgtgtat acacgtatgc  44280
gtacctgtgt atatatatgc atgcatgtgc atgcatatgt gtgcgtgtgt acacatatat  44340
gtgtacgtgt acacatatat gtgtatatgt gtacacgtgt acacatatat gtgtatatat  44400
atacgtgtgt gtgtacatat atttacatat atatatattt tttttttag gatacaggat  44460
ctcactttgt tccccaggct ggtctcaaac tcctgagctc aagcaatctt cccatctcag  44520
cctcccaagt agctgggatt ataggcaccc agctatgaga aatattttaa atatcagatc  44580
cttacaaaaa aaatagtatt cttttattgg aacttcactt ggtttgcact tccaacacct  44640
gttagtttat ccagtcaggc actccatatt tggaaggaag gaggataata tttggggaga  44700
ggaaaggtaa gagaggggtg agttggcagt gatggaaagc aaagtcaacc ccacttggtc  44760
acgactcact aacctccaat ggagaaagtg tgtgagtctg catgtatgtt tgatttttga  44820
tacatgaaag aacataaaaa tatgacatta gactattata cttcaatttt taaaacttaa  44880
gttttttaaa gaaaagtacg tttaatgttt tacaaaaatt attgtattta tatttaatag  44940
cattatattc cattataaaa atttcattta ttgtagcaac caaggagtta aaaaaaacca  45000
aggatagaca aataacaaga aatgtacaag gcctgtatgg agaaaacatt agatctccag  45060
tgatggacat ttaagaacac tggaggaaat gtgaaggcat ttcttatctt aaagaagacg  45120
ttaaatattt tagagtcaac tggacatggt ggctcacgcc tgtaattcca gcactgtggg  45180
agaccaaggc agggaggatc acttgaatcc aggagtttga gactagcctg ggcaacatag  45240
tgagaccctg tctctgcaaa ataaaaaaaa atattgggca ttggtggcat gtgcctgtag  45300
tcccagctac ttgggaggct gaggcaggag gattgcttga gcccaggaag ttaaaactgc  45360
```

-continued

```
agtgggctat gattgcacca ctgcacttcg tctgggtgac agagcaagac cctgtccccc  45420
caaaaaatta tagtcatatt gtccttagat taatcccata aattccaatg taaacccaat  45480
tttgtggcca aaaacacttt aaatatggtg gaaatacaaa aagcaagctg aaaagatagt  45540
tgaaacaatg tagtacacac atttaatatt tgtaattcac agaatactct taaaaataag  45600
tcaggtgggc tgggcacggt ggctcacacc tgtaatctca gcactttggg aggccgaggc  45660
aggtggatca cgaggtcatg agatcaagac catcctggca aacatggtga aaccctgtct  45720
ctcttaaaaa tacaaaaaaa aaaaaaaaaa acccaaaaca aacaaaaaac ctagctgggc  45780
gtggtggcat gcacctgtaa tcccagctac ttaggaggct gaggcaggag aatcgcttga  45840
acctgggagg cagaggtggc agtgagccga gatcgtgcca ctgcactcca gcttggtgat  45900
agagcgagac tctgtctaaa aaataaaaat aaaataagtc aggtgaaaag gctgggcgtg  45960
gtggctcacg cctataatcc cagcaatttg ggaagccgag gagggtggat cacttgaagt  46020
caggagttcg agaccagcct ggtcaacatg gcgaaacccc atttctactt aaaatacaaa  46080
attagctggt cgtggtggca catgcctgta atcccagtta cttgggaagc tgaggcagga  46140
gaattcttga acctggatga tggaggtcat gccactgcac tccagcctgg gtgacagaac  46200
gagactttat ctcaaaaaaa ataaataaat aaataaatca ggtgaaaaac aacccaagag  46260
acctaatagg agacttcaca aaagaggata cagaaataaa caaaggaaaa tatctttaac  46320
ctcaggagta tctgaagaaa aataagtaaa agtgagatac agtttttcat ttatcagact  46380
aacagatttt aacattaaac tgttggtaaa ggtataggaa ataggcatca ttaggaagac  46440
aagttgcagt gtttgtgaac agttttgcaa atatgttaaa gtttgcatat ttcttaaccc  46500
acaaatacta cttttacaca tttaaactaa aaagaagtca tcacttgtgc aactgtactt  46560
gtaaaaaaca cattatataa agcaaaaaaa tcaaaccaaa acaaaaagga cctaccaaaa  46620
tgctcatcat tgtttaaata aggtactatg tgatcccttc gtataaggga atgctccaaa  46680
accactaaaa aggatcctat ataagccggg cgcggtggct cacccctgta atcccagcac  46740
tttgagaggc cgaggcgggc agatcacttg aggttgggag ttcaagacca gcctgaccaa  46800
catggagaaa ccccgtctct actaaaaaat ataaaattag ccgggcgtgg tggcgcacgc  46860
ctctaatccc agctactcgg taggctgagg caggagaatc acttgagcct gggaggtgga  46920
ggttgcggtg agccgagatt gtgccattgc actccagcct gggcaacaag agtgaaactc  46980
cgtctcagga aaaaaaaaaa aaaaaaaagg atcattcata tatatgtgtg nnnnnnnnnn  47040
nnnnnnnnnn nnnnnnnnnn nnnnnnnnnn nnnnnnnnnn nnnnnnnnnn nnnnnnnnnn  47100
nnnnnnnnnn nnnnnnnnnn nnnnnnnnnn nnnnnnnnnn nnnnnnnnnn nnnnnnnnnn  47160
nnnnnnnnnn nnnnnnnnnn nnnnnnnnnn nnnnnnnnnn nnnnnnnnnn nnnnnnnnnn  47220
nnnnnnnnnn nnnnnnnnnn nnnnnnnnnn nnnnnnnnnn nnnnnnnnnn nnnnnnnnnn  47280
nnnnnnnnnn nnnnnnnnnn nnnnnnnnnn nnnnnnnnnn nnnnnnnnnn nnnnnnnnnn  47340
nnnnnnnnnn nnnnnnnnnn nnnnnnnnnn nnnnnnnnnn nnnnnnnnnn nnnnnnnnnn  47400
nnnnnnnnnn nnnnnnnnnn nnnnnnnnnn nnnnnnnnnn nnnnnnnnnn nnnnnnnnnn  47460
nnnnnnnnnn nnnnnnnnnn nnnnnnnnnn nnnnnnnnnn nnnnnnnnnn nnnnnnnnnn  47520
nnnnnnnnnn nnnnnnnnnn nnnnnnnnnn nnnnnnnnnn nnnnnnnnnn nnnnnnnnnn  47580
nnnnnnnnnn nnnnnnnnnn nnnnnnnnnn nnnnnnnnnn nnnnnnnnnn nnnnnnnnnn  47640
nnnnnnnnnn nnnnnnnnnn nnnnnnnnnn nnnnnnnnnn nnnnnnnnnn nnnnnnnnnn  47700
nnnnnnnnnn nnnnnnnnnn nnnnnnnnnn nnnnnnnnnn nnnnnnnnnn nnnnnnnnnn  47760
```

-continued

```
nnnnnnnnnn nnnnnnnnnn nnnnnnnnnn nnnnnnnnnn nnnnnnnnnn nnnnnnnnnn  47820
nnnnnnnnnn nnnnnnnnnn nnnnnnnnnn nnnnnnnnnn nnnnnnnnnn nnnnnnnnnn  47880
nnnnnnnnnn nnnnnnnnnn nnnnnnnnnn nnnnnnnnnn nnnnnnnnnn atagcattaa  47940
atattaaact cttcaaatgg taattgtcag taaaaacaac ttttaaacca aaacaactag  48000
tagcatttct gctttagtag ttaattagag gaagtggagg tggttgcatg caacagtatt  48060
aatttaagaa aagtctttat gtgaaagtgt ctgttaatat tacttgacta ttatgggact  48120
tactgtaaat agttgagttt ttcagttaat cagtggttgt gaaataatag ttttctgaca  48180
aaattagaaa aatttgtttg acatttttat catagtttca ttaaacggtc tccgcataat  48240
tttaaagata actaatttat agctgaaact atttcaatca atgatctaat aacaaagata  48300
agctttgaca gctttaaaaa tatttaaatt ttgtaaggac atcatttgca cagtgattaa  48360
ataaatgcaa aatttaaagg tactgaattt aggctatcag gtttccatgg ttacaccttt  48420
ccaagttatt ttgtgtattg tgtaaatagg tctgtgagtc actggtaatt atttgttttt  48480
ttgtttgttc tgttggtaat tctgtgttta gctgaattta atacagttca cacggcgtgc  48540
tttggtttat gtatatttta gtgtttgtga ttgacagtga ttgagcattt cttatggagt  48600
gcttgccttt tttgtcataa gtgatgtatg ttggtagtgc ttgaaatgta aataagttct  48660
tcctgtatca ctgtttaata aacaggaatt tttatgcaaa gaagacttct tgatacattt  48720
aaacaataag gtttgttgag ctctgaaata tttctgctaa acagattgtg caccaagaca  48780
aataggttta aattcttaca aactgaggtt accaagggca acgttaaagt ttatggctaa  48840
gcacagcatt gactgaatgg tatttagtaa cagaataaaa aaggctgaat tctttttttt  48900
ttttgagaca gggtctcact ttgttgccca ggctggaatg cagtggtgca atctccactc  48960
actacagcct cagcctcctg ggctcaagtc atcctcccac ctcagtcttc tgagtagctg  49020
ggactacagg agcatgccac cacgcctggc taatttttgt atttttcata gagatgcggt  49080
ttcaccatgt tgccccaggc tggccttgaa ctcctgagct caaaggatcc gcacacctcg  49140
gcctcccaaa gtgctcagat tataggcgtg agccactgcg ctcagccaaa atagcagcat  49200
tctgatctaa ctcttaaaat tgtttgtgat agtacacttt acagggaatg tcttcaatgc  49260
aaagtagaat cttcctataa cataatttct cccatcccac cctttgcaca aatttaagaa  49320
gtattcttat atgtttagaa agatatgatt cttgaaaaaa gccagggcct tttatggatg  49380
taggaaggaa ttttccttag acctcaccat taaccatcag catactagca agggcccagc  49440
aggaactctc aggaaaacat caaaattagg ctgtccgtaa ttcatcctac tgagtgtgag  49500
ccttctctca tacactacaa tcatgaaatg ctgtccagtt tgtaaagtgt ttctacatct  49560
gcagtctcat ttggggttca ggttggccct gtgatggagt gaggagaggc ccagtgcttt  49620
ggatggtgtc acttttaagt agcagctctg ggacccaacc taggatctca tgattacttt  49680
gtgaattact tgctttgtgg attatccaag gcacatttta aaattcaggc tggtttctac  49740
ctactgatta gtccatttta gagtgacctc ctcccacagt caggtaacca atgatagtaa  49800
ttaccattta ttgagtgctt accttatgcc actttcgata tatcatgtca tacaattatc  49860
atagcaaccc tgtgaggaag gtattattat ccacattaac aaatgaagaa actaaggctt  49920
aaagaattta actaacttgt ttaagtaaac caatagtact cagagaagga aaaccaattt  49980
aaacaagagc tcaagtgaat ataaatagga aggcatatct tttggaggaa attctcatgg  50040
tgcattcaca agcaaaatat aaaattttaa atttcacact gtttccttct tttttacccc  50100
```

-continued caaattgact ataccttatt aggcattgaa gagttgaggt ttctttgtaa cactccagta 50160
gaagcatact tcaaaaagtg tcccatcccc tcagacaata aatatgtttc aaatgtttta 50220
cacatcaaat attttggtat tgtggcaata ttaaaaactt taaatatgag atgatgaatt 50280
tgtcatttta ctgtgtgaat aatcttggtg ttggctaagg ttttcaagta atgtgttttc 50340
agatatgaga agcaagcagc ctgctatata cagataaaga gtacatgttt ttttggtggt 50400
tggggtggtt ttaattttta acgtttttaa atttttattt tattttaact tttttaaggc 50460
agggtttcgc tctgttgcct aggctgaagt gcagcagcgc aatcttggct cactgcaacc 50520
tctgcctcct gggctcaaac ggtcttccca ccccaacctc ccaagtagct gggactacag 50580
ttgtgtgcca ccatgcctgg ctaatgtttg tatttttttgt agaaacaagg tttcaccatg 50640
tttcccaggc tggtctcaaa ttcctggact caagcgattc acaggcctta gtctcccaaa 50700
gtgctgggtt tataggcgtc agcctggctt aatttttaat ctttagtaca aaaagtaaca 50760
gatagttgaa cattcatatc cttaaatata taagtatata tatttaaata aatgtttatt 50820
tatatttatg tttacttata tacatatatt tacttatata catatttata tttatgttta 50880
cttatataca tatacacaca catacacata tatatgggcc aaattgtaag caggcatcta 50940
tggagctccc cttttaagcc tgtgccattt taacactttg tactttttga attaatacca 51000
aaaactgtcg agtgagtatt catatggtca accaggtata cctagtagaa ttgagtgtaa 51060
aattatttgg gcaacataac tataccagtc caaaaagctg ccttcagaaa atttggagct 51120
tttgctttta ctaaagaggt tactgtatac tttctcttta tttttctggt tgaaaataac 51180
tccttgatga gtgatcttgg cttctgttgt cttgaatctg tgtactctca actgcagaag 51240
cttggaaata tattgttttc ctgaagcatt agctttctca ttttaggtag taattattga 51300
cctatctacc taccgattta ccactcctat tgactggtta cagggcagag acaaaactcc 51360
tacagttgtc aaaataccac gataagattg atattcaaat gttttctttc tatcccatgc 51420
ctttcactta gagatgtaca gtgaaaatct tctcaggaag tttaagatgt agggtttttt 51480 gtttttgtc ttatttgttt ttgatattga tactacaatt ttggtcaaag ctctgagcta 51540
tttcatccca atggtttgct tgtgtggcaa taactttcaa tggcccattg aaaagaaaaa 51600
aggaaagaaa gacatccagc aatataccta gggcatgctg tatctagaat tcagttgaca 51660
ctattgtaat atgaagacta aaatcatgct cttttcaaat gctttaatgt aatttaaaaa 51720
tatattaaag ctgtgctttt gatcatagat tataagccct catatcttct gttattgggc 51780
attttaatac aaaataacta atattttaag tagtatatga cagtagtatt tatgaatagt 51840
ctggaggttt ttttaagaat taaagaagga ttttgttact atatcagttt ttttttaaaa 51900
aactcatgat gtttttatat agactttctc taaaattcag ttccatgtgt gattcctatg 51960
aaattgctct ttctggttct gatttgtgtg ctttaatata aaatcattct attttcctct 52020
tctttaacca aagtgtgtga ggtaacagga atgtttcttt tgagagactt tggaaggttg 52080
aaatttgcca gatgttctgt gctaacctag aagtgtgcat tccctgggta gcaggactgt 52140
gtgaaattct ttcctataac tttgacagag catttggttt tggttcattt tagtgttgtg 52200
cttctactct gatcagagct tgtcttttat tctgtgttta aatgatatta aggcatccag 52260
aaaatctgac aaagaaaatg atattttgat gacatttttc acagggctca actagaatga 52320
attattacat tttaaccacg gccctaataa acagcttctt tatttcctct gtaaggatac 52380
aatatttctt tgtccaagaa gttgcctgag tatatgtatt gttgaagtgc taaaaagctg 52440
cttttctcta aactttagct gagagacaat gggatttgcc aagtatatac catttcattg 52500

-continued

```
tgactcaata ctttataaag atgaatttaa tttaaatttt gaagtaaact ttttttgtct  52560
caaatggaga aattccatgc aatagcccta ttgtacaaat taaacatttc tatgtaactt  52620
ctacttatcc accaaatgat cagcttttag ttttatactt gagttctgac tataatcttt  52680
ggcacccttc ccccagctat aattcggcta gcctaaagga attttttttc ctagactcac  52740
aagcaggagc ctatattatt aagtaggaat gtttatagat ctgtgtttct agagtaggtt  52800
gaggtgtttt agtttcccaa aaagagggga atgcttcttg ttttaaatac agatgcctgt  52860
gtgctggtgg tgtacattag tgaataatca catattaaca gatttagctt ttgtaaagaa  52920
gcaaaatgaa gtgttttcgt aaaccatttc tgaacttgtc attgatgtta tactctatca  52980
gttgctattg ataattttat ttaaaggagg aggtatatag tatagcgcca acttcctgat  53040
taggccttgg ggaaggtcac gttttgcagt gacctgggca ccactcttaa atgttgttat  53100
tattggaaga gggtaccctc aggctgctgc ccttcctctc cccagaagcg ctctgtgact  53160
gactttccag ttcatctttt ctagaaccaa gactcccagg ctgtagatga attctgacat  53220
ctacagacca gtatccatct caacttcatt tgaggtgaat tttattagta gtagtgaccc  53280
agtcctacct taatatgaga atgatgcatc ctcataaaaa ttgcaaactt agagcagtaa  53340
acaactagga taaactttta tgtttcagca taaaagtgag ttatgacttt tttgtcattt  53400
aaaatattgc acacatttcc tttttatttc tgtgggatct ttgttactgt tttagtggtc  53460
ttaagtaaaa ataacttcaa ggacaacacg gttggatgtg aggtagaata tttatttcag  53520
acaagtatta tgcccacata ttttagattc aactatgtgc tttattttca gcattaaaga  53580
aaatgagctg ttttccaaca cctgcatacc aactgggcct gcatcctctt tagaaatgtt  53640
gtttaataaa cactgtggct ttatcatcca gaggctgttg ccaaatgctg ttaattaggc  53700
caaaaaaatg ttttttaaag gttggtgaaa cagatccact tttctctctg taatggcatc  53760
ttagcttgaa atccaggaag cagtggtgta tggtgtccat atccatgatt tcctgcattg  53820
gagaaaaagt gtggaaagca tctggggaaa aggaggctct ttaccagctt gtttcctgta  53880
agttcaattg gaagaccttg tctgtgcaaa tagatttcaa aatagagcct gccctttgac  53940
tgtctccata attacatggc tcgctctgta ttttatttgg cagccagagc agttaacccc  54000
tggaaggaag gggctgatgg tatggccagc ttggcttccc aggcatgtcc atgggaatga  54060
ataaaccact gtttggagaa gcccatagct aaaaacacac tagaatagtc tgtaactgaa  54120
ctgaaactct tttaaaacaa gttcactaat gtttattatg atcggttaaa aaacttaact  54180
ttgtccttat tgtgtagatt atagagctgt attaattgtt ttaaaaattg ggaattgggg  54240
gagttccttg ttgctttgat gtaatcaaca tctgtcaaca gatgaatttg cttttgttta  54300
gtttcaaggg ctcttgtcct ttagctttgc ccaatcagta tctgcttcag cctggggcat  54360
tccctagtag tgcatgtggt tttttttccc tcagcaaatg cataggttat ttctcatgaa  54420
atgtgagctt ctcttctgct ttatagttgc cttgagatgg gaaggaacct tcaatctttc  54480
tcatttattt tgaaacgtac accttagtac tagattataa aaatcaataa aagagttata  54540
tcaagtgatg cagactattt aatttttctt tagcaacatt tgtacaagtt atgaaacatg  54600
tcaagcaatc agtgttttag gtcaagaaat ataaggcatg gatgcatttg cagtgttctc  54660
atggacttga agcacacagc gctgtaagag cctgtgctcc tactctgagt aattggttgg  54720
agttcatgaa gtgtgatctt tctgtgggtc taaatcagca ccccgaaaat atattcctat  54780
gctatagtcc cttctgagct tactgtagga ggcaacattt ttaaacagtt aaaaatgtat  54840
```

-continued

```
cagattgctg tcacaaagta agttgggttt tttttcttgt taaagttaat atattattaa  54900
gcaaatcatt tggtttaaaa ttaaaatcat caatgaatgt aagaaccata tttgaaaatg  54960
aattagcaaa acattgttgt ttttctctct tggtaatcat aaatcattta aatctggcag  55020
gcattcctct cttcatccaa aataattgcc tccatttgta aaatcaatta gatgttaaca  55080
tgctataaat aatagttttg ttactagact ttggcattta ctgatcatta tgaaaaaata  55140
tattcagtaa gacattttac agggtgtctt ttaaatcaca tattatctct ggttgacatt  55200
gttagctaat gtaaagtagt gccaagctac attattgtgt tgttttctac ccagatattt  55260
gatacctctg cagtgtaacg taactgagga ttgatggcac actgcagggt gaaagtgctt  55320
ccctggaaac atacaatgaa aaatatatgt gttggtagtc caaacttgag tacaaatgta  55380
ctttgttcag ttttacaact gcttaaaata ataagcattt taaatgtctc tttgaaagtt  55440
cattcagacc tctcccttaa aaatacttat tgaccaaaag aaaactcaca ttttcaggga  55500
taaaatcagc ttaattaagg gtcattagta aaggtgcaca tgaaaaccca gggctcagtg  55560
ggtgaaatgg aagcatttca ttatgtggta taggatgcat gagcagataa caattaaaat  55620
ggaccctgag taagaggcca ataaatatag ggcatgttgt gtgcagcaac attcgttatt  55680
taaaatgcat tcctcctggc caggcacggt ggctcatgcc tgtaatccca gcactttggg  55740
aggcccgagg tgggccggat cacgaggtca gggagatcga gaccatcctg gccaacatgg  55800
tgaaacccgt ctctattaaa aatacaaaaa ttagctggac gtggtggtgg gtgcctgtaa  55860
tcccagctac tcgggaggct gaggcaggaa aatgacttga acccgggagg cagaggttgc  55920
agtgagccga gatcgtgcta ctgcactcta gcctggtgac agagcaagaa gactctgtct  55980
caaaataaat aaataaataa ataaataaaa tgcattcctc cctccatcat acttgaattc  56040
tataatccta ccttcagatt taacctataa aggaaaataa aatgcagctt ttagaaatgg  56100
atgttattac tgaatatgaa aatatttaaa accataacct agatttacat tccaaataca  56160
aattttaaat atgaaaaaat gtgctgcagg atccagagga catagagcaa tttcaagaga  56220
tgttcagact gcacagtgtg ctcttccatg gagtgcagga agaagttgcc tataattttc  56280
agcgttcaac tcagactagg tgctgataga atttttgtaa cactaaaaat aattcttatt  56340
attacctttg ataacagtaa ctattctagt attcataaaa aataacatgt agatttactc  56400
cctaagaaaa ccctatatag agttgctgtt aggtcatcaa cagtagcaat actacgatca  56460
tctcttgcaa gatcaaatta gtataaagca actcctcact gttctgggct ctcctactcc  56520
cctgaggttt ctggtgattt cccactggtg tctctaaaaa catcagatta gtccacttgc  56580
cccttgtagt aattagtaca cacctgagtc ttgtttcccc aaatagcttt accaaaacac  56640
cgtgtgcagt gaatcctgaa tgaatgatag tgtgtgggag acggagggac tatttctgtc  56700
tctgaagatg gtcatcatgc atcaaatttg ttgtaacatt ggtggtagca atttggaaat  56760
tagatgtagt tataaggtat cagcagtgct tttgtcaaga aatgaattat ataggaaatt  56820
caagagacca tttctacatt gatctacatt agttactgta gttcgggtat cctttctgtg  56880
accctgaata taatagagac tggggatttt aattttgctc actctgcatt tagaaaattt  56940
actacttatt tgtattgtga taaacaaagt tgagggcccg cccctctttc tttgccaggc  57000
tagttggagg accattatct tctaaaggta ccatgactta tgcccatttc ttcatttccc  57060
ctgtgaaaac accagatttt atttctaata aaaagatgga atcatttgta atgagtagtt  57120
agtggaataa acacagtatg gcaccttatt atcctgttgc cttgtgacaa catttgtaag  57180
ggtgtctttc atcagattga aagaaaagaa ttcgtttcaa atacaaaagt gtcttatgaa  57240
```

-continued

```
agtgaaattg ctgaatacag tgtagaacca taattgtcaa cagattggat atgttcaggc  57300
tgtgttcctg acgtttcgaa ttttaccatc cagtcatgtg tgggtgtgtc tgcatctttt  57360
cggcagtgag gctgtcattt ggcaggacag gtaccttggc aacactgttc atcctaaaag  57420
tgaatgtctc aaaagcctca tccagatatc tagtggaggc ctgatgactt catgcttcaa  57480
gtttaagtac atagaaaaga ttccccctat aatgactgtg tacttgaact tgataacact  57540
gataaagatg atcttttgtg taatcaacca cattgaaaaa aatcttcatg agtcctaaaa  57600
ttgatcagag gctacatctt cccatttcct gggatgtagc atgacaatca gatggtgctg  57660
aatgaaggca cacatttcag agctgaaggg acctcaaaga ttgtgaagcc caactctcat  57720
tttactgagc ttctgcatct cacagggtaa tgtctttgaa gtactcagca ccgagcttgg  57780
caccagtaag ctcttggtca gtcagcatcc actgttattg ttattgctca agatcacata  57840
gctcttagca ggaccagggg tagaactttc tgtccaatgc tgtgccactt tggttatttt  57900
ttcatcatgc atagcactgt ctgatgtaat caaatgcatt tgttgatttg cctatgtctg  57960
cctcccacta caaggatgta agctccctgg gagtcgggac cttgtcacct cattcaccac  58020
tgaattctct aatccagagc atggcacatg caatgagttc attaagtagt tgttgaatga  58080
atgaaggcat ttagagaccc cacaggtaaa catgttgaag aatggagaag gaaaaggaaa  58140
agaaaggagc atttatggag cacctatttt ttaaaagatg gtttacctat ttatgttatc  58200
tcagcaaatg ctcacatcag ctcgtggtag ggagagcact actactccca tttaatagtg  58260
aagaaaatga gtctcagaag ttttggtaac tcacacctgt ttgacctcca agctcatgct  58320
gttgtcacta ccatagtgcc tcccaactgg atcatttcta agaattttca tgaaaagtgt  58380
cttcattcta aatgctaact agttacatga tatttacatt tttcatgata aaaaaaactg  58440
accttgaaat ctagtaccct gaaagaatac attatgtaac aaaacacact agcgaataga  58500
actcatagag cccctgcaca ctgctgagag gcaactggaa tggcagacac agccctggat  58560
ttgcatttac aggattaagc ttggggcctg gtcattgatt accagacttg tgagccttag  58620
ttcctcatct ataaagcagt gatgttaaca gctacctgcc taatgacaga gctggtaaga  58680
ggtaatgtat gtagagcacc tagcactgag cttaatctaa gtgtccatta aattttaacc  58740
actgttatta ttactattta tattagcatt atcattatta atagtaatta taatactttc  58800
ctcagaagag aaacacttgt gagtttgtgt cttgtatgtg gtcctgccta gcaatgcaat  58860
tagggaggtg gaatcataga ttgagtccac ctgtgtcttt ccaaattttc catttcatat  58920
ccacagactg tccaactaat agttctggca gccacctccc caaagcgtgt gtttggtcag  58980
cgaaggcagc ttggcttaag gtagtgggtg gattaggcca acccatcacc acttttggaa  59040
aaataatagt agtagtaaca atagttttgt gatgcctttt caattttctg ggtatttccc  59100
tgtgttttag ctcctgtttt ttctcatgcc tgtgagagaa gtaatacatt ttgtagaggc  59160
aacttagcct gctttccctc tcagctttgg cacttactgc atgttccttt gtgtgcctca  59220
gtatcttcaa ctgtgacatg gagtaataac agttcacaat tcatacagtt tctgtgaaga  59280
ttaatgagct aacatatgta aagtgcctag tacagtaatt gaggcataat aagtgttcag  59340
tattagaagc tatactggag gtcatgtttt ctttcccatt ttattttttg tgcagacttt  59400
tttttttttt ttgagacagg atcttactct gttgcccagg ctggagtgca gtggtgtgat  59460
catagctcag tgcataactc agtgatcata gctccagggc tcaagtgatt ctcctgcctc  59520
agcctcctga gtagctggac tcctgagtag ctggactgac tcctgagtag ctgaactcct  59580
```

-continued

```
gagtagctgg actacagtag ctgatggccc aagccaccac atctggctaa ttcttttatt  59640
ttttgtagag atgggatctc acgatcctcc cacctcgacc tcccaaagcg ctgggattac  59700
aggtttttat gtattcttga aagaactatt atttattggg tatcttctta aatgcaagac  59760
actttcacat ttcttatttc aattctcacc tgagactgaa atgaagaaac ttgtgcaggg  59820
ccacacagct aataagtggt agagctgaaa caaaagtcca ggcttctgcc ttccaactgt  59880
ctgcttttcc taggacacta ccctgtccct catatatcag ttgacaatac tagggttggt  59940
gatattgtca ttagggaaat attatacttt aaaagcttta cacaatacat acctgcctct  60000
atcaagcaac tttttttttt ttagagagac aggagtcttg ctttgttgcc caagctggtc  60060
tcagactcct gggtttaagc aatcccacat cagctgccct ccaaagtagc tgggactaca  60120
tgtatgtgcc actgtacctg agttttgtaa cttcttttta aagaaatgat attactgaca  60180
ttttgtctag tgcttgaaat tgtttaaaat agtaccaaaa acacctctat aagttagatt  60240
caacaatatt gcagtccact ttaaggaggg acataattga gtgaaaccta tcaccctgaa  60300
tcactgatca ttgcggtttg tttgcatcag tgcctttccc caagtcaatt agagatccag  60360
agttttgaag ccagtactta cctgcaattc acgttttcat tatgtttcac agctgaaatg  60420
ttactctagg ccagttctca agcttcgtgt gcgtcaggat tacctgaggg ctggttaagg  60480
cacagattgc ccgcctccat caccagtttc tatgtttgta ggtcgatacg gggcccaaga  60540
atttgcatct tttttctttt tctttctttc tttctttttt tttttttctg agacagagtc  60600
ttgctctgtc acccaggctg gagtgcagtg gcgcgatctt ggctcactgc accctctgcc  60660
ttccgggttc gagtagttct cctgccttag cctcccgagt agctgggatt acaggcgcgc  60720
gccaccatgc ccggctaatt tttgtatttt tagtagagac aaggtgtggg attacaggcg  60780
tgacccaccg cactcagcct tgcatctttt ttctatgtga cattatactg ctggtctgtg  60840
aacctcattt taaggactac tgctctagac caggattcag caaatgtctc ctgtagaggg  60900
ccaaagagta catttttttag gctctgtgga acatgtgttc acaactactc agctaccact  60960
gtagctcaaa atcctccata gacatttgta agcaaatgag ggtagctatg gtccaatgaa  61020
ccttttattt atgggcacca agatttgaat ttcatgtatt acaaaatatt gggttaaaaa  61080
gttttttttca accatttata aatgtaaaaa cctttttagg ttttgtgctg tataaaaaca  61140
gtcagcagtc cagatttggc ccttgagctg tagttttctg acccctgcca tgtagttgtg  61200
acctgttggg gacttctaaa actattgttc tggccaggcg cggtggctac gcccgtaatc  61260
ccagcacttt gggagaccaa ggcgggcaga ttacgaggtc aggagattga gaccagcatg  61320
gccaacatgg tgaaaccccg tctctactaa aaatacaaaa aaattagccg ggcctggtgg  61380
tgcgcgcctg cagtcccagc tactctggag gctgaggcag gagaattgct tggacctggg  61440
aggcggaggt tgcagtgagc caagatcgcg ccactgtact ccagcctggg cgactgagtg  61500
agactccgtc tcaaaaaaaa gaaaccaaaa aacaaaaaac aaaaaaaaga ttgttctaaa  61560
tatgaaagta ataaaatgaa tcaaaatgtc ttcctggctg gatgcagtag ctcacgcctg  61620
taacctcaac actttgggag gccgaggtgg gaggatcgct tgagcccagg agtttaaaac  61680
cagcctgggc cacatagcag gaccccatct ctacaaaaaa tacaaaaatt agccaggcat  61740
ggtagcatgt gcctgtggtt ccagctactc aagaggctga agtgggagga ttccttgagc  61800
ctgggaatcc aaggctgcag tgaaccatga tcgcaccact gttgccttag cctgggcgac  61860
agagcaagac cctgtctcaa aaaaaaaaaa aaaaaaaaag tcttcctctc tacctctagc  61920
cccaaccaca agccacagaa agagccactg tttacaaata tcaatttcca gaaattttat  61980
```

-continued gagcacgtgc aagcttatat aaatgtataa gctcctttta cattaatggg ctttttatat 62040
gtatttgtta agcattcact tttttcctaa cagtgtattg tgacctcttt ccatatcaac 62100
acatagagat gatgatttag cctattcttt ttaatagctc cagaattttc tgtaagtata 62160
ccataatata tttaatcagt cccctactgg tatttcctat ttggaaacat ttgagttgtt 62220
tcccactttc ttctaccaca aataatgctg ccatgagggt acatcttcat tcatccatca 62280
gtgcatagtg tctgcaggat aaagtcctag gagatgaact gctgagtcaa aggatatgtg 62340
catttaaaat tttgatagac atttctaaat tcctgttgtg agtacttcaa accctatatt 62400
cattttcttt cagtgttata cttacatttt tgctatttag tctttatctg acttgaacat 62460
tcatcacaat gaatttcagt ataatgcctc actgcacgtg aacttaacac agagtagtaa 62520
tcctatggag ggcaaaaagt gcagctggca atttgtccgt gattcttgaa aggaaacggc 62580
tttacagagt ataaagccat caaaacagtg ccctgaatct agggtcgtct tggacattgc 62640
cacataaggt attacagcag aaattgttct ttttacagac ctggtgctta gcagatgttt 62700
ctatatgttt gtttcccgtt agagtagagt tttccattgt cacgcattta tgtaaacata 62760
gtattagcta ataaatacgc tgtgttacta ttgtactaga attcagaata ccactgtttt 62820
catttctatt tggggctttt cctttttcag tcaataaggt attagaataa tgatttaata 62880
gacaacacca caacatctta aagtggagga ctgtgttagg ttgttttttt acttaaaata 62940
tgtctgtttc tgctcacagg ttctcataga attttctctt caccactcaa tcatatctac 63000
ttacacaagc agtcaagcag tcaacaaaga agaaatttct tttttcggag acaaagagat 63060
atttcacaca gtatagtttt gccggctgca gtttcttcag ctcatccggt tcctaaggta 63120
ctgtattgcc tattatctcc tgctttttcc agccaagata aaagttgact gcagaagtga 63180
tcaaatattt ttgcaccttt gatttctgag ccatttgggt tttaattttc aaactaggtt 63240
tgtgatctaa aactgtgatt tgagaagttt taatatcctg caattctata gcattaattt 63300
tttaaaacaa agctctaagc tttcaattgc ttagagtatt tagaattaaa atttttaaca 63360
tgaaattttc tatattaaat ttctaacatg aagataaaac tatacgtatg tagttttcta 63420
actgttttag agaaaaaaat tgactataaa attgtgatga ttcaaaagag attacttaaa 63480
actaacatac tagatttttt taagcctgtt cttacatttt ccttgttatt gatgctggtg 63540
tctttgaatt gtcttttaga ctaaattaaa taaaatatgt ctcagagcag tcttggcttt 63600
ttttttcag agattgcaat tctgtggaaa ggcaatctat ccatttttca aaatgcaata 63660
taaagggagt gtgcgagtga gccctttagg aagaaggaga gtagctaaag aaatatagat 63720
tggtcacaaa aatcatctgc tttctccctt ttatgaactt tgtttacagc gagcccatat 63780
ttagtatgtt atacttctga aggtgagtgg cccactttta tggcaaaggc cagtgacaca 63840
gaagggccac caggatgtat cccctggcct ggccatcaca gtgagagtga gaatttggta 63900
ttagttacaa aactgacact tttttcctta gaagaaaaga aaaagaaatc tctggtgagg 63960
tgaattgtat tgctttagcc atttcagtca atttcagcat gacagcccaa cagcccttct 64020
gcctgcaagt tataaccttg ccagatcaca gagcagagtg gagacaagaa cacaggctct 64080
ttgggggaga cctggtgagc atttgtgggc atttgtggtg tagctgtggg agagtagatg 64140
ttcctctgga gctcagctgt ggcaaaccag gcagtagtgt tacctgtatc agaaaaccca 64200
tctgaacagg ggagcaagtg aagacccgta actcctgcag gacaggcttc acaaagaaga 64260
gagccctaac ctcagccctt ccagagctgc tgcaatgttt caattgaaga gtgttatctc 64320

-continued

```
cctcagcttc ctgtcccaaa ctgctgtgga gcctaactgt ggactgtcca ataatgctta  64380
tagtttgtaa tgcattataa actataaata gtttgtaaag agctgtgcaa aaccttggga  64440
ctgaaagaag ctttgtgtgt aagatggtat ttatttcctg aatactgccc atggtggaga  64500
atggtctgca aaagtgatca gggttgcacg tcttgagttt tggggtggct ttttgtttac  64560
tcttgacaaa taatggaaat gttctaggta atttttatgt atttgaagaa taaaacttgt  64620
ttcattttat tctagtgtct cagtgtaagt acggttgcaa aatgtaagaa aagtgtatat  64680
gtaataggct ttagggaact tgatagtcag cctttttaca tatgttcatt ttgagagggt  64740
gttgggagct atcttttgca taaattatat ttttgtgtta agaagatgaa agtgctctta  64800
attaaccatt tggtgaattg gaagcttggt gctatttttc atcaatggtg aatatgcttc  64860
taactgggtt gggaggagga aaaagagaaa actactgttt gttttgacca gaagtctact  64920
tcagtccagt ttgactcaaa gcatggtaag gttaacagac catccagagg cagcactaac  64980
aggcaatgtt aagttcaaaa gggcagggga aggaactggg ggcagcctgg agggtctgtt  65040
gtgctggctt cggaggtcgg tgctccggca ggaagggcag agctccatga agcaggaggc  65100
tgtgtctgaa aaaatgatcc cattgtcgtg cgctgggttc tgatcttcgt tttcaatcct  65160
ttttcctcaa gcacataaag aagccagact atgtgacgac aggcattgta ccagactggg  65220
gagacagcat agaagttaag aatgaagatc agattcaagg gcttcatcag gcttgtcagc  65280
tggcccgcca cgtcctcctc ttggctggga agagtttaaa ggtggcgtct caccaagcct  65340
cagaacgact tacataaggg gcaacaaaca ctcctctttt tttccttctc cttaactctt  65400
cttttaggtt gacatctaat ttgttttaaa aatttatttg ttttaaatta atttgttttt  65460
aaaaattaag taaagccttg ggatggggaa aaggaatttt attattttat gtgtttattc  65520
aagaagtaat ttaaaatcca aattcaattt taactagcag aattctagag atactttggt  65580
ctcagtcaac ctatccaagt tgatcaatgg cagacagctt tgatttttgc ccccctactc  65640
ctgcctgtag tttcagcttt tactccccac attatttctg tgtgcttgaa gatttgctct  65700
accttgtcct ttgtctccta ttttcttgca tttgccctgc aaagaaagat cagatcacat  65760
acacaaagct gtaggtaata tagcagtgta attacataca acttcctact acaagattta  65820
gttcttttag gccaggcgca gtgactcatg gctgtggatc atttgaggtc aggagttcga  65880
gaccagcctg gccaacatgg tgaaacccca cctctactaa aaatataaaa attagccagg  65940
catggtggcg ggcacctgta gtcccagcta cttgggaggc tgaggcagga gaatcacttg  66000
aacccaggag gtggaggttg cagtgagcca agatcatgct actgtactcc agtctgggca  66060
acagagtgag actccatctc aaaaaaaaaa aaaaaaagat ttagttcttt catttagttc  66120
tttcataata atctgaagca cccttctgta taaggattat aaaagaaaaa tatgagccta  66180
ttttctgcca aaaggtgggc agaatttagg aagtgagact caaagataaa atcactcaca  66240
gtatcttctg tgtaataaac ttacaacacg gctaaacata atgtatatat acaaaatgaa  66300
gaaaattatt gaagaaatgg ttaattttta ataaaagatt ttatttttgt tttagaattt  66360
tatttatgtt tatggagttt atggaaatag tcttcatata cttataaaac tcaatttcag  66420
ttttctttta gtttgggagc aatttagttt ggaatacctt tagtaaggaa aaaatatttt  66480
aaaaattaca tttatttaga catgaaagaa atgaagatta cttaaaatca aatctctaca  66540
aactatatta gactcactct tttaaatatc aaccataatc tctgtgccat tgctgcaaaa  66600
cccctgtaat gttttactga gataaaaaga tgcgagttga cctacttttc aagcttttca  66660
aggttcaact gatgaacctt ttgagcattt attcacatgc gctgggtagc ccagggcacc  66720
```

-continued

```
aatcattgag aaagagtaag gaattgccga agaacataat tttgaaatcc tcaggccaaa  66780
agggagttat gtcatttaat gactcacaaa tgatttagag gatcgtaggg tttaacattt  66840
ctatttccta atggtccata acaccatcat atgcccaaat gattgtccac aaggcacagt  66900
tgaggattct aacactaatc ataattaatt caaatgttgt accataactt tatcatagta  66960
aatttataca gtctcacatg gaagtactgt tgctatagca tagttgataa atacaagaaa  67020
tgtcttcaat tgttgctgca caatttcttt atttaacatt ttaggttgac atgacaactg  67080
aagagataga tgctcttgtt catcgggaaa tcatcagtca taatgcctat ccctcacctc  67140
taggctatgg aggttttcca aaatctgttt gtacctctgt aaacaacgtg ctctgtcatg  67200
gtattcctga caggtattca gttcttaata acatattgtt cctttggaaa ctaaaacatg  67260
aagctaagat ctgtaacata tgttgaaaga cactatcatt caattgaaac ccaccggtaa  67320
acttctgaaa ttgattatga taaaacagaa attttgaagt attttacttc taaatggata  67380
caccaccacc atttaatgtt tgttaaagca gtgcataatc taaatggggg ttgtgcatta  67440
cgtatgtctt ttacttctta gattttaatc atataagtgg taaaattcaa atgtggcaaa  67500
tttttcttat caactcttgt tttggttctt ggcaaaatta aggtaataaa ttaagtgcat  67560
cttttgaaat aaagattaga tttagttatc ctgtgtagtc ctccttcact ccaaattatc  67620
actgcatccc attgggtttg tgacagtagt cattaagtat ttatttttat tttcctttta  67680
ttgagatctg tctatcacca tttttttttc tgtttacgtt ttagtcgacc tcttcaggat  67740
ggagatatta tcaacattga tgtcacagtg agtaaatcat ataaaaaatt gtctttgatc  67800
aacttcagaa ttgctggtag caacaggaag agtggattga aaatgtgaac tgcaccagtg  67860
gaagtgctgt ttacttctag acccagacgc aagcagctgg tttccttttt tgtctttaac  67920
tctgtgttta ttccaagtaa acccaggcct gacttgaatt tagggctgca atcagatgca  67980
ctgagatcaa tgttggccta agtgaaatgt caacccaatc ctgctatgtg tcatgttttt  68040
gagaaggtgt aattgttatt gatccactgt gtagttaacg cagagcacca cagcactggg  68100
cagctgctga agctagatat gtatgagatg agctaacacg aagaaagcca gcatttttcc  68160
ttcactctgc caagattgat cttcctcttc ctgctgattt tgagtggggc ctgtcattat  68220
cttactctgt cattaggggc tacattggcc tgtgtatgtc agtctatttg gacagcaact  68280
cttttgctag ccgtgttccc tagatttatt aaaatccctg aaggtaacgt tgagttccat  68340
ttctggtata gagagccttg tgctcaaagt aagcagagtg gttttttttgt ctgaacttaa  68400
gttttcacca aatggttaat agcctttctt ttaagtaaca agcctaagta atttatcata  68460
gggacttcaa attgtacaag atgtagcttt ttctcatttt cttagccttt taccattctc  68520
agacttggat tatatgtgct tttacatttc tgtttattaa agaattttgt aatgatacct  68580
ttggattacc tagattataa ataaattctg tacatctaat gattaacaaa tacattttaa  68640
ataaataaac aaaatttaaa catcttagga gaactagttg aaatgacaat attcagggaa  68700
tacaatttct attaataagg aagtgttttt aagaatagta tctagaccat gaaactgaag  68760
taggagtggg aatgagataa aaataggaat ccaatggtgg aattcagtct gacttttagt  68820
ttaagttaac taaacctttt ttcttcatat caatcatatg aggagatagc caacgattct  68880
ttcattgctg atgctatttc ctgtatcatt ttatcctact taaaatgctt gaacacttgc  68940
accacataca tcctgttggt atctttccaa ctcagaatca tgtggaagga ggtattttat  69000
gaagtatacc taaaacagag ttcttttcat gagacacttt tattttggat tgtacctgat  69060
```

-continued

```
tttacggttt tacatctatt ttctcatcta gtcaccctat catgaaatgt taccatttta  69120
atgttttgaa tgaaatcaac tactcttccc tactgtttcc agtgtgtcca aagaaaatac  69180
tctattcctt ttctaagttt cctgaatact taataaacag ttttgtattt aacattcaaa  69240
ttacttcaca attgcaaaac ttataaagca aagtgaaata tttccaagtg tctagaaatg  69300
tgaaggaatc taggaaacat ataggtccat atcttaacaa attatatttc ttataaaata  69360
ttttattaag tgaaggactc cattatcaga tcctatgttt ctatcagaaa atactcattg  69420
catcttagaa ttattgacgt ctagtataca tcacaagaaa ttagatttcc ttcccccctt  69480
taaaactgaa aaatgttttt cttaaagaca atgcgatgtc catagtagtt gctcaataaa  69540
tatttgttaa atgaagtaca agggccaggc gcagtggctc atgcctgaaa tcccagcact  69600
ttgggaggcc aaggcaggcg gatcacctga ggtcaggagt tcaagaccag cctggccaac  69660
atggtgaaat cccatctcta ctaaaaatac taaaaatata aaaattagcc ctgtgtgggg  69720
gcaggagcct ctaatcccag ctacttagga ggctgaggca gggagaattg cttgaacctg  69780
agaggcagag gttgcagtga gctgaaatcg cgcccctgca ctccagcctg ggtgacagag  69840
cgagactctg tctcaaaaaa taaataaata aataaatgaa gtacaagtac tagtttatgg  69900
gtataaatag aaattgtaga tgactgccac agactttcaa aagtattgta tttctgtata  69960
tagtgaatct tttaagtagt cttttttttt ttcagacgga gtttccctct gttgcccagg  70020
ctggagcaca atggcaggat ctcagctcac tgcaaactcc gccttaaggg ttcaagtgat  70080
tctcctgcct cagcctcccc agtaactgag actacaggca cacgccacca cacccagcta  70140
atttttgtat tttaagtaga ggctgggttt accatgttgg ccagactggt cttgaactcc  70200
tgacctcaag tgatccgccc acctccgcct cccaaagtgc tggaattatg ggtgtgagcc  70260
actgcaccag tctcaaatag tcattttgat attccttcct tccttccttc cttccttcgt  70320
tcctcccttc ctccctccct tcctcccttc ctttcttttt ctttttcttt gtttcctttt  70380
cttttttttac tttttcagat atagggtctt gctctgtcac tcaggatgca gtgcagtggt  70440
gccatcatgg cttactgtaa gcttgaactc ctgggctcaa gtgatccttc taccgtagcc  70500
tcccaagtag ctagaactac aggcgtgtgc caccacacct ggttaatttt ttaattttgt  70560
agagatgggg tttcactatg tttcccaagc tggtcttaaa ctcctggtct cacgcaatcc  70620
tctcatccca gcctcccaaa ggattgcagg cgtgagctac tgcacccagc ctcaagtaat  70680
cattttcaaa gctaggaaaa agtaatatga aaagatgaat aaagattttt taaaatagta  70740
catttttact taaaaagcag ttatataaac attcatttat acattttctt gactacgcct  70800
atattagcaa attttatatt cttgtatttt gaatgaaatc gtattttgta ttttgaaata  70860
gtattcttgt attttgaatg aaatataaga atataaaaat ttgaattttt gaacgaaatc  70920
agcatagtct tccctactgt ttccaatgtg tccaaagaga atactctatt ccttttctaa  70980
gtttcctgaa gacttttaat agtttcatta ttaacattca aactatttca aaattgtaaa  71040
acctatgaag caaagtgaaa tactgccaag tgtataaaat aaaaactcat actttcctgg  71100
attgcaaagg actgtaagtg ggagtaaatg tataaaacac tattctgttg caaggtaatt  71160
aagataattt gatatagtag agaaaacact cgattagaag ccaataatcc atcatattaa  71220
cctgaatcta cctctatatt ctgccaccaa ccttaaacaa gttacttatc tgtgcctcag  71280
tttcctgaat tataaactga agatctaata aagacctttc ttgcttcctt cacagaatat  71340
gagagcattt tttaagaaat gcagagtagt atacagattt aagacattaa ttcagtatca  71400
caacagactg aaagctcata taaacatctt ttttataaca gtttctacat tctaccttat  71460
```

-continued

```
gagcaagaga aatgtgaaaa ataattagat aggacaaatt tatgcaaagt agcaaattcc  71520
atgctacatc aaaggatcag tatccaaaca gttgcctctg ccttttatat ttactatagt  71580
gcttggttat caatgattta taatgaatct ggtatctttc aagatcctac ttggcttctg  71640
aatcactgaa gactgataaa attatacttt ctgtaattgt gcttttaagc ttgttttatt  71700
atattctaat tctttagata tccatatata gtgctttctg ttaacgttcg gctgtctgga  71760
acatttgatt aagatttcac ttctagacat aggattttc tgtaacacat ttcattccta  71820
tatggaacca cttcaattct tagaactgaa ttctcctatt tgtttgttag aatacagaca  71880
tgtctatctt acttcttctt gtcattatat atcacttcaa atgtagaact ggtaaataca  71940
aaatcaagta agtcttcatg acattgaaga aacttttcac tatgttaaat actttttggt  72000
tctctaaacc tgttgtggta attgtagatc aaggtctttg gctactaatt tttgcttata  72060
taattttgtc ttctcagaaa taaagtgagg aatcaaaata ttacagtagt attgttcatc  72120
ataatgctga aataaccata ctagttaaca tagttgtttt taaattttgc aatatcattg  72180
catggcttca tcttttaaat ttctgcaagg tttcaatata tctatttctt ctttttttga  72240
taggcaaatg aataattctg gaagggtaaa acatgagtct actaaataca taaatgaata  72300
caatgtatac tttaggaaag tagattttta aacaaggaca tatttttaaa tttctgctta  72360
tgtttaggtc tattacaatg gctaccatgg agacacctct gaaacatttt tggtgggcaa  72420
tgtggacgaa tgtggtaaaa agttagtgga ggttgccagg aggtgtagag atgaagcaat  72480
tgcagcttgc agagcagggg ctcccttctc tgtaattgga aacacaatca ggtaagcctt  72540
acattgacaa gtaaagggag ggttggcaaa tggtacaaag gttattggtg gcttggtata  72600
aagttgatga catgttttat gattcagaac catcatttca gtctgatatc agtatgtgaa  72660
ctgccaggct gcaatattgt tccctgagtt gaaaaaaaaa aaagatttta taaaaatgaa  72720
ttataccagg gtcagcaaag aaacttatag aaggagcaag caatatttac atggctgctt  72780
ttgttttagc ttgacatact ggtctatagt ttccctttat tcaaaatcac accaaatatg  72840
gaagggagta cctaagaagg ggatgagcat ctcaaccctg gggtttttaa taagacagga  72900
gaaaaactaa attttataaa ggaatgaagt gaaatgtatt tctgtgatat gaagataata  72960
aagtgttagt tcaagcaagc cttacctttc aaattggtag attaacaaat agcctgaaac  73020
ggtgatcttc tgttcttttt ttgtctggtt catttttcct gtaaaccgtt gtttattttt  73080
cacagagtat tctatcctta ctttttgaat gtatgtgtat gtgtgttttc tgaatttaag  73140
acttttcttt ataatctgtt acctactttt aggtcttttt tcccccataa ctgttttgaa  73200
gtagacatgc cgaatatatg ttttcatttt aaagtaatgc attctgttaa agatgatcac  73260
atcagtgccc tttaaagtac tgttctcatt aatatgaacc attgaatact tcccatttgt  73320
ctaaaggatg gaaggcttag tcaccttgaa aagatgctgc cttttttttct tcgtaagcct  73380
tcaaatactt taagaaaaaa gccagtaaaa tatcagttaa atgtatttat ggctttaaaa  73440
atattgtaac agtgtctgaa tcaaacttta gtaaaatctc tttgggttat atctgagaag  73500
cttttattga agactttgaa caaaattgtg tttttgacag ttttaaatta taggctaact  73560
agcctgggaa aaaaggatag tgtctctctg ttctttcata ggaaatgttg aatcagaccc  73620
ctactgggaa aagaaattta atgcatatct cactatctta ctgtccatga atataataga  73680
aatgaattca aaatgcagtt ttatttttgc aaatgggatg agtcgataga tgcacctcat  73740
atttttgaac acctagggtt caacaaattt actggtggtg ctcttgcatt ttaacaaaat  73800
```

-continued

```
ttattcttca gtagaagggg gcagagaaca ctagattctt attcaagcat tctatcgagc  73860
tctgcattca tggctgtgtc taaagggcat gtcagccttt gattctctct gagaggtaat  73920
tatccttttc ctgtcacgga acaacaaatg atagctaact acagaggcac atttgcagta  73980
gtcacattca tcaactgcag aaaaaaaaat tcaatttaat tgtgcaacac agctgcacat  74040
gggcttttga gcatttctgt tgttctccct gtctcgctat tcctccctcc agatctattt  74100
tttaaacttt ttttctggtt attttttccc ctttttgtct cttcttccat ttttactctc  74160
tgtactttct tgttaaagta attttccttt gtggctctca ttctttttcc cccattgaag  74220
gctatgaatg tagaaaatta tcacaattac tcatataatt gagcctcttt gtagcaagtg  74280
caactccagt agcctttctc catcagaaaa ggtttcatta tagggttttt catattctct  74340
gacaccatct acacagagga acaggcgtgc agatgagatg tgctaggaac aggctagatc  74400
agtaaggtca cagtaggaat aattagctct gctatggaaa gagcatctag gccttttact  74460
gctacataaa tgtactgtcc atggctttta gtcacaaaaa aaacttacta acaaatggag  74520
ctcccgccta ctactttgaa aaaaagattt gtatcaacac tacaattttc catcattaag  74580
actaataaca cagagcctag tatacatcaa ggggaataaa aagaaaaatc tcacattcaa  74640
gtggcggctg ggtgctgacc tttgttccct ttttttgtgt acgacttaac tctttacaaa  74700
aaagagccac acgccacacc aacatgcagg tgaactccag ctagtactag caaagcatag  74760
cattcagttg gaaaatttga taaatctcca tgcaggataa tgcatttcat tacatattca  74820
ctacattaat tctagctaca ttaaaaaaaa aagaagaaga agaagaagag tagaattgaa  74880
agtgacattg gattttagct atctggatac aaaggtcagt tttcacagag tatgaatttg  74940
catgtacaag ctttttttgaa aaccagatca gtcagtccca acaactgcac ttaaaaaaac  75000
tatgtggaaa ataacagaca atgaactttt tacttgtacc ctaatacatt tcattattta  75060
gatggtttat gtctgccgct agaaaggaaa ctggccccga ttctaacaaa tatttgttct  75120
gatgtgttaa agcagtgttt ctggacacct attatcttgc cttttcttat tctggcaaaa  75180
tcttagggga ataagtaaac aaaccatatt tacctttaag ccaaaagtac ttgaaatcat  75240
tacagaccaa aggtttacaa acatctttca actcggtctt gtttatttta agatattcac  75300
catcttttgc gtagcctctc tctactgata cactaggaaa agaacaagca acttgtatta  75360
gtatcatgtt atcaaaaacc ttgagatctc tacaggaaat tttggaattc tcctctgaaa  75420
cctaaagaag ataatgtctt tgaggaagta tcagctaaaa tgttttaatg gaaagagttc  75480
tctctgggcc cttttgcttt tgtgaggaat gtctagtaat ctttaggtca tagtgttact  75540
agactcactg tatctccatt tgctttaaaa tatttctaaa tctgtatttt tataattatc  75600
tctagattat acaatctgta catatgagta tattgtgaat gtgtagattc atgcatcatg  75660
aatatgtgac agttcaatca aaaataattt aaacttgtaa atgtcatgat gaaagtatca  75720
ataaatggtt tttaatgttt aattcataac tatatgtttt gatattaatt tggaacaata  75780
taaagcagat ttttaaaaaa taatctcttt ctattagatt acgcacattt aaacaataag  75840
tggctcaggc aaaataagtc attttaatgt catctgtgat ggatttttct tgacagctac  75900
tgtaaattac aattatactg cttctctctg cacatgaaag taagcattgc aataaattat  75960
cttttatttc aatccatcat gtctgctttt cagaaacaga aaacctcaaa taaaagttca  76020
gcactattgt aagaaaaata cagtaatttg tgatctggtt tgaaacaaaa aaaatctact  76080
actttttgg aaaacagttg ttggctttca aaaatattac taattgtact taaacattcc  76140
ttttcattag aaggaatccc tggatttgtg catttcttca ttcataacta ctgcctaaaa  76200
```

-continued

```
taaatatcta gaaagagtaa agaaaaattt cataacttat gaaataacat gccatttgag  76260
atcatttatt agagatgtga ctatttggag attagtgctg tttataggat taatgtaaaa  76320
ttggcaataa atctattttc atgtgcattt ttatttcttt ataacagcat gtacgtaaac  76380
atagtactcc tctgccctct tggggaatgt atttttagtc aaaaaactag ttgaaaagta  76440
ttaagaaatt taatttacct aggtgacatt taaattgagt ataactgcct catgaaaagg  76500
aattaaactg aagaaaatgg tcacaagatg aaattcctta aaagaggtat ctttttcatg  76560
tataaactgt aactacaaca tgaattgtaa tcagacagta taataggaaa gtaagttcat  76620
aaacaacctt tatgtatcct cctctccctc tccaaatatt ccatataaaa ggcctcaaat  76680
cacaagtgtg cttgggttca tgggcagatg tcacactgtc ttaaaggatt tttagttaga  76740
gaaaatcaga agatctacta ccaggagaat tcttttcagt aggtttcagc agagcgaaga  76800
cagattttat ccgtgaaatg tccagggcaa gaaaactctt gtgcacagca aaagggttat  76860
ggcctgtggt gactggtgtt tgggagcact tcggtgcttc tgcctgccct gctgtttcca  76920
ttttccccag catgccagtc aagagctgca gacatactcc aactccccat gccacagtta  76980
gggttaccag tactttcttt caaattagag gagtgaaatt tgctactact ggtcacttgg  77040
attgtctctg tgaatttgga cttaaaccct acaatcaggt aaataatctt gtgctcccca  77100
tttattccaa aataatagaa agggaatgct tttaaacagt aattaggaat attaatgaga  77160
tcctatctga cttagttcca gtaagtgcta aaaaccacct accaatccag aaggaaaata  77220
ctctgcaaag caaacaggag tgtatactca gctcctgaga gtcaggcatt aagatgtgct  77280
caagcaggga actgggggaa atttggcctg ttcttttcct ctttccacct ggctgtgaaa  77340
tcctctaacc tttgcatcca tgacacacag attctatgat actcctggag ccagaagttc  77400
cagcaggacc cacggagtaa attgttgtag gagaatgctc ttagatatct ttagccacct  77460
agtaattgca cagcttcttt tatgcagagg aacgagaggt atgatggggg gagggaccct  77520
aagtgttttt tcagagtggg ctttcttcct ctcctctcat cggaaattaa aatgaagatt  77580
gccattgtaa cacacattta agatgtagcc gtgatgcctg ccaatcagcc ggatcctcta  77640
aaaacaaaaa aaaaagaacc tagatttttt tttttagaag agaaaataga atagtttata  77700
ttgagtgttc ttagaatcat tgaggtttgt tgggattgaa ctaacataat ttataggttt  77760
agggagaaac tgttcctgta aaaaaaaaaa aatctagatt attatgtcct atttaattat  77820
ctttcttcca ccctgtattc actcttcatc ctcagtgttt attcagaaac tgtgtggcac  77880
aaataaaaac accttgggaa acaccaaata gaaatacttg cccaccaaag atccacagaa  77940
ataaccataa agtacaacgt aagagataaa aaccttgact taccgttcct gtcctcaaca  78000
tatgtatagc ttacctattt ctgcactaac agttacatca aaattaaatc tgaataagag  78060
gctgcccatc tgctggttat agtgacatcc aggtctaagt gaagctgtct tacaagtctg  78120
gggatggtta aaattattta gaaaaatgta taaacatgaa tggccataaa gatgctggct  78180
gaaagcctgt gggttcatgt taaactaaac ttagagtctg ttagagactc tagtttgaga  78240
tctagaaact tagttctgtt aataattgaa atagtagtcc tgtaaatccc aatctagtgt  78300
tagggttagg ggcattttgc cctttgtcca catgaaaata taaattctta atagtatata  78360
tgttcttgtt tgtctgatgc tccccaaaat aaacatgtta gctgatttca aggactactt  78420
ttcaatcttg tagatgaaga ttttagaatt ggagtctgtg tgcttggttt cagatggaat  78480
gtaaaacatt tgcatgtaac taatgtagtg catgcaatgt acttctccac atacatgtaa  78540
```

-continued

```
tgaagtaact aatgaagcac taagaattgg gaatcacaat actagcttat cttaagcatc  78600
ctagtgatta aaaagcattc tttatgaatt ttgttaatgg tgcaggtctt gaatggaact  78660
ctcaaatgat ctcacggttt tggagtattt caagaatatt gacaaagtag attgagcttt  78720
tcgtgtgagt gtgcctgttg gtaaaatgtg taacactttg aaatagagca gaaaaaggga  78780
accatagaag tagaaagtca tatttctata ttgtaatttg ttttatattt ggttccccaa  78840
tcaggagtaa tttatagtct ttttgtgaaa cctcaaaaaa gccaggcagg tttttatgac  78900
ctgcattata tgcacatata tcccggttat gtatggcaat cactatgtgt gtatacacac  78960
tcacttgttg tctaaaagtg gctttgtttg aatgctgtac aaaggtaaat gactcaaacg  79020
actgtgttgg atagatatgt accttctctc ttcatatatc caaagacagt ggttgcaggc  79080
aacagcaaaa attaaaatta ttacagcata atgaaaacac atgaatgtta ttatctgact  79140
ctaaatatta ctgacttttt ctttttcaga gaatatttta aagtgacttt gttttatctt  79200
agtatgcctg aaaaacttat ctaatttaat taaatatttt ttggtcactt ttaaagccac  79260
ataactcatc agaatggttt tcaagtctgt ccacattttg tgggacatgg aataggatct  79320
tactttcatg gacatccaga aatttggcat catggtaaga aagttcattt ggaggctgtt  79380
tcttgatcag agatcaagat gtggcagctt tgaccctgaa gctcttcctc tgactttgaa  79440
tctgcattat caaccttgtg tttgtgtgtg tgtttatgtg caggggggcag gggagggggg  79500
tctgcttaat tttaaccggg acattactgt gttactggat tagagcccag ctgtttcaat  79560
cccaaaataa ggtttatttt gctctctgtc ttctcctgaa gggtgcatgg ctggaaggca  79620
caagggatat ttgtgtagaa aaagttactg aaaacaaaac gccactgcat cagtgtccca  79680
gcagcatgca catatgactg tttctgtttt tctttttcta ccccctttc tagctgctga  79740
ctgttgtggt taaacttcat tacatcctac acagcgttga cagctgatgt atttagcagc  79800
atgtactcct tcgtgatttc tagattatgc ccacccttgt cttccttccc cagaatctct  79860
tgtttttcac tgcctgggtg tgcaccctat agtgagaaga caggggtggg cccagagggg  79920
tgggaggatt tggattgagg taggaggcag ctcagtggag caccctcaag gcaggtccac  79980
acctggacgg ggatcaaagg aaagttggtc ctggggcctt gacctgtgcc cctatggact  80040
tgattggtcc atagaaggac tactctttcg gacccatgcc ctcgaggatc gctggacacc  80100
cagcaggtcc aaaccctctt tggaccaaag agcccccacc taggcagctc aagaggttca  80160
ggtgagagtg cagaaacggc ttgtcagcct tgtgccctac ctggtgccaa tgtctggagt  80220
gaagctattt gaagtcaggc ccctgctccc cacaacctgc accaaaggag gcttccctcc  80280
tttgcatcct tccccaggac ttctttgagt gaggggtgtg ggcaaggccc aggacccagt  80340
agtaggctgg gagacctagt agcctggggg acagggagag ggggcgagga agcctgacgt  80400
gtctgaaaca accaggctgc ccctgccagg ccttggaaaa ctcttctggg ggagtcttga  80460
cccagagcac agataatgca aagactcagg cccagtagcc ccgtgtttaa ctcctggtca  80520
ctatccagga ctccagaaat ctccaccctt ccttctctaa aagaagagaa ataaaacgac  80580
caagtttttt aaaggggcct gacccctgta atctgttttt tttttctgtc ctccccattt  80640
cctattctca ccccccatgt tttttgtttt gcagcaaacg acagtgatct acccatggag  80700
gagggcatgg cattcactat aggtaaattg agctcctctt ccgagtgagt gcgtagctcc  80760
tggtggaagc ttttgccact ggcctaggcc cggcagtccg gtgaaggacc aataaagcca  80820
atcagtgtaa tgaaataatt cggatgcact ggaaatctga ttaaataata tcctcaagcc  80880
ccatcttcct aaatcagata cttaccgaca catttaggag aaggcagcca tccaacctct  80940
```

-continued aattctgtta ccagcataat gtggtgttgg gttttttgtt ttgttttgtt ttttcattaa 81000
cacccagtaa ctagacacga ttatgtccct tgctccctgt cagcaagtgg catgtgctct 81060
ctggtggccc gttcctggct gatcctgtga ttggtatcac caccaaattc cagtcaccta 81120
gggccgtaaa gacatcctgt ttctgactgt gggacttaat ggagaagcaa ttagagtgaa 81180
ataagaaaat tgttatttgc tgatgaatga acatctcgag catgttttta aaatttaaat 81240
atttttttaa aaattggtat ttataagagg gactggtgtt tgggtggtta ttatccacgg 81300
ggtcctaatt aaagcttgat taaaatgccc ttctttctct aaaaaattac gaactaggca 81360
acttcataca ttttgaatgg cgcagtgttt cctcttccaa ctgtttagtt tgtagtatac 81420
tatgtaagca acatcaatta tcaacccttg caagatgaca acatgagcct gtgggggaag 81480
cacttgaggg gagggaggag aaacttctct tttttaataa tcagccggaa acaatgttta 81540
acaagaatct gatgaggtca ctgcagtaaa tattttttcct cttacagagc caatcatcac 81600
ggagggatcc cctgaattta aagtcctgga ggatgcatgg actgtggtct ccctagacaa 81660
tcaaaggtgt ttgctttctg ctctgttgct tttaaattgt atgggaaagg aagattggtc 81720
cgacggcgcg cttgtggccc ggccggagct tgcgtgcgcg ttctgacggc tgggtgctgt 81780
gttacaggtc ggcgcagttc gagcacacgg ttctgatcac gtcgaggggc gcgcagatcc 81840
tgaccaaact accccatgag gcctgaggag ccgcccgaag gtcgcggtga cctggtgcct 81900
ttttaaataa attgctgaaa tttggctgga gaacttttag aagaaacagg gaaatgaccg 81960
gtggtgcggt aacctgcgtg gctcctgata gcgtttggaa gaacgcgggg gagactgaag 82020
agcaactggg aactcggatc tgaagccctg ctggggtcgc gcggctttgg aaaaacaaat 82080
cctggccctg gactcggttt cccagcgcgg tcaacgcatc tggaggggac tggaggaaac 82140
ccccttgttg gaagagattc caagagaagc acggttttct ctttcccttg ccctgactgt 82200
tggagtaaaa aacctcttaa atccattgta tcagaggtcc ttacctctct gacagttaca 82260
atgatctttg tatctgaact ttgcacgtct gccgaaaaat ccgaacctgt tgactgggat 82320
ttttaagaat ccgtttctcc cttttgtgta ttccatattg gccggcccca aggatgctcg 82380
cagaagccag cccccaaccc cagcccttcc gtatctttcc cctccatcgc ggctttgcga 82440
tgaaagatta gcccgcgaac agaggcattg attacaaaca tgtccttggc agtggactct 82500
gggcctggcc attcttcagg tttctgtcaa tccagaaacg cgactttcct ggacccctgc 82560
ggctcttcct cccccgccca catccagccc tccaaggcca gtccagaggt gaagtttgag 82620
gccctccccc cacccacccc acacgcacgc acgcacgcta gagcgtttgc tgcactagga 82680
attcgagctt gggccccact cgcccaggtg tgaacagtgg ctgattagtg ggcggtctag 82740
tctctaaaat gacccctccc cagactggcc cttctcgcat cgggacccgc gcttgcacgc 82800
tgcaggagcc gcaaacgtca gctgttctgg aaaccgagag ggtcccagag agaggagata 82860
cgggcgcatt tgagagcaag ggcctacttg gccgggactg aagcttgcga gttgagctcc 82920
agttcggccg gcagttccat cccgcttcag gaacaggaat ccaagggccc acgctctgtc 82980
tgccaagggc cattcctgcc cggagcaccc tcctttccct tgcgcttgct ctccggtacc 83040
tgttccgcac ctgagctcaa gggcagggag aggccgggcc tctggcagtc cacgaaggaa 83100
gccgtctgcc ttcggttatg attttaggaa caagtccaac gagggtgttc aagcagttaa 83160
tggttgtgct aactcttgtt tctactgaag cgggttttgc aaagctgaca tcccttaaag 83220
ataacttggg ctttcggaag cggcaaggaa atggcacctg tagttgccag gacaggtggt 83280

-continued

```
gtcctcggcc aggactaaga gccagctcat ctttgtaaca ttcataatac gggaaactga  83340

ggaccaggtg gctcggaaaa gagatgagtt ccagctttta cctaacacag ggttctctcg  83400

tcgtccccca acccctccag ctcggcttct ttgtgtccag ggttgtagat ttttggatag  83460

aggtgtttct gattctagtg agtctgagaa ctggaaaaga ccaaggaggg gttgatgatt  83520

tacaaggtcc atagaaaaac tttttgtgtg gtcggaagtt ggccaagcag aggcccacag  83580

cctgatgcta ctgcccccca cccccccaaa gatctgaatt ccctaaagat caagagggtt  83640

cagctggcct tgggagatgt ttgctggaga atgacttcag ttttctccta aggcaatcag  83700

attgcaacca ttagcattgt atcttatctg caaatcagtt tactccgagg ttccccaagg  83760

atagttttat taggaccaca ggactttact aaccactgag gtaacacgct gcttgtgcag  83820

caattatttt gaggtggagg tatttatggg acaagtttat aattccattt attaaaggga  83880

ctaacctaaa gtgtgtgggt gtatatatat atgtgtgtat gtgtgtacca acactcagca  83940

gctccctaaa gaactccctt taacatgctt tgaagttgag attaggaagt agatttaaaa  84000

atacctcgtc cacgccttcc tgtccctctt ccagctgaac tggccgaaaa cctcacccag  84060

agccactggg attccagcca agagtggctg cggctaacac caccaggacc tcctggtcct  84120

gaggtgactc cagtaggctc catgaggaat cccggaccct caggacaaat gggagagttt  84180

tgttttctct cagagtgagg gcaggcaaca atttaagcaa accggcattc agaacaggtg  84240

tcaccttagc agtagggggt gggagggatc cactccaagt tcactgagtg cagctaagat  84300

cccacattga gaaaccagct accgccagcg gctcggcatc agagggcccg cgctcagtgc  84360

tcctccctag acctttctga gctaagaaat aattcccgga gtgtagccat ctcttgctca  84420

cacacaaccc gcttctaaat taagcaaggc tctgaaacag tatcccgagg ggctcatgcc  84480

ggacttttgt tccaa                                                   84495
```

<210> SEQ ID NO 4
<211> LENGTH: 289
<212> TYPE: PRT
<213> ORGANISM: Arabidopsis Thaliana

<400> SEQUENCE: 4

```
Glu Thr Lys Ser Lys Val Arg Arg Asn Pro Pro Leu Arg Arg Gly Arg
 1               5                  10                  15

Val Ser Pro Arg Leu Leu Val Pro Asp His Ile Pro Arg Pro Pro Tyr
            20                  25                  30

Val Glu Ser Gly Val Leu Pro Asp Ile Ser Ser Glu Phe Gln Ile Pro
        35                  40                  45

Gly Pro Glu Gly Ile Ala Lys Met Arg Ala Ala Cys Glu Leu Ala Ala
    50                  55                  60

Arg Val Leu Asn Tyr Ala Gly Thr Leu Val Lys Pro Ser Val Thr Thr
65                  70                  75                  80

Asn Glu Ile Asp Lys Ala Val His Asp Met Ile Ile Glu Ala Gly Ala
                85                  90                  95

Tyr Pro Ser Pro Leu Gly Tyr Gly Gly Phe Pro Lys Ser Val Cys Thr
            100                 105                 110

Ser Val Asn Glu Cys Met Cys His Gly Ile Pro Asp Ser Arg Gln Leu
        115                 120                 125

Gln Ser Gly Asp Ile Ile Asn Ile Asp Val Thr Val Tyr Leu Asp Gly
    130                 135                 140

Tyr His Gly Asp Thr Ser Arg Thr Phe Phe Cys Gly Glu Val Asp Glu
145                 150                 155                 160
```

```
Gly Phe Lys Arg Leu Val Lys Val Thr Glu Glu Cys Leu Glu Arg Gly
                165                 170                 175

Ile Ala Val Cys Lys Asp Gly Ala Ser Phe Lys Lys Ile Gly Lys Arg
            180                 185                 190

Ile Ser Glu His Ala Glu Lys Phe Gly Tyr Asn Val Val Glu Arg Phe
        195                 200                 205

Val Gly His Gly Val Gly Pro Val Phe His Ser Glu Pro Leu Ile Tyr
    210                 215                 220

His Tyr Arg Asn Asp Glu Pro Gly Leu Met Val Glu Gly Gln Thr Phe
225                 230                 235                 240

Thr Ile Glu Pro Ile Leu Thr Ile Gly Thr Thr Glu Cys Val Thr Trp
                245                 250                 255

Pro Asp Asn Trp Thr Thr Leu Thr Ala Asp Gly Gly Val Ala Ala Gln
            260                 265                 270

Phe Glu His Thr Ile Leu Ile Thr Arg Thr Gly Ser Glu Ile Leu Thr
        275                 280                 285

Lys


<210> SEQ ID NO 5
<211> LENGTH: 289
<212> TYPE: PRT
<213> ORGANISM: Arabidopsis Thaliana

<400> SEQUENCE: 5

Glu Thr Lys Ser Lys Val Arg Arg Asn Pro Pro Leu Arg Arg Gly Arg
 1               5                  10                  15

Val Ser Pro Arg Leu Leu Val Pro Asp His Ile Pro Arg Pro Pro Tyr
            20                  25                  30

Val Glu Ser Gly Val Leu Pro Asp Ile Ser Ser Glu Phe Gln Ile Pro
        35                  40                  45

Gly Pro Glu Gly Ile Ala Lys Met Arg Ala Ala Cys Glu Leu Ala Ala
    50                  55                  60

Arg Val Leu Asn Tyr Ala Gly Thr Leu Val Lys Pro Ser Val Thr Thr
65                  70                  75                  80

Asn Glu Ile Asp Lys Ala Val His Asp Met Ile Ile Glu Ala Gly Ala
                85                  90                  95

Tyr Pro Ser Pro Leu Gly Tyr Gly Gly Phe Pro Lys Ser Val Cys Thr
            100                 105                 110

Ser Val Asn Glu Cys Met Cys His Gly Ile Pro Asp Ser Arg Gln Leu
        115                 120                 125

Gln Ser Gly Asp Ile Ile Asn Ile Asp Val Thr Val Tyr Leu Asp Gly
    130                 135                 140

Tyr His Gly Asp Thr Ser Arg Thr Phe Phe Cys Gly Glu Val Asp Glu
145                 150                 155                 160

Gly Phe Lys Gln Leu Val Lys Val Thr Glu Glu Cys Leu Glu Lys Gly
                165                 170                 175

Ile Ala Val Cys Lys Asp Gly Ala Ser Phe Lys Lys Ile Gly Lys Arg
            180                 185                 190

Ile Ser Glu His Ala Glu Lys Phe Gly Tyr Asn Val Val Glu Arg Phe
        195                 200                 205

Val Gly His Gly Val Gly Pro Val Phe His Ser Glu Pro Leu Ile Tyr
    210                 215                 220

His Tyr Arg Asn Asp Glu Pro Gly Leu Met Val Glu Gly Gln Thr Phe
225                 230                 235                 240
```

-continued

```
Thr Ile Glu Pro Ile Leu Thr Ile Gly Thr Thr Glu Cys Val Thr Trp
                245                 250                 255

Pro Asp Asn Trp Thr Thr Leu Thr Ala Asp Gly Gly Val Ala Ala Gln
            260                 265                 270

Phe Glu His Thr Ile Leu Ile Thr Arg Thr Gly Ser Glu Ile Leu Thr
        275                 280                 285

Lys
```

ISOLATED HUMAN PROTEASE PROTEINS, NUCLEIC ACID MOLECULES ENCODING HUMAN PROTEASE PROTEINS, AND USES THEREOF

RELATED APPLICATIONS

The present application is a continuation-in-part of U.S. Ser. No. 09/797,000, filed Mar. 2, 2001 now abandoned.

FIELD OF THE INVENTION

The present invention is in the field of protease proteins that are related to the methionine aminopeptidase subfamily, recombinant DNA molecules, and protein production. The present invention specifically provides novel peptides and proteins that effect protein cleavage/processing/turnover and nucleic acid molecules encoding such peptide and protein molecules, all of which are useful in the development of human therapeutics and diagnostic compositions and methods.

BACKGROUND OF THE INVENTION

The proteases may be categorized into families by the different amino acid sequences (generally between 2 and 10 residues) located on either side of the cleavage site of the protease.

The proper functioning of the cell requires careful control of the levels of important structural proteins, enzymes, and regulatory proteins. One of the ways that cells can reduce the steady state level of a particular protein is by proteolytic degradation. Further, one of the ways cells produce functioning proteins is to produce pre or pro-protein precursors that are processed by proteolytic degradation to produce an active moiety. Thus, complex and highly-regulated mechanisms have been evolved to accomplish this degradation.

Proteases regulate many different cell proliferation, differentiation, and signaling processes by regulating protein turnover and processing. Uncontrolled protease activity (either increased or decreased) has been implicated in a variety of disease conditions including inflammation, cancer, arteriosclerosis, and degenerative disorders.

An additional role of intracellular proteolysis is in the stress-response. Cells that are subject to stress such as starvation, heat-shock, chemical insult or mutation respond by increasing the rates of proteolysis. One function of this enhanced proteolysis is to salvage amino acids from non-essential proteins. These amino acids can then be re-utilized in the synthesis of essential proteins or metabolized directly to provide energy. Another function is in the repair of damage caused by the stress. For example, oxidative stress has been shown to damage a variety of proteins and cause them to be rapidly degraded.

The International Union of Biochemistry and Molecular Biology (IUBMB) has recommended to use the term peptidase for the subset of peptide bond hydrolases (Subclass E.C 3.4). The widely used term protease is synonymous with peptidase. Peptidases comprise two groups of enzymes: the endopeptidases and the exopeptidases, which cleave peptide bonds at points within the protein and remove amino acids sequentially from either N or C-terminus respectively. The term proteinase is also used as a synonym word for endopeptidase and four mechanistic classes of proteinases are recognized by the IUBMB: two of these are described below (also see: *Handbook of Proteolytic Enzymes* by Barrett, Rawlings, and Woessner AP Press, NY 1998). Also, for a review of the various uses of proteases as drug targets, see: Weber M, Emerging treatments for hypertension: potential role for vasopeptidase inhibition; Am J Hypertens 1999 Nov;12(11 Pt 2):139S–147S; Kentsch M, Otter W, Novel neurohormonal modulators in cardiovascular disorders. The therapeutic potential of endopeptidase inhibitors, Drugs R D 1999 Apr;1(4):331–8; Scarborough R M, Coagulation factor Xa: the prothrombinase complex as an emerging therapeutic target for small molecule inhibitors, J Enzym Inhib 1998;14 (1):15–25; Skotnicki J S, et al., Design and synthetic considerations of matrix metalloproteinase inhibitors, Ann N Y Acad Sci 1999 Jun. 30;878:61–72; McKerrow J H, Engel J C, Caffrey C R, Cysteine protease inhibitors as chemotherapy for parasitic infections, Bioorg Med Chem 1999 Apr;7(4):639–44; Rice K D, Tanaka R D, Katz B A, Numerof R P, Moore W R, Inhibitors of tryptase for the treatment of mast cell-mediated diseases, Curr Pharm Des 1998 Oct;4(5):381–96; Materson B J, Will angiotensin converting enzyme genotype, receptor mutation identification, and other miracles of molecular biology permit reduction of NNT Am J Hypertens 1998 Aug;11(8 Pt 2):138S–142S.

Serine Proteases

The serine proteases (SP) are a large family of proteolytic enzymes that include the digestive enzymes, trypsin and chymotrypsin, components of the complement cascade and of the blood-clotting cascade, and enzymes that control the degradation and turnover of macromolecules of the extracellular matrix. SP are so named because of the presence of a serine residue in the active catalytic site for protein cleavage. SP have a wide range of substrate specificities and can be subdivided into subfamilies on the basis of these specificities. The main sub-families are trypases (cleavage after arginine or lysine), aspases (cleavage after aspartate), chymases (cleavage after phenylalanine or leucine), metases (cleavage after methionine), and serases (cleavage after serine).

A series of six SP have been identified in murine cytotoxic T-lymphocytes (CTL) and natural killer (NK) cells. These SP are involved with CTL and NK cells in the destruction of virally transformed cells and tumor cells and in organ and tissue transplant rejection (Zunino, S. J. et al. (1990) J. Immunol. 144:2001–9; Sayers, T. J. et al. (1994) J. Immunol. 152:2289–97). Human homologs of most of these enzymes have been identified (Trapani, J. A. et al. (1988) Proc. Natl. Acad. Sci. 85:6924–28; Caputo, A. et al. (1990) J. Immunol. 145:737–44). Like all SP, the CTL-SP share three distinguishing features: 1) the presence of a catalytic triad of histidine, serine, and aspartate residues which comprise the active site; 2) the sequence GDSGGP which contains the active site serine; and 3) an N-terminal IIGG sequence which characterizes the mature SP.

The SP are secretory proteins which contain N-terminal signal peptides that serve to export the immature protein across the endoplasmic reticulum and are then cleaved (von Heijne (1986) Nuc. Acid. Res. 14:5683–90). Differences in these signal sequences provide one means of distinguishing individual SP. Some SP, particularly the digestive enzymes, exist as inactive precursors or preproenzymes, and contain a leader or activation peptide sequence 3' of the signal peptide. This activation peptide may be 2–12 amino acids in length, and it extends from the cleavage site of the signal peptide to the N-terminal IIGG sequence of the active, mature protein. Cleavage of this sequence activates the enzyme. This sequence varies in different SP according to the biochemical pathway and/or its substrate (Zunino et al, supra; Sayers et al, supra). Other features that distinguish various SP are the presence or absence of N-linked glycosylation sites that provide membrane anchors, the number and distribution of cysteine residues that determine the secondary structure of the SP, and the sequence of a substrate binding sites such as S'. The S' substrate binding region is defined by residues extending from approximately +17 to +29 relative to the N-terminal I (+1). Differences in this region of the molecule are believed to determine SP substrate specificities (Zunino et al, supra).

Trypsinogens

The trypsinogens are serine proteases secreted by exocrine cells of the pancreas (Travis J and Roberts R. Biochemistry 1969; 8: 2884–9; Mallory P and Travis J, Biochemistry 1973; 12: 2847–51). Two major types of trypsinogen isoenzymes have been characterized, trypsinogen-1, also called cationic trypsinogen, and trypsinogen-2 or anionic trypsinogen. The trypsinogen proenzymes are activated to trypsins in the intestine by enterokinase, which removes an activation peptide from the N-terminus of the trypsinogens. The trypsinogens show a high degree of sequence homology, but they can be separated on the basis of charge differences by using electrophoresis or ion exchange chromatography. The major form of trypsinogen in the pancreas and pancreatic juice is trypsinogen-1 (Guy CO et al., Biochem Biophys Res Commun 1984; 125: 516–23). In serum of healthy subjects, trypsinogen-1 is also the major form, whereas in patients with pancreatitis, trypsinogen-2 is more strongly elevated (Itkonen et al., J Lab Clin Med 1990; 115:712–8). Trypsinogens also occur in certain ovarian tumors, in which trypsinogen-2 is the major form (Koivunen et al., Cancer Res 1990; 50: 2375–8). Trypsin-1 in complex with alpha-1-antitrypsin, also called alpha-1-antiprotease, has been found to occur in serum of patients with pancreatitis (Borgstrom A and Ohlsson K, Scand J Clin Lab Invest 1984; 44: 381–6) but determination of this complex has not been found useful for differentiation between pancreatic and other gastrointestinal diseases (Borgstrom et al., Scand J Clin Lab Invest 1989; 49:757–62).

Trypsinogen-1 and -2 are closely related immunologically (Kimland et al., Clin Chim Acta 1989; 184: 31–46; Itkonen et al., 1990), but by using monoclonal antibodies (Itkonen et al., 1990) or by absorbing polyclonal antisera (Kimland et al., 1989) it is possible to obtain reagents enabling specific measurement of each form of trypsinogen.

When active trypsin reaches the blood stream, it is inactivated by the major trypsin inhibitors alpha-2-macroglobulin and alpha-1-antitrypsin (AAT). AAT is a 58 kilodalton serine protease inhibitor synthesized in the liver and is one of the main protease inhibitors in blood. Whereas complexes between trypsin-1 and AAT are detectable in serum (Borgstrom and Ohlsson, 1984) the complexes with alpha -2-macroglobulin are not measurable with antibody-based assays (Ohlsson K, Acta Gastroenterol Belg 1988; 51: 3–12).

Inflammation of the pancreas or pancreatitis may be classified as either acute or chronic by clinical criteria. With treatment, acute pancreatitis can often be cured and normal function restored. Chronic pancreatitis often results in permanent damage. The precise mechanisms which trigger acute inflammation are not understood. However, some causes in the order of their importance are alcohol ingestion, biliary tract disease, post-operative trauma, and hereditary pancreatitis. One theory provides that autodigestion, the premature activation of proteolytic enzymes in the pancreas rather than in the duodenum, causes acute pancreatitis. Any number of other factors including endotoxins, exotoxins, viral infections, ischemia, anoxia, and direct trauma may activate the proenzymes. In addition, any internal or external blockage of pancreatic ducts can also cause an accumulation of pancreatic juices in the pancreas resulting cellular damage.

Anatomy, physiology, and diseases of the pancreas are reviewed, inter alia, in Guyton AC (1991) Textbook of Medical Physiology, W B Saunders Co, Philadelphia Pa.; Isselbacher K J et al (1994) Harrison's Principles of Internal Medicine, McGraw-Hill, New York City; Johnson K E (1991) Histology and Cell Biology, Harwal Publishing, Media Pa.; and The Merck Manual of Diagnosis and Therapy (1992) Merck Research Laboratories, Rahway N.J.

Metalloprotease

The metalloproteases may be one of the older classes of proteinases and are found in bacteria, fungi as well as in higher organisms. They differ widely in their sequences and their structures but the great majority of enzymes contain a zinc atom which is catalytically active. In some cases, zinc may be replaced by another metal such as cobalt or nickel without loss of the activity. Bacterial thermolysin has been well characterized and its crystallographic structure indicates that zinc is bound by two histidines and one glutamic acid. Many enzymes contain the sequence HEXXH, which provides two histidine ligands for the zinc whereas the third ligand is either a glutamic acid (thermolysin, neprilysin, alanyl aminopeptidase) or a histidine (astacin). Other families exhibit a distinct mode of binding of the Zn atom. The catalytic mechanism leads to the formation of a non covalent tetrahedral intermediate after the attack of a zinc-bound water molecule on the carbonyl group of the scissile bond. This intermediate is further decomposed by transfer of the glutamic acid proton to the leaving group.

Metalloproteases contain a catalytic zinc metal center which participates in the hydrolysis of the peptide backbone (reviewed in Power and Harper, in Protease Inhibitors, A. J. Barrett and G. Salversen (eds.) Elsevier, Amsterdam, 1986, p. 219). The active zinc center differentiates some of these proteases from calpains and trypsins whose activities are dependent upon the presence of calcium. Examples of metalloproteases include carboxypeptidase A, carboxypeptidase B, and thermolysin.

Metalloproteases have been isolated from a number of procaryotic and eucaryotic sources, e.g. Bacillus subtilis (McConn et al., 1964, J. Biol. Chem. 239:3706); Bacillus megaterium; Serratia (Miyata et al., 1971, Agr. Biol. Chem. 35:460); Clostridium bifermentans (MacFarlane et al., 1992, App. Environ. Microbiol. 58:1195–1200), Legionella pneumophila (Moffat et al., 1994, Infection and Immunity 62:751–3). In particular, acidic metalloproteases have been isolated from broad-banded copperhead venoms (Johnson and Ownby, 1993, Int. J. Biochem. 25:267–278), rattlesnake venoms (Chlou et al., 1992, Biochem. Biophys. Res. Commun. 187:389–396) and articular cartilage (Treadwell et al., 1986, Arch. Biochem. Biophys. 251:715–723). Neutral metalloproteases, specifically those having optimal activity at neutral pH have, for example, been isolated from Aspergillus sojae (Sekine, 1973, Agric. Biol. Chem. 37:1945–1952). Neutral metalloproteases obtained from Aspergillus have been classified into two groups, npl and npII (Sekine, 1972, Agric. Biol. Chem. 36:207–216). So far, success in obtaining amino acid sequence information from these fungal neutral metalloproteases has been limited. An npII metalloprotease isolated from Aspergillus oryzae has been cloned based on amino acid sequence presented in the literature (Tatsumi et al., 1991, Mol. Gen. Genet. 228:97–103). However, to date, no npI fungal metalloprotease has been cloned or sequenced. Alkaline metalloproteases, for example, have been isolated from Pseudomonas aeruginosa (Baumann et al., 1993, EMBO J 12:3357–3364) and the insect pathogen Xenorhabdus luminescens (Schmidt et al., 1998, Appl. Environ. Microbiol. 54:2793–2797).

Metalloproteases have been devided into several distinct families based primarily on activity and sturcture: 1) water nucleophile; water bound by single zinc ion ligated to two His (within the motif HEXXH) and Glu, His or Asp; 2) water nucleophile; water bound by single zinc ion ligated to His, Glu (within the motif HXXE) and His; 3) water nucleophile; water bound by single zinc ion ligated to His, Asp and His; 4) Water nucleophile; water bound by single zinc ion ligated to two His (within the motif HXXEH) and Glu and 5) water nucleophile; water bound by two zinc ions ligated by Lys, Asp, Asp, Asp, Glu.

Examples of members of the metalloproteinase family include, but are not limited to, membrane alanyl aminopeptidase (Homo sapiens), germinal peptidyl-dipeptidase A (Homo sapiens), thimet oligopeptidase (Rattus norvegicus), oligopeptidase F (Lactococcus lactis), mycolysin (Streptomyces cacaoi), immune inhibitor A (Bacillus thuringiensis), snapalysin (Streptomyces lividans), leishmanolysin (Leishmania major), microbial collagenase (Vibrio alginolyticus), microbial collagenase, class I (Clostridium perfringens), collagenase 1 (Homo sapiens), serralysin (Serratia marcescens), fragilysin (Bacteroides fragilis), gametolysin (Chlamydomonas reinhardtii), astacin (Astacus fluviatilis), adamalysin (Crotalus adamanteus), ADAM 10 (Bos taurus), neprilysin (Homo sapiens), carboxypeptidase A (Homo sapiens), carboxypeptidase E (Bos taurus), gamma-D-glutamyl-(L)-meso-diaminopimelate peptidase I (Bacillus sphaericus), vanY D-Ala-D-Ala carboxypeptidase (Enterococcus faecium), endolysin (bacteriophage A118), pitrilysin (Escherichia coli), mitochondrial processing peptidase (Saccharomyces cerevisiae), leucyl aminopeptidase (Bos taurus), aminopeptidase I (Saccharomyces cerevisiae), membrane dipeptidase (Homo sapiens), glutamate carboxypeptidase (Pseudomonas sp.), Gly-X carboxypeptidase (Saccharomyces cerevisiae), O-sialoglycoprotein endopeptidase (Pasteurella haemolytica), beta-lytic metalloendopeptidase (Achromobacter lyticus), methionyl aminopeptidase I (Escherichia coli), X-Pro aminopeptidase (Escherichia coli), X-His dipeptidase (Escherichia coli), IgA1-specific metalloendopeptidase (Streptococcus sanguis), tentoxilysin (Clostridium tetani), leucyl aminopeptidase (Vibrio proteolyticus), aminopeptidase (Streptomyces griseus), IAP aminopeptidase (Escherichia coli), aminopeptidase T (Thermus aquaticus), hyicolysin (Staphylococcus hyicus), carboxypeptidase Taq (Thermus aquaticus), anthrax lethal factor (Bacillus anthracis), penicillolysin (Penicillium citrinum), fungalysin (Aspergillus fumigatus), lysostaphin (Staphylococcus simulans), beta-aspartyl dipeptidase (Escherichia coli), carboxypeptidase Ssl (Sulfolobus solfataricus), FtsH endopeptidase (Escherichia coli), glutamyl aminopeptidase (Lactococcus lactis), cytophagalysin (Cytophaga sp.), metalloendopeptidase (vaccinia virus), VanX D-Ala-D-Ala dipeptidase (Enterococcus faecium), Ste24p endopeptidase (Saccharomyces cerevisiae), dipeptidyl-peptidase III (Rattus norvegicus), S2P protease (Homo sapiens), sporulation factor SpoIVFB (Bacillus subtilis), and HYBD endopeptidase (Escherichia coli).

Metalloproteases have been found to have a number of uses. For example, there is strong evidence that a metalloprotease is involved in the in vivo proteolytic processing of the vasoconstrictor, endothelin-1. Rat metalloprotease has been found to be involved in peptide hormone processing. One important subfamily of the metalloproteases are the matrix metalloproteases.

A number of diseases are thought to be mediated by excess or undesired metalloprotease activity or by an imbalance in the ratio of the various members of the protease family of proteins. These include: a) osteoarthritis (Woessner, et al., J. Biol. Chem. 259(6), 3633, 1984; Phadke, et al., J. Rheumatol. 10, 852, 1983), b) rheumatoid arthritis (Mullins, et al., Biochim. Biophys. Acta 695, 117, 1983; Woolley, et al., Arthritis Rheum. 20, 1231, 1977; Gravallese, et al., Arthritis Rheum. 34, 1076, 1991), c) septic arthritis (Williams, et al., Arthritis Rheum. 33, 533, 1990), d) tumor metastasis (Reich, et al., Cancer Res. 48, 3307, 1988, and Matrisian, et al., Proc. Nat'l. Acad. Sci., USA 83, 9413, 1986), e) periodontal diseases (Overall, et al., J. Periodontal Res. 22, 81, 1987), f) corneal ulceration (Bums, et al., Invest. Opthalmol. Vis. Sci. 30, 1569, 1989), g) proteinuria (Baricos, et al., Biochem. J. 254, 609, 1988), h) coronary thrombosis from atherosclerotic plaque rupture (Henney, et al., Proc. Nat'l. Acad. Sci., USA 88, 8154–8158, 1991), i) aneurysmal aortic disease (Vine, et al., Clin. Sci. 81, 233, 1991),j) birth control (Woessner, et al., Steroids 54, 491, 1989), k) dystrophobic epidermolysis bullosa (Kronberger, et al., J. Invest. Dermatol. 79, 208, 1982), and 1) degenerative cartilage loss following traumatic joint injury, m) conditions leading to inflammatory responses, osteopenias mediated by MMP activity, n) tempero mandibular joint disease, o) demyelating diseases of the nervous system (Chantry, et al., J. Neurochem. 50, 688, 1988).

Aspartic protease

Aspartic proteases have been divided into several distinct families based primarily on activity and structure. These include 1) water nucleophile; water bound by two Asp from monomer or dimer; all endopeptidases, from eukaryote organisms, viruses or virus-like organisms and 2) endopeptidases that are water nucleophile and are water bound by Asp and Asn.

Most of aspartic proteases belong to the pepsin family. The pepsin family includes digestive enzymes such as pepsin and chymosin as well as lysosomal cathepsins and processing enzymes such as renin, and certain fligal proteases (eondcillopepsin, rhizopuspepsin, endothiapepsin). A second family comprises viral proteases such as the protease from the AIDS virus (HIV) also called retropepsin. Crystallographic studies have shown that these enzymes are biwbed molecules with the active site located between two homologous lobes. Each lobe contributes one aspartate residue of the catalytically active diad of aspartates. These two aspartyl residues are in close geometric proximity in the active molecule and one aspartate is ionized whereas the second one is unionized at the optimum pH range of 2–3. Retropepsins, are monomeric, i.e carry only one catalytic aspartate and then dimerization is required to form an active enzyme.

In contrast to serine and cysteine proteases, catalysis by aspartic protease do not involve a covalent intermediate though a tetrahedral intermediate exists. The nucleophilic attack is achieved by two simultaneous proton transfer: one from a water molecule to the diad of the two carboxyl groups and a second one from the diad to the carbonyl oxygen of the substrate with the concurrent CO—NH bond cleavage. This general acid-base catalysis, which may be called a "push-pull" mechanism leads to the formation of a non covalent neutral tetrahedral intermediate.

Examples of the aspartic protease family of proteins include, but are not limited to, pepsin A (Homo sapiens), HIV1 retropepsin (human immunodeficiency virus type 1), endopeptidase (cauliflower mosaic virus), bacilliform virus putative protease (rice tungro bacilliform virus), aspergillopepsin II (Aspergillus niger), thermopsin (Sulfolobus acidocaldarius), nodavirus endopeptidase (flock house virus), pseudomonapepsin (Pseudomonas sp. 101), signal peptidase II (Escherichia coli), polyprotein peptidase (human spumaretrovirus), copia transposon (Drosophila melanogaster), SIRE-1 peptidase (Glycine max), retrotransposon bs 1 endopeptidase (Zea mays), retrotransposon peptidase (Drosophila buzzatii), Tas retrotransposon peptidase (Ascaris lumbricoides), Pao retrotransposon peptidase (Bombyx mori), putative proteinase of Skippy retrotransposon (Fusarium oxysporum), tetravirus endopeptidase (Nudaurelia capensis omega virus), presenilin 1 (Homo sapiens).

Proteases and Cancer

Proteases are critical elements at several stages in the progression of metastatic cancer. In this process, the proteolytic degradation of structural protein in the basal membrane allows for expansion of a tumor in the primary site, evasion from this site as well as homing and invasion in distant, secondary sites. Also, tumor induced angiogenesis is required for tumor growth and is dependent on proteolytic tissue remodeling. Transfection experiments with various types of proteases have shown that the matrix metalloproteases play a dominant role in these processes in particular gelatinases A and B (MMP-2 and MMP-9, respectively). For an overview of this field see Mullins, et al., Biochim. Biophys. Acta 695, 177, 1983; Ray, et al., Eur. Respir. J. 7, 2062, 1994; Birkedal-Hansen, et al., Crit. Rev. Oral Biol. Med. 4, 197, 1993.

Furthermore, it was demonstrated that inhibition of degradation of extracellular matrix by the native matrix metalloprotease inhibitor TIMP-2 (a protein) arrests cancer growth (DeClerck, et al., Cancer Res. 52, 701, 1992) and that TIMP-2 inhibits tumor-induced angiogenesis in experimental systems (Moses, et al. Science 248, 1408, 1990). For a review, see DeClerck, et al., Ann. N. Y. Acad. Sci. 732, 222, 1994. It was further demonstrated that the synthetic matrix metalloprotease inhibitor batimastat when given intraperitoneally inhibits human colon tumor growth and spread in an orthotopic model in nude mice (Wang, et al. Cancer Res. 54, 4726, 1994) and prolongs the survival of mice bearing human ovarian carcinoma xenografts (Davies, et. al., Cancer Res. 53, 2087, 10 1993). The use of this and related compounds has been described in Brown, et al., WO-9321942 A2.

There are several patents and patent applications claiming the use of metalloproteinase inhibitors for the retardation of metastatic cancer, promoting tumor regression, inhibiting cancer cell proliferation, slowing or preventing cartilage loss associated with osteoarthritis or for treatment of other diseases as noted above (e.g. Levy, et al., WO-9519965 A1; Beckett, et al., WO-9519956 A1; Beckett, et al., WO-9519957 A1; Beckett, et al., WO-9519961 A1; Brown, et al., WO-9321942 A2; Crimmin, et al., WO-9421625 A1; Dickens, et al., U.S. Pat. No. 4,599,361; Hughes, et al., U.S. Pat. No. 5,190,937; Broadhurst, et al., EP 574758 A1; Broadhurst, et al., EP 276436; and Myers, et al., EP 520573 A1.

Arabidopsis thaliana has been used as a model organism to study the methionine aminopeptidase. Methionine aminopeptidases were found in the cytoplasm and in the organelles. For more information see a review of Giglione et al., EMBO J 2000 Nov 1;19(21):5916–29.

Protease proteins, particularly members of the methionine aminopeptidase subfamily, are a major target for drug action and development. Accordingly, it is valuable to the field of pharmaceutical development to identify and characterize previously unknown members of this subfamily of protease proteins. The present invention advances the state of the art by providing a previously unidentified human protease proteins that have homology to members of the methionine aminopeptidase subfamily.

SUMMARY OF THE INVENTION

The present invention is based in part on the identification of amino acid sequences of human protease peptides and proteins that are related to the methionine aminopeptidase subfamily, as well as allelic variants and other mammalian orthologs thereof. These unique peptide sequences, and nucleic acid sequences that encode these peptides, can be used as models for the development of human therapeutic targets, aid in the identification of therapeutic proteins, and serve as targets for the development of human therapeutic agents that modulate protease activity in cells and tissues that express the protease. Experimental data as provided in FIG. 1 indicates expression in the adrenal cortico adenoma for cushing's syndrome, prostate embryonal carcinoma, colon tumor, adult brain, heaptocellular carcinoma, pooled (fetal lung, testis and b cell), kidney,prostate.

DESCRIPTION OF THE FIGURE SHEETS

FIG. 1 provides the nucleotide sequence of a cDNA molecule or transcript sequence that encodes the protease protein of the present invention. (SEQ ID NO:1) In addition, structure and functional information is provided, such as ATG start, stop and tissue distribution, where available, that allows one to readily determine specific uses of inventions based on this molecular sequence. Experimental data as provided in FIG. 1 indicates expression in the adrenal cortico adenoma for cushing's syndrome, prostate embryonal carcinoma, colon tumor, adult brain, heaptocellular carcinoma, pooled (fetal lung, testis and b cell), kidney, prostate.

FIG. 2 provides the predicted amino acid sequence of the protease of the present invention. (SEQ ID NO:2) In addition structure and functional information such as protein family, function, and modification sites is provided where available, allowing one to readily determine specific uses of inventions based on this molecular sequence.

FIG. 3 provides genomic sequences that span the gene encoding the protease protein of the present invention. (SEQ ID NO:3) In addition structure and functional information, such as intron/exon structure, promoter location, etc., is provided where available, allowing one to readily determine specific uses of inventions based on this molecular sequence. 21 SNPs, including 6 indels, have been identified in the gene encoding the aminopeptidase protein provided by the present invention and are given in FIG. 3.

DETAILED DESCRIPTION OF THE INVENTION

General Description

The present invention is based on the sequencing of the human genome. During the sequencing and assembly of the human genome, analysis of the sequence information revealed previously unidentified fragments of the human genome that encode peptides that share structural and/or sequence homology to protein/peptide/domains identified and characterized within the art as being a protease protein or part of a protease protein and are related to the methionine aminopeptidase subfamily. Utilizing these sequences, additional genomic sequences were assembled and transcript and/or cDNA sequences were isolated and characterized. Based on this analysis, the present invention provides amino acid sequences of human protease peptides and proteins that are related to the methionine aminopeptidase subfamily, nucleic acid sequences in the form of transcript sequences, cDNA sequences and/or genomic sequences that encode these protease peptides and proteins, nucleic acid variation (allelic information), tissue distribution of expression, and information about the closest art known protein/peptide/domain that has structural or sequence homology to the protease of the present invention.

In addition to being previously unknown, the peptides that are provided in the present invention are selected based on their ability to be used for the development of commercially important products and services. Specifically, the present peptides are selected based on homology and/or structural relatedness to known protease proteins of the methionine aminopeptidase subfamily and the expression pattern observed. Experimental data as provided in FIG. 1 indicates expression in the adrenal cortico adenoma for cushing's syndrome, prostate embryonal carcinoma, colon tumor, adult brain, heaptocellular carcinoma, pooled (fetal lung, testis and b cell), kidney, prostate. The art has clearly established the commercial importance of members of this family of proteins and proteins that have expression patterns similar to that of the present gene. Some of the more specific features of the peptides of the present invention, and the uses thereof, are described herein, particularly in the Background of the Invention and in the annotation provided in the Figures, and/or are known within the art for each of the known methionine aminopeptidase family or subfamily of protease proteins.

Specific Embodiments

Peptide Molecules

The present invention provides nucleic acid sequences that encode protein molecules that have been identified as being members of the protease family of proteins and are related to the methionine aminopeptidase subfamily (protein sequences are provided in FIG. 2, transcript/cDNA sequences are provided in FIG. 1 and genomic sequences are provided in FIG. 3). The peptide sequences provided in FIG. 2, as well as the obvious variants described herein, particularly allelic variants as identified herein and using the information in FIG. 3, will be referred herein as the protease peptides of the present invention, protease peptides, or peptides/proteins of the present invention.

The present invention provides isolated peptide and protein molecules that consist of, consist essentially of, or comprise the amino acid sequences of the protease peptides disclosed in the FIG. 2, (encoded by the nucleic acid molecule shown in FIG. 1, transcript/cDNA or FIG. 3, genomic sequence), as well as all obvious variants of these peptides that are within the art to make and use. Some of these variants are described in detail below.

As used herein, a peptide is said to be "isolated" or "purified" when it is substantially free of cellular material or free of chemical precursors or other chemicals. The peptides of the present invention can be purified to homogeneity or other degrees of purity. The level of purification will be based on the intended use. The critical feature is that the preparation allows for the desired function of the peptide, even if in the presence of considerable amounts of other components (the features of an isolated nucleic acid molecule is discussed below).

In some uses, "substantially free of cellular material" includes preparations of the peptide having less than about 30% (by dry weight) other proteins (i.e., contaminating protein), less than about 20% other proteins, less than about 10% other proteins, or less than about 5% other proteins. When the peptide is recombinantly produced, it can also be substantially free of culture medium, i.e., culture medium represents less than about 20% of the volume of the protein preparation.

The language "substantially free of chemical precursors or other chemicals" includes preparations of the peptide in which it is separated from chemical precursors or other chemicals that are involved in its synthesis. In one embodiment, the language "substantially free of chemical precursors or other chemicals" includes preparations of the protease peptide having less than about 30% (by dry weight) chemical precursors or other chemicals, less than about 20% chemical precursors or other chemicals, less than about 10% chemical precursors or other chemicals, or less than about 5% chemical precursors or other chemicals.

The isolated protease peptide can be purified from cells that naturally express it, purified from cells that have been altered to express it (recombinant), or synthesized using known protein synthesis methods. Experimental data as provided in FIG. 1 indicates expression in the adrenal cortico adenoma for cushing's syndrome, prostate embryonal carcinoma, colon tumor, adult brain, heaptocellular carcinoma, pooled (fetal lung, testis and b cell), kidney, prostate. For example, a nucleic acid molecule encoding the protease peptide is cloned into an expression vector, the expression vector introduced into a host cell and the protein expressed in the host cell. The protein can then be isolated from the cells by an appropriate purification scheme using standard protein purification techniques. Many of these techniques are described in detail below.

Accordingly, the present invention provides proteins that consist of the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). The amino acid sequence of such a protein is provided in FIG. 2. A protein consists of an amino acid sequence when the amino acid sequence is the final amino acid sequence of the protein.

The present invention further provides proteins that consist essentially of the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). A protein consists essentially of an amino acid sequence when such an amino acid sequence is present with only a few additional amino acid residues, for example from about 1 to about 100 or so additional residues, typically from 1 to about 20 additional residues in the final protein.

The present invention further provides proteins that comprise the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). A protein comprises an amino acid sequence when the amino acid sequence is at least part of the final amino acid sequence of the protein. In such a fashion, the protein can be only the peptide or have additional amino acid molecules, such as amino acid residues (contiguous encoded sequence) that are naturally associated with it or heterologous amino acid residues/peptide sequences. Such a protein can have a few additional amino acid residues or can comprise several hundred or more additional amino acids. The preferred classes of proteins that are comprised of the protease peptides of the present invention are the naturally occurring mature proteins. A brief description of how various types of these proteins can be made/isolated is provided below.

The protease peptides of the present invention can be attached to heterologous sequences to form chimeric or fusion proteins. Such chimeric and fusion proteins comprise a protease peptide operatively linked to a heterologous protein having an amino acid sequence not substantially homologous to the pratease peptide. "Operatively linked" indicates that the protease peptide and the heterologous protein are fused in-frame. The heterologous protein can be fused to the N-terminus or C-terminus of the protease peptide.

In some uses, the fusion protein does not affect the activity of the protease peptide per se. For example, the fusion protein can include, but is not limited to, enzymatic fusion proteins, for example beta-galactosidase fusions, yeast two-hybrid GAL fusions, poly-His fusions, MYC-tagged, HI-tagged and Ig fusions. Such fusion proteins, particularly poly-His fusions, can facilitate the purification of recombinant protease peptide. In certain host cells (e.g., mammalian host cells), expression and/or secretion of a protein can be increased by using a heterologous signal sequence.

A chimeric or fusion protein can be produced by standard recombinant DNA techniques. For example, DNA fragments coding for the different protein sequences are ligated together in-frame in accordance with conventional techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see Ausubel et al., *Current Protocols in Molecular Biology*, 1992). Moreover, many expression vectors are commercially available that already encode a fusion moiety (e.g., a GST protein). A protease peptide-encoding nucleic acid can be cloned into such an expression vector such that the fusion moiety is linked in-frame to the protease peptide.

As mentioned above, the present invention also provides and enables obvious variants of the amino acid sequence of the proteins of the present invention, such as naturally occurring mature forms of the peptide, allelic/sequence variants of the peptides, non-naturally occurring recombinantly derived variants of the peptides, and orthologs and paralogs of the peptides. Such variants can readily be generated using art-known techniques in the fields of recombinant nucleic acid technology and protein biochemistry. It is understood, however, that variants exclude any amino acid sequences disclosed prior to the invention.

Such variants can readily be identified/made using molecular techniques and the sequence information disclosed herein. Further, such variants can readily be distinguished from other peptides based on sequence and/or structural homology to the protease peptides of the present invention. The degree of homology/identity present will be based primarily on whether the peptide is a functional variant or non-functional variant, the amount of divergence present in the paralog family and the evolutionary distance between the orthologs.

To determine the percent identity of two amino acid sequences or two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, at least 30%, 40%, 50%, 60%, 70%, 80%, or 90% or more of the length of a reference sequence is aligned for comparison purposes. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity and similarity between two sequences can be accomplished using a mathematical algorithm. (*Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of sequence Data*, Part 1, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991). In a preferred embodiment, the percent identity between two amino acid sequences is determined using the Needleman and Wunsch (*J Mol. Biol.* (48):444–453 (1970)) algorithm which has been incorporated into the GAP program in the GCG software package (available at http://www.gcg.com), using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (Devereux, J., et al., *Nucleic Acids Res.* 12(1):387 (1984)) (available at http:H/www.gcg.com), using a NWS-gapdna.CMP matrix and a gap weight of40, 50, 60, 70, or 80 and a length weight of 1, 2, 3, 4, 5, or 6. In another embodiment, the percent identity between two amino acid or nucleotide sequences is determined using the algorithm of E. Myers and W. Miller (CABIOS, 4:11–17 (1989)) which has been incorporated into the ALIGN program (version 2.0), using a PAM120 weight residue table, a gap length penalty of 12 and a gap penalty of 4.

The nucleic acid and protein sequences of the present invention can further be used as a "query sequence" to perform a search against sequence databases to, for example, identify other family members or related sequences. Such searches can be performed using the NBLAST and XBLAST programs (version 2.0) of Altschul, et al. (*J. Mol.*

*Biol.* 215:403–10 (1990)). BLAST nucleotide searches can be performed with the NBLAST program, score=100, wordlength=12 to obtain nucleotide sequences homologous to the nucleic acid molecules of the invention. BLAST protein searches can be performed with the XBLAST program, score=50, wordlength=3 to obtain amino acid sequences homologous to the proteins of the invention. To obtain gapped alignments for comparison purposes, Gapped BLAST can be utilized as described in Altschul et al. (*Nucleic Acids Res.* 25(17):3389–3402 (1997)). When utilizing BLAST and gapped BLAST programs, the default parameters of the respective programs (e.g., XBLAST and NBLAST) can be used.

Full-length pre-processed forms, as well as mature processed forms, of proteins that comprise one of the peptides of the present invention can readily be identified as having complete sequence identity to one of the protease peptides of the present invention as well as being encoded by the same genetic locus as the protease peptide provided herein. As indicated by the data presented in FIG. 3, the map position was determined to be on chromosome 2 by ePCR.

Allelic variants of a protease peptide can readily be identified as being a human protein having a high degree (significant) of sequence homology/identity to at least a portion of the protease peptide as well as being encoded by the same genetic locus as the protease peptide provided herein. Genetic locus can readily be determined based on the genomic information provided in FIG. 3, such as the genomic sequence mapped to the reference human. As indicated by the data presented in FIG. 3, the map position was determined to be on chromosome 2 by ePCR. As used herein, two proteins (or a region of the proteins) have significant homology when the amino acid sequences are typically at least about 70–80%, 80–90%, and more typically at least about 90–95% or more homologous. A significantly homologous amino acid sequence, according to the present invention, will be encoded by a nucleic acid sequence that will hybridize to a protease peptide encoding nucleic acid molecule under stringent conditions as more fully described below.

FIG. 3 provides information on SNPs that have been identified in a gene encoding the protease protein of the present invention. 21 SNP variants were found, including 6 indels (indicated by a "-") and 1 SNPs in exons.

Paralogs of a protease peptide can readily be identified as having some degree of significant sequence homology/identity to at least a portion of the protease peptide, as being encoded by a gene from humans, and as having similar activity or function. Two proteins will typically be considered paralogs when the amino acid sequences are typically at least about 60% or greater, and more typically at least about 70% or greater homology through a given region or domain. Such paralogs will be encoded by a nucleic acid sequence that will hybridize to a protease peptide encoding nucleic acid molecule under moderate to stringent conditions as more fully described below.

Orthologs of a protease peptide can readily be identified as having some degree of significant sequence homology/identity to at least a portion of the protease peptide as well as being encoded by a gene from another organism. Preferred orthologs will be isolated from mammals, preferably primates, for the development of human therapeutic targets and agents. Such orthologs will be encoded by a nucleic acid sequence that will hybridize to a protease peptide encoding nucleic acid molecule under moderate to stringent conditions, as more fully described below, depending on the degree of relatedness of the two organisms yielding the proteins. As indicated by the data presented in FIG. 3, the map position was determined to be on chromosome 2 by ePCR.

FIG. 3 provides information on SNPs that have been identified in a gene encoding the protease protein of the present invention. 21 SNP variants were found, including 6 indels (indicated by a "-") and 1 SNPs in exons.

Non-naturally occurring variants of the protease peptides of the present invention can readily be generated using recombinant techniques. Such variants include, but are not limited to deletions, additions and substitutions in the amino acid sequence of the protease peptide. For example, one class of substitutions are conserved amino acid substitution. Such substitutions are those that substitute a given amino acid in a protease peptide by another amino acid of like characteristics. Typically seen as conservative substitutions are the replacements, one for another, among the aliphatic amino acids Ala, Val, Leu, and Ile; interchange of the hydroxyl residues Ser and Thr; exchange of the acidic residues Asp and Glu; substitution between the amide residues Asn and Gln; exchange of the basic residues Lys and Arg; and replacements among the aromatic residues Phe and Tyr. Guidance concerning which amino acid changes are likely to be phenotypically silent are found in Bowie et al., *Science* 247:1306–1310 (1990).

Variant protease peptides can be fully functional or can lack function in one or more activities, e.g. ability to bind substrate, ability to cleave substrate, ability to participate in a signaling pathway, etc. Fully functional variants typically contain only conservative variation or variation in non-critical residues or in non-critical regions. FIG. 2 provides the result of protein analysis and can be used to identify critical domains/regions. Functional variants can also contain substitution of similar amino acids that result in no change or an insignificant change in function. Alternatively, such substitutions may positively or negatively affect function to some degree.

Non-functional variants typically contain one or more non-conservative amino acid substitutions, deletions, insertions, inversions, or truncation or a substitution, insertion, inversion, or deletion in a critical residue or critical region.

Amino acids that are essential for function can be identified by methods known in the art, such as site-directed mutagenesis or alanine-scanning mutagenesis (Cunningham et al., *Science* 244:1081–1085 (1989)), particularly using the results provided in FIG. 2. The latter procedure introduces single alanine mutations at every residue in the molecule. The resulting mutant molecules are then tested for biological activity such as protease activity or in assays such as an in vitro proliferative activity. Sites that are critical for binding partner/substrate binding can also be determined by structural analysis such as crystallization, nuclear magnetic resonance or photoaffinity labeling (Smith et al., *J. Mol. Biol.* 224:899–904 (1992); de Vos et al. *Science* 255:306–312 (1992)).

The present invention further provides fragments of the protease peptides, in addition to proteins and peptides that comprise and consist of such fragments, particularly those comprising the residues identified in FIG. 2. The fragments to which the invention pertains, however, are not to be construed as encompassing fragments that may be disclosed publicly prior to the present invention.

As used herein, a fragment comprises at least 8, 10, 12, 14, 16, or more contiguous amino acid residues from a protease peptide. Such fragments can be chosen based on the ability to retain one or more of the biological activities of the protease peptide or could be chosen for the ability to perform a function, e.g. bind a substrate or act as an immunogen. Particularly important fragments are biologically active fragments, peptides that are, for example, about 8 or more amino acids in length. Such fragments will typically comprise a domain or motif of the protease peptide, e.g., active site, a transmembrane domain or a substrate-binding domain. Further, possible fragments include, but are not limited to, domain or motif containing fragments, soluble peptide fragments, and fragments containing immunogenic structures. Predicted domains and functional sites are readily identifiable by computer programs well known and readily available to those of skill in the art (e.g., PROSITE analysis). The results of one such analysis are provided in FIG. 2.

Polypeptides often contain amino acids other than the 20 amino acids commonly referred to as the 20 naturally occurring amino acids. Further, many amino acids, including the terminal amino acids, may be modified by natural processes, such as processing and other post-translational modifications, or by chemical modification techniques well known in the art. Common modifications that occur naturally in protease peptides are described in basic texts, detailed monographs, and the research literature, and they are well known to those of skill in the art (some of these features are identified in FIG. 2).

Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well known to those of skill in the art and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as *Proteins—Structure and Molecular Properties*, 2nd Ed., T. E. Creighton, W. H.

Freeman and Company, New York (1993). Many detailed reviews are available on this subject, such as by Wold, F., *Posttranslational Covalent Modification of proteins*, B. C. Johnson, Ed., Academic Press, New York 1–12 (1983); Seifter et al. (*Meth. Enzymol.* 182: 626–646 (1990)) and Rattan et al. (*Ann. N.Y. Acad. Sci.* 663:48–62 (1992)).

Accordingly, the protease peptides of the present invention also encompass derivatives or analogs in which a substituted amino acid residue is not one encoded by the genetic code, in which a substituent group is included, in which the mature protease peptide is fused with another compound, such as a compound to increase the half-life of the protease peptide (for example, polyethylene glycol), or in which the additional amino acids are fused to the mature protease peptide, such as a leader or secretory sequence or a sequence for purification of the mature protease peptide or a pro-protein sequence.

Protein/Peptide Uses

The proteins of the present invention can be used in substantial and specific assays related to the functional information provided in the Figures; to raise antibodies or to elicit another immune response; as a reagent (including the labeled reagent) in assays designed to quantitatively determine levels of the protein (or its binding partner or ligand) in biological fluids; and as markers for tissues in which the corresponding protein is preferentially expressed (either constitutively or at a particular stage of tissue differentiation or development or in a disease state). Where the protein binds or potentially binds to another protein or ligand (such as, for example, in a protease-effector protein interaction or protease-ligand interaction), the protein can be used to identify the binding partner/ligand so as to develop a system to identify inhibitors of the binding interaction. Any or all of these uses are capable of being developed into reagent grade or kit format for commercialization as commercial products.

Methods for performing the uses listed above are well known to those skilled in the art. References disclosing such methods include "Molecular Cloning: A Laboratory Manual", 2d ed., Cold Spring Harbor Laboratory Press, Sambrook, J., E. F. Fritsch and T. Maniatis eds., 1989, and "Methods in Enzymology: Guide to Molecular Cloning Techniques", Academic Press, Berger, S. L. and A. R. Kimmel eds., 1987.

The potential uses of the peptides of the present invention are based primarily on the source of the protein as well as the class/action of the protein. For example, proteases isolated from humans and their human/mammalian orthologs serve as targets for identifying agents for use in mammalian therapeutic applications, e.g. a human drug, particularly in modulating a biological or pathological response in a cell or tissue that expresses the protease. Experimental data as provided in FIG. 1 indicates that aminopeptidase proteins of the present invention are expressed in the in the adrenal cortico adenoma for cushing's syndrome, prostate embryonal carcinoma,colon tumor, adult brain, heaptocellular carcinoma, pooled (fetal lung, testis and b cell), kidney, prostate by a virtual northern blot. In addition, PCR-based tissue screening panel indicates expression in human fetal whole brain. A large percentage of pharmaceutical agents are being developed that modulate the activity of protease proteins, particularly members of the methionine aminopeptidase subfamily (see Background of the Invention). The structural and functional information provided in the Background and Figures provide specific and substantial uses for the molecules of the present invention, particularly in combination with the expression information provided in FIG. 1. Experimental data as provided in FIG. 1 indicates expression in the adrenal cortico adenoma for cushing's syndrome, prostate embryonal carcinoma, colon tumor, adult brain, heaptocellular carcinoma, pooled (fetal lung, testis and b cell), kidney,prostate. Such uses can readily be determined using the information provided herein, that which is known in the art, and routine experimentation.

The proteins of the present invention (including variants and fragments that may have been disclosed prior to the present invention) are useful for biological assays related to proteases that are related to members of the methionine aminopeptidase subfamily. Such assays involve any of the known protease functions or activities or properties useful for diagnosis and treatment of protease-related conditions that are specific for the subfamily of proteases that the one of the present invention belongs to, particularly in cells and tissues that express the protease. Experimental data as provided in FIG. 1 indicates that aminopeptidase proteins of the present invention are expressed in the in the adrenal cortico adenoma for cushing's syndrome, prostate embryonal carcinoma,colon tumor, adult brain, heaptocellular carcinoma, pooled (fetal lung, testis and b cell), kidney, prostate by a virtual northern blot. In addition, PCR-based tissue screening panel indicates expression in human fetal whole brain.

The proteins of the present invention are also useful in drug screening assays, in cell-based or cell-free systems. Cell-based systems can be native, i.e., cells that normally express the protease, as a biopsy or expanded in cell culture. Experimental data as provided in FIG. 1 indicates expression in the adrenal cortico adenoma for cushing's syndrome, prostate embryonal carcinoma, colon tumor, adult brain, heaptocellular carcinoma, pooled (fetal lung, testis and b cell), kidney,prostate. In an alternate embodiment, cell-based assays involve recombinant host cells expressing the protease protein.

The polypeptides can be used to identify compounds that modulate protease activity of the protein in its natural state or an altered form that causes a specific disease or pathology associated with the protease. Both the proteases of the present invention and appropriate variants and fragments can be used in high-throughput screens to assay candidate compounds for the ability to bind to the protease. These compounds can be further screened against a functional protease to determine the effect of the compound on the protease activity. Further, these compounds can be tested in animal or invertebrate systems to determine activity/effectiveness. Compounds can be identified that activate (agonist) or inactivate (antagonist) the protease to a desired degree.

Further, the proteins of the present invention can be used to screen a compound for the ability to stimulate or inhibit interaction between the protease protein and a molecule that normally interacts with the protease protein, e.g. a substrate or a component of the signal pathway that the protease protein normally interacts (for example, a protease). Such assays typically include the steps of combining the protease protein with a candidate compound under conditions that allow the protease protein, or fragment, to interact with the target molecule, and to detect the formation of a complex between the protein and the target or to detect the biochemical consequence of the interaction with the protease protein and the target, such as any of the associated effects of signal transduction such as protein cleavage, cAMP turnover, and adenylate cyclase activation, etc.

Candidate compounds include, for example, 1) peptides such as soluble peptides, including Ig-tailed fusion peptides and members of random peptide libraries (see, e.g., Lam et al., *Nature* 354:82–84 (1991); Houghten et al., *Nature* 354:84–86 (1991)) and combinatorial chemistry-derived molecular libraries made of D- and/or L- configuration amino acids; 2) phosphopeptides (e.g., members of random and partially degenerate, directed phosphopeptide libraries, see, e.g., Songyang et al., *Cell* 72:767–778 (1993)); 3) antibodies (e.g., polyclonal, monoclonal, humanized, anti-idiotypic, chimeric, and single chain antibodies as well as Fab, $F(ab')_2$, Fab expression library fragments, and epitope-binding fragments of antibodies); and 4) small organic and inorganic molecules (e.g., molecules obtained from combinatorial and natural product libraries).

One candidate compound is a soluble fragment of the receptor that competes for substrate binding. Other candidate compounds include mutant proteases or appropriate fragments containing mutations that affect protease function and thus compete for substrate. Accordingly, a fragment that competes for substrate, for example with a higher affinity, or a fragment that binds substrate but does not allow release, is encompassed by the invention.

The invention further includes other end point assays to identify compounds that modulate (stimulate or inhibit) protease activity. The assays typically involve an assay of events in the signal transduction pathway that indicate protease activity. Thus, the cleavage of a substrate, inactivation/activation of a protein, a change in the expression of genes that are up- or down-regulated in response to the protease protein dependent signal cascade can be assayed.

Any of the biological or biochemical functions mediated by the protease can be used as an endpoint assay. These include all of the biochemical or biochemical/biological events described herein, in the references cited herein, incorporated by reference for these endpoint assay targets, and other functions known to those of ordinary skill in the art or that can be readily identified using the information provided in the Figures, particularly FIG. 2. Specifically, a biological function of a cell or tissues that expresses the protease can be assayed. Experimental data as provided in FIG. 1 indicates that aminopeptidase proteins of the present invention are expressed in the in the adrenal cortico adenoma for cushing's syndrome, prostate embryonal carcinoma,colon tumor, adult brain, heaptocellular carcinoma, pooled (fetal lung, testis and b cell), kidney, prostate by a virtual northern blot. In addition, PCR-based tissue screening panel indicates expression in human fetal whole brain.

Binding and/or activating compounds can also be screened by using chimeric protease proteins in which the amino terminal extracellular domain, or parts thereof, the entire transmembrane domain or subregions, such as any of the seven transmembrane segments or any of the intracellular or extracellular loops and the carboxy terminal intracellular domain, or parts thereof, can be replaced by heterologous domains or subregions. For example, a substrate-binding region can be used that interacts with a different substrate then that which is recognized by the native protease. Accordingly, a different set of signal transduction components is available as an end-point assay for activation. This allows for assays to be performed in other than the specific host cell from which the protease is derived.

The proteins of the present invention are also useful in competition binding assays in methods designed to discover compounds that interact with the protease (e.g. binding partners and/or ligands). Thus, a compound is exposed to a protease polypeptide under conditions that allow the compound to bind or to otherwise interact with the polypeptide. Soluble protease polypeptide is also added to the mixture. If the test compound interacts with the soluble protease polypeptide, it decreases the amount of complex formed or activity from the protease target. This type of assay is particularly useful in cases in which compounds are sought that interact with specific regions of the protease. Thus, the soluble polypeptide that competes with the target protease region is designed to contain peptide sequences corresponding to the region of interest.

To perform cell free drug screening assays, it is sometimes desirable to immobilize either the protease protein, or fragment, or its target molecule to facilitate separation of complexes from uncomplexed forms of one or both of the proteins, as well as to accommodate automation of the assay.

Techniques for immobilizing proteins on matrices can be used in the drug screening assays. In one embodiment, a fusion protein can be provided which adds a domain that allows the protein to be bound to a matrix. For example, glutathione-S-transferase fusion proteins can be adsorbed onto glutathione sepharose beads (Sigma Chemical, St. Louis, Mo.) or glutathione derivatized microtitre plates, which are then combined with the cell lysates (e.g., $^{35}$S-labeled) and the candidate compound, and the mixture incubated under conditions conducive to complex formation (e.g., at physiological conditions for salt and pH). Following incubation, the beads are washed to remove any unbound label, and the matrix immobilized and radiolabel determined directly, or in the supernatant after the complexes are dissociated. Alternatively, the complexes can be dissociated from the matrix, separated by SDS-PAGE, and the level of protease-binding protein found in the bead fraction quantitated from the gel using standard electrophoretic techniques. For example, either the polypeptide or its target molecule can be immobilized utilizing conjugation of biotin and streptavidin using techniques well known in the art. Alternatively, antibodies reactive with the protein but which do not interfere with binding of the protein to its target molecule can be derivatized to the wells of the plate, and the protein trapped in the wells by antibody conjugation. Preparations of a protease-binding protein and a candidate compound are incubated in the protease protein-presenting wells and the amount of complex trapped in the well can be quantitated. Methods for detecting such complexes, in addition to those described above for the GST-immobilized complexes, include immunodetection of complexes using antibodies reactive with the protease protein target molecule, or which are reactive with protease protein and compete with the target molecule, as well as enzyme-linked assays which rely on detecting an enzymatic activity associated with the target molecule.

Agents that modulate one of the proteases of the present invention can be identified using one or more of the above assays, alone or in combination. It is generally preferable to use a cell-based or cell free system first and then confirm activity in an animal or other model system. Such model systems are well known in the art and can readily be employed in this context.

Modulators of protease protein activity identified according to these drug screening assays can be used to treat a subject with a disorder mediated by the protease pathway, by treating cells or tissues that express the protease. Experimental data as provided in FIG. 1 indicates expression in the adrenal cortico adenoma for cushing's syndrome, prostate embryonal carcinoma, colon tumor, adult brain, heaptocellular carcinoma, pooled (fetal lung, testis and b cell), kidney, prostate. These methods of treatment include the steps of administering a modulator of protease activity in a pharmaceutical composition to a subject in need of such treatment, the modulator being identified as described herein.

In yet another aspect of the invention, the protease proteins can be used as "bait proteins" in a two-hybrid assay or three-hybrid assay (see, e.g., U.S. Pat. No. 5,283,317; Zervos et al. (1993) *Cell* 72:223–232; Madura et al. (1993) *J. Biol. Chem.* 268:12046–12054; Bartel et al. (1993) *Biotechniques* 14:920–924; Iwabuchi et al. (1993) *Oncogene* 8:1693–1696; and Brent WO94/10300), to identify other proteins, which bind to or interact with the protease and are involved in protease activity. Such protease-binding proteins are also likely to be involved in the propagation of signals by the protease proteins or protease targets as, for example, downstream elements of a protease-mediated signaling pathway. Alternatively, such protease-binding proteins are likely to be protease inhibitors.

The two-hybrid system is based on the modular nature of most transcription factors, which consist of separable DNA-binding and activation domains. Briefly, the assay utilizes two different DNA constructs. In one construct, the gene that codes for a protease protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a protease-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the protease protein.

This invention further pertains to novel agents identified by the above-described screening assays. Accordingly, it is within the scope of this invention to further use an agent identified as described herein in an appropriate animal model. For example, an agent identified as described herein (e.g., a protease-modulating agent, an antisense protease nucleic acid molecule, a protease-specific antibody, or a protease-binding partner) can be used in an animal or other model to determine the efficacy, toxicity, or side effects of treatment with such an agent. Alternatively, an agent identified as described herein can be used in an animal or other model to determine the mechanism of action of such an agent. Furthermore, this invention pertains to uses of novel agents identified by the above-described screening assays for treatments as described herein.

The protease proteins of the present invention are also useful to provide a target for diagnosing a disease or predisposition to disease mediated by the peptide. Accordingly, the invention provides methods for detecting the presence, or levels of, the protein (or encoding mRNA) in a cell, tissue, or organism. Experimental data as provided in FIG. 1 indicates expression in the adrenal cortico adenoma for cushing's syndrome, prostate embryonal carcinoma, colon tumor, adult brain, heaptocellular carcinoma, pooled (fetal lung, testis and b cell), kidney, prostate. The method involves contacting a biological sample with a compound capable of interacting with the protease protein such that the interaction can be detected. Such an assay can be provided in a single detection format or a multi-detection format such as an antibody chip array.

One agent for detecting a protein in a sample is an antibody capable of selectively binding to protein. A biological sample includes tissues, cells and biological fluids isolated from a subject, as well as tissues, cells and fluids present within a subject.

The peptides of the present invention also provide targets for diagnosing active protein activity, disease, or predisposition to disease, in a patient having a variant peptide, particularly activities and conditions that are known for other members of the family of proteins to which the present one belongs. Thus, the peptide can be isolated from a biological sample and assayed for the presence of a genetic mutation that results in aberrant peptide. This includes amino acid substitution, deletion, insertion, rearrangement, (as the result of aberrant splicing events), and inappropriate post-translational modification. Analytic methods include altered electrophoretic mobility, altered tryptic peptide digest, altered protease activity in cell-based or cell-free assay, alteration in substrate or antibody- binding pattern, altered isoelectric point, direct amino acid sequencing, and any other of the known assay techniques useful for detecting mutations in a protein. Such an assay can be provided in a single detection format or a multi-detection format such as an antibody chip array.

In vitro techniques for detection of peptide include enzyme linked immunosorbent assays (ELISAs), Western blots, immunoprecipitations and immunofluorescence using a detection reagent, such as an antibody or protein binding agent. Alternatively, the peptide can be detected in vivo in a subject by introducing into the subject a labeled anti-peptide antibody or other types of detection agent. For example, the antibody can be labeled with a radioactive marker whose presence and location in a subject can be detected by standard imaging techniques. Particularly useful are methods that detect the allelic variant of a peptide expressed in a subject and methods which detect fragments of a peptide in a sample.

The peptides are also useful in pharmacogenomic analysis. Pharmacogenomics deal with clinically significant hereditary variations in the response to drugs due to altered drug disposition and abnormal action in affected persons. See, e.g., Eichelbaum, M. (*Clin. Exp. Pharmacol. Physiol.* 23(10–11):983–985 (1996)), and Linder, M. W. (*Clin. Chem.* 43(2):254–266 (1997)). The clinical outcomes of these variations result in severe toxicity of therapeutic drugs in certain individuals or therapeutic failure of drugs in certain individuals as a result of individual variation in metabolism. Thus, the genotype of the individual can determine the way a therapeutic compound acts on the body or the way the body metabolizes the compound. Further, the activity of drug metabolizing enzymes effects both the intensity and duration of drug action. Thus, the pharmacogenomics of the individual permit the selection of effective compounds and effective dosages of such compounds for prophylactic or therapeutic treatment based on the individual's genotype. The discovery of genetic polymorphisms in some drug metabolizing enzymes has explained why some patients do not obtain the expected drug effects, show an exaggerated drug effect, or experience serious toxicity from standard drug dosages. Polymorphisms can be expressed in the phenotype of the extensive metabolizer and the phenotype of the poor metabolizer. Accordingly, genetic polymorphism may lead to allelic protein variants of the protease protein in which one or more of the protease functions in one population is different from those in another population. The peptides thus allow a target to ascertain a genetic predisposition that can affect treatment modality. Thus, in a ligand-based treatment, polymorphism may give rise to amino terminal extracellular domains and/or other substrate-binding regions that are more or less active in substrate binding, and protease activation. Accordingly, substrate dosage would necessarily be modified to maximize the therapeutic effect within a given population containing a polymorphism. As an alternative to genotyping, specific polymorphic peptides could be identified.

The peptides are also useful for treating a disorder characterized by an absence of, inappropriate, or unwanted expression of the protein. Experimental data as provided in FIG. 1 indicates expression in the adrenal cortico adenoma for cushing's syndrome, prostate embryonal carcinoma, colon tumor, adult brain, heaptocellular carcinoma, pooled (fetal lung, testis and b cell), kidney,prostate. Accordingly, methods for treatment include the use of the protease protein or fragments.

Antibodies

The invention also provides antibodies that selectively bind to one of the peptides of the present invention, a protein comprising such a peptide, as well as variants and fragments thereof. As used herein, an antibody selectively binds a target peptide when it binds the target peptide and does not significantly bind to unrelated proteins. An antibody is still considered to selectively bind a peptide even if it also binds to other proteins that are not substantially homologous with the target peptide so long as such proteins share homology with a fragment or domain of the peptide target of the antibody. In this case, it would be understood that antibody binding to the peptide is still selective despite some degree of cross-reactivity.

As used herein, an antibody is defined in terms consistent with that recognized within the art: they are multi-subunit proteins produced by a mammalian organism in response to an antigen challenge. The antibodies of the present invention include polyclonal antibodies and monoclonal antibodies, as well as fragments of such antibodies, including, but not limited to, Fab or $F(ab')_2$, and Fv fragments.

Many methods are known for generating and/or identifying antibodies to a given target peptide. Several such methods are described by Harlow, Antibodies, Cold Spring Harbor Press, (1989).

In general, to generate antibodies, an isolated peptide is used as an immunogen and is administered to a mammalian organism, such as a rat, rabbit or mouse. The full-length protein, an antigenic peptide fragment or a fusion protein can be used. Particularly important fragments are those covering functional domains, such as the domains identified in FIG. 2, and domain of sequence homology or divergence amongst the family, such as those that can readily be identified using protein alignment methods and as presented in the Figures.

Antibodies are preferably prepared from regions or discrete fragments of the protease proteins. Antibodies can be prepared from any region of the peptide as described herein. However, preferred regions will include those involved in function/activity and/or protease/binding partner interaction. FIG. 2 can be used to identify particularly important regions while sequence alignment can be used to identify conserved and unique sequence fragments.

An antigenic fragment will typically comprise at least 8 contiguous amino acid residues. The antigenic peptide can comprise, however, at least 10, 12, 14, 16 or more amino acid residues. Such fragments can be selected on a physical property, such as fragments correspond to regions that are located on the surface of the protein, e.g., hydrophilic regions or can be selected based on sequence uniqueness (see FIG. 2).

Detection on an antibody of the present invention can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

Antibody Uses

The antibodies can be used to isolate one of the proteins of the present invention by standard techniques, such as affinity chromatography or immunoprecipitation. The antibodies can facilitate the purification of the natural protein from cells and recombinantly produced protein expressed in host cells. In addition, such antibodies are useful to detect the presence of one of the proteins of the present invention in cells or tissues to determine the pattern of expression of the protein among various tissues in an organism and over the course of normal development. Experimental data as provided in FIG. 1 indicates that aminopeptidase proteins of the present invention are expressed in the in the adrenal cortico adenoma for cushing's syndrome, prostate embryonal carcinoma,colon tumor, adult brain, heaptocellular carcinoma, pooled (fetal lung, testis and b cell), kidney, prostate by a virtual northern blot. In addition, PCR-based tissue screening panel indicates expression in human fetal whole brain. Further, such antibodies can be used to detect protein in situ, in vitro, or in a cell lysate or supernatant in order to evaluate the abundance and pattern of expression. Also, such antibodies can be used to assess abnormal tissue distribution or abnormal expression during development or progression of a biological condition. Antibody detection of circulating fragments of the full length protein can be used to identify turnover.

Further, the antibodies can be used to assess expression in disease states such as in active stages of the disease or in an individual with a predisposition toward disease related to the protein's function. When a disorder is caused by an inappropriate tissue distribution, developmental expression, level of expression of the protein, or expressed/processed form, the antibody can be prepared against the normal protein. Experimental data as provided in FIG. 1 indicates expression in the adrenal cortico adenoma for cushing's syndrome, prostate embryonal carcinoma, colon tumor, adult brain, heaptocellular carcinoma, pooled (fetal lung, testis and b cell), kidney,prostate. If a disorder is characterized by a specific mutation in the protein, antibodies specific for this mutant protein can be used to assay for the presence of the specific mutant protein.

The antibodies can also be used to assess normal and aberrant subcellular localization of cells in the various tissues in an organism. Experimental data as provided in FIG. 1 indicates expression in the adrenal cortico adenoma for cushing's syndrome, prostate embryonal carcinoma, colon tumor, adult brain, heaptocellular carcinoma, pooled (fetal lung, testis and b cell), kidney,prostate. The diagnostic uses can be applied, not only in genetic testing, but also in monitoring a treatment modality. Accordingly, where treatment is ultimately aimed at correcting expression level or the presence of aberrant sequence and aberrant tissue distribution or developmental expression, antibodies directed against the protein or relevant fragments can be used to monitor therapeutic efficacy.

Additionally, antibodies are useful in pharmacogenomic analysis. Thus, antibodies prepared against polymorphic proteins can be used to identify individuals that require modified treatment modalities. The antibodies are also useful as diagnostic tools as an immunological marker for aberrant protein analyzed by electrophoretic mobility, isoelectric point, tryptic peptide digest, and other physical assays known to those in the art.

The antibodies are also useful for tissue typing. Experimental data as provided in FIG. 1 indicates expression in the adrenal cortico adenoma for cushing's syndrome, prostate embryonal carcinoma, colon tumor, adult brain, heaptocellular carcinoma, pooled (fetal lung, testis and b cell), kidney, prostate. Thus, where a specific protein has been correlated with expression in a specific tissue, antibodies that are specific for this protein can be used to identify a tissue type.

The antibodies are also useful for inhibiting protein function, for example, blocking the binding of the protease peptide to a binding partner such as a substrate. These uses can also be applied in a therapeutic context in which treatment involves inhibiting the protein's function. An antibody can be used, for example, to block binding, thus modulating (agonizing or antagonizing) the peptides activity. Antibodies can be prepared against specific fragments containing sites required for function or against intact protein that is associated with a cell or cell membrane. See FIG. 2 for structural information relating to the proteins of the present invention.

The invention also encompasses kits for using antibodies to detect the presence of a protein in a biological sample. The kit can comprise antibodies such as a labeled or labelable antibody and a compound or agent for detecting protein in a biological sample; means for determining the amount of protein in the sample; means for comparing the amount of protein in the sample with a standard; and instructions for use. Such a kit can be supplied to detect a single protein or epitope or can be configured to detect one of a multitude of epitopes, such as in an antibody detection array. Arrays are described in detail below for nucleic acid arrays and similar methods have been developed for antibody arrays.

Nucleic Acid Molecules

The present invention further provides isolated nucleic acid molecules that encode a protease peptide or protein of the present invention (cDNA, transcript and genomic sequence). Such nucleic acid molecules will consist of, consist essentially of, or comprise a nucleotide sequence that encodes one of the protease peptides of the present invention, an allelic variant thereof, or an ortholog or paralog thereof.

As used herein, an "isolated" nucleic acid molecule is one that is separated from other nucleic acid present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. However, there can be some flanking nucleotide sequences, for example up to about 5 KB, 4 KB, 3 KKB, 2KB, or 1 KB or less, particularly contiguous peptide encoding sequences and peptide encoding sequences within the same gene but separated by introns in the genomic sequence. The important point is that the nucleic acid is isolated from remote and unimportant flanking sequences such that it can be subjected to the specific manipulations described herein such as recombinant expression, preparation of probes and primers, and other uses specific to the nucleic acid sequences.

Moreover, an "isolated" nucleic acid molecule, such as a transcript/cDNA molecule, can be substantially free of other cellular material, or culture medium when produced by recombinant techniques, or chemical precursors or other chemicals when chemically synthesized. However, the nucleic acid molecule can be fused to other coding or regulatory sequences and still be considered isolated.

For example, recombinant DNA molecules contained in a vector are considered isolated. Further examples of isolated DNA molecules include recombinant DNA molecules maintained in heterologous host cells or purified (partially or substantially) DNA molecules in solution. Isolated RNA molecules include in vivo or in vitro RNA transcripts of the isolated DNA molecules of the present invention. Isolated nucleic acid molecules according to the present invention further include such molecules produced synthetically.

Accordingly, the present invention provides nucleic acid molecules that consist of the nucleotide sequence shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule consists of a nucleotide sequence when the nucleotide sequence is the complete nucleotide sequence of the nucleic acid molecule.

The present invention further provides nucleic acid molecules that consist essentially of the nucleotide sequence shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule consists essentially of a nucleotide sequence when such a nucleotide sequence is present with only a few additional nucleic acid residues in the final nucleic acid molecule.

The present invention further provides nucleic acid molecules that comprise the nucleotide sequences shown in FIG. 1 or 3 (SEQ ID NO: 1, transcript sequence and SEQ ID NO:3, genomic sequence), or any nucleic acid molecule that encodes the protein provided in FIG. 2, SEQ ID NO:2. A nucleic acid molecule comprises a nucleotide sequence when the nucleotide sequence is at least part of the final nucleotide sequence of the nucleic acid molecule. In such a fashion, the nucleic acid molecule can be only the nucleotide sequence or have additional nucleic acid residues, such as nucleic acid residues that are naturally associated with it or heterologous nucleotide sequences. Such a nucleic acid molecule can have a few additional nucleotides or can comprises several hundred or more additional nucleotides. A brief description of how various types of these nucleic acid molecules can be readily made/isolated is provided below.

In FIGS. 1 and 3, both coding and non-coding sequences are provided. Because of the source of the present invention, humans genomic sequence (FIG. 3) and cDNA/transcript sequences (FIG. 1), the nucleic acid molecules in the Figures will contain genomic intronic sequences, 5' and 3' non-coding sequences, gene regulatory regions and non-coding intergenic sequences. In general such sequence features are either noted in FIGS. 1 and 3 or can readily be identified using computational tools known in the art. As discussed below, some of the non-coding regions, particularly gene regulatory elements such as promoters, are useful for a variety of purposes, e.g. control of heterologous gene expression, target for identifying gene activity modulating compounds, and are particularly claimed as fragments of the genomic sequence provided herein.

The isolated nucleic acid molecules can encode the mature protein plus additional amino or carboxyl-terminal amino acids, or amino acids interior to the mature peptide (when the mature form has more than one peptide chain, for instance). Such sequences may play a role in processing of a protein from precursor to a mature form, facilitate protein trafficking, prolong or shorten protein half-life or facilitate manipulation of a protein for assay or production, among other things. As generally is the case in situ, the additional amino acids may be processed away from the mature protein by cellular enzymes.

As mentioned above, the isolated nucleic acid molecules include, but are not limited to, the sequence encoding the protease peptide alone, the sequence encoding the mature peptide and additional coding sequences, such as a leader or secretory sequence (e.g., a pre-pro or pro-protein sequence), the sequence encoding the mature peptide, with or without the additional coding sequences, plus additional non-coding sequences, for example introns and non-coding 5' and 3' sequences such as transcribed but non-translated sequences that play a role in transcription, mRNA processing (including splicing and polyadenylation signals), ribosome binding and stability of mRNA. In addition, the nucleic acid molecule may be fused to a marker sequence encoding, for example, a peptide that facilitates purification.

Isolated nucleic acid molecules can be in the form of RNA, such as mRNA, or in the form DNA, including cDNA and genomic DNA obtained by cloning or produced by chemical synthetic techniques or by a combination thereof. The nucleic acid, especially DNA, can be double-stranded or single-stranded. Single-stranded nucleic acid can be the coding strand (sense strand) or the non-coding strand (anti-sense strand).

The invention further provides nucleic acid molecules that encode fragments of the peptides of the present invention as well as nucleic acid molecules that encode obvious variants of the protease proteins of the present invention that are described above. Such nucleic acid molecules may be naturally occurring, such as allelic variants (same locus), paralogs (different locus), and orthologs (different organism), or may be constructed by recombinant DNA methods or by chemical synthesis. Such non-naturally occurring variants may be made by mutagenesis techniques, including those applied to nucleic acid molecules, cells, or organisms. Accordingly, as discussed above, the variants can contain nucleotide substitutions, deletions, inversions and insertions. Variation can occur in either or both the coding and non-coding regions. The variations can produce both conservative and non-conservative amino acid substitutions.

The present invention further provides non-coding fragments of the nucleic acid molecules provided in FIGS. 1 and 3. Preferred non-coding fragments include, but are not limited to, promoter sequences, enhancer sequences, gene modulating sequences and gene termination sequences. Such fragments are useful in controlling heterologous gene expression and in developing screens to identify gene-modulating agents. A promoter can readily be identified as being 5' to the ATG start site in the genomic sequence provided in FIG. 3.

A fragment comprises a contiguous nucleotide sequence greater than 12 or more nucleotides. Further, a fragment could at least 30, 40, 50, 100, 250 or 500 nucleotides in length. The length of the fragment will be based on its intended use. For example, the fragment can encode epitope bearing regions of the peptide, or can be useful as DNA probes and primers. Such fragments can be isolated using the known nucleotide sequence to synthesize an oligonucleotide probe. A labeled probe can then be used to screen a cDNA library, genomic DNA library, or mRNA to isolate nucleic acid corresponding to the coding region. Further, primers can be used in PCR reactions to clone specific regions of gene.

A probe/primer typically comprises substantially a purified oligonucleotide or oligonucleotide pair. The oligonucleotide typically comprises a region of nucleotide sequence that hybridizes under stringent conditions to at least about 12, 20, 25, 40, 50 or more consecutive nucleotides.

Orthologs, homologs, and allelic variants can be identified using methods well known in the art. As described in the Peptide Section, these variants comprise a nucleotide sequence encoding a peptide that is typically 60–70%, 70–80%, 80–90%, and more typically at least about 90–95% or more homologous to the nucleotide sequence shown in the Figure sheets or a fragment of this sequence. Such nucleic acid molecules can readily be identified as being able to hybridize under moderate to stringent conditions, to the nucleotide sequence shown in the Figure sheets or a fragment of the sequence. Allelic variants can readily be determined by genetic locus of the encoding gene.

As used herein, the term "hybridizes under stringent conditions" is intended to describe conditions for hybridization and washing under which nucleotide sequences encoding a peptide at least 60–70% homologous to each other typically remain hybridized to each other. The conditions can be such that sequences at least about 60%, at least about 70%, or at least about 80% or more homologous to each other typically remain hybridized to each other. Such stringent conditions are known to those skilled in the art and can be found in *Current Protocols in Molecular Biology*, John Wiley & Sons, N.Y. (1989), 6.3.1–6.3.6. One example of stringent hybridization conditions are hybridization in 6X sodium chloride/sodium citrate (SSC) at about 45C, followed by one or more washes in 0.2×SSC, 0.1% SDS at 50–65C. Examples of moderate to low stringency hybridization conditions are well known in the art.

Nucleic Acid Molecule Uses

The nucleic acid molecules of the present invention are useful for probes, primers, chemical intermediates, and in biological assays. The nucleic acid molecules are useful as a hybridization probe for messenger RNA, transcript/cDNA and genomic DNA to isolate full-length cDNA and genomic clones encoding the peptide described in FIG. 2 and to isolate cDNA and genomic clones that correspond to variants (alleles, orthologs, etc.) producing the same or related peptides shown in FIG. 2. 21 SNPs, including 6 indels, have been identified in the gene encoding the aminopeptidase protein provided by the present invention and are given in FIG. 3.

The probe can correspond to any sequence along the entire length of the nucleic acid molecules provided in the Figures. Accordingly, it could be derived from 5' noncoding regions, the coding region, and 3' noncoding regions. However, as discussed, fragments are not to be construed as encompassing fragments disclosed prior to the present invention.

The nucleic acid molecules are also useful as primers for PCR to amplify any given region of a nucleic acid molecule and are useful to synthesize antisense molecules of desired length and sequence.

The nucleic acid molecules are also useful for constructing recombinant vectors. Such vectors include expression vectors that express a portion of, or all of, the peptide sequences. Vectors also include insertion vectors, used to integrate into another nucleic acid molecule sequence, such as into the cellular genome, to alter in situ expression of a gene and/or gene product. For example, an endogenous coding sequence can be replaced via homologous recombination with all or part of the coding region containing one or more specifically introduced mutations.

The nucleic acid molecules are also useful for expressing antigenic portions of the proteins.

The nucleic acid molecules are also useful as probes for determining the chromosomal positions of the nucleic acid molecules by means of in situ hybridization methods. As indicated by the data presented in FIG. 3, the map position was determined to be on chromosome 2 by ePCR.

The nucleic acid molecules are also useful in making vectors containing the gene regulatory regions of the nucleic acid molecules of the present invention.

The nucleic acid molecules are also useful for designing ribozymes corresponding to all, or a part, of the mRNA produced from the nucleic acid molecules described herein.

The nucleic acid molecules are also useful for making vectors that express part, or all, of the peptides.

The nucleic acid molecules are also useful for constructing host cells expressing a part, or all, of the nucleic acid molecules and peptides.

The nucleic acid molecules are also useful for constructing transgenic animals expressing all, or a part, of the nucleic acid molecules and peptides.

The nucleic acid molecules are also useful as hybridization probes for determining the presence, level, form and distribution of nucleic acid expression. Experimental data as provided in FIG. 1 indicates that aminopeptidase proteins of the present invention are expressed in the in the adrenal cortico adenoma for cushing's syndrome, prostate embryonal carcinoma,colon tumor, adult brain, heaptocellular carcinoma, pooled (fetal lung, testis and b cell), kidney, prostate by a virtual northern blot. In addition, PCR-based tissue screening panel indicates expression in human fetal whole brain. Accordingly, the probes can be used to detect the presence of, or to determine levels of, a specific nucleic acid molecule in cells, tissues, and in organisms. The nucleic acid whose level is determined can be DNA or RNA. Accordingly, probes corresponding to the peptides described herein can be used to assess expression and/or gene copy number in a given cell, tissue, or organism. These uses are relevant for diagnosis of disorders involving an increase or decrease in protease protein expression relative to normal results.

In vitro techniques for detection of mRNA include Northern hybridizations and in situ hybridizations. In vitro techniques for detecting DNA includes Southern hybridizations and in situ hybridization.

Probes can be used as a part of a diagnostic test kit for identifying cells or tissues that express a protease protein, such as by measuring a level of a protease-encoding nucleic acid in a sample of cells from a subject e.g., mRNA or genomic DNA, or determining if a protease gene has been mutated. Experimental data as provided in FIG. 1 indicates that aminopeptidase proteins of the present invention are expressed in the in the adrenal cortico adenoma for cushing's syndrome, prostate embryonal carcinoma,colon tumor, adult brain, heaptocellular carcinoma, pooled (fetal lung, testis and b cell), kidney, prostate by a virtual northern blot. In addition, PCR-based tissue screening panel indicates expression in human fetal whole brain.

Nucleic acid expression assays are useful for drug screening to identify compounds that modulate protease nucleic acid expression.

The invention thus provides a method for identifying a compound that can be used to treat a disorder associated with nucleic acid expression of the protease gene, particularly biological and pathological processes that are mediated by the protease in cells and tissues that express it. Experimental data as provided in FIG. 1 indicates expression in the adrenal cortico adenoma for cushing's syndrome, prostate embryonal carcinoma, colon tumor, adult brain, heaptocellular carcinoma, pooled (fetal lung, testis and b cell), kidney, prostate. The method typically includes assaying the ability of the compound to modulate the expression of the protease nucleic acid and thus identifying a compound that can be used to treat a disorder characterized by undesired protease nucleic acid expression. The assays can be performed in cell-based and cell-free systems. Cell-based assays include cells naturally expressing the protease nucleic acid or recombinant cells genetically engineered to express specific nucleic acid sequences.

The assay for protease nucleic acid expression can involve direct assay of nucleic acid levels, such as mRNA levels, or on collateral compounds involved in the signal pathway. Further, the expression of genes that are up- or down-regulated in response to the protease protein signal pathway can also be assayed. In this embodiment the regulatory regions of these genes can be operably linked to a reporter gene such as luciferase.

Thus, modulators of protease gene expression can be identified in a method wherein a cell is contacted with a candidate compound and the expression of mRNA determined. The level of expression of protease mRNA in the presence of the candidate compound is compared to the level of expression of protease mRNA in the absence of the candidate compound. The candidate compound can then be identified as a modulator of nucleic acid expression based on this comparison and be used, for example to treat a disorder characterized by aberrant nucleic acid expression. When expression of mRNA is statistically significantly greater in the presence of the candidate compound than in its absence, the candidate compound is identified as a stimulator of nucleic acid expression. When nucleic acid expression is statistically significantly less in the presence of the candidate compound than in its absence, the candidate compound is identified as an inhibitor of nucleic acid expression.

The invention further provides methods of treatment, with the nucleic acid as a target, using a compound identified through drug screening as a gene modulator to modulate protease nucleic acid expression in cells and tissues that express the protease. Experimental data as provided in FIG. 1 indicates that aminopeptidase proteins of the present invention are expressed in the in the adrenal cortico adenoma for cushing's syndrome, prostate embryonal carcinoma,colon tumor, adult brain, heaptocellular carcinoma, pooled (fetal lung, testis and b cell), kidney, prostate by a virtual northern blot. In addition, PCR-based tissue screening panel indicates expression in human fetal whole brain. Modulation includes both up-regulation (i.e. activation or agonization) or down-regulation (suppression or antagonization) or nucleic acid expression.

Alternatively, a modulator for protease nucleic acid expression can be a small molecule or drug identified using the screening assays described herein as long as the drug or small molecule inhibits the protease nucleic acid expression in the cells and tissues that express the protein. Experimental data as provided in FIG. 1 indicates expression in the adrenal cortico adenoma for cushing's syndrome, prostate embryonal carcinoma, colon tumor, adult brain, heaptocellular carcinoma, pooled (fetal lung, testis and b cell), kidney, prostate.

The nucleic acid molecules are also useful for monitoring the effectiveness of modulating compounds on the expression or activity of the protease gene in clinical trials or in a treatment regimen. Thus, the gene expression pattern can serve as a barometer for the continuing effectiveness of treatment with the compound, particularly with compounds to which a patient can develop resistance. The gene expression pattern can also serve as a marker indicative of a physiological response of the affected cells to the compound. Accordingly, such monitoring would allow either increased administration of the compound or the administration of alternative compounds to which the patient has not become resistant. Similarly, if the level of nucleic acid expression falls below a desirable level, administration of the compound could be commensurately decreased.

The nucleic acid molecules are also useful in diagnostic assays for qualitative changes in protease nucleic acid expression, and particularly in qualitative changes that lead to pathology. The nucleic acid molecules can be used to detect mutations in protease genes and gene expression products such as mRNA. The nucleic acid molecules can be used as hybridization probes to detect naturally occurring genetic mutations in the protease gene and thereby to determine whether a subject with the mutation is at risk for a disorder caused by the mutation. Mutations include deletion, addition, or substitution of one or more nucleotides in the gene, chromosomal rearrangement, such as inversion or transposition, modification of genomic DNA, such as aberrant methylation patterns or changes in gene copy number, such as amplification. Detection of a mutated form of the protease gene associated with a dysfunction provides a diagnostic tool for an active disease or susceptibility to disease when the disease results from overexpression, underexpression, or altered expression of a protease protein.

Individuals carrying mutations in the protease gene can be detected at the nucleic acid level by a variety of techniques. FIG. 3 provides information on SNPs that have been identified in a gene encoding the protease protein of the present invention. 21 SNP variants were found, including 6 indels (indicated by a "-") and 1 SNPs in exons. As indicated by the data presented in FIG. 3, the map position was determined to be on chromosome 2 by ePCR. Genomic DNA can be analyzed directly or can be amplified by using PCR prior to analysis. RNA or cDNA can be used in the same way. In some uses, detection of the mutation involves the use of a probe/primer in a polymerase chain reaction (PCR) (see, e.g. U.S. Pat. Nos. 4,683,195 and 4,683,202), such as anchor PCR or RACE PCR, or, alternatively, in a ligation chain reaction (LCR) (see, e.g., Landegran et al., *Science* 241:1077–1080 (1988); and Nakazawa et al., *PNAS* 91:360–364 (1994)), the latter of which can be particularly useful for detecting point mutations in the gene (see Abravaya et al., *Nucleic Acids Res.* 23:675–682 (1995)). This method can include the steps of collecting a sample of cells from a patient, isolating nucleic acid (e.g., genomic, mRNA or both) from the cells of the sample, contacting the nucleic acid sample with one or more primers which specifically hybridize to a gene under conditions such that hybridization and amplification of the gene (if present) occurs, and detecting the presence or absence of an amplification product, or detecting the size of the amplification product and comparing the length to a control sample. Deletions and insertions can be detected by a change in size of the amplified product compared to the normal genotype. Point mutations can be identified by hybridizing amplified DNA to normal RNA or antisense DNA sequences.

Alternatively, mutations in a protease gene can be directly identified, for example, by alterations in restriction enzyme digestion patterns determined by gel electrophoresis.

Further, sequence-specific ribozymes (U.S. Pat. No. 5,498,531) can be used to score for the presence of specific mutations by development or loss of a ribozyme cleavage site. Perfectly matched sequences can be distinguished from mismatched sequences by nuclease cleavage digestion assays or by differences in melting temperature.

Sequence changes at specific locations can also be assessed by nuclease protection assays such as RNase and S1 protection or the chemical cleavage method. Furthermore, sequence differences between a mutant protease gene and a wild-type gene can be determined by direct DNA sequencing. A variety of automated sequencing procedures can be utilized when performing the diagnostic assays (Naeve, C. W., (1995) *Biotechniques* 19:448), including sequencing by mass spectrometry (see, e.g., PCT International Publication No. WO 94/16101; Cohen et al., *Adv. Chromatogr.* 36:127–162 (1996); and Griffin et al., *Appl. Biochem. Biotechnol.* 38:147–159 (1993)).

Other methods for detecting mutations in the gene include methods in which protection from cleavage agents is used to detect mismatched bases in RNA/RNA or RNA/DNA duplexes (Myers et al., *Science* 230:1242 (1985)); Cotton et al., *PNAS* 85:4397 (1988); Saleeba et al., *Meth. Enzymol.* 217:286–295 (1992)), electrophoretic mobility of mutant and wild type nucleic acid is compared (Orita et al., *PNAS* 86:2766 (1989); Cotton et al., *Mutat. Res.* 285:125–144 (1993); and Hayashi et al., *Genet. Anal. Tech. Appl.* 9:73–79 (1992)), and movement of mutant or wild-type fragments in polyacrylamide gels containing a gradient of denaturant is assayed using denaturing gradient gel electrophoresis (Myers et al., *Nature* 313:495 (1985)). Examples of other techniques for detecting point mutations include selective oligonucleotide hybridization, selective amplification, and selective primer extension.

The nucleic acid molecules are also useful for testing an individual for a genotype that while not necessarily causing the disease, nevertheless affects the treatment modality. Thus, the nucleic acid molecules can be used to study the relationship between an individual's genotype and the individual's response to a compound used for treatment (pharmacogenomic relationship). Accordingly, the nucleic acid molecules described herein can be used to assess the mutation content of the protease gene in an individual in order to select an appropriate compound or dosage regimen for treatment.

Thus nucleic acid molecules displaying genetic variations that affect treatment provide a diagnostic target that can be used to tailor treatment in an individual. Accordingly, the production of recombinant cells and animals containing these polymorphisms allow effective clinical design of treatment compounds and dosage regimens.

The nucleic acid molecules are thus useful as antisense constructs to control protease gene expression in cells, tissues, and organisms. A DNA antisense nucleic acid molecule is designed to be complementary to a region of the gene involved in transcription, preventing transcription and hence production of protease protein. An antisense RNA or DNA nucleic acid molecule would hybridize to the mRNA and thus block translation of mRNA into protease protein. FIG. 3 provides information on SNPs that have been identified in a gene encoding the protease protein of the present invention. 21 SNP variants were found, including 6 indels (indicated by a "-") and 1 SNPs in exons.

Alternatively, a class of antisense molecules can be used to inactivate mRNA in order to decrease expression of protease nucleic acid. Accordingly, these molecules can treat a disorder characterized by abnormal or undesired protease nucleic acid expression. This technique involves cleavage by means of ribozymes containing nucleotide sequences complementary to one or more regions in the mRNA that attenuate the ability of the mRNA to be translated. Possible regions include coding regions and particularly coding regions corresponding to the catalytic and other functional activities of the protease protein, such as substrate binding.

The nucleic acid molecules also provide vectors for gene therapy in patients containing cells that are aberrant in protease gene expression. Thus, recombinant cells, which include the patient's cells that have been engineered ex vivo and returned to the patient, are introduced into an individual where the cells produce the desired protease protein to treat the individual.

The invention also encompasses kits for detecting the presence of a protease nucleic acid in a biological sample. Experimental data as provided in FIG. 1 indicates that aminopeptidase proteins of the present invention are expressed in the in the adrenal cortico adenoma for cushing's syndrome, prostate embryonal carcinoma,colon tumor, adult brain, heaptocellular carcinoma, pooled (fetal lung, testis and b cell), kidney, prostate by a virtual northern blot. In addition, PCR-based tissue screening panel indicates expression in human fetal whole brain. For example, the kit can comprise reagents such as a labeled or labelable nucleic acid or agent capable of detecting protease nucleic acid in a biological sample; means for determining the amount of protease nucleic acid in the sample; and means for comparing the amount of protease nucleic acid in the sample with a standard. The compound or agent can be packaged in a suitable container. The kit can further comprise instructions for using the kit to detect protease protein mRNA or DNA.

Nucleic Acid Arrays

The present invention further provides nucleic acid detection kits, such as arrays or microarrays of nucleic acid molecules that are based on the sequence information provided in FIGS. 1 and 3 (SEQ ID NOS:1 and 3).

As used herein "Arrays" or "Microarrays" refers to an array of distinct polynucleotides or oligonucleotides synthesized on a substrate, such as paper, nylon or other type of membrane, filter, chip, glass slide, or any other suitable solid support. In one embodiment, the microarray is prepared and used according to the methods described in U.S. Pat. 5,837,832, Chee et al., PCT application WO95/11995 (Chee et al.), Lockhart, D. J. et al. (1 996; Nat. Biotech. 14: 1675–1680) and Schena, M. et al. (1996; Proc. Natl. Acad. Sci. 93: 10614–10619), all of which are incorporated herein in their entirety by reference. In other embodiments, such arrays are produced by the methods described by Brown et at, U.S. Pat. No. 5,807,522.

The microarray or detection kit is preferably composed of a large number of unique, single-stranded nucleic acid sequences, usually either synthetic antisense oligonucleotides or fragments of cDNAs, fixed to a solid support. The oligonucleotides are preferably about 6–60 nucleotides in length, more preferably 15–30 nucleotides in length, and most preferably about 20–25 nucleotides in length. For a certain type of microarray or detection kit, it may be preferable to use oligonucleotides that are only 7–20 nucleotides in length. The microarray or detection kit may contain oligonucleotides that cover the known 5', or 3', sequence, sequential oligonucleotides which cover the full length sequence; or unique oligonucleotides selected from particular areas along the length of the sequence. Polynucleotides used in the microarray or detection kit may be oligonucleotides that are specific to a gene or genes of interest.

In order to produce oligonucleotides to a known sequence for a microarray or detection kit, the gene(s) of interest (or an ORF identified from the contigs of the present invention) is typically examined using a computer algorithm which starts at the 5' or at the 3' end of the nucleotide sequence. Typical algorithms will then identify oligomers of defined length that are unique to the gene, have a GC content within a range suitable for hybridization, and lack predicted secondary structure that may interfere with hybridization. In certain situations it may be appropriate to use pairs of oligonucleotides on a microarray or detection kit. The "pairs" will be identical, except for one nucleotide that preferably is located in the center of the sequence. The second oligonucleotide in the pair (mismatched by one) serves as a control. The number of oligonucleotide pairs may range from two to one million. The oligomers are synthesized at designated areas on a substrate using a light-directed chemical process. The substrate may be paper, nylon or other type of membrane, filter, chip, glass slide or any other suitable solid support.

In another aspect, an oligonucleotide may be synthesized on the surface of the substrate by using a chemical coupling procedure and an ink jet application apparatus, as described in PCT application WO95/251116 (Baldeschweiler et al.) which is incorporated herein in its entirety by reference. In another aspect, a "gridded" array analogous to a dot (or slot) blot may be used to arrange and link cDNA fragments or oligonucleotides to the surface of a substrate using a vacuum system, thermal, UV, mechanical or chemical bonding procedures. An array, such as those described above, may be produced by hand or by using available devices (slot blot or dot blot apparatus), materials (any suitable solid support), and machines (including robotic instruments), and may contain 8, 24, 96, 384, 1536, 6144 or more oligonucleotides, or any other number between two and one million which lends itself to the efficient use of commercially available instrumentation.

In order to conduct sample analysis using a microarray or detection kit, the RNA or DNA from a biological sample is made into hybridization probes. The mRNA is isolated, and cDNA is produced and used as a template to make antisense RNA (aRNA). The aRNA is amplified in the presence of fluorescent nucleotides, and labeled probes are incubated with the microarray or detection kit so that the probe sequences hybridize to complementary oligonucleotides of the microarray or detection kit. Incubation conditions are adjusted so that hybridization occurs with precise complementary matches or with various degrees of less complementarity. After removal of nonhybridized probes, a scanner is used to determine the levels and patterns of fluorescence. The scanned images are examined to determine degree of complementarity and the relative abundance of each oligonucleotide sequence on the microarray or detection kit. The biological samples may be obtained from any bodily fluids (such as blood, urine, saliva, phlegm, gastric juices, etc.), cultured cells, biopsies, or other tissue preparations. A detection system may be used to measure the absence, presence, and amount of hybridization for all of the distinct sequences simultaneously. This data may be used for large-scale correlation studies on the sequences, expression patterns, mutations, variants, or polymorphisms among samples.

Using such arrays, the present invention provides methods to identify the expression of the protease proteins/peptides of the present invention. In detail, such methods comprise incubating a test sample with one or more nucleic acid molecules and assaying for binding of the nucleic acid molecule with components within the test sample. Such assays will typically involve arrays comprising many genes, at least one of which is a gene of the present invention and or alleles of the protease gene of the present invention. FIG. 3 provides information on SNPs that have been identified in a gene encoding the protease protein of the present invention. 21 SNP variants were found, including 6 indels (indicated by a "-") and 1 SNPs in exons.

Conditions for incubating a nucleic acid molecule with a test sample vary. Incubation conditions depend on the format employed in the assay, the detection methods employed, and the type and nature of the nucleic acid molecule used in the assay. One skilled in the art will recognize that any one of the commonly available hybridization, amplification or array assay formats can readily be adapted to employ the novel fragments of the Human genome disclosed herein. Examples of such assays can be found in Chard, T, *An Introduction to Radioimmunoassay and Related Techniques*, Elsevier Science Publishers, Amsterdam, The Netherlands (1986); Bullock, G. R. et al., *Techniques in Immunocytochemistry*, Academic Press, Orlando, Fla. Vol. 1 (1982), Vol. 2 (1983), Vol. 3 (1985); Tijssen, P., *Practice and Theory ofEnzyme Immunoassays: Laboratory Techniques in Biochemistry and Molecular Biology*, Elsevier Science Publishers, Amsterdam, The Netherlands (1985).

The test samples of the present invention include cells, protein or membrane extracts of cells. The test sample used in the above-described method will vary based on the assay format, nature of the detection method and the tissues, cells or extracts used as the sample to be assayed. Methods for preparing nucleic acid extracts or of cells are well known in the art and can be readily be adapted in order to obtain a sample that is compatible with the system utilized.

In another embodiment of the present invention, kits are provided which contain the necessary reagents to carry out the assays of the present invention.

Specifically, the invention provides a compartmentalized kit to receive, in close confinement, one or more containers which comprises: (a) a first container comprising one of the nucleic acid molecules that can bind to a fragment of the Human genome disclosed herein; and (b) one or more other containers comprising one or more of the following: wash reagents, reagents capable of detecting presence of a bound nucleic acid.

In detail, a compartmentalized kit includes any kit in which reagents are contained in separate containers. Such containers include small glass containers, plastic containers, strips of plastic, glass or paper, or arraying material such as silica. Such containers allows one to efficiently transfer reagents from one compartment to another compartment such that the samples and reagents are not cross-contaminated, and the agents or solutions of each container can be added in a quantitative fashion from one compartment to another. Such containers will include a container which will accept the test sample, a container which contains the nucleic acid probe, containers which contain wash reagents (such as phosphate buffered saline, Tris-buffers, etc.), and containers which contain the reagents used to detect the bound probe. One skilled in the art will readily recognize that the previously unidentified protease gene of the present invention can be routinely identified using the sequence information disclosed herein can be readily incorporated into one of the established kit formats which are well known in the art, particularly expression arrays.

Vectors/host cells

The invention also provides vectors containing the nucleic acid molecules described herein. The term "vector" refers to a vehicle, preferably a nucleic acid molecule, which can transport the nucleic acid molecules. When the vector is a nucleic acid molecule, the nucleic acid molecules are covalently linked to the vector nucleic acid. With this aspect of the invention, the vector includes a plasmid, single or double stranded phage, a single or double stranded RNA or DNA viral vector, or artificial chromosome, such as a BAC, PAC, YAC, OR MAC.

A vector can be maintained in the host cell as an extrachromosomal element where it replicates and produces additional copies of the nucleic acid molecules. Alternatively, the vector may integrate into the host cell genome and produce additional copies of the nucleic acid molecules when the host cell replicates.

The invention provides vectors for the maintenance (cloning vectors) or vectors for expression (expression vectors) of the nucleic acid molecules. The vectors can function in prokaryotic or eukaryotic cells or in both (shuttle vectors).

Expression vectors contain cis-acting regulatory regions that are operably linked in the vector to the nucleic acid molecules such that transcription of the nucleic acid molecules is allowed in a host cell. The nucleic acid molecules can be introduced into the host cell with a separate nucleic acid molecule capable of affecting transcription. Thus, the second nucleic acid molecule may provide a trans-acting factor interacting with the cis-regulatory control region to allow transcription of the nucleic acid molecules from the vector. Alternatively, a trans-acting factor may be supplied by the host cell. Finally, a trans-acting factor can be produced from the vector itself. It is understood, however, that in some embodiments, transcription and/or translation of the nucleic acid molecules can occur in a cell-free system.

The regulatory sequence to which the nucleic acid molecules described herein can be operably linked include promoters for directing mRNA transcription. These include, but are not limited to, the left promoter from bacteriophage λ, the lac, TRP, and TAC promoters from *E. coli*, the early and late promoters from SV40, the CMV immediate early promoter, the adenovirus early and late promoters, and retrovirus long-terminal repeats.

In addition to control regions that promote transcription, expression vectors may also include regions that modulate transcription, such as repressor binding sites and enhancers. Examples include the SV40 enhancer, the cytomegalovirus immediate early enhancer, polyoma enhancer, adenovirus enhancers, and retrovirus LTR enhancers.

In addition to containing sites for transcription initiation and control, expression vectors can also contain sequences necessary for transcription termination and, in the transcribed region a ribosome binding site for translation. Other regulatory control elements for expression include initiation and termination codons as well as polyadenylation signals. The person of ordinary skill in the art would be aware of the numerous regulatory sequences that are useful in expression vectors. Such regulatory sequences are described, for example, in Sambrook et al., *Molecular Cloning: A Laboratory Manual*. 2nd ed., Cold Spring Harbor Laboratory Press, Cold Spring Harbor, N.Y., (1989).

A variety of expression vectors can be used to express a nucleic acid molecule. Such vectors include chromosomal, episomal, and virus-derived vectors, for example vectors derived from bacterial plasmids, from bacteriophage, from yeast episomes, from yeast chromosomal elements, including yeast artificial chromosomes, from viruses such as baculoviruses, papovaviruses such as SV40, Vaccinia viruses, adenoviruses, poxviruses, pseudorabies viruses, and retroviruses. Vectors may also be derived from combinations of these sources such as those derived from plasmid and bacteriophage genetic elements, e.g. cosmids and phagemids. Appropriate cloning and expression vectors for prokaryotic and eukaryotic hosts are described in Sambrook et al., *Molecular Cloning. A Laboratory Manual*. 2nd ed., Cold Spring Harbor Laboratory Press, Cold Spring Harbor, N.Y., (1989).

The regulatory sequence may provide constitutive expression in one or more host cells (i.e. tissue specific) or may provide for inducible expression in one or more cell types such as by temperature, nutrient additive, or exogenous factor such as a hormone or other ligand. A variety of vectors providing for constitutive and inducible expression in prokaryotic and eukaryotic hosts are well known to those of ordinary skill in the art.

The nucleic acid molecules can be inserted into the vector nucleic acid by well-known methodology. Generally, the DNA sequence that will ultimately be expressed is joined to an expression vector by cleaving the DNA sequence and the expression vector with one or more restriction enzymes and then ligating the fragments together. Procedures for restriction enzyme digestion and ligation are well known to those of ordinary skill in the art.

The vector containing the appropriate nucleic acid molecule can be introduced into an appropriate host cell for propagation or expression using well-known techniques. Bacterial cells include, but are not limited to, *E. coli*, Streptomyces, and Salmonella typhimurium. Eukaryotic cells include, but are not limited to, yeast, insect cells such as Drosophila, animal cells such as COS and CHO cells, and plant cells.

As described herein, it may be desirable to express the peptide as a fusion protein. Accordingly, the invention provides fusion vectors that allow for the production of the peptides. Fusion vectors can increase the expression of a recombinant protein, increase the solubility of the recombinant protein, and aid in the purification of the protein by acting for example as a ligand for affinity purification. A proteolytic cleavage site may be introduced at the junction of the fusion moiety so that the desired peptide can ultimately be separated from the fusion moiety. Proteolytic enzymes include, but are not limited to, factor Xa, thrombin, and enteroprotease. Typical fusion expression vectors include pGEX (Smith et al., *Gene* 67:31–40 (1988)), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. Examples of suitable inducible non-fusion *E. coli* expression vectors include pTrc (Amann et al., *Gene* 69:301–315 (1988)) and pET 11d (Studier et al., *Gene Expression Technology: Methods in Enzymology* 185:60–89 (1990)).

Recombinant protein expression can be maximized in host bacteria by providing a genetic background wherein the host cell has an impaired capacity to proteolytically cleave the recombinant protein. (Gottesman, S., *Gene Expression Technology: Methods in Enzymology* 185, Academic Press, San Diego, Calif. (1990)119–128). Alternatively, the sequence of the nucleic acid molecule of interest can be altered to provide preferential codon usage for a specific host cell, for example *E coli*. (Wada et al., Nucleic Acids Res. 20:2111–2118 (1992)).

The nucleic acid molecules can also be expressed by expression vectors that are operative in yeast. Examples of vectors for expression in yeast e.g., S. cerevisiae include pYepSec1 (Baldari, et al., *EMBO J*. 6:229–234 (1987)), pMFa (Kujan et al., *Cell* 30:933–943(1982)), pJRY88 (Schultz et al., *Gene* 54:113–123 (1987)), and pYES2 (Invitrogen Corporation, San Diego, Calif.).

The nucleic acid molecules can also be expressed in insect cells using, for example, baculovirus expression vectors. Baculovirus vectors available for expression of proteins in cultured insect cells (e.g., Sf 9 cells) include the pAc series (Smith et al., *Mol. Cell Biol*. 3:2156–2165 (1983)) and the pVL series (Lucklowet al., *Virology* 170:31–39 (1989)).

In certain embodiments of the invention, the nucleic acid molecules described herein are expressed in mammalian cells using mammalian expression vectors. Examples of mammalian expression vectors include pCDM8 (Seed, B. *Nature* 329:840(1987)) and pMT2PC (Kaulman et al., *EMBO J*. 6:187–195 (1987)).

The expression vectors listed herein are provided by way of example only of the well-known vectors available to those of ordinary skill in the art that would be useful to express the nucleic acid molecules. The person of ordinary skill in the art would be aware of other vectors suitable for maintenance propagation or expression of the nucleic acid molecules described herein. These are found for example in Sambrook, J., Fritsh, E. F., and Maniatis, *T. Molecular Cloning: A Laboratory Manual*. 2nd, ed, *Cold Spring Harbor Laboratory*, Cold Spring Harbor Laboratory Press, Cold Spring Harbor, N.Y., 1989.

The invention also encompasses vectors in which the nucleic acid sequences described herein are cloned into the vector in reverse orientation, but operably linked to a regulatory sequence that permits transcription of antisense RNA. Thus, an antisense transcript can be produced to all, or to a portion, of the nucleic acid molecule sequences described herein, including both coding and non-coding regions. Expression of this antisense RNA is subject to each of the parameters described above in relation to expression of the sense RNA (regulatory sequences, constitutive or inducible expression, tissue-specific expression).

The invention also relates to recombinant host cells containing the vectors described herein. Host cells therefore include prokaryotic cells, lower eukaryotic cells such as yeast, other eukaryotic cells such as insect cells, and higher eukaryotic cells such as mammalian cells.

The recombinant host cells are prepared by introducing the vector constructs described herein into the cells by techniques readily available to the person of ordinary skill in the art. These include, but are not limited to, calcium phosphate transfection, DEAE-dextran-mediated transfection, cationic lipid-mediated transfection, electroporation, transduction, infection, lipofection, and other techniques such as those found in Sambrook, et al. (*Molecular Cloning: A Laboratory Manual*. 2nd, ed, *Cold Spring Harbor Laboratory*, Cold Spring Harbor Laboratory Press, Cold Spring Harbor, N.Y., 1989).

Host cells can contain more than one vector. Thus, different nucleotide sequences can be introduced on different vectors of the same cell. Similarly, the nucleic acid molecules can be introduced either alone or with other nucleic acid molecules that are not related to the nucleic acid molecules such as those providing trans-acting factors for expression vectors. When more than one vector is introduced into a cell, the vectors can be introduced independently, co-introduced or joined to the nucleic acid molecule vector.

In the case of bacteriophage and viral vectors, these can be introduced into cells as packaged or encapsulated virus by standard procedures for infection and transduction. Viral vectors can be replication-competent or replication-defective. In the case in which viral replication is defective, replication will occur in host cells providing functions that complement the defects.

Vectors generally include selectable markers that enable the selection of the subpopulation of cells that contain the recombinant vector constructs. The marker can be contained in the same vector that contains the nucleic acid molecules described herein or may be on a separate vector. Markers include tetracycline or ampicillin-resistance genes for prokaryotic host cells and dihydrofolate reductase or neomycin resistance for eukaryotic host cells. However, any marker that provides selection for a phenotypic trait will be effective.

While the mature proteins can be produced in bacteria, yeast, mammalian cells, and other cells under the control of the appropriate regulatory sequences, cell-free transcription and translation systems can also be used to produce these proteins using RNA derived from the DNA constructs described herein.

Where secretion of the peptide is desired, which is difficult to achieve with multi-transmembrane domain containing proteins such as proteases, appropriate secretion signals are incorporated into the vector. The signal sequence can be endogenous to the peptides or heterologous to these peptides.

Where the peptide is not secreted into the medium, which is typically the case with proteases, the protein can be isolated from the host cell by standard disruption procedures, including freeze thaw, sonication, mechanical disruption, use of lysing agents and the like. The peptide can then be recovered and purified by well-known purification methods including ammonium sulfate precipitation, acid extraction, anion or cationic exchange chromatography, phosphocellulose chromatography, hydrophobic-interaction chromatography, affinity chromatography, hydroxylapatite chromatography, lectin chromatography, or high performance liquid chromatography.

It is also understood that depending upon the host cell in recombinant production of the peptides described herein, the peptides can have various glycosylation patterns, depending upon the cell, or maybe non-glycosylated as when produced in bacteria. In addition, the peptides may include an initial modified methionine in some cases as a result of a host-mediated process.

Uses of vectors and host cells

The recombinant host cells expressing the peptides described herein have a variety of uses. First, the cells are useful for producing a protease protein or peptide that can be further purified to produce desired amounts of protease protein or fragments. Thus, host cells containing expression vectors are useful for peptide production.

Host cells are also useful for conducting cell-based assays involving the protease protein or protease protein fragments, such as those described above as well as other formats known in the art. Thus, a recombinant host cell expressing a native protease protein is useful for assaying compounds that stimulate or inhibit protease protein function.

Host cells are also useful for identifying protease protein mutants in which these functions are affected. If the mutants naturally occur and give rise to a pathology, host cells containing the mutations are useful to assay compounds that have a desired effect on the mutant protease protein (for example, stimulating or inhibiting function) which may not be indicated by their effect on the native protease protein.

Genetically engineered host cells can be further used to produce non-human transgenic animals. A transgenic animal is preferably a mammal, for example a rodent, such as a rat or mouse, in which one or more of the cells of the animal include a transgene. A transgene is exogenous DNA which is integrated into the genome of a cell from which a transgenic animal develops and which remains in the genome of the mature animal in one or more cell types or tissues of the transgenic animal. These animals are useful for studying the function of a protease protein and identifying and evaluating modulators of protease protein activity. Other examples of transgenic animals include non-human primates, sheep, dogs, cows, goats, chickens, and amphibians.

A transgenic animal can be produced by introducing nucleic acid into the male pronuclei of a fertilized oocyte, e.g., by microinjection, retroviral infection, and allowing the oocyte to develop in a pseudopregnant female foster animal. Any of the protease protein nucleotide sequences can be introduced as a transgene into the genome of a non-human animal, such as a mouse.

Any of the regulatory or other sequences useful in expression vectors can form part of the transgenic sequence. This includes intronic sequences and polyadenylation signals, if not already included. A tissue-specific regulatory sequence (s) can be operably linked to the transgene to direct expression of the protease protein to particular cells.

Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of the transgene in its genome and/or expression of transgenic mRNA in tissues or cells of the animals. A transgenic founder animal can then be used to breed additional animals carrying the transgene. Moreover, transgenic animals carrying a transgene can further be bred to other transgenic animals carrying other transgenes. A transgenic animal also includes animals in which the entire animal or tissues in the animal have been produced using the homologously recombinant host cells described herein.

In another embodiment, transgenic non-human animals can be produced which contain selected systems that allow for regulated expression of the transgene. One example of such a system is the cre/loxP recombinase system of bacteriophage P1. For a description of the cre/loxP recombinase system, see, e.g., Lakso et al. *PNAS* 89:6232–6236 (1992). Another example of a recombinase system is the FLP recombinase system of S. cerevisiae (O'Gorman et al. *Science* 251:1351–1355 (1991). If a cre/loxP recombinase system is used to regulate expression of the transgene, animals containing transgenes encoding both the Cre recombinase and a selected protein is required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. *Nature* 385:810–813 (1997) and PCT International Publication Nos. WO 97/07668 and WO 97/07669. In brief, a cell, e.g., a somatic cell, from the transgenic animal can be isolated and induced to exit the growth cycle and enter GO phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyst and then transferred to pseudopregnant female foster animal. The offspring born of this female foster animal will be a clone of the animal from which the cell, e.g., the somatic cell, is isolated.

Transgenic animals containing recombinant cells that express the peptides described herein are useful to conduct the assays described herein in an in vivo context. Accordingly, the various physiological factors that are present in vivo and that could effect substrate binding, protease protein activity/activation, and signal transduction, may not be evident from in vitro cell-free or cell-based assays. Accordingly, it is useful to provide non-human transgenic animals to assay in vivo protease protein function, including substrate interaction, the effect of specific mutant protease proteins on protease protein function and substrate interaction, and the effect of chimeric protease proteins. It is also possible to assess the effect of null mutations, that is mutations that substantially or completely eliminate one or more protease protein functions.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the above-described modes for carrying out the invention which are obvious to those skilled in the art field of molecular biology or related fields are intended to be within the scope of the following claims.

That which is claimed is:

1. An isolated nucleic acid molecule ending a methionine amino peptidase consisting of a nucleotide sequence selected from the group consisting of:

(a) a nucleotide sequence that encodes a protein comprising the amino acid sequence of SEQ ID NO:2;

(b) a nucleic acid molecule consisting of the nucleic acid sequence of SEQ ID NO:1; and (c) a nucleic acid molecule consisting of the nucleic acid sequence of SEQ ID NO:3.

2. A nucleic acid vector comprising a nucleic acid molecule of claim 1.

3. A host cell containing the vector of claim 2.

4. A process for producing a polypeptide comprising culturing the host cell of claim 3 under conditions sufficient for the production of said polypeptide, and recovering the peptide from the host cell culture.

5. An isolated polynucleotide consisting of a nucleotide sequence set forth in SEQ ID NO:1.

6. An isolated polynucleotide consisting of a nucleotide sequence set forth in SEQ ID NO:3.

7. A vector according to claim 2, wherein said vector is selected from the group consisting of a plasmid, virus, and bacteriophage.

8. A vector according to claim 2, wherein said isolated nucleic acid molecule is inserted into said vector in proper orientation and correct reading frame such that the protein of SEQ ID NO:2 may be expressed by a cell transformed with said vector.

9. A vector according to claim 8, wherein said isolated nucleic acid molecule is operatively linked to a promoter sequence.

10. An isolated nucleic acid molecule consisting of a nucleotide sequence that is completely complementary to a nucleotide sequence of claim 4.

* * * * *